(12) United States Patent
Gocho et al.

(10) Patent No.: US 12,342,093 B2
(45) Date of Patent: *Jun. 24, 2025

(54) SOLID-STATE IMAGE SENSOR

(71) Applicant: SONY SEMICONDUCTOR SOLUTIONS CORPORATION, Kanagawa (JP)

(72) Inventors: Tetsuo Gocho, Kanagawa (JP); Masami Nagata, Kanagawa (JP)

(73) Assignee: Sony Semiconductor Solutions Corporation, Kanagawa (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/631,205

(22) Filed: Apr. 10, 2024

(65) Prior Publication Data
US 2024/0267654 A1    Aug. 8, 2024

Related U.S. Application Data

(63) Continuation of application No. 17/292,276, filed as application No. PCT/JP2019/045680 on Nov. 21, 2019, now Pat. No. 11,985,443.

(30) Foreign Application Priority Data

Nov. 21, 2018  (JP) ................................. 2018-218695
Jun. 25, 2019  (JP) ................................. 2019-116983

(51) Int. Cl.
*H04N 25/77*      (2023.01)
*G02B 23/24*      (2006.01)
(Continued)

(52) U.S. Cl.
CPC ............. *H04N 25/77* (2023.01); *H10F 39/18* (2025.01); *H10F 39/80373* (2025.01);
(Continued)

(58) Field of Classification Search
CPC .... H04N 25/77; H04N 25/587; H04N 25/778; H04N 25/78; H04N 25/79;
(Continued)

(56) References Cited

U.S. PATENT DOCUMENTS 8,514,308 B2*  8/2013  Itonaga ............... H01L 27/1469
                                                              348/340
9,685,480 B2*  6/2017  Yamagishi ............ H01L 23/481
(Continued)

FOREIGN PATENT DOCUMENTS

CN        102468317        5/2012
EP        2518768 A       10/2012
(Continued)

OTHER PUBLICATIONS

International Search Report and Written Opinion for International (PCT) Patent Application No. PCT/JP2019/045680, dated Feb. 10, 2020, 8 pages.
(Continued)

*Primary Examiner* — Shahbaz Nazrul
(74) *Attorney, Agent, or Firm* — Sheridan Ross PC

(57) ABSTRACT

A solid-state image sensor according to the present disclosure includes a first semiconductor substrate having a photoelectric conversion element and a second semiconductor substrate facing the first semiconductor substrate with an insulating film interposed therebetween, in which the second semiconductor substrate has an amplification transistor that amplifies an electrical signal output from the photoelectric conversion element on a first main surface (MSa), has a region having a resistance lower than a resistance of the second semiconductor substrate on a second main surface (MSb) opposite to the first main surface (MSa), and is grounded via the region.

20 Claims, 95 Drawing Sheets

(51) Int. Cl.
*H10F 39/00* (2025.01)
*H10F 39/18* (2025.01)
*A61B 1/05* (2006.01)

(52) U.S. Cl.
CPC ............ *A61B 1/05* (2013.01); *G02B 23/2407* (2013.01); *H10F 39/011* (2025.01); *H10F 39/806* (2025.01); *H10F 39/807* (2025.01)

(58) Field of Classification Search
CPC ......... H01L 27/14614; H01L 27/14643; H01L 27/14625; H01L 27/1463; H01L 27/14683; H01L 27/14687; H01L 27/1469; H01L 27/14623; H01L 27/1464; H01L 27/14603; H01L 27/14634; H01L 27/14636; H01L 27/14641; H01L 27/14609; A61B 1/05; G02B 23/2407; H10F 39/18; H10F 39/80373; H10F 39/011; H10F 39/806; H10F 39/807; H10F 39/018; H10F 39/026; H10F 39/811; H10F 39/199; H10F 39/813; H10F 39/809; H10F 39/8057; H10F 39/802; H10F 39/803
See application file for complete search history.

(56) References Cited

U.S. PATENT DOCUMENTS

| | | | |
|---|---|---|---|
| 10,090,352 B2 * | 10/2018 | Kumano | ............... H01L 23/481 |
| 10,840,278 B2 * | 11/2020 | Yamashita | ........ H01L 27/14612 |
| 2011/0155893 A1 | 6/2011 | Endo | |
| 2013/0141617 A1 | 6/2013 | Soda | |
| 2015/0091114 A1 | 4/2015 | Mansoorian et al. | |
| 2015/0365567 A1 * | 12/2015 | Umebayashi | ..... H01L 27/14645 348/308 |
| 2016/0037111 A1 | 2/2016 | Dai et al. | |
| 2016/0118425 A1 | 4/2016 | Kurokawa | |
| 2018/0294300 A1 | 10/2018 | Ishida et al. | |
| 2021/0057479 A1 | 2/2021 | Mizuta | |
| 2021/0400224 A1 | 12/2021 | Gocho et al. | |

FOREIGN PATENT DOCUMENTS

| | | |
|---|---|---|
| EP | 3358620 | 8/2018 |
| JP | 2000-196089 | 7/2000 |
| JP | 2010-245506 | 10/2010 |
| JP | 2013-118345 | 6/2013 |
| JP | 2015032687 A | 2/2015 |
| JP | 2016-086164 | 5/2016 |
| JP | 2018-050028 | 3/2018 |
| KR | 10-2017-0093709 | 8/2017 |
| KR | 10-2018-0048900 | 5/2018 |
| TW | 201839967 A | 11/2018 |
| TW | 201840005 A | 11/2018 |
| WO | WO-2011077580 A1 | 6/2011 |
| WO | WO 2013/161331 | 10/2013 |
| WO | WO 2017/057277 | 4/2017 |

OTHER PUBLICATIONS

Official Action for U.S. Appl. No. 17/292,276, dated Sep. 14, 2023, 13 pages.
Notice of Allowance for U.S. Appl. No. 17/292,276, dated Jan. 10, 2024, 9 pages.
Corrected Notice of Allowance for U.S. Appl. No. 17/292,276, dated Mar. 7, 2024, 4 pages.

* cited by examiner

FIG. 8
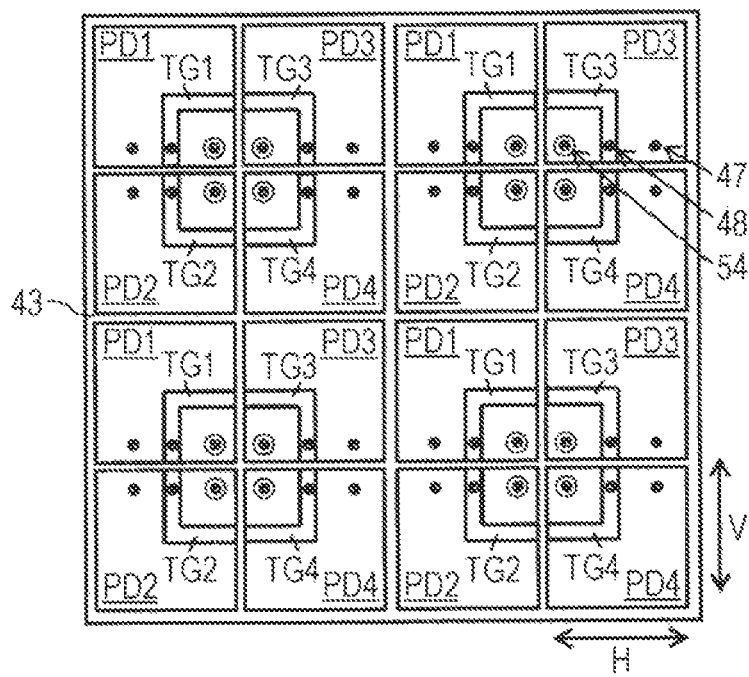
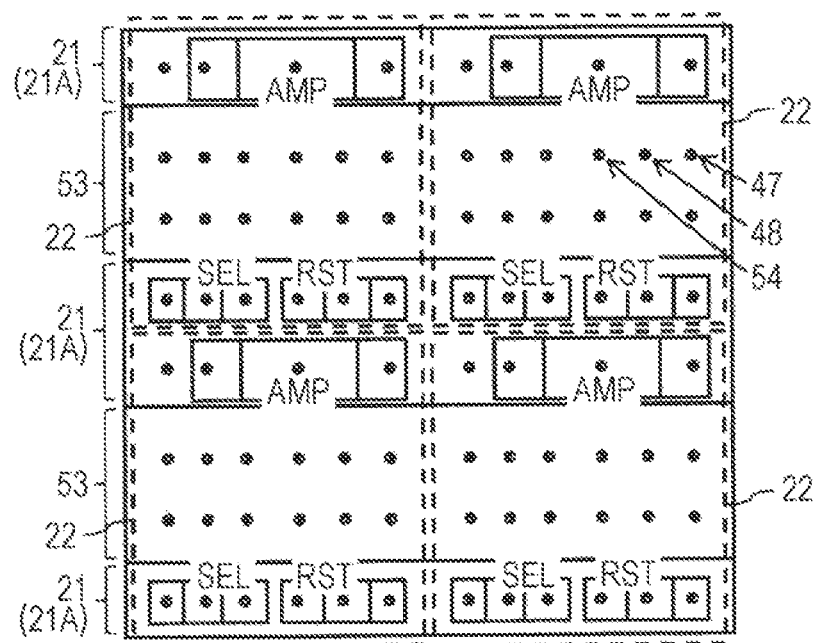

FIG. 13
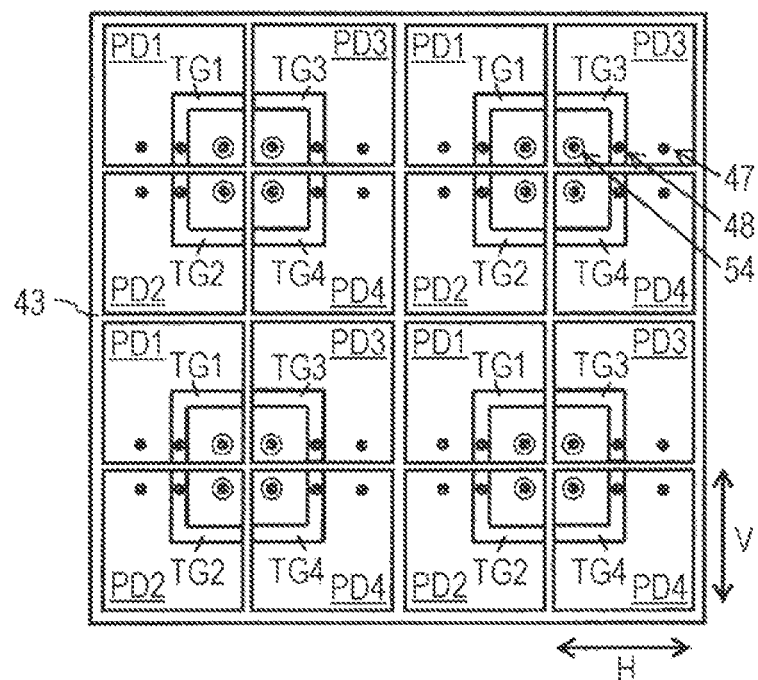
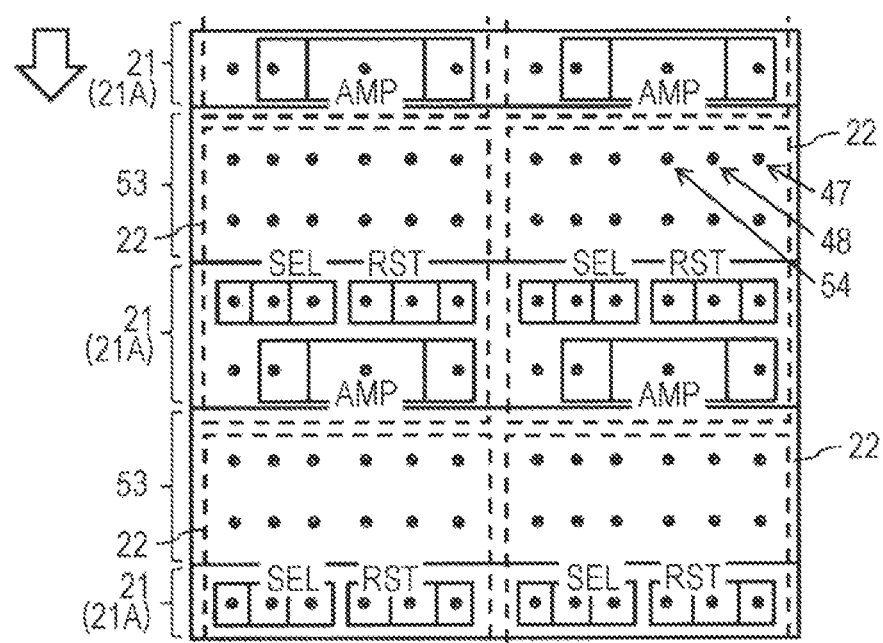

FIG. 14
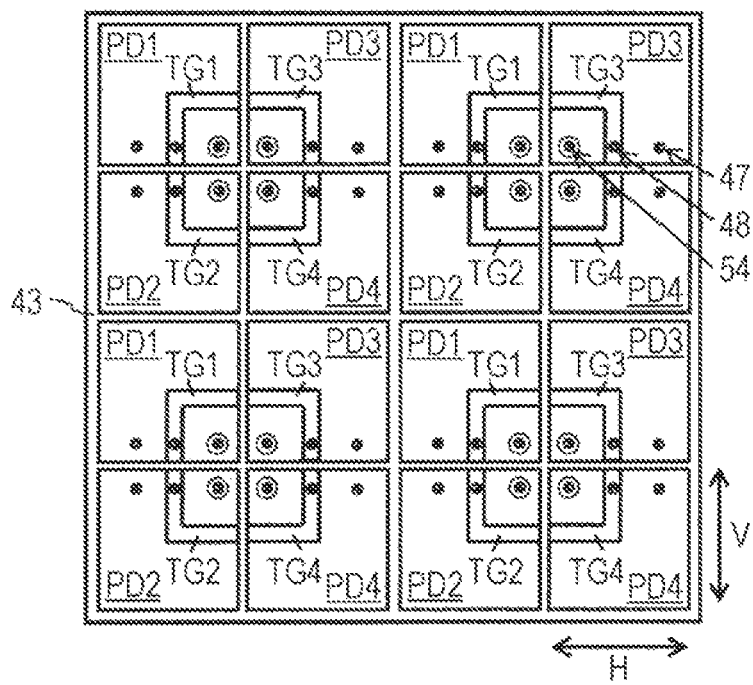
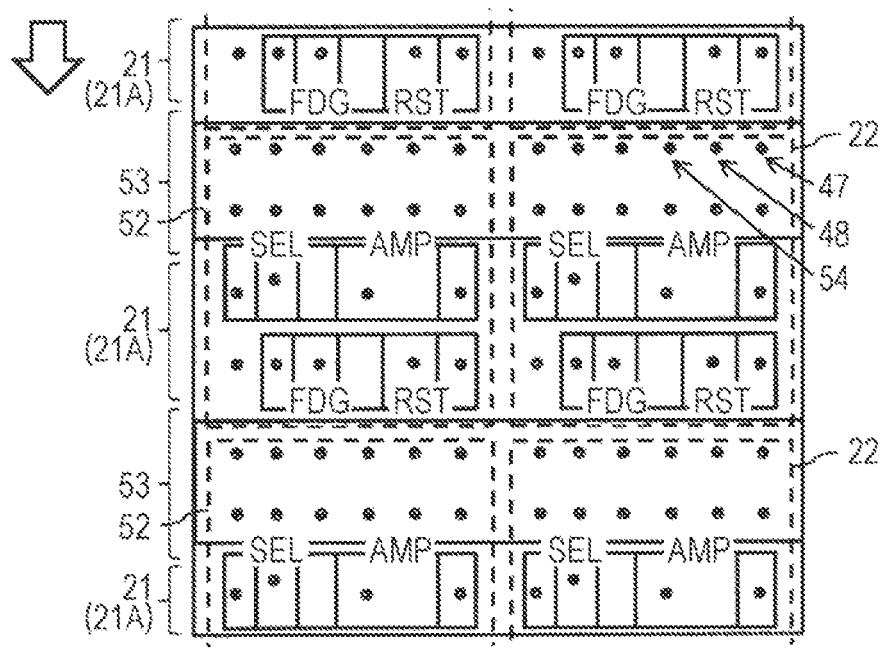

FIG. 26
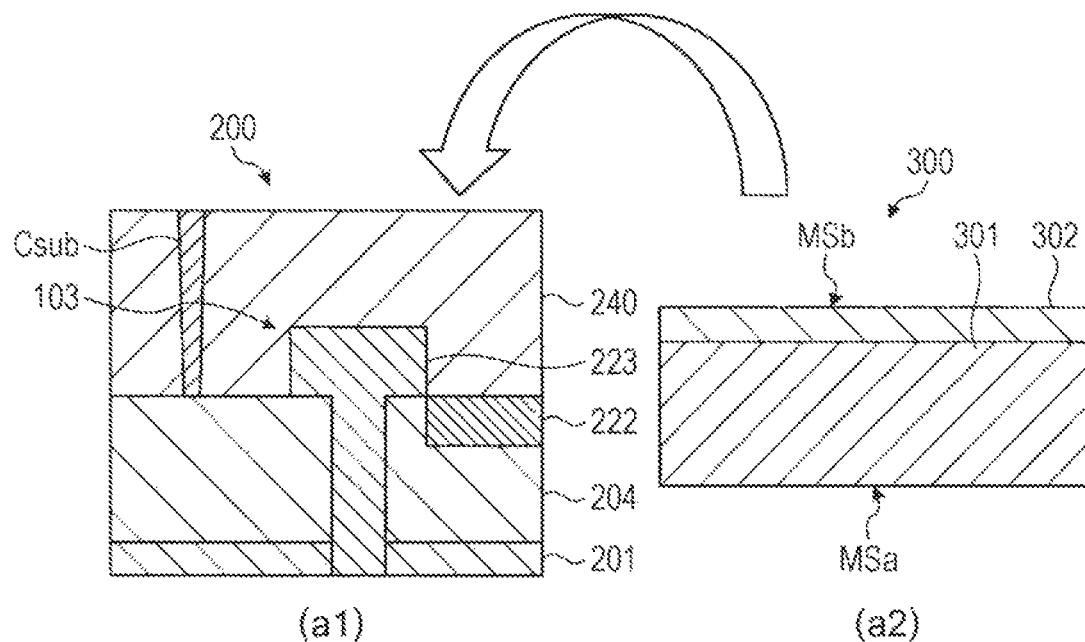
(a1)   (a2)
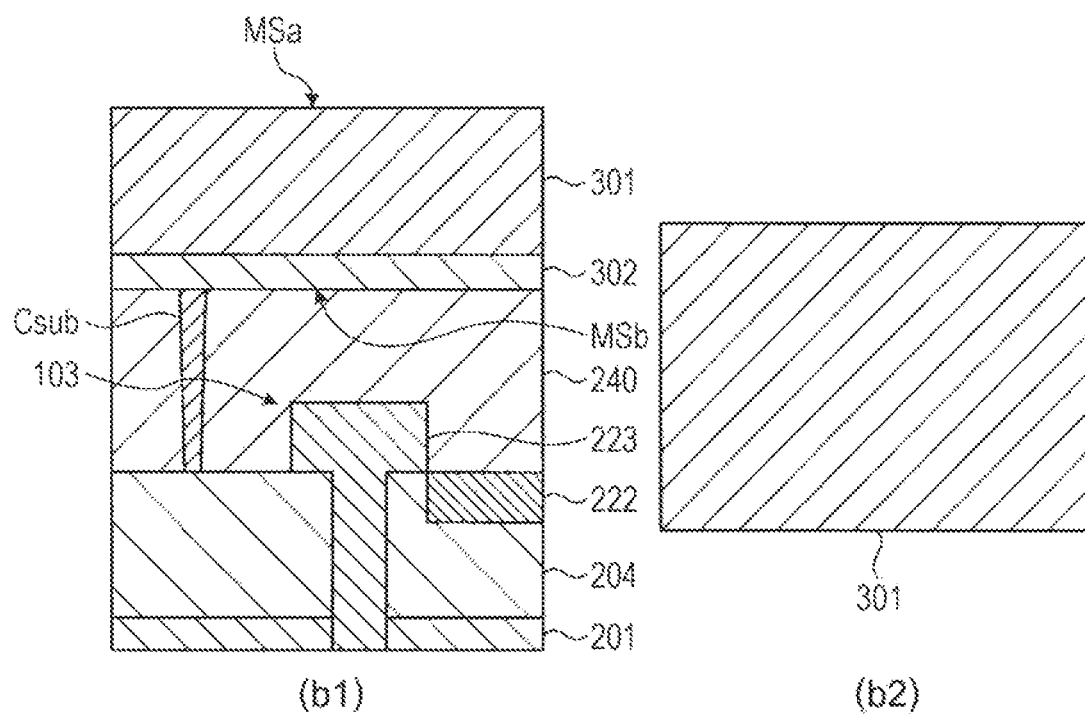
(b1)   (b2)

FIG. 27
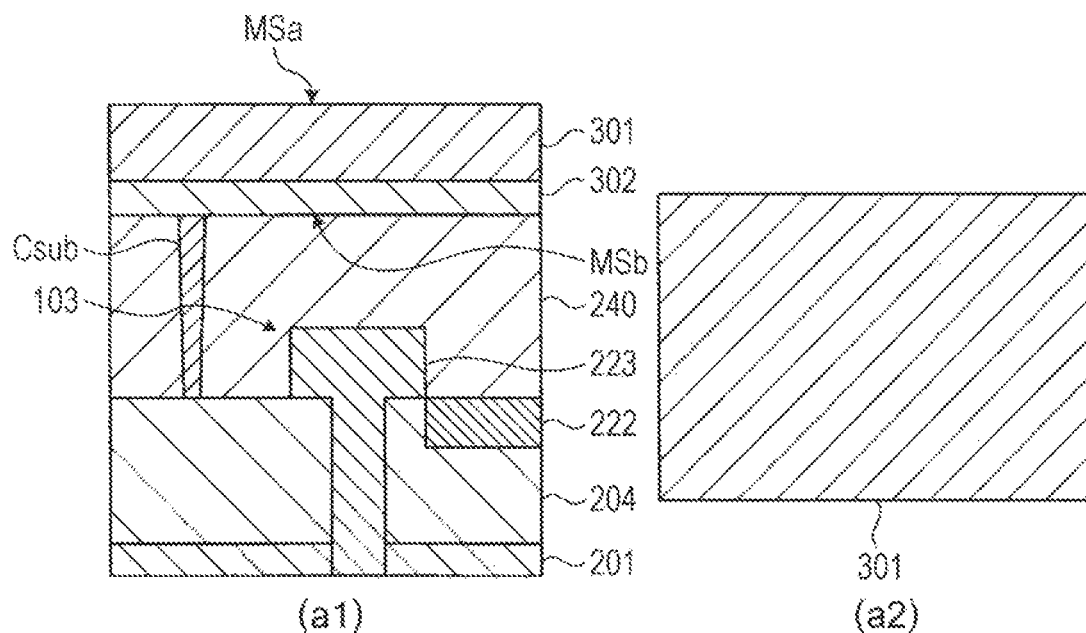
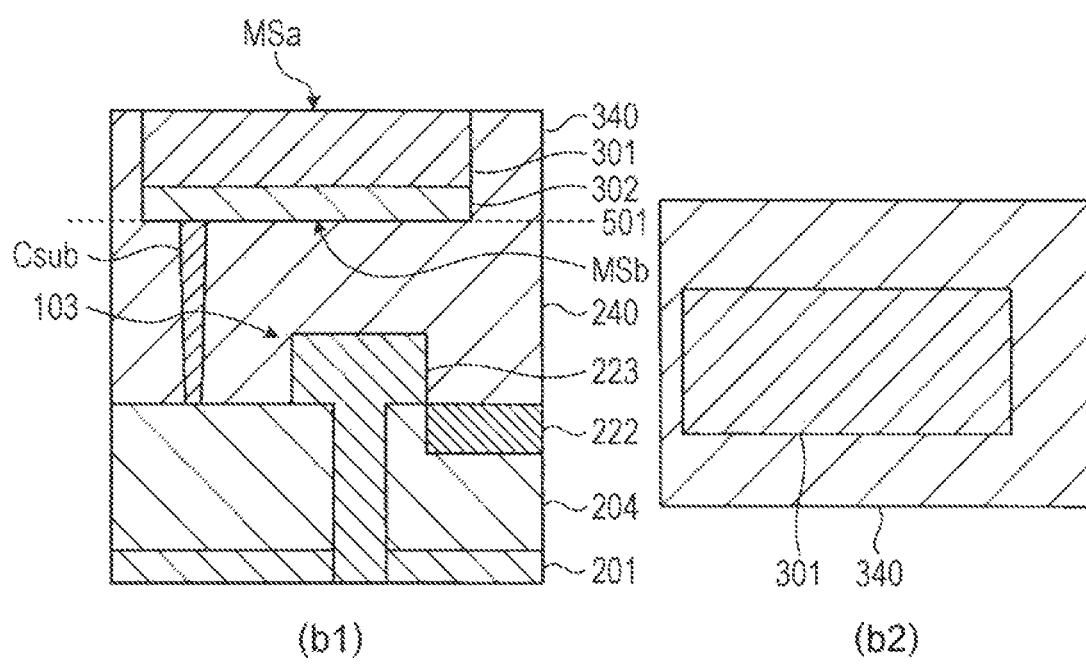

FIG. 28
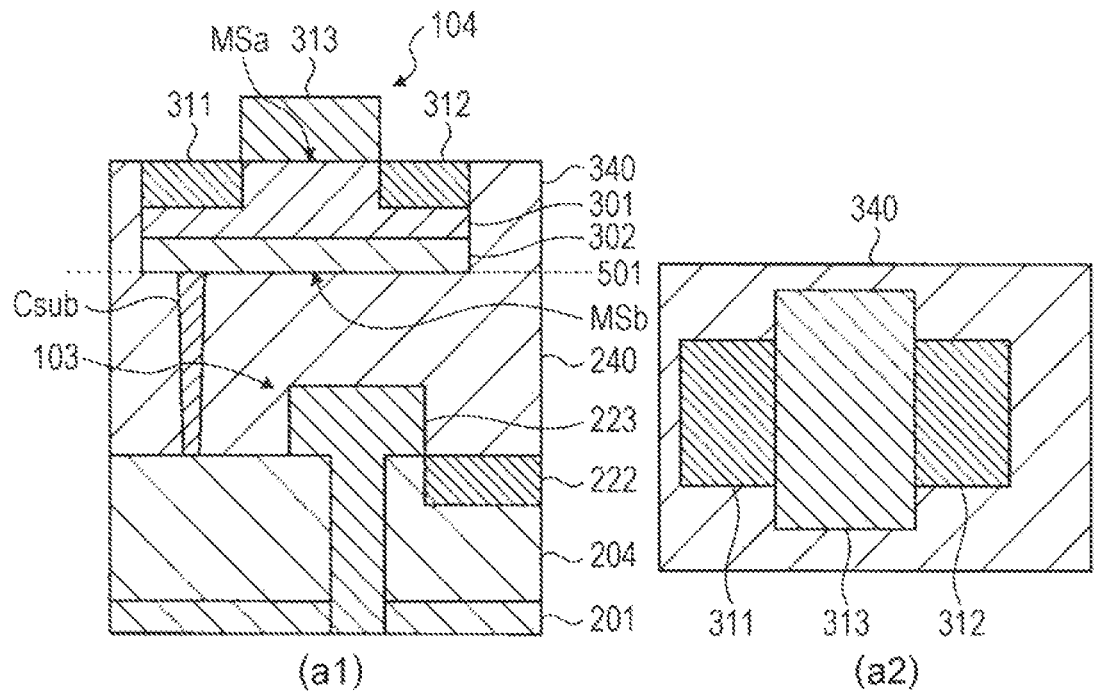
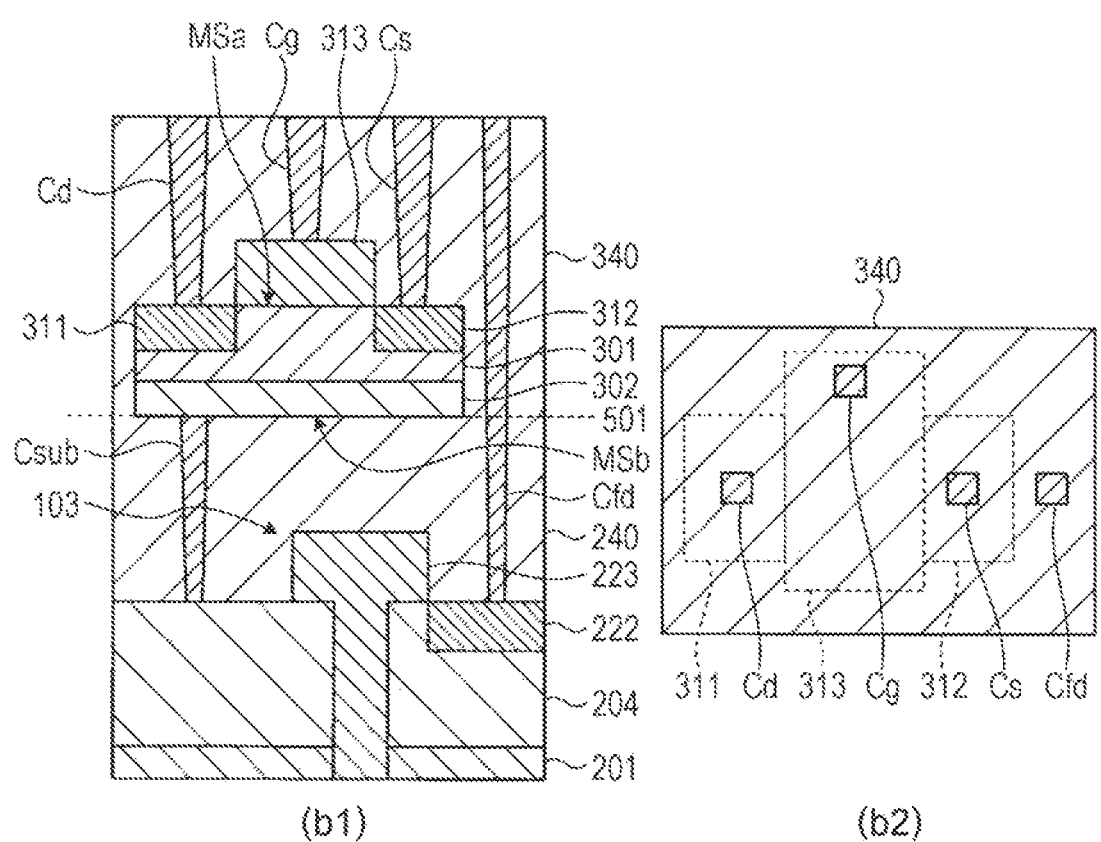

FIG. 29

| | COMPARATIVE EXAMPLE 1 | COMPARATIVE EXAMPLE 2 | FIRST EMBODIMENT |
|---|---|---|---|
| CROSS-SECTIONAL VIEW | | ST1, 302 | |
| TOP VIEW | | 302 ST1 | |
| AMP Tr SIZE (RELATIVE RATIO) | 3 | 1 | 3 |
| SUBSTRATE POTENTIAL | INDEFINITE | FIXED | FIXED |
| RTS NOISE LEVEL (RELATIVE RATIO) | 0.33 | 1 | 0.33 |

FIG. 30
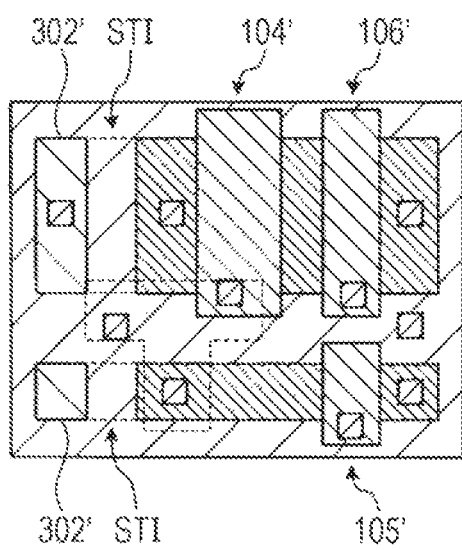
(a)
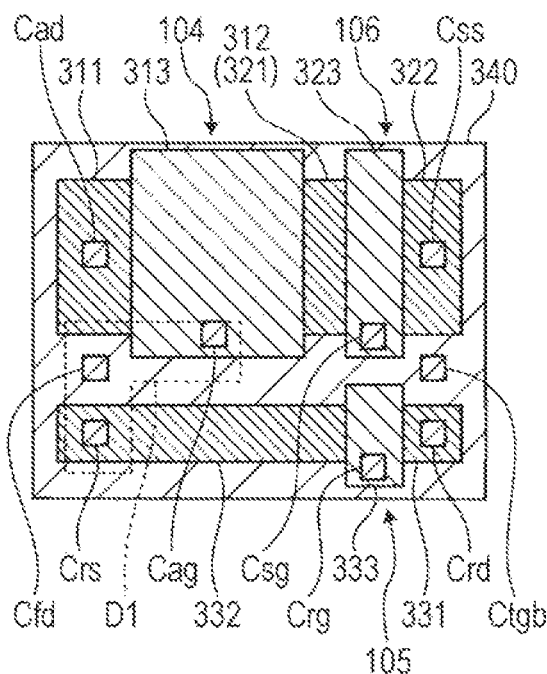
(b)
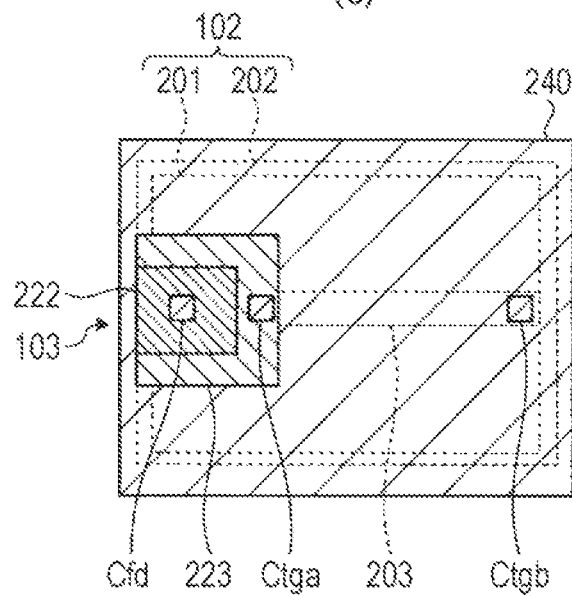
(c)

FIG. 36
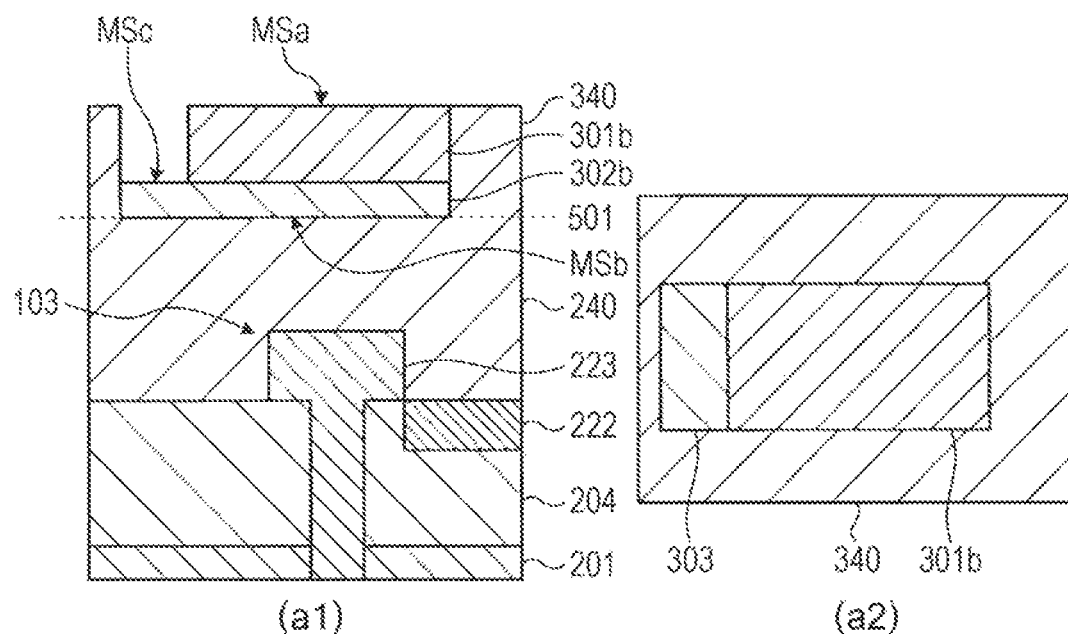
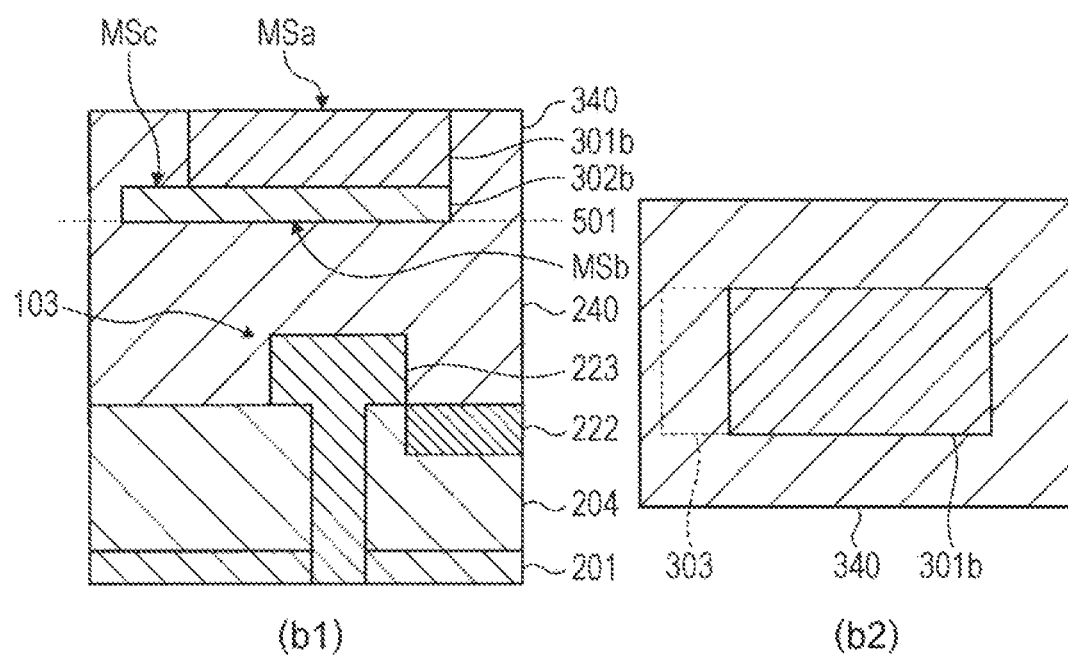

FIG. 37
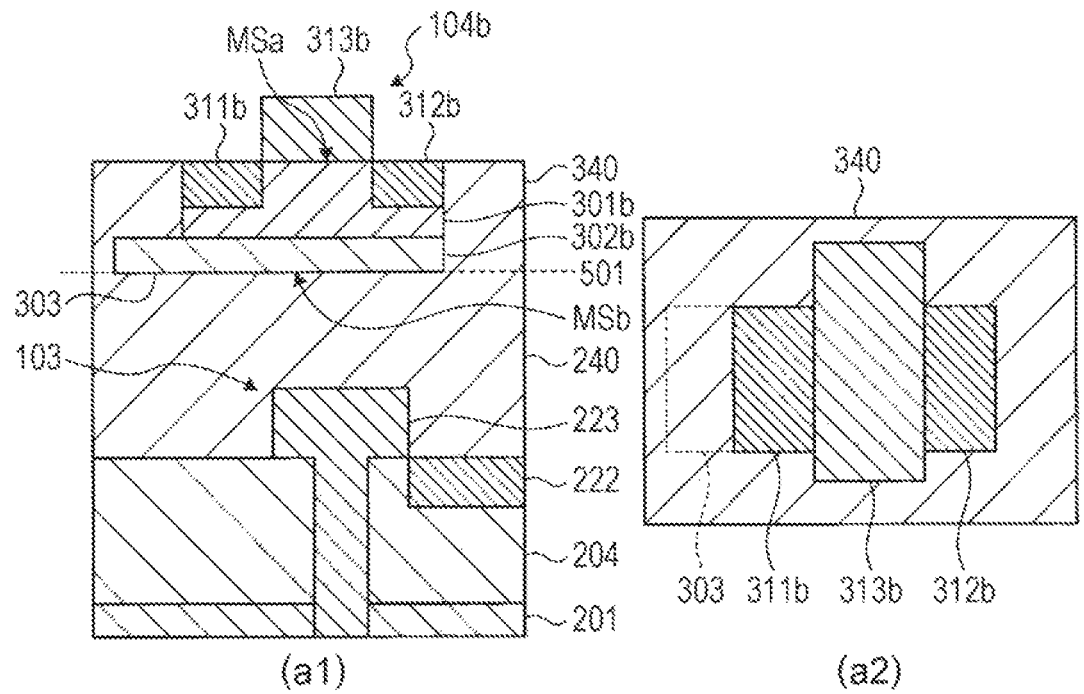
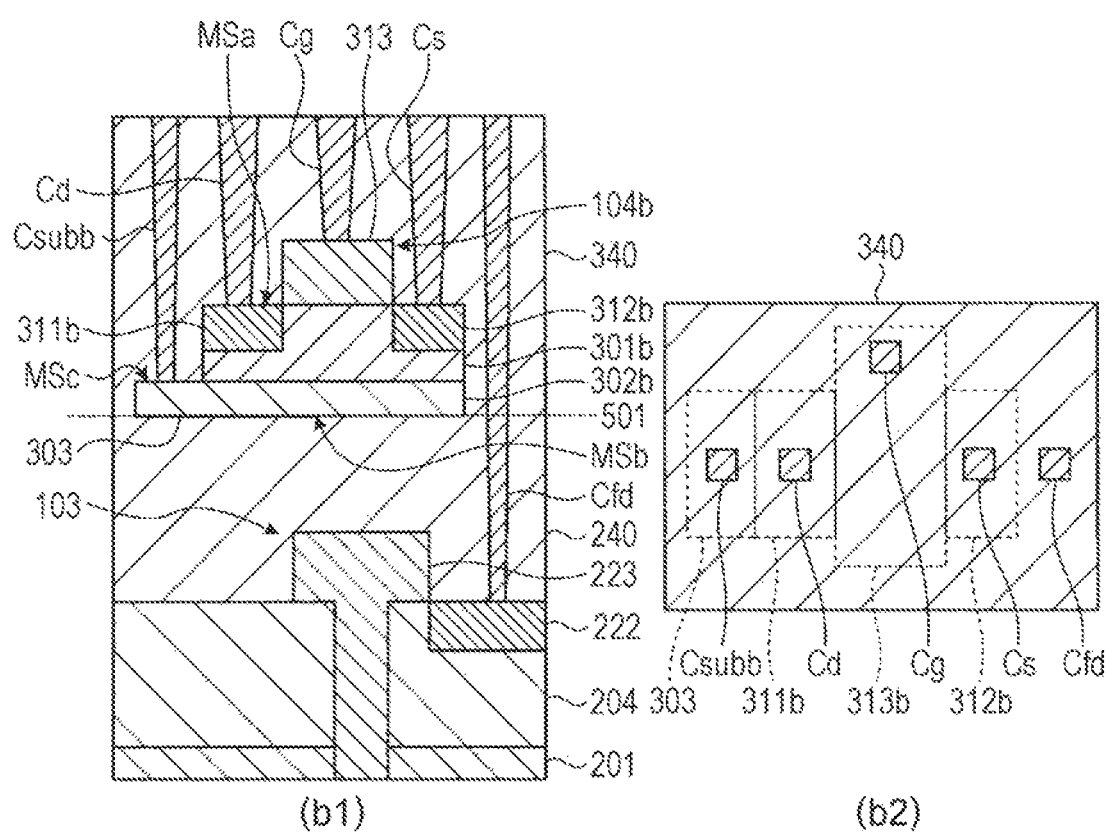

FIG. 38

| | COMPARATIVE EXAMPLE 1 | COMPARATIVE EXAMPLE 2 | SECOND EMBODIMENT |
|---|---|---|---|
| CROSS-SECTIONAL VIEW | | | |
| TOP VIEW | | | |
| AMP Tr SIZE (RELATIVE RATIO) | 3 | 1 | 2 |
| SUBSTRATE POTENTIAL | INDEFINITE | FIXED | FIXED |
| RTS NOISE LEVEL (RELATIVE RATIO) | 0.33 | 1 | 0.5 |

FIG. 43

FIG. 55
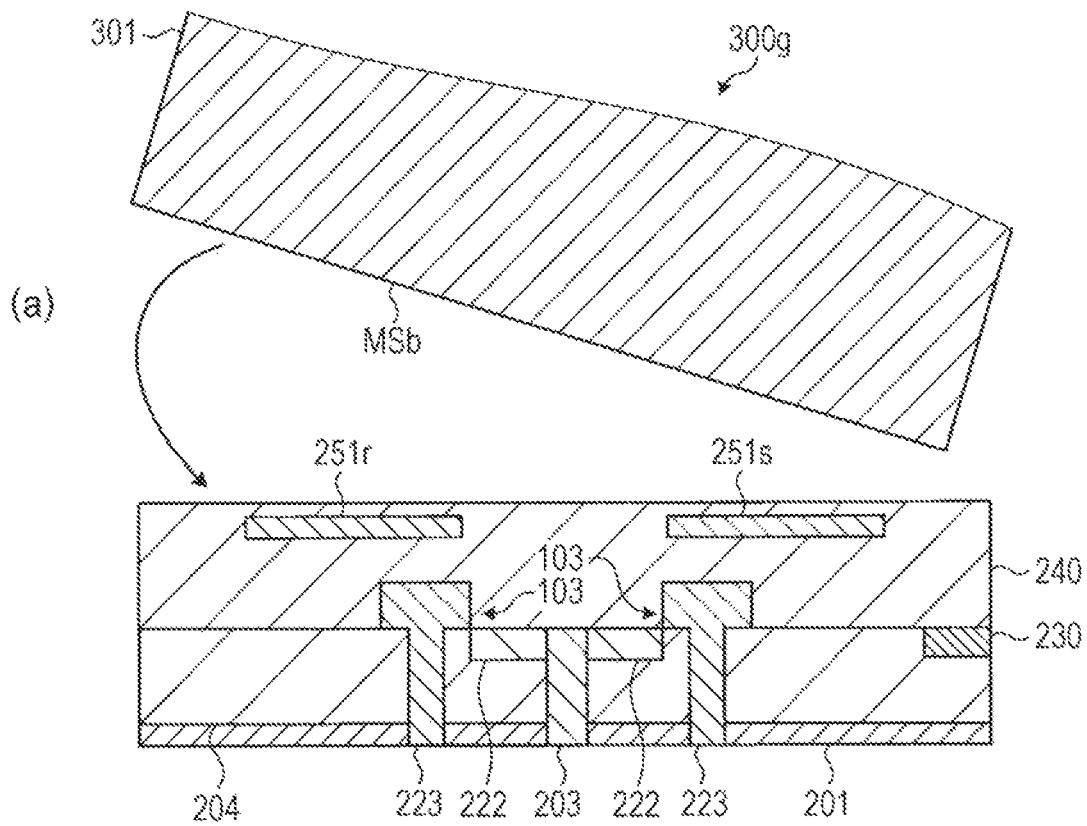
(a)
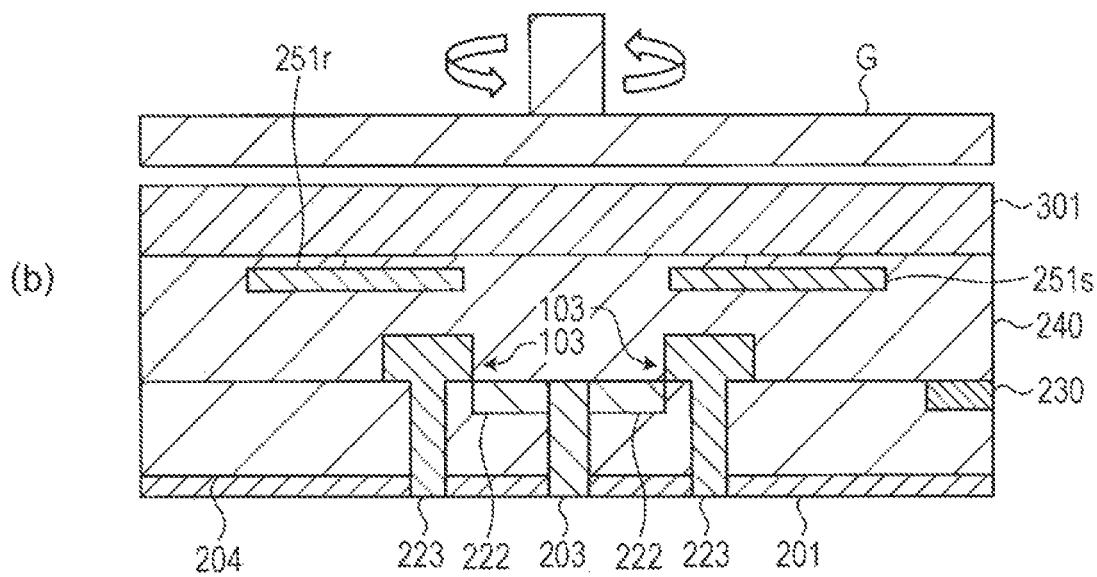
(b)

FIG. 56
(a)
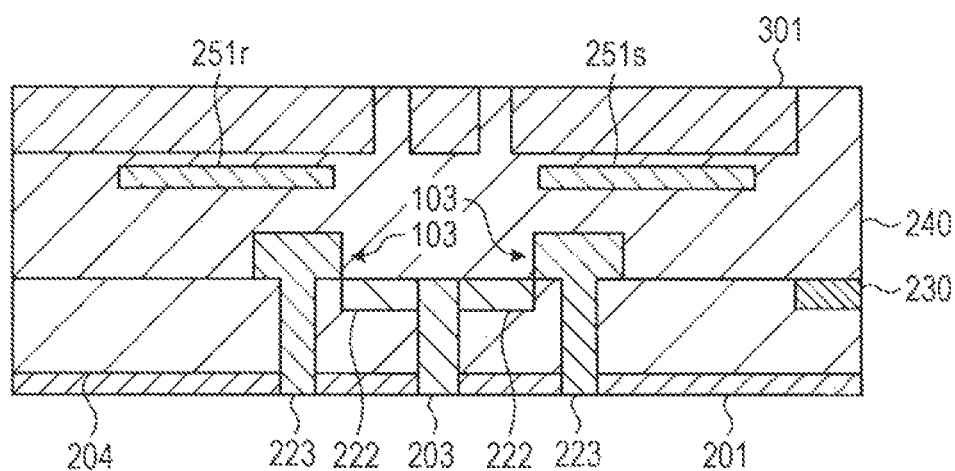
(b)
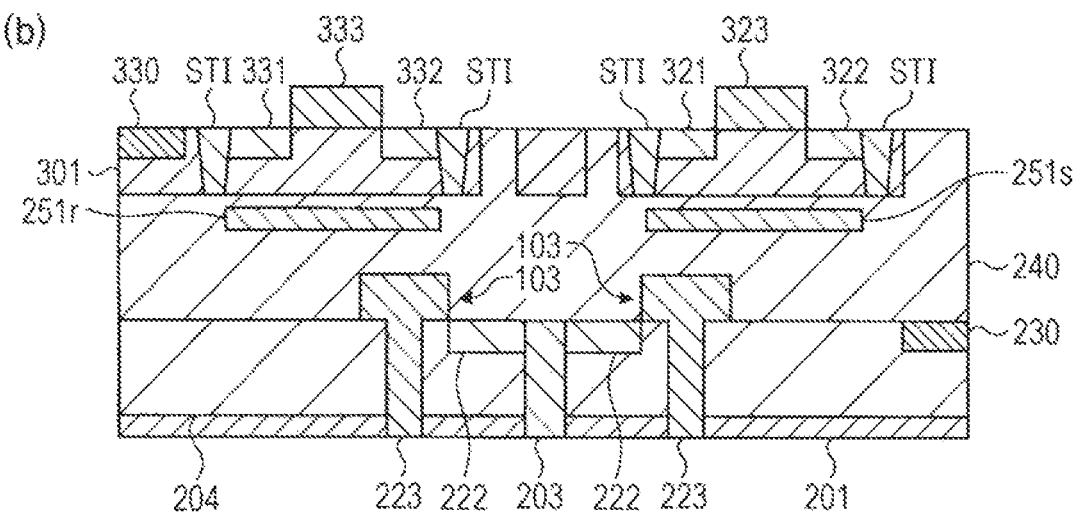

FIG. 57
(a)
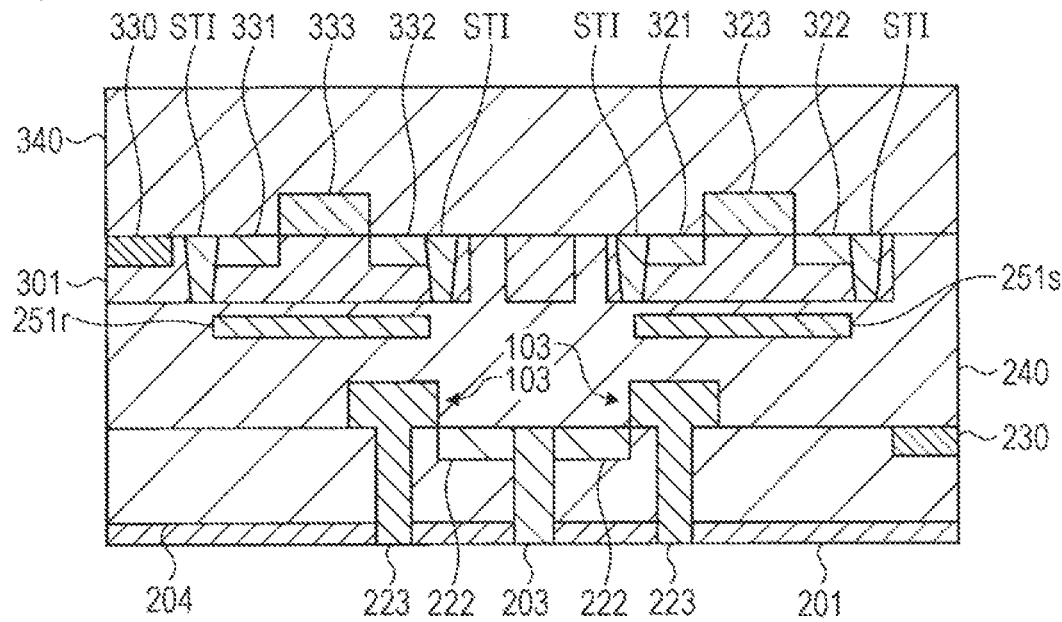
(b)
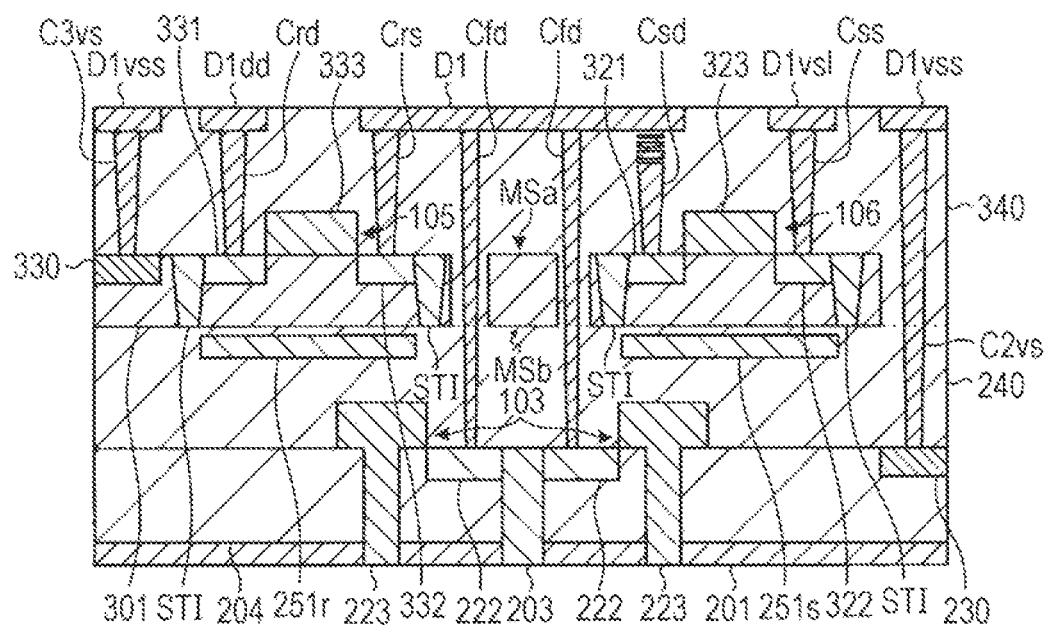

FIG. 58
(a)
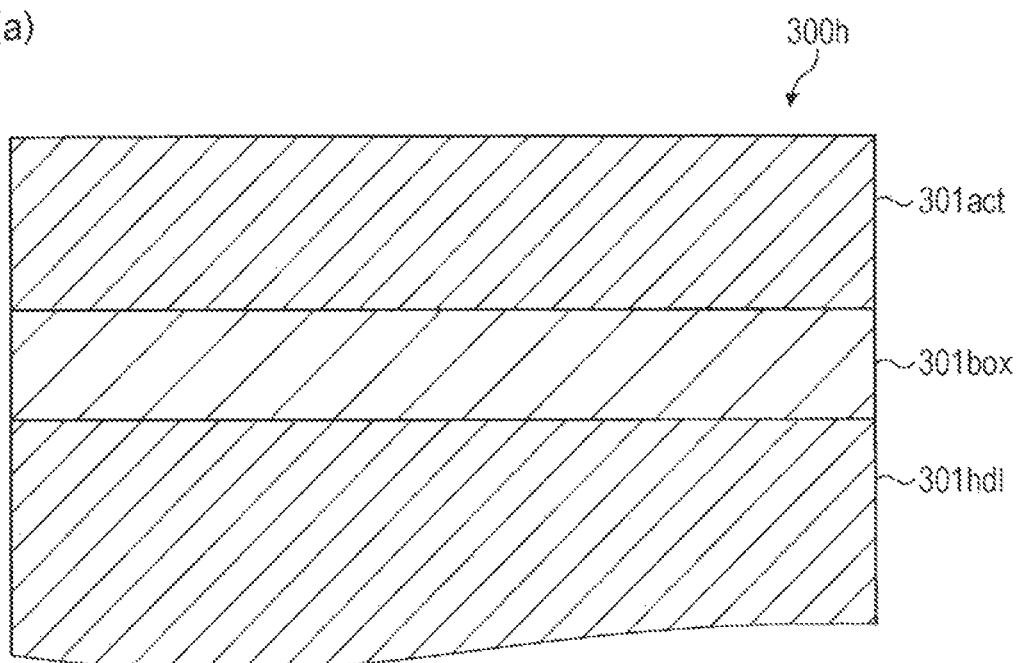
(b)
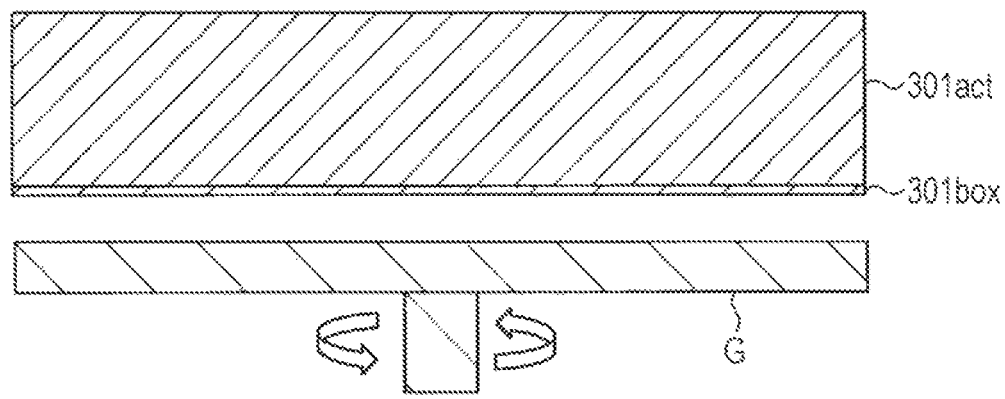

FIG. 59
(a)
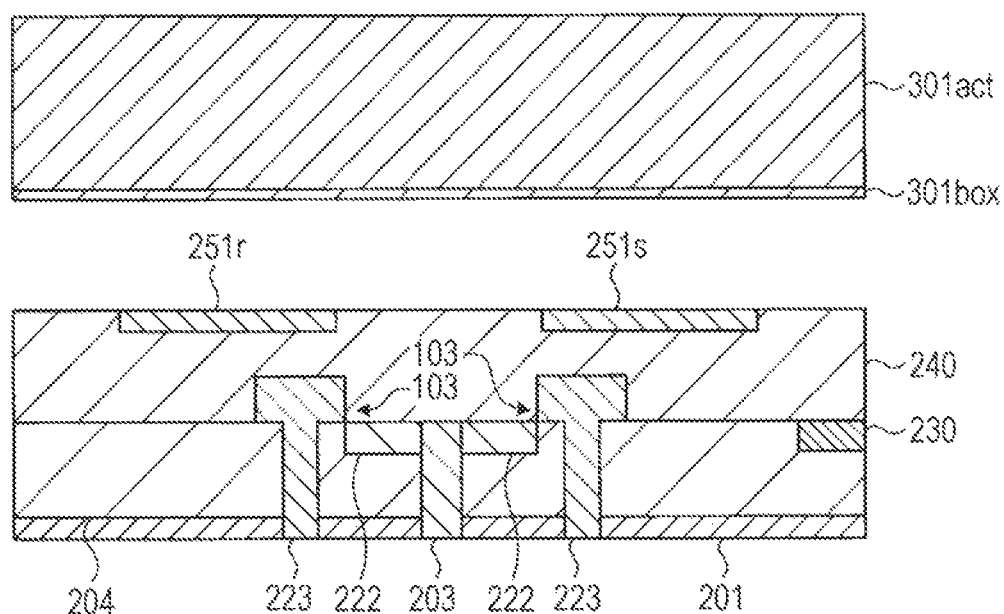
(b)
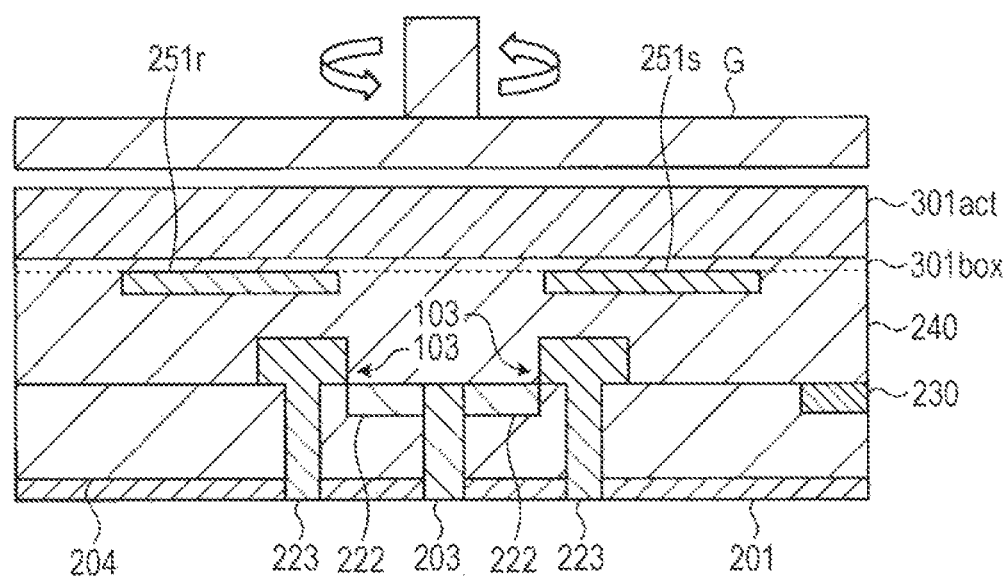

SOLID-STATE IMAGE SENSOR

CROSS REFERENCE TO RELATED APPLICATIONS

This application is a continuation of U.S. patent application Ser. No. 17/292,276, filed May 7, 2021, which is a national stage application under 35 U.S.C. 371 and claims the benefit of PCT Application No. PCT/JP2019/045680 having an international filing date of Nov. 21, 2019, which designated the United States, which PCT application claimed the benefit of Japanese Patent Application Nos. 2018-218695, filed Nov. 21, 2018 and 2019-116983, filed Jun. 25, 2019, the entire disclosures of each of which are incorporated herein by reference.

TECHNICAL FIELD

The present disclosure relates to a solid-state image sensor.

BACKGROUND ART

There is a three-dimensional mounting technology for stacking a plurality of semiconductor substrates. For example, in a solid-state image sensor, it is known that a first semiconductor substrate in which a pixel region is formed and a second semiconductor substrate in which a logic circuit is formed are stacked (see, for example, Patent Document 1).

CITATION LIST

Patent Document

Patent Document 1: Japanese Patent Application Laid-Open No. 2010-245506

SUMMARY OF THE INVENTION

Problems to be Solved by the Invention

In the solid-state image sensor disclosed in Patent Document 1, a sufficient space for arranging pixel transistors cannot be secured. Accordingly, for example, it is conceivable to further separate and stack a substrate in which photoelectric conversion elements are formed and a substrate in which pixel transistors are formed.

However, in such a configuration, the potential of the substrate in which the pixel transistors are formed is not fixed, and the operation of the pixel transistors becomes unstable.

Accordingly, the present disclosure proposes a solid-state image sensor capable of fixing the potentials of stacked substrates while securing a space for arranging transistors.

Solutions to Problems

A solid-state image sensor according to the present disclosure includes a first semiconductor substrate having a photoelectric conversion element, and a second semiconductor substrate facing the first semiconductor substrate with an insulating film interposed therebetween, in which the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region.

BRIEF DESCRIPTION OF DRAWINGS

FIG. 8 is a view representing an example of a cross-sectional configuration of the solid-state image sensor of FIG. 1 in the horizontal direction.

FIG. 13 is a view representing a modification example of the cross-sectional configuration of the solid-state image sensor of FIG. 1 in the horizontal direction.

FIG. 14 is a view representing a modification example of the cross-sectional configuration of the solid-state image sensor of FIG. 1 in the horizontal direction.

FIG. 26 is a flow view illustrating an example of a procedure of a manufacturing process of the solid-state image sensor according to the first embodiment of the present disclosure.

FIG. 27 is a flow view illustrating an example of a procedure of the manufacturing process of the solid-state image sensor according to the first embodiment of the present disclosure.

FIG. 28 is a flow view illustrating an example of a procedure of the manufacturing process of the solid-state image sensor according to the first embodiment of the present disclosure.

FIG. 29 is a diagram for comparing solid-state image sensors according to the first embodiment of the present disclosure and comparative examples 1 and 2.

FIG. 30 is a view illustrating arrangements of pixel transistors of the solid-state image sensor according to the first embodiment of the present disclosure and comparative example 2.

FIG. 36 is a flow view illustrating an example of a procedure of a manufacturing process of the solid-state image sensor according to the second embodiment of the present disclosure.

FIG. 37 is a flow view illustrating an example of a procedure of the manufacturing process of the solid-state image sensor according to the second embodiment of the present disclosure.

FIG. 38 is a diagram for comparing the solid-state image sensors according to the second embodiment of the present disclosure and comparative examples 1 and 2.

FIG. 43 is a diagram for comparing the solid-state image sensors according to the second embodiment of the present disclosure, modification example 2 thereof, and comparative examples 1 and 2.

FIG. 55 is a flow view illustrating the example of the procedure of the manufacturing process of the solid-state image sensor according to the fifth embodiment of the present disclosure.

FIG. 56 is a flow view illustrating the example of the procedure of the manufacturing process of the solid-state image sensor according to the fifth embodiment of the present disclosure.

FIG. 57 is a flow view illustrating the example of the procedure of the manufacturing process of the solid-state image sensor according to the fifth embodiment of the present disclosure.

FIG. 58 is a flow view illustrating an example of a procedure of a manufacturing process of a solid-state image sensor according to modification example 1 of the fifth embodiment of the present disclosure.

FIG. 59 is a flow view illustrating an example of the procedure of the manufacturing process of the solid-state image sensor according to modification example 1 of the fifth embodiment of the present disclosure.

FIG. 103 is a schematic plan view representing another example of a pixel separation part illustrated in FIG. 73A and the like.

MODE FOR CARRYING OUT THE INVENTION

Figure 1:
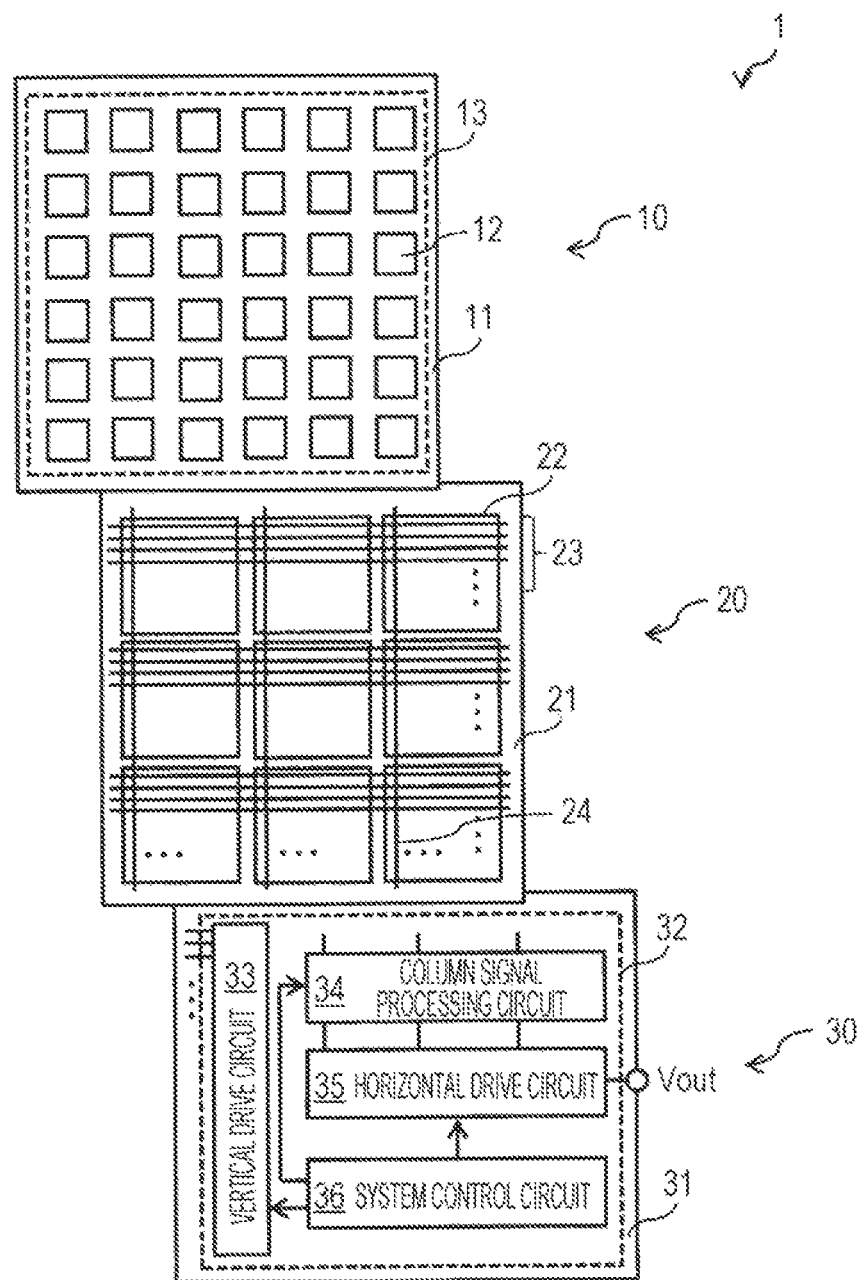
FIG. 1 is a diagram illustrating an example of a schematic configuration of a solid-state image sensor applied to each embodiment of the present disclosure.

Hereinafter, embodiments of the present disclosure will be described in detail on the basis of drawings. Note that in each of embodiments below, the same parts are designated by the same reference numerals, and thereby duplicate description will be omitted.

Schematic Configuration Example of Solid-State Image Sensor

A schematic configuration example of a solid-state image sensor will be described with reference to FIGS. 1 to 19.

Circuit Configuration Example of Solid-State Image Sensor

FIG. 1 is a diagram illustrating an example of a schematic configuration of a solid-state image sensor 1 applied to each embodiment of the present disclosure. The solid-state image sensor 1 converts a received light into an electrical signal and outputs it as a pixel signal. In this example, the solid-state image sensor 1 is formed as a complementary metal oxide semiconductor (CMOS) image sensor.

As illustrated in FIG. 1, the solid-state image sensor 1 includes three substrates, a first substrate 10, a second substrate 20, and a third substrate 30. The solid-state image sensor 1 is an imaging device having a three-dimensional structure formed by bonding these three substrates together. The first substrate 10, the second substrate 20, and the third substrate 30 are stacked in this order.

The first substrate 10 has a plurality of sensor pixels 12 that performs photoelectric conversion on a semiconductor substrate 11. The plurality of sensor pixels 12 is provided in a matrix in a pixel region 13 of the first substrate 10. The second substrate 20 has one readout circuit 22 for every four sensor pixels 12 on the semiconductor substrate 21 to output a pixel signal based on charges output from the sensor pixels 12. The second substrate 20 has a plurality of pixel drive lines 23 extending in a row direction and a plurality of vertical signal lines 24 extending in a column direction. The third substrate 30 has a logic circuit 32 for processing a pixel signal on the semiconductor substrate 31. The logic circuit 32 includes, for example, a vertical drive circuit 33, a column signal processing circuit 34, a horizontal drive circuit 35, and a system control circuit 36. The logic circuit 32, more specifically, the horizontal drive circuit 35 outputs an output voltage Vout of every sensor pixel 12 to the outside. In the logic circuit 32, for example, a low resistance region including a silicide such as $CoSi_2$ or NiSi formed using a self-aligned silicide (SALICIDE) process may be formed on the surface of an impurity diffusion region in contact with a source electrode and a drain electrode.

The vertical drive circuit 33 selects, for example, a plurality of sensor pixels 12 in order in row units. The column signal processing circuit 34 performs, for example, correlated double sampling (CDS) processing on a pixel signal output from each sensor pixel 12 in a row selected by the vertical drive circuit 33. The column signal processing circuit 34 extracts, for example, the signal level of the pixel signal by performing the CDS processing, and holds pixel data corresponding to the amount of light received by each sensor pixel 12. The horizontal drive circuit 35 sequentially outputs the pixel data held in the column signal processing circuit 34 to the outside, for example. The system control circuit 36 controls driving of each block of the vertical drive circuit 33, the column signal processing circuit 34, and the horizontal drive circuit 35 in the logic circuit 32, for example.

FIGS. 2 to 5 are diagrams representing examples of the sensor pixel 12 and the readout circuit 22. A case where the four sensor pixels 12 share one readout circuit 22 will be described below. Here, "sharing" means that outputs of the four sensor pixels 12 are input to the common readout circuit 22. However, as the unit of sharing, the number of pixels is of no question. For example, as in first and second embodiments as described later, an output of one sensor pixel 12 may be input to one readout circuit 22. Furthermore, similarly to the present example, outputs of the four sensor pixels 12 may be input to one readout circuit 22 as in a third embodiment.

Figure 2:
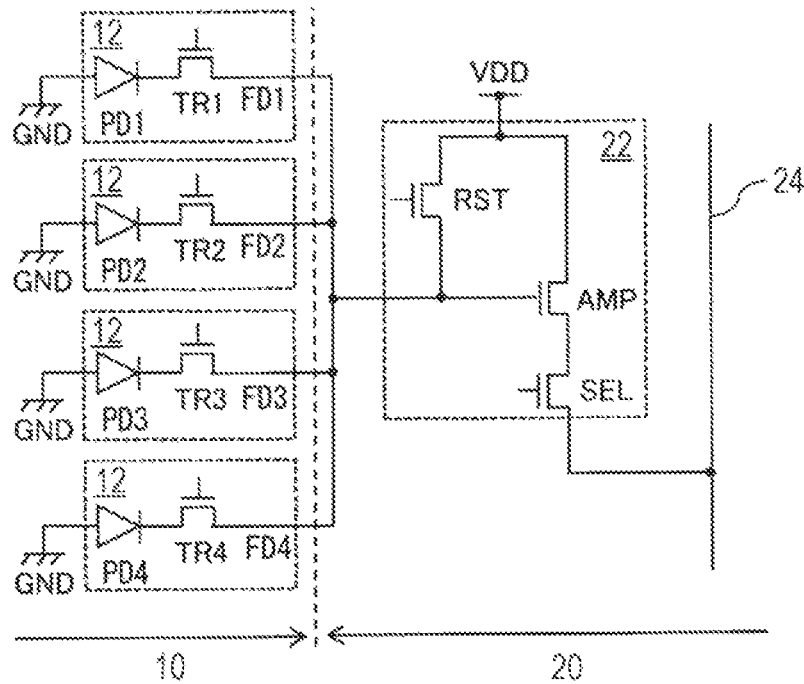
FIG. 2 is a diagram representing an example of sensor pixels and a readout circuit of FIG. 1.

As illustrated in FIG. 2, the sensor pixels 12 each have components common to each other. In FIG. 2, an identification number 1, 2, 3, 4 is added to the end of each reference sign of components of the respective sensor pixels 12 in order to distinguish the components of the respective sensor pixels 12 from each other. In the following, in a case where it is necessary to distinguish the components of the respective sensor pixels 12 from each other, an identification number is added to the end of each reference sign of the components of the respective sensor pixels 12. In a case where it is not necessary to distinguish the components of the respective sensor pixels 12 from each other, the identification number at the end of each reference sign of the components of the respective sensor pixels 12 is omitted.

Each of the sensor pixels 12 has, for example, a photodiode PD, a transfer transistor TR electrically connected to the photodiode PD, and a floating diffusion FD that temporarily holds a charge output from the photodiode PD via the transfer transistor TR. The photodiode PD corresponds to a specific example of a "photoelectric conversion element" of the present disclosure. The photodiode PD performs photoelectric conversion to generate a charge corresponding to the amount of received light. A cathode of the photodiode PD is electrically connected to a source of the transfer transistor TR, and an anode of the photodiode PD is electrically connected to a reference potential line such as a ground wire (GND). A drain of the transfer transistor TR is electrically connected to the floating diffusion FD, and a gate of the transfer transistor TR is electrically connected to a pixel drive line 23 (see FIG. 1). The transfer transistor TR is, for example, a CMOS transistor.

The floating diffusions FD of the respective sensor pixels 12 that share one readout circuit 22 are electrically connected to each other and are electrically connected to an input end of the common readout circuit 22. The readout circuit 22 has, for example, a reset transistor RST, a selection transistor SEL, and an amplification transistor AMP. Note that the selection transistor SEL may be omitted if necessary. A source of the reset transistor RST, which is the input end of the readout circuit 22, is electrically connected to the floating diffusions FD, and a drain of the reset transistor RST is electrically connected to a power supply line VDD and a drain of the amplification transistor AMP. A gate of the reset transistor RST is electrically connected to the pixel drive line 23 (see FIG. 1). A source of the amplification transistor AMP is electrically connected to a drain of the selection transistor SEL, and a gate of the amplification transistor AMP is electrically connected to the source of the reset transistor RST. A source of the selection transistor SEL, which is an output end of the readout circuit 22, is electrically connected to a vertical signal line 24, and a gate of the selection transistor SEL is electrically connected to the pixel drive line 23 (see FIG. 1).

When the transfer transistor TR is turned on, the charge of the photodiode PD is transferred to the floating diffusion FD. The reset transistor RST resets the potential of the floating diffusion FD to a predetermined potential. When the reset transistor RST is turned on, the potential of the floating diffusion FD is reset to the potential of the power supply line VDD. The selection transistor SEL controls the output timing of a pixel signal from the readout circuit 22. The amplification transistor AMP generates as a pixel signal a signal with a voltage corresponding to the level of a charge held in the floating diffusion FD. The amplification transistor AMP forms a source follower type amplifier, and outputs the pixel signal with the voltage corresponding to the level of a charge generated by the photodiode PD. When the selection transistor SEL is turned on, the amplification transistor AMP amplifies the potential of the floating diffusion FD and outputs a voltage corresponding to the potential to the column signal processing circuit 34 via the vertical signal line 24. The reset transistor RST, the amplification transistor AMP, and the selection transistor SEL are, for example, CMOS transistors.

Figure 3:
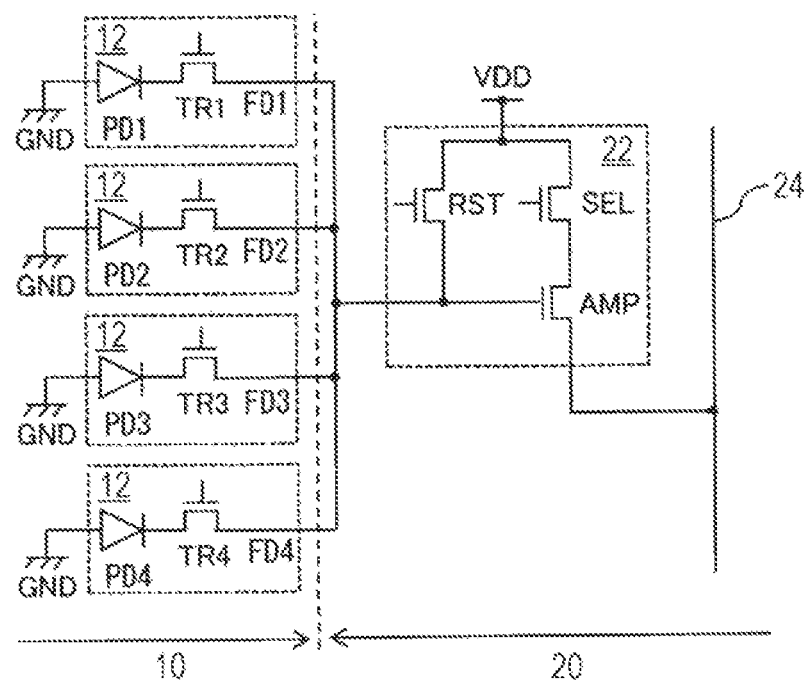
FIG. 3 is a diagram representing an example of the sensor pixels and the readout circuit of FIG. 1.

Note that as illustrated in FIG. 3, the selection transistor SEL may be provided between the power supply line VDD and the amplification transistor AMP. In this case, the drain of the reset transistor RST is electrically connected to the power supply line VDD and the drain of the selection transistor SEL. The source of the selection transistor SEL is electrically connected to the drain of the amplification transistor AMP, and the gate of the selection transistor SEL is electrically connected to the pixel drive line 23 (see FIG. 1). The source of the amplification transistor AMP, which is the output end of the readout circuit 22, is electrically connected to the vertical signal line 24, and the gate of the amplification transistor AMP is electrically connected to the source of the reset transistor RST.

Figure 4:
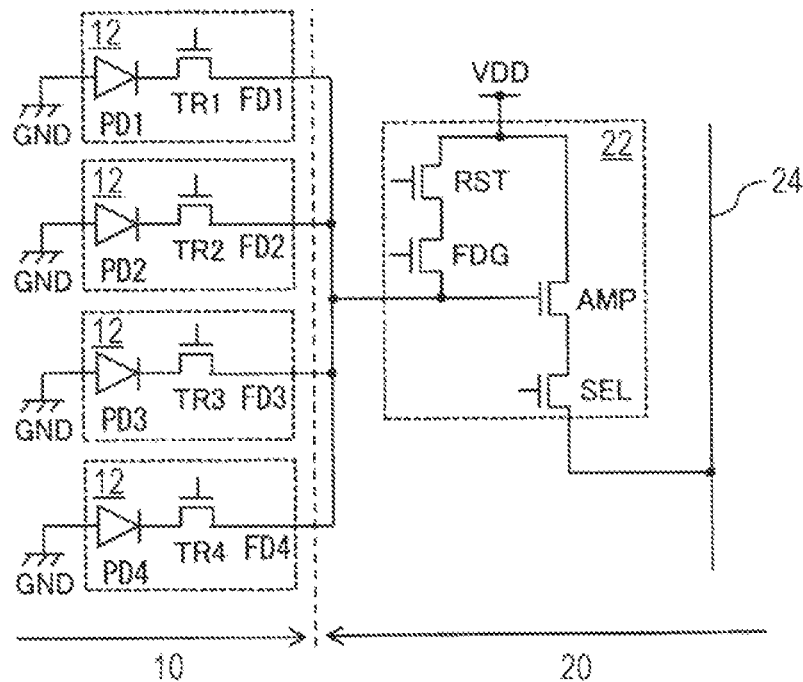
FIG. 4 is a diagram representing an example of the sensor pixels and the readout circuit of FIG. 1.
Figure 5:
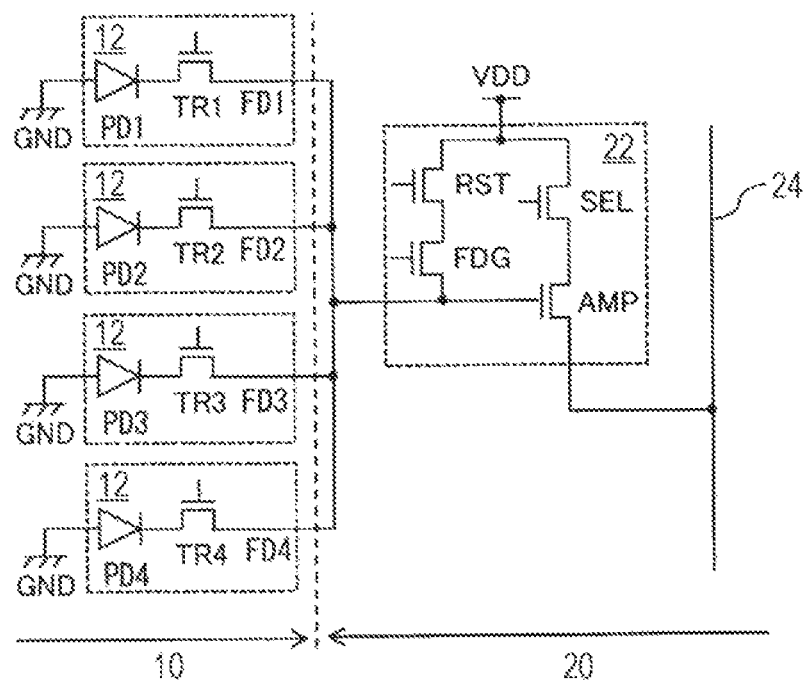
FIG. 5 is a diagram representing an example of the sensor pixels and the readout circuit of FIG. 1.

Furthermore, as illustrated in FIGS. 4 and 5, an FD transfer transistor FDG may be provided between the source of the reset transistor RST and the gate of the amplification transistor AMP. The FD transfer transistor FDG is used to switch conversion efficiency. Generally, the pixel signal is small when capturing an image in a dark place. If FD capacitance C of the floating diffusion FD is large when performing charge-voltage conversion on the basis of Q=CV, voltage V when converted by the amplification transistor AMP becomes small. On the other hand, in a bright place, the pixel signal becomes large, and thus unless the FD capacitance C is large, the floating diffusion FD cannot receive the charge of the photodiode PD. Moreover, the FD capacitance C needs to be large so that the voltage V when converted by the amplification transistor AMP does not become too large. Based on these factors, when the FD transfer transistor FDG is turned on, the gate capacitance for the amount of the FD transfer transistor FDG increases, and thus the overall FD capacitance C increases. On the other hand, when the FD transfer transistor FDG is turned off, the overall FD capacitance C decreases. By switching the FD transfer transistor FDG on and off in this manner, the FD capacitance C can be made variable and conversion efficiency can be switched.

Figure 6:
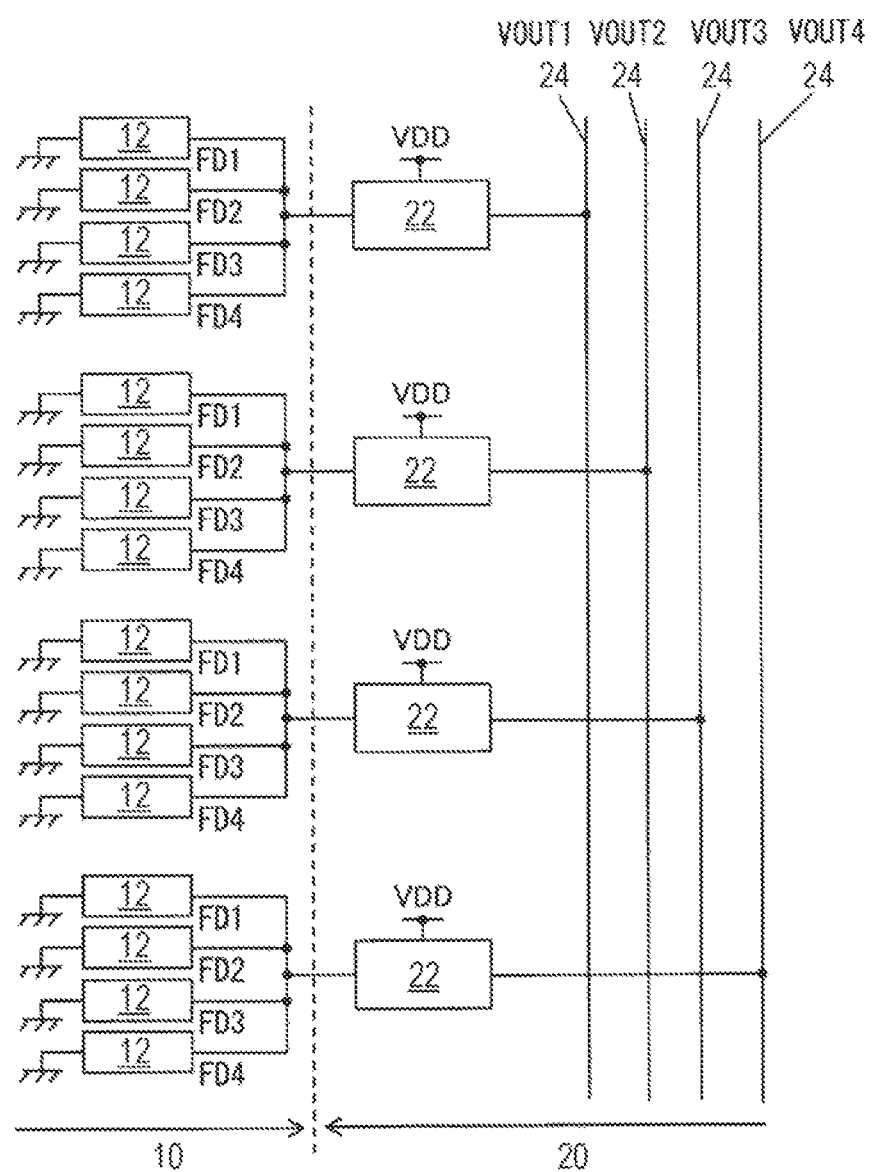
FIG. 6 is a diagram representing an example of a connection mode of a plurality of readout circuits and a plurality of vertical signal lines.

FIG. 6 is a diagram representing an example of a connection mode of a plurality of readout circuits 22 and a plurality of vertical signal lines 24. In a case where the plurality of readout circuits 22 is arranged to line up in the column direction that is the extending direction of the vertical signal lines 24, one of the plurality of vertical signal lines 24 may be assigned to each of the readout circuits 22. For example, as illustrated in FIG. 6, in a case where four readout circuits 22 are arranged to line up in the extending direction of the vertical signal lines 24, one of four vertical signal lines 24 may be assigned to each of the readout circuits 22. Note that in FIG. 6, an identification number 1, 2, 3, 4 is added to the end of the reference sign of each vertical signal line 24 in order to distinguish each vertical signal line 24.

(Physical Configuration Example of Solid-State Image Sensor)

Figure 7:
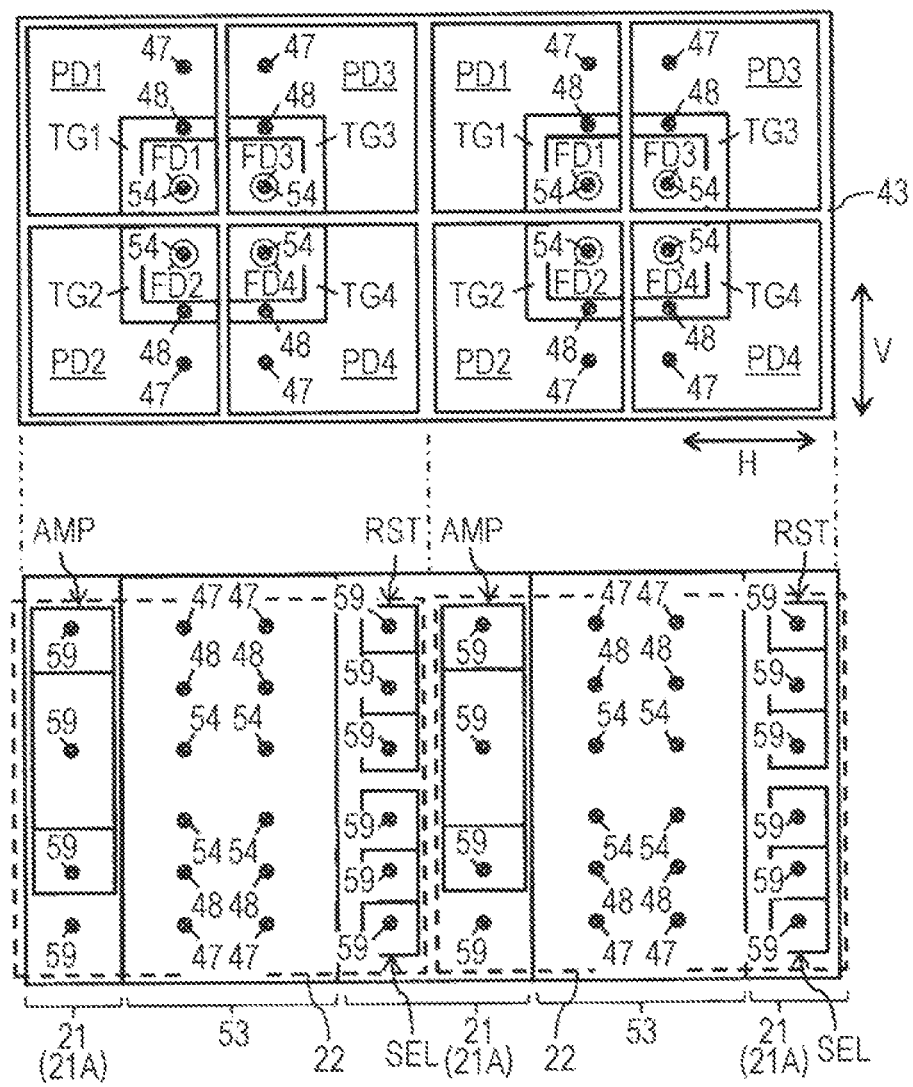
FIG. 7 is a view representing an example of a cross-sectional configuration of the solid-state image sensor of FIG. 1 in a horizontal direction.

FIGS. 7 and 8 are views representing examples of the cross-sectional configuration of the solid-state image sensor 1 in a horizontal direction. Views on upper sides of FIGS. 7 and 8 are views representing an example of a cross-sectional configuration of the first substrate 10 of FIG. 1 in the horizontal direction. Views on lower sides of FIGS. 7 and 8 are views representing an example of a cross-sectional configuration of the second substrate 20 of FIG. 1 in the horizontal direction. FIG. 7 exemplifies a configuration in which two sets of 2×2, four sensor pixels 12 are arranged in a second direction H, and FIG. 8 exemplifies a configuration in which four sets of 2×2, four sensor pixels 12 are arranged in a first direction V and the second direction H. Note that in the cross-sectional views on the upper sides of FIGS. 7 and 8, a view representing an example of a surface configuration of the semiconductor substrate 11 is superimposed on a view representing an example of a cross-sectional configuration of the first substrate 10 of FIG. 1 in the horizontal direction. Furthermore, in the cross-sectional views on the lower sides of FIGS. 7 and 8, a view representing an example of a surface configuration of the semiconductor substrate 21 is superimposed on a view representing an example of a cross-sectional configuration of the second substrate 20 in FIG. 1 in the horizontal direction.

As illustrated in FIGS. 7 and 8, a plurality of through wirings 54, a plurality of through wirings 48, and a plurality of through wirings 47 are arranged to line up in a band shape in the first direction V, which is a vertical direction of FIG. 7, or in the second direction H, which is a left-right direction of FIG. 8 in the plane of the first substrate 10. Note that FIGS. 7 and 8 exemplify a case where the plurality of through wirings 54, the plurality of through wirings 48, and the plurality of through wirings 47 are arranged to line up in two lines in the first direction V or the second direction H. The first direction V or the second direction H is parallel to, for example, the column direction, which is one arrangement direction of the row direction and the column direction, which are the two arrangement directions of the plurality of sensor pixels 12 arranged in a matrix. In the four sensor pixels 12 sharing the readout circuit 22, the four floating diffusions FD are arranged close to each other, for example, with a pixel separation part 43 interposed therebetween. In the four sensor pixels 12 sharing the readout circuit 22, gate electrodes TG of the four transfer transistors TR are arranged so as to surround the four floating diffusions FD, and for example, the four gate electrodes TG form a ring shape.

An insulating layer 53 existing in a portion of the above-mentioned semiconductor substrate 21 through which the plurality of through wirings 54 penetrates includes a plurality of blocks extending in the first direction V or the second direction H. The semiconductor substrate 21 includes a plurality of island-shaped blocks 21A that extends in the first direction V or the second direction H and is arranged to line up in the first direction V or the second direction H orthogonal to each other, with the insulating layer 53 described above interposed therebetween. Each block 21A is provided with, for example, a plurality of sets of a reset transistor RST, an amplification transistor AMP, and a selection transistor SEL. One readout circuit 22 shared by four sensor pixels 12 includes, for example, a reset transistor RST, an amplification transistor AMP, and a selection transistor SEL located in a region facing the four sensor pixels 12. One readout circuit 22 shared by the four sensor pixels 12 includes, for example, an amplification transistor AMP in the left adjacent block 21A of the insulating layer 53 described above, and a reset transistor RST and a selection transistor SEL in the right adjacent block 21A of the insulating layer 53.

FIGS. 9 to 12 are views representing an example of a wiring layout of the solid-state image sensor 1 in a horizontal plane. FIGS. 9 to 12 exemplify a case where one readout circuit 22 shared by the four sensor pixels 12 is provided in the region facing the four sensor pixels 12. Wirings illustrated in FIGS. 9 to 12 are provided in mutually different layers of wiring layers, which are not illustrated, provided on the pixel transistors described above, for example. A wiring layer has, for example, a plurality of pixel drive lines 23 and a plurality of vertical signal lines 24, a pad electrode (not illustrated) which is exposed on a surface of the wiring layer and is used for electrical connection between the second substrate 20 and the third substrate 30, and so on.

Figure 9:
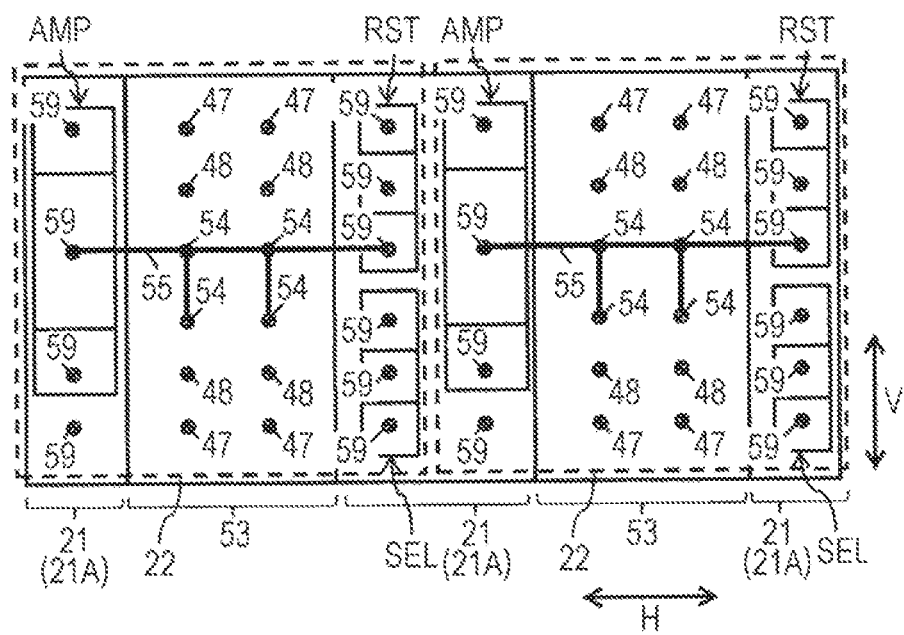
FIG. 9 is a view representing an example of a wiring layout of the solid-state image sensor of FIG. 1 in a horizontal plane.

The four through wirings 54 adjacent to each other are electrically connected to a connection wiring 55, for example, as illustrated in FIG. 9. The four through wirings 54 adjacent to each other are further electrically connected to, for example, the gate of the amplification transistor AMP included in the left adjacent block 21A of the insulating layer 53 and the gate of the reset transistor RST included in the right adjacent block 21A of the insulating layer 53 via the connection wiring 55 and a connection portion 59.

Figure 10:
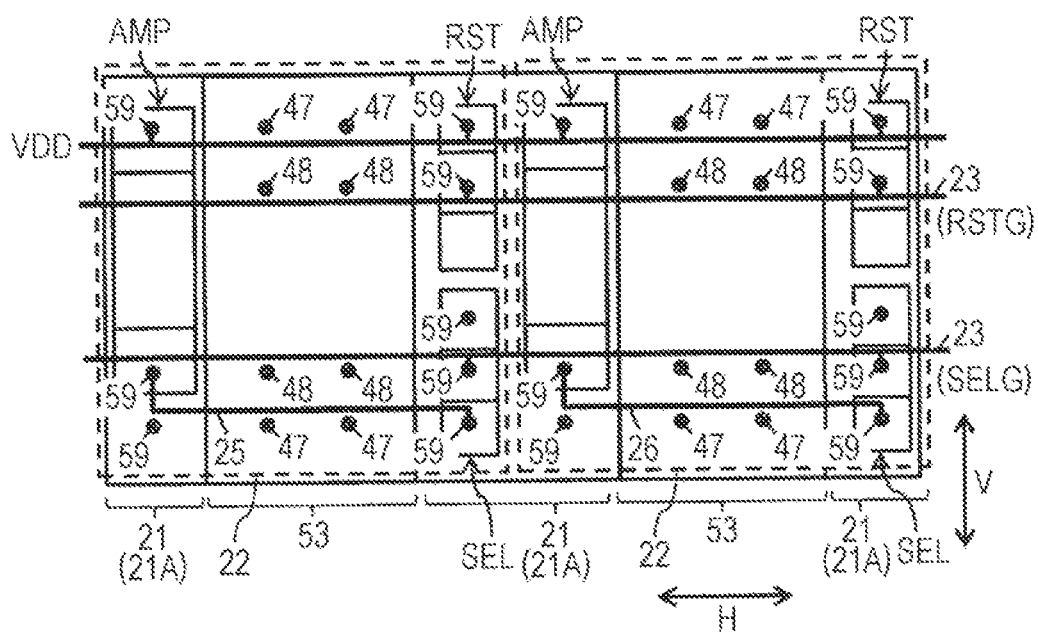
FIG. 10 is a view representing an example of a wiring layout of the solid-state image sensor of FIG. 1 in the horizontal plane.

As illustrated in FIG. 10, for example, the power supply line VDD is arranged at a position facing respective readout circuits 22 arranged to line up in the second direction H. The power supply line VDD is electrically connected to the drain of the amplification transistor AMP and the drain of the reset transistor RST of the respective readout circuits 22 arranged to line up in the second direction H, for example, via the connection portion 59. Two pixel drive lines 23 are arranged at positions facing the respective readout circuits 22 arranged to line up in the second direction H, for example. One pixel drive line 23 is, for example, a wiring RSTG electrically connected to the gates of the reset transistors RST of the respective readout circuits 22 arranged to line up in the second direction H. The other pixel drive line 23 is, for example, a wiring SELG electrically connected to the gates of the selection transistors SEL of the respective readout circuits 22 arranged to line up in the second direction H. In each readout circuit 22, the source of the amplification transistor AMP and the drain of the selection transistor SEL are electrically connected to each other, for example, via a wiring 25.

Figure 11:
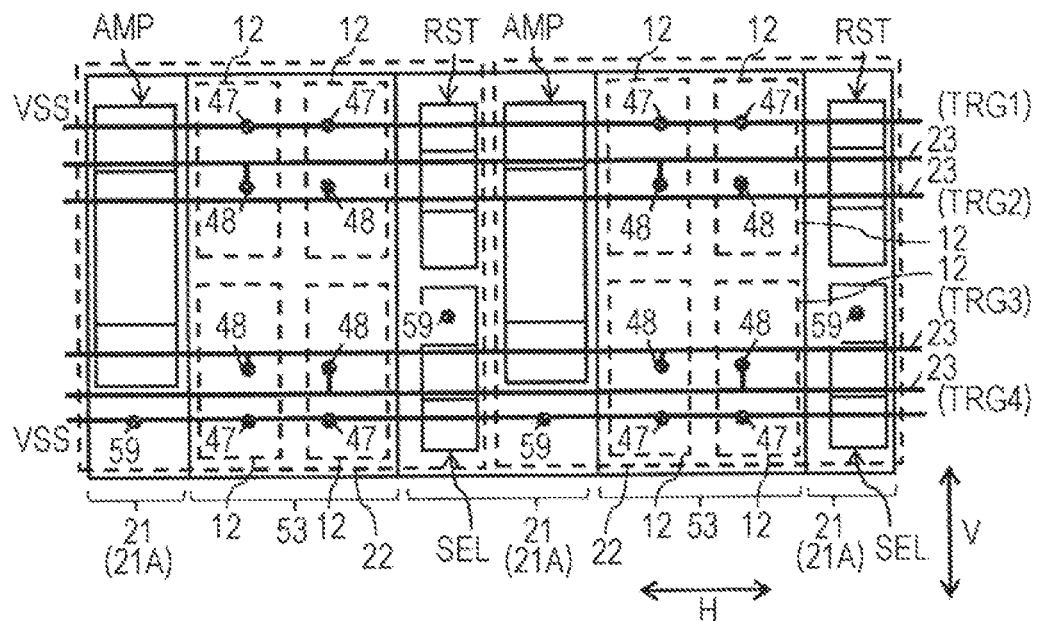
FIG. 11 is a view representing an example of a wiring layout of the solid-state image sensor of FIG. 1 in the horizontal plane.

As illustrated in FIG. 11, two power supply line VSSs are arranged at positions facing the respective readout circuits 22 arranged to line up in the second direction H, for example. Each power supply line VSS is electrically connected to the plurality of through wirings 47, for example, at positions facing respective sensor pixels 12 arranged to line up in the second direction H. Four pixel drive lines 23 are arranged at positions facing the respective readout circuits 22 arranged to line up in the second direction H, for example. Each of the four pixel drive lines 23 is a wiring TRG electrically connected to, for example, the through wiring 48 of one sensor pixel 12 among the four sensor pixels 12 corresponding to each of the readout circuits 22 arranged to line up in the second direction H. That is, the four pixel drive lines 23 that function as control lines are electrically connected to the gate electrodes TG of the transfer transistors TR of the respective sensor pixels 12 arranged to line up in the second direction H. In FIG. 11, identifiers 1, 2, 3, and 4 are added to ends of respective wirings TRG in order to distinguish the respective wirings TRG.

Figure 12:
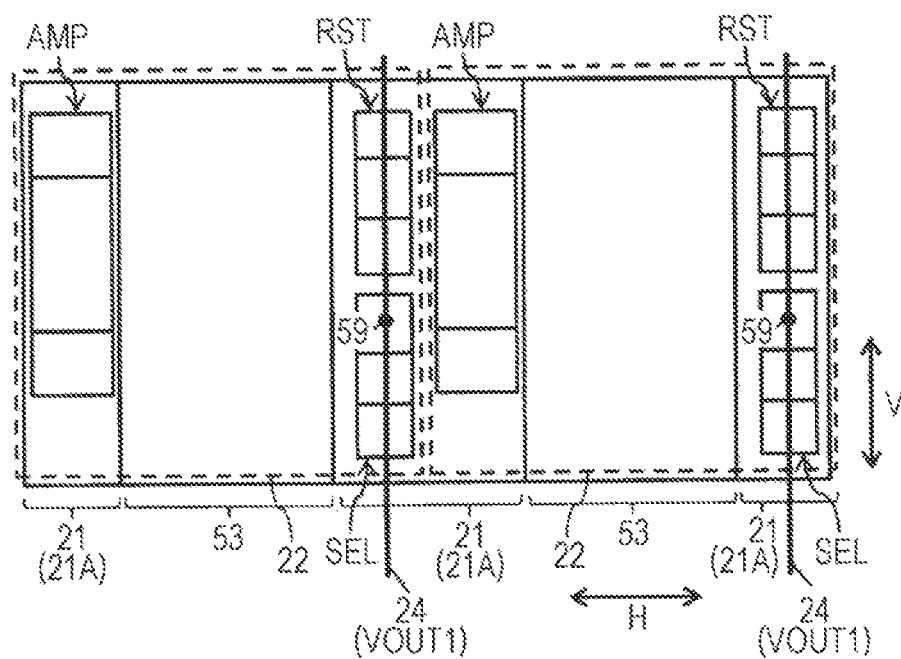
FIG. 12 is a view representing an example of a wiring layout of the solid-state image sensor of FIG. 1 in the horizontal plane.

As illustrated in FIG. 12, for example, the vertical signal lines 24 are arranged at positions facing the respective readout circuits 22 arranged to line up in the first direction V. The vertical signal lines 24 that function as output lines are electrically connected to, for example, the sources of the amplification transistors AMP, which are the output ends of the respective readout circuits 22 arranged to line up in the first direction V.

Modification Example 1

FIGS. 13 and 14 are views representing modification examples of the cross-sectional configuration of the solid-state image sensor 1 described above in the horizontal direction. Views on upper sides of FIGS. 13 and 14 depict a modification example of the cross-sectional configuration of the first substrate 10 of FIG. 1 in the horizontal direction, and a view on a lower side of FIG. 13 depicts a modification example of the cross-sectional configuration of the second substrate 20 of FIG. 1 in the horizontal direction. Note that in the cross-sectional views on the upper sides of FIGS. 13 and 14, a view representing a modification example of the surface configuration of the semiconductor substrate 11 of FIG. 1 is superposed on a view representing a modification example of the cross-sectional configuration of the first substrate 10 of FIG. 1 in the horizontal direction. Furthermore, in the cross-sectional views on the lower sides of FIGS. 13 and 14, a view representing a modification example of the surface configuration of the semiconductor substrate 21 is superimposed on a view representing a modification example of the cross-sectional configuration of the second substrate 20 of FIG. 1 in the horizontal direction.

As illustrated in FIGS. 13 and 14, the plurality of through wirings 54, the plurality of through wirings 48, and the plurality of through wirings 47, which are illustrated as a plurality of dots arranged in a matrix in the figure, are arranged to line up in a band shape in the second direction H, which is the left-right direction of FIGS. 13 and 14, in the plane of the first substrate 10. Note that FIGS. 13 and 14 exemplify a case where the plurality of through wirings 54, the plurality of through wirings 48, and the plurality of through wirings 47 are arranged to line up in two lines in the second direction H. In the four sensor pixels 12 sharing the readout circuit 22, the four floating diffusions FD are arranged close to each other, for example, with a pixel separation part 43 interposed therebetween. In the four sensor pixels 12 sharing the readout circuit 22, the four transfer gates TG1, TG2, TG3, and TG4 are arranged so as to surround the four floating diffusions FD, and for example, the four transfer gates TG form a ring shape.

The insulating layer 53 includes a plurality of blocks extending in the second direction H. The semiconductor substrate 21 includes a plurality of island-shaped blocks 21A that extends in the second direction H and is arranged to line up in the first direction V orthogonal to the second direction H with the insulating layer 53 interposed therebetween. Each block 21A is provided with, for example, a reset transistor RST, an amplification transistor AMP, and a selection transistor SEL. One readout circuit 22 shared by the four sensor pixels 12 is not arranged to directly face the four sensor pixels 12 but is arranged, for example, to be displaced in the first direction V.

In FIG. 13, one readout circuit 22 shared by the four sensor pixels 12 includes a reset transistor RST, an amplification transistor AMP, and a selection transistor SEL located in a region displaced from the region facing the four sensor pixels 12 in the first direction V in the second substrate 20 One readout circuit 22 shared by the four sensor pixels 12 includes, for example, an amplification transistor AMP, a reset transistor RST, and a selection transistor SEL in one block 21A.

In FIG. 14, one readout circuit 22 shared by the four sensor pixels 12 includes a reset transistor RST, an amplification transistor AMP, a selection transistor SEL, and an FD transfer transistor FDG located in a region displaced from the region facing the four sensor pixels 12 in the first direction V in the second substrate 20. One readout circuit 22 shared by the four sensor pixels 12 includes, for example, an amplification transistor AMP, a reset transistor RST, a selection transistor SEL, and an FD transfer transistor FDG in one block 21A.

In this modification example, one readout circuit 22 shared by the four sensor pixels 12 is, for example, not arranged to directly face the four sensor pixels 12 but is arranged to be displaced in the first direction V from a position directly facing the four sensor pixels 12. In this case, the wiring 25 (see FIG. 10) can be shortened, or the wiring 25 can be omitted and the source of the amplification transistor AMP and the drain of the selection transistor SEL can be formed in a common impurity region. Consequently, the size of the readout circuit 22 can be reduced, and the sizes of other parts of the readout circuit 22 can be increased.

Modification Example 2

Figure 15:
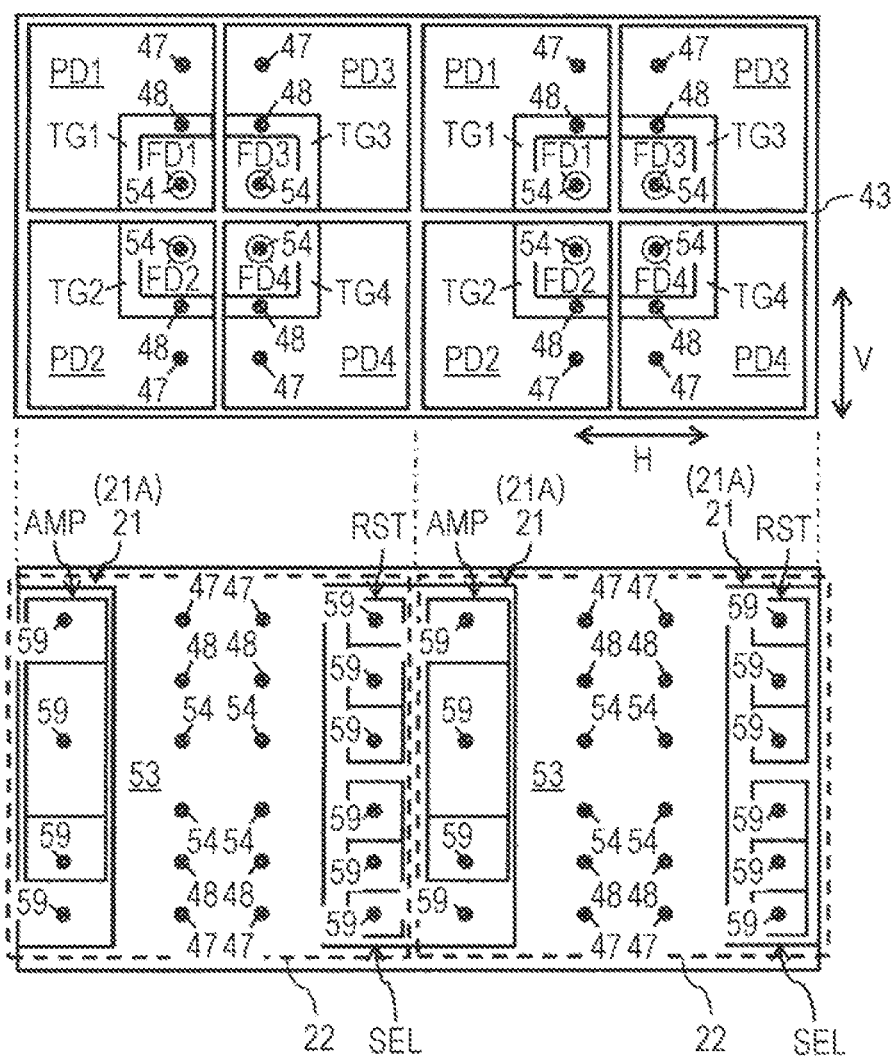
FIG. 15 is a view representing a modification example of the cross-sectional configuration of the solid-state image sensor of FIG. 1 in the horizontal direction.

FIG. 15 is a view representing a modification example of the cross-sectional configuration of the solid-state image sensor 1 described above in the horizontal direction. FIG. 15 illustrates a modification example of the cross-sectional configuration of FIG. 7.

In this modification example, the semiconductor substrate 21 includes a plurality of island-shaped blocks 21A arranged to line up in the first direction V and the second direction H with the insulating layer 53 interposed therebetween. Each block 21A is provided with, for example, a set of a reset transistor RST, an amplification transistor AMP, and a selection transistor SEL. In this case, crosstalk between the readout circuits 22 adjacent to each other can be suppressed by the insulating layer 53, and resolution deterioration on the reproduced image and image quality deterioration due to color mixing can be suppressed.

Modification Example 3

Figure 16:
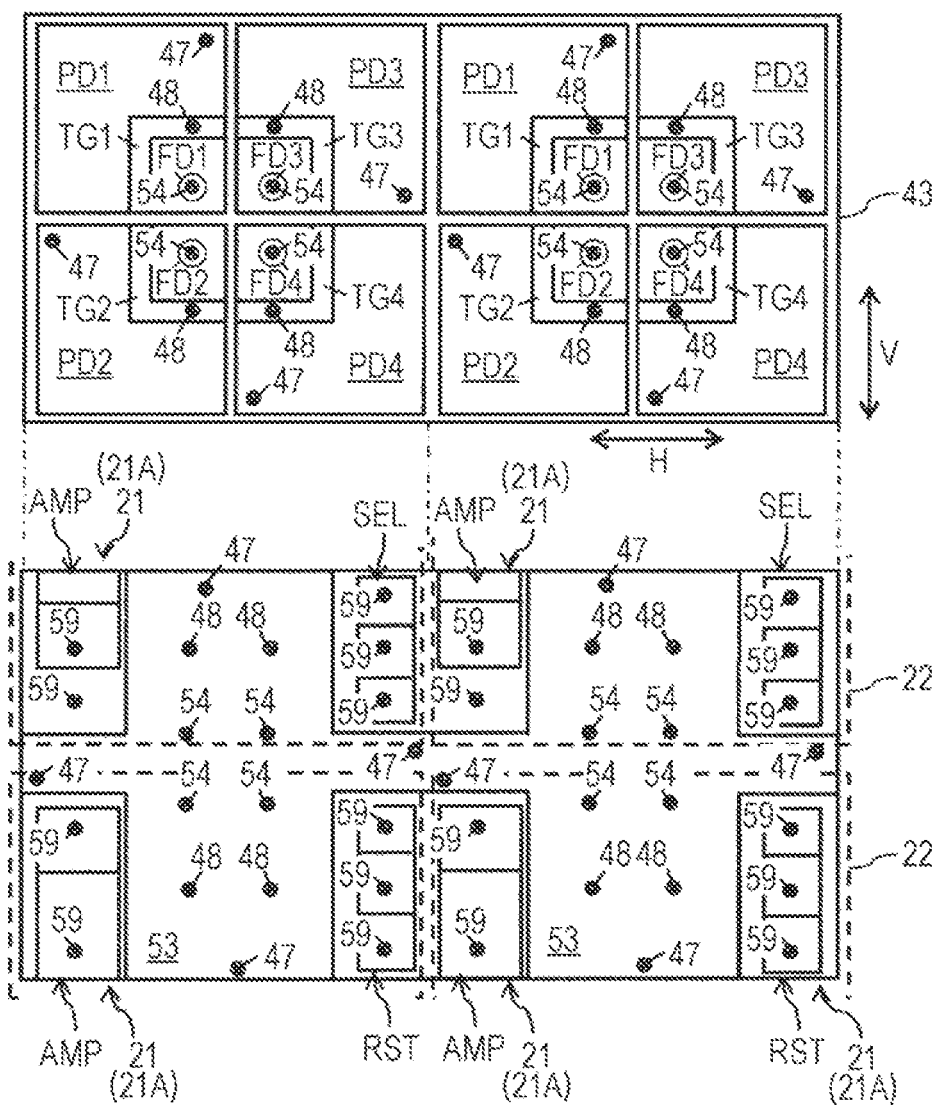
FIG. 16 is a view representing a modification example of the cross-sectional configuration of the solid-state image sensor of FIG. 1 in the horizontal direction.

FIG. 16 is a view representing a modification example of the cross-sectional configuration of the solid-state image sensor 1 described above in the horizontal direction. FIG. 16 illustrates a modification example of the cross-sectional configuration of FIG. 15.

In this modification example, one readout circuit 22 shared by the four sensor pixels 12 is, for example, not arranged to directly face the four sensor pixels 12 but is arranged to be displaced in the first direction V. In this modification example, similarly to modification example 2, the semiconductor substrate 21 includes a plurality of island-shaped blocks 21A arranged to line up in the first direction V and the second direction H with the insulating layer 53 interposed therebetween. Each block 21A is provided with, for example, a set of a reset transistor RST, an amplification transistor AMP, and a selection transistor SEL. In this modification example, a plurality of through wirings 47 and a plurality of through wirings 54 are further arranged in the second direction H. Specifically, a plurality of through wirings 47 is arranged between four through wirings 54 sharing a certain readout circuit 22 and four through wirings 54 sharing another readout circuit 22 adjacent to the readout circuit 22 in the second direction H. In this case, crosstalk between the readout circuits 22 adjacent to each other can be suppressed by the insulating layer 53 and the through wiring 47, and resolution deterioration on the reproduced image and image quality deterioration due to color mixing can be suppressed.

Modification Example 4

Figure 17:
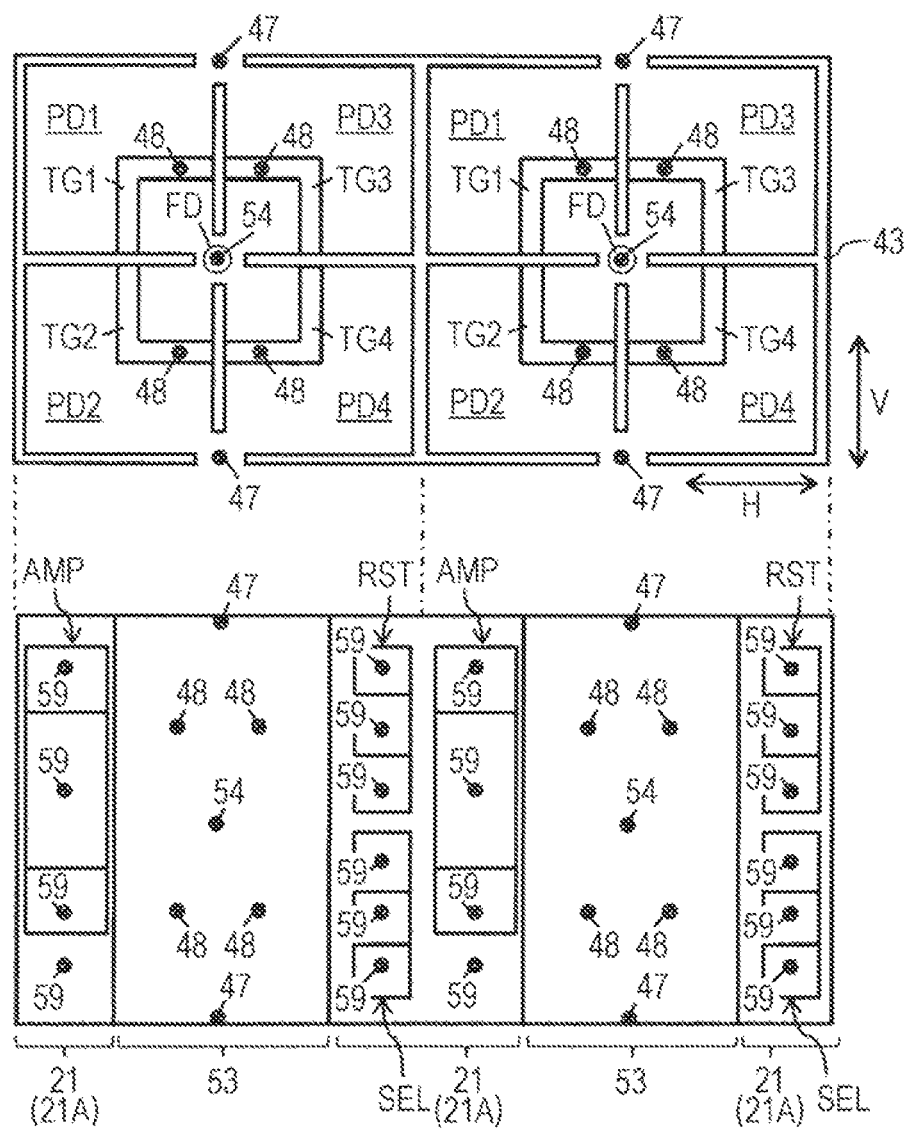
FIG. 17 is a view representing a modification example of the cross-sectional configuration of the solid-state image sensor of FIG. 1 in the horizontal direction.

FIG. 17 is a view representing an example of the cross-sectional configuration of the solid-state image sensor 1 described above in the horizontal direction. FIG. 17 illustrates a modification example of the cross-sectional configuration of FIG. 7.

In this modification example, the first substrate 10 has a photodiode PD and a transfer transistor TR for every sensor pixel 12, and a floating diffusion FD is shared by every four sensor pixels 12. Therefore, in this modification example, one through wiring 54 is provided for every four sensor pixels 12.

In the plurality of sensor pixels 12 arranged in a matrix, the four sensor pixels 12 corresponding to a region obtained by displacing a unit region corresponding to the four sensor pixels 12 sharing one floating diffusion FD in the first direction V by one sensor pixel 12 will be referred to as four sensor pixels 12A for convenience. At this time, in this modification example, the first substrate 10 shares the through wiring 47 by every four sensor pixels 12A. Therefore, in this modification example, one through wiring 47 is provided for every four sensor pixels 12A.

In this modification example, the first substrate 10 has a pixel separation part 43 that separates the photodiode PD and the transfer transistor TR for every sensor pixel 12. The pixel separation part 43 does not completely surround the sensor pixels 12 when viewed from a normal direction of the semiconductor substrate 11, and has gaps that are unformed regions near the through wiring 54 connected to the floating diffusion FD and near the through wiring 47. Then, the gaps allow the four sensor pixels 12 to share one through wiring 54 and the four sensor pixels 12A to share one through wiring 47. In this modification example, the second substrate 20 has a readout circuit 22 for every four sensor pixels 12 that share the floating diffusion FD.

Figure 18:
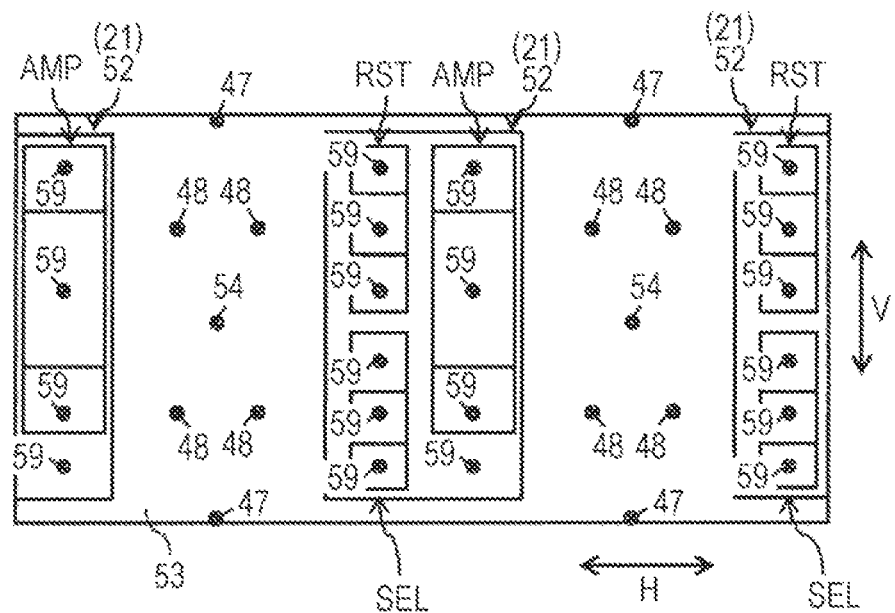
FIG. 18 is a view representing a modification example of the cross-sectional configuration of the solid-state image sensor of FIG. 1 in the horizontal direction.

FIG. 18 is a view representing an example of the cross-sectional configuration of the solid-state image sensor 1 in the horizontal direction according to this modification example. FIG. 18 illustrates a modification example of the cross-sectional configuration of FIG. 15. In this modification example, the first substrate 10 has a photodiode PD and a transfer transistor TR for every sensor pixel 12, and a floating diffusion FD is shared by every four sensor pixels 12. Moreover, the first substrate 10 has a pixel separation part 43 that separates the photodiode PD and the transfer transistor TR for every sensor pixel 12.

Figure 19:
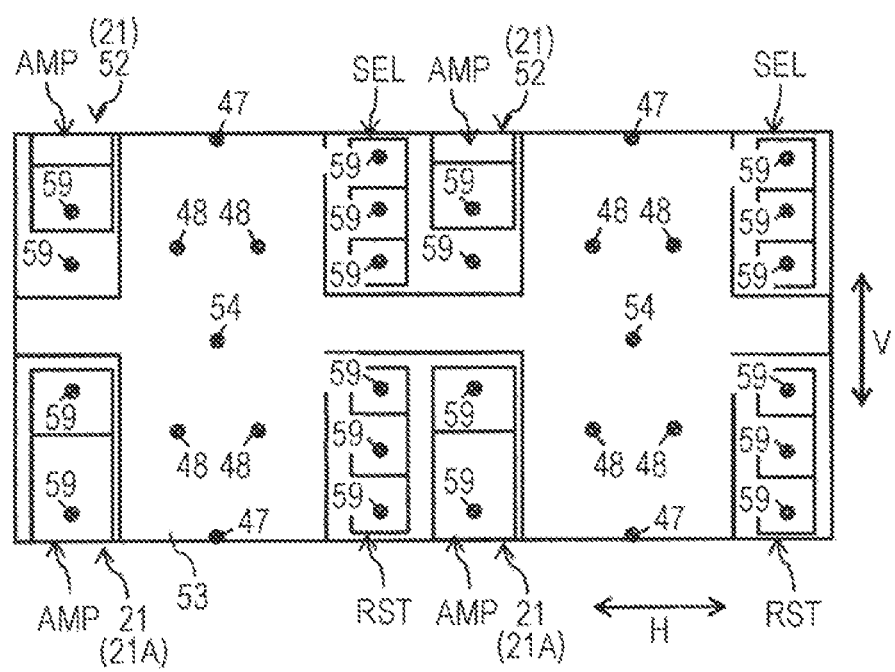
FIG. 19 is a view representing a modification example of the cross-sectional configuration of the solid-state image sensor of FIG. 1 in the horizontal direction.

FIG. 19 is a view representing an example of the cross-sectional configuration of the solid-state image sensor 1 in the horizontal direction according to this modification example. FIG. 19 illustrates a modification example of the cross-sectional configuration of FIG. 16. In this modification example, the first substrate 10 has a photodiode PD and a transfer transistor TR for every sensor pixel 12, and a floating diffusion FD is shared by every four sensor pixels 12.

Moreover, the first substrate 10 has a pixel separation part 43 that separates the photodiode PD and the transfer transistor TR for every sensor pixel 12.

Modification Example 5

Figure 20:
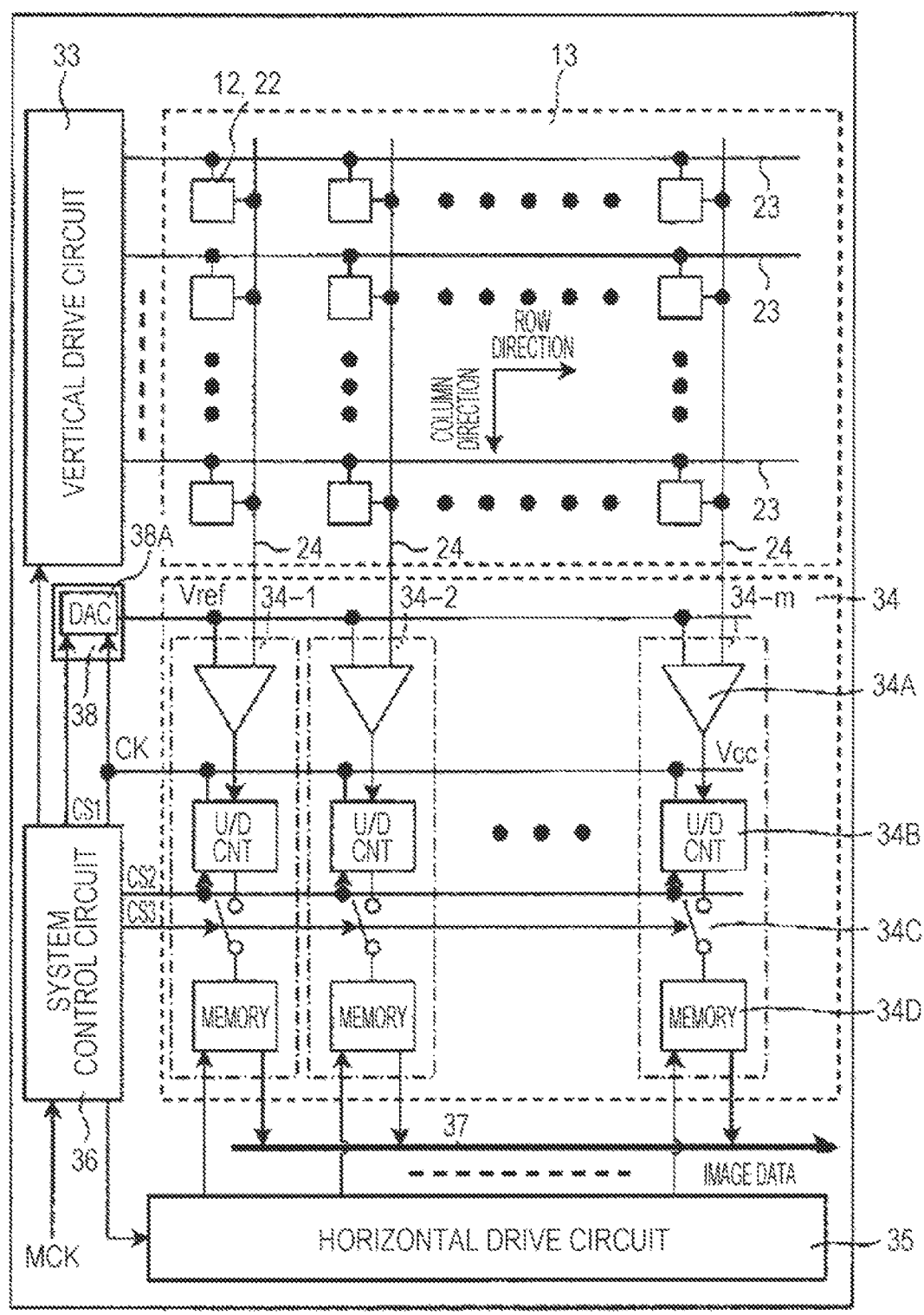
FIG. 20 is a diagram representing a modification example of a circuit configuration of the solid-state image sensor according to the configuration of FIG. 1 and a modification example thereof.

FIG. 20 is a view representing an example of the circuit configuration of the solid-state image sensor 1 according to a modification example. The solid-state image sensor 1 according to this modification example is a CMOS image sensor equipped with a column-parallel ADC.

As illustrated in FIG. 20, the solid-state image sensor 1 according to this modification example includes the vertical drive circuit 33, the column signal processing circuit 34, a reference voltage supply unit 38, the horizontal drive circuit 35, a horizontal output line 37, and a system control circuit 36, in addition to the pixel region 13 in which the plurality of sensor pixels 12 including the photoelectric conversion elements is arranged in a matrix in two dimensions.

In this system configuration, the system control circuit 36 generates a clock signal, a control signal, and the like to be references for operation of the vertical drive circuit 33, the column signal processing circuit 34, the reference voltage supply unit 38, the horizontal drive circuit 35, and the like on the basis of a master clock MCK, and gives the generated signals to the vertical drive circuit 33, the column signal processing circuit 34, the reference voltage supply unit 38, the horizontal drive circuit 35, and the like.

Furthermore, the vertical drive circuit 33 is formed on the first substrate 10 together with the respective sensor pixels 12 in the pixel region 13, and is further formed on the second substrate 20 on which the readout circuits 22 are formed. The column signal processing circuit 34, the reference voltage supply unit 38, the horizontal drive circuit 35, the horizontal output line 37, and the system control circuit 36 are formed on the third substrate 30.

Although not illustrated here, for the sensor pixels 12, for example, it is possible to use a configuration having a transfer transistor TR that transfers a charge obtained by photoelectric conversion by the photodiode PD to the floating diffusion FD, besides the photodiode PD. Furthermore, although not illustrated here, as the readout circuit 22, for example, it is possible to use one with a three-transistor configuration having a reset transistor RST that controls the potential of the floating diffusion FD, an amplification transistor AMP that outputs a signal corresponding to the potential of the floating diffusion FD, and a selection transistor SEL for selecting a pixel.

In the pixel region 13, the sensor pixels 12 are arranged two-dimensionally, the pixel drive line 23 is wired for every row and the vertical signal line 24 is wired for every column with respect to the pixel arrangement of m rows and n columns. Each end of the plurality of pixel drive lines 23 is connected to each output end corresponding to each row of the vertical drive circuit 33. The vertical drive circuit 33 includes a shift register and so on, and controls the row address and row scan of the pixel region 13 via the plurality of pixel drive lines 23.

The column signal processing circuit 34 has, for example, ADCs (analog-to-digital conversion circuits) 34-1 to 34-$m$ provided for every pixel row in the pixel region 13, that is, for every vertical signal line 24, and converts an analog signal output from each sensor pixel 12 of the pixel region 13 by every column into a digital signal and outputs the digital signal.

The reference voltage supply unit 38 has, for example, a digital-to-analog conversion circuit (DAC) 38A as a method for generating a reference voltage Vref of what is called a ramp (RAMP) waveform whose level changes in an inclined manner over time. Note that the method for generating the reference voltage Vref with a lamp waveform is not limited to the DAC 38A.

The DAC 38A generates the reference voltage Vref with a lamp waveform on the basis of a clock CK given by the system control circuit 36 under control of a control signal CS1 given by the system control circuit 36, and supplies the reference voltage Vref to the ADCs 34-1 to 34-$m$ of a column processing unit 15.

Note that each of the ADCs 34-1 to 34-$m$ is configured to be capable of selectively performing AD conversion operation corresponding to respective operation modes of a normal frame rate mode with a progressive scanning method for reading information of all the sensor pixels 12 and a high-speed frame rate mode in which the exposure time of the sensor pixels 12 is set to 1/N to increase the frame rate to N times, double for example, compared to when it is the normal frame rate mode. This switching of operation mode is executed by control by control signals CS2 and CS3 given from the system control circuit 36. Furthermore, the system control circuit 36 is given instruction information for switching the respective operation modes of the normal frame rate mode and the high-speed frame rate mode by an external system controller (not illustrated).

The ADCs 34-1 to 34-$m$ all have the same configuration, and here, the ADC 34-$m$ will be described as an example. The ADC 34-$m$ includes a comparator 34A, an up-down counter (U/DCNT) 34B, which is a counting means for example, a transfer switch 34C, and a memory device 34D.

The comparator 34A compares a signal voltage Vx of the vertical signal line 24 corresponding to a signal output from each sensor pixel 12 in the n-th column of the pixel region 13 with the reference voltage Vref with a lamp waveform supplied from the reference voltage supply unit 38. For example, when the reference voltage Vref becomes larger than the signal voltage Vx, an output Vco becomes an "H" level, and when the reference voltage Vref is equal to or less than the signal voltage Vx, the output Vco becomes an "L" level.

The up-down counter 34B is an asynchronous counter, and the clock CK is given from the system control circuit 36 at the same time as the DAC 18A under the control by the control signal CS2 given from the system control circuit 36, and performs a down count or an up count in synchronization with the clock CK, thereby measuring a comparison period from the start of the comparison operation to the end of the comparison operation in the comparator 34A.

Specifically, in the normal frame rate mode, in a signal reading operation from one sensor pixel 12, a down count is performed during a first reading operation to measure a comparison time at a time of first readout operation, and an up count is performed during a second reading operation to measure a comparison time at a time of second readout operation.

On the other hand, in the high-speed frame rate mode, the count result for the sensor pixels 12 in a certain row is held as it is, the down count is continuously performed for the sensor pixels 12 in the next row during the first readout operation from the previous count result to thereby measure a comparison time at the time of the first readout operation, and the up count is performed during the second readout operation to thereby measure a comparison time at the time of the second readout operation.

Under the control of the control signal CS3 given from the system control circuit 36, in the normal frame rate mode, the transfer switch 34C turns on (closed) at a point when the count operation of the up-down counter 34B for the sensor pixels 12 in a certain row is completed, and transfers the count result of the up-down counter 34B to the memory device 34D.

On the other hand, for example, at the high-speed frame rate of N=2, the transfer switch 34C remains to be off (opened) at a point when the count operation of the up-down counter 34B for the sensor pixel 12 of a certain row is completed, and subsequently turns on at a point when the count operation of the up-down counter 34B for the sensor pixel 12 of the next row is completed, and transfers count results for two vertical pixels of the up-down counter 34B to the memory device 34D.

Thus, the analog signal supplied from each sensor pixel 12 in the pixel region 13 via the vertical signal line 24 by every column is converted into an N-bit digital signal by the respective operations of the comparator 34A and the up-down counter 34B in the ADCs 34-1 to 34-$m$, and is stored in the memory device 34D.

The horizontal drive circuit 35 includes a shift register and so on, and controls column addresses and column scans of the ADCs 34-1 to 34-$m$ in the column signal processing circuit 34. Under the control of the horizontal drive circuit 35, the N-bit digital signals AD-converted by the respective ADCs 34-1 to 34-$m$ are sequentially read out to the horizontal output line 37 and output as imaging data via the horizontal output line 37.

Note that although not illustrated in particular because it is not directly related to the present disclosure, it is possible to provide a circuit or the like that performs various signal processing on the imaging data output via the horizontal output line 37 besides the components described above.

In the solid-state image sensor 1 equipped with the column-parallel ADC according to this modification example of the configuration described above, the count result of the up-down counter 34B can be selectively transferred to the memory device 34D via the transfer switch 34C, and thus it is possible to independently control the count operation of the up-down counter 34B and the readout operation of the count result of the up-down counter 34B to the horizontal output line 37.

Figure 21:
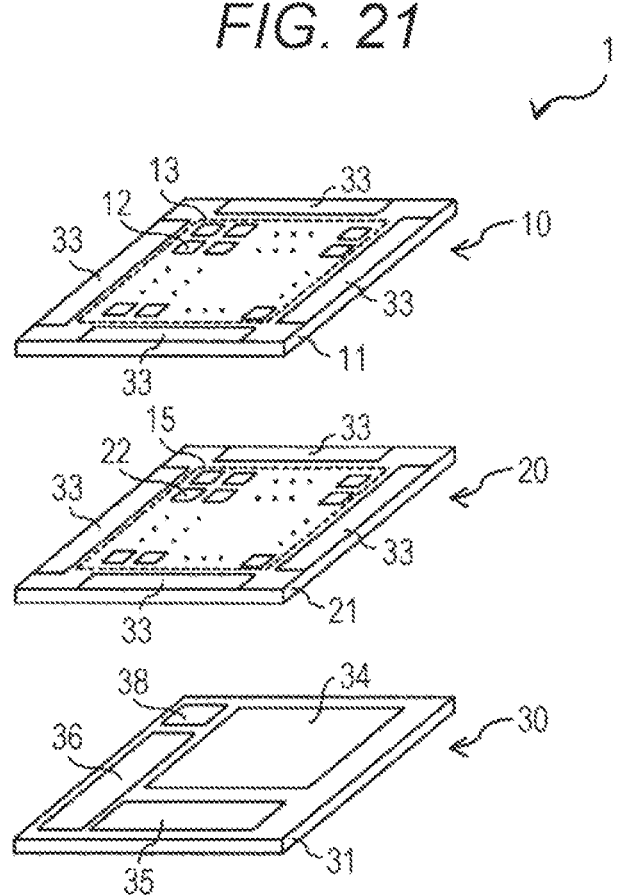
FIG. 21 is a view representing an example in which the solid-state image sensor of FIG. 20 is formed by stacking three substrates.

FIG. 21 represents an example in which the solid-state image sensor 1 of FIG. 20 is formed by stacking the three substrates, the first substrate 10, the second substrate 20, and the third substrate 30.

In this modification example, in the first substrate 10, the pixel region 13 including the plurality of sensor pixels 12 is formed in a central portion, and the vertical drive circuit 33 is formed around the pixel region 13.

Furthermore, in the second substrate 20, a readout circuit region 15 including a plurality of readout circuits 22 is formed in a central portion, and the vertical drive circuit 33 is formed around the readout circuit region 15.

Furthermore, in the third substrate 30, the column signal processing circuit 34, the horizontal drive circuit 35, the system control circuit 36, the horizontal output line 37, and the reference voltage supply unit 38 are formed.

With the configuration described above, as in the configuration of FIG. 1 and the modification examples thereof, increase in the chip size or hindrance to miniaturization of the area per pixel due to the structure of electrically connecting substrates with each other will not occur. Consequently, it is possible to provide a solid-state image sensor 1 having a three-layer structure that does not hinder the miniaturization of the area per pixel with a chip size equivalent to those in the past. Note that the vertical drive circuit 33 may be formed only on the first substrate 10 or only on the second substrate 20.

Modification Example 6

Figure 22:
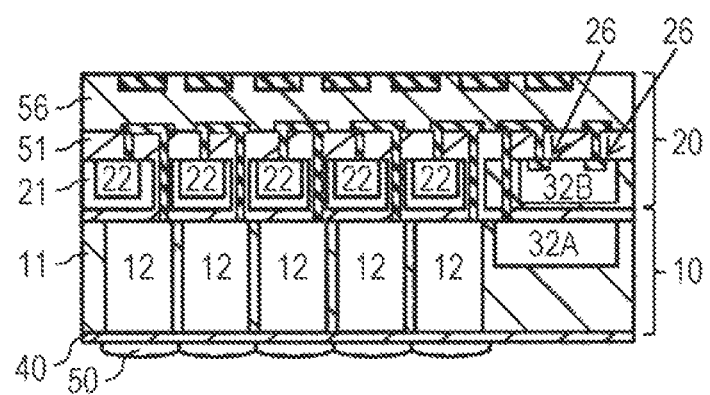
FIG. 22 is a view representing an example in which a logic circuit is divided between a substrate provided with sensor pixels and a substrate provided with a readout circuit.

FIG. 22 illustrates a modification example of the cross-sectional configuration of the solid-state image sensor 1 according to this modification example. In the configuration of FIG. 1 described above and the modification examples thereof, the solid-state image sensor 1 is formed by stacking three substrates, the first substrate 10, the second substrate 20, and the third substrate 30. However, in the configuration of FIG. 1 described above and the modification examples thereof, the solid-state image sensor 1 may be configured by stacking two substrates, the first substrate 10 and the second substrate 20.

At this time, for example, as illustrated in FIG. 22, the logic circuit 32 is formed by dividing between the first substrate 10 and the second substrate 20. Here, in a circuit 32A provided on the first substrate 10 side of the logic circuit 32, a transistor having a gate structure is provided in which a high dielectric constant film formed by a material (for example, high-k) capable of withstanding a high temperature process and a metal gate electrode are stacked. On the other hand, in a circuit 32B provided on the second substrate 20 side, a low resistance region including a silicide such as $CoSi_2$ or NiSi formed using a self-aligned silicide (SALICIDE) process is formed on the surface of an impurity diffusion region in contact with a source electrode and a drain electrode. The low resistance region including a silicide including a compound of the material of the semiconductor substrate and metal.

Thus, a high temperature process such as thermal oxidation can be used when forming the sensor pixels 12. Furthermore, in a case where, in the circuit 32B provided on the second substrate 20 side of the logic circuit 32, a low resistance region 26 including a silicide is provided on the surface of an impurity diffusion region in contact with a source electrode and a drain electrode, contact resistance can be reduced. Consequently, the calculation speed in the logic circuit 32 can be increased.

Figure 23:
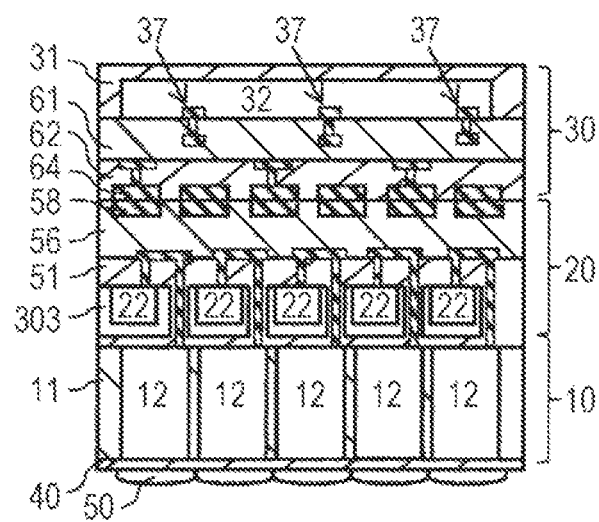
FIG. 23 is a view representing an example in which the logic circuit is formed on a third substrate.

FIG. 23 represents a modification example of the cross-sectional configuration of the solid-state image sensor 1 according to the configuration of FIG. 1 described above and the modification examples thereof. In the logic circuit 32 of the third substrate 30 according to the configuration of FIG. 1 described above and the modification examples thereof, a low resistance region 37 including a silicide such as $CoSi_2$ or NiSi formed using a self-aligned silicide (SALICIDE) process may be formed on the surface of an impurity diffusion region in contact with a source electrode and a drain electrode. Thus, a high temperature process such as thermal oxidation can be used when forming the sensor pixels 12. Furthermore, in a case where the low resistance region 37 including a silicide is provided on the surface of an impurity diffusion region in contact with a source electrode and a drain electrode in the logic circuit 32, contact resistance can be reduced. Consequently, the calculation speed in the logic circuit 32 can be increased.

First Embodiment

A solid-state image sensor of a first embodiment will be described with reference to FIGS. 24 to 34.

[Example of Overall Configuration of Solid-State Image Sensor]

Figure 24:
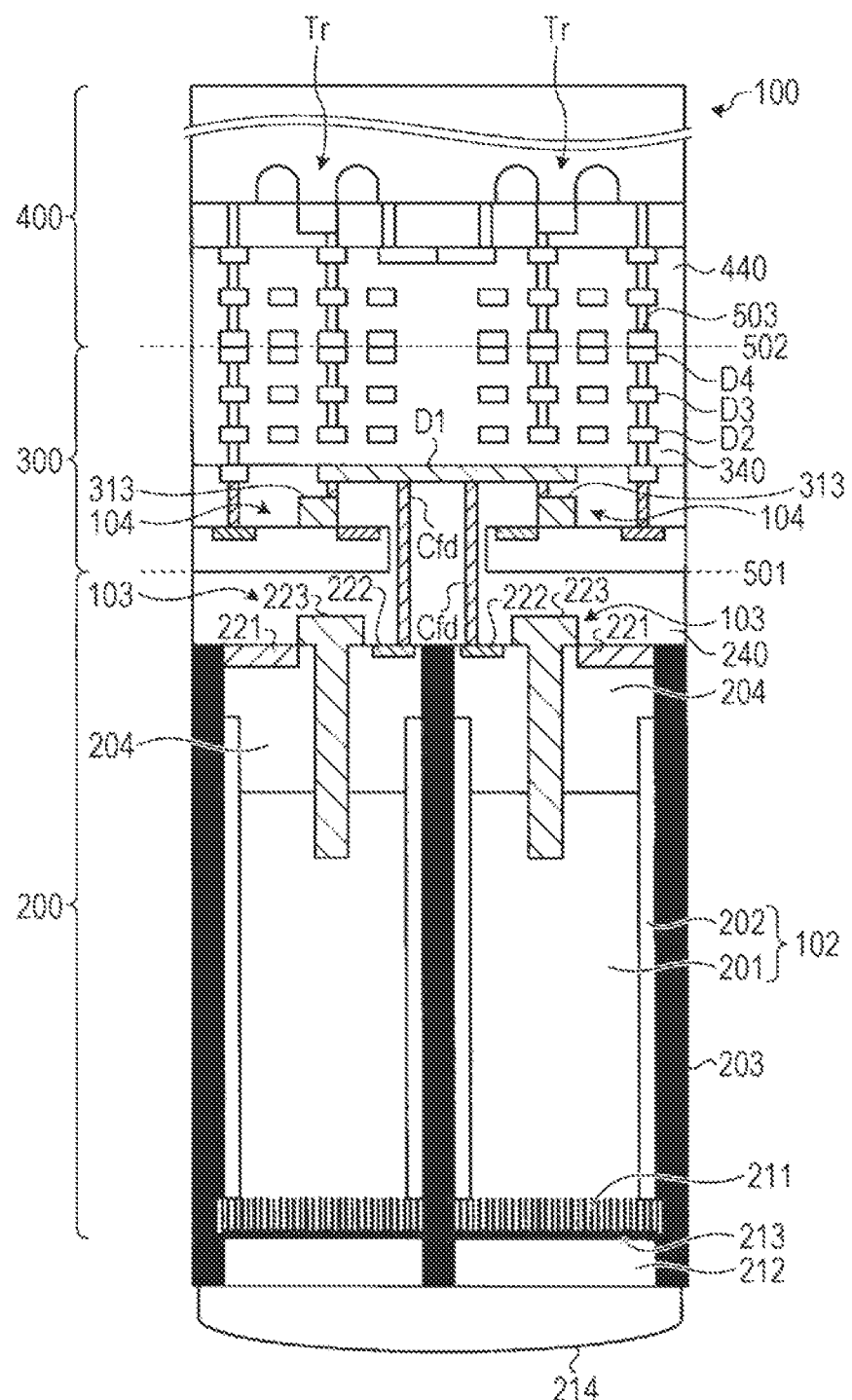
FIG. 24 is a diagram illustrating a part of a cross section of a solid-state image sensor according to a first embodiment of the present disclosure.

FIG. 24 is a diagram illustrating a part of a cross section of a solid-state image sensor 100 according to the first embodiment of the present disclosure. As illustrated in FIG. 24, the solid-state image sensor 100 includes a structure in which a substrate 200, a substrate 300, and a substrate 400 are bonded together. A surface 501 illustrated in FIG. 24 indicates a surface on which the substrate 200 and the substrate 300 are bonded together. Furthermore, a surface 502 illustrated in FIG. 24 indicates a surface on which the substrate 300 and the substrate 400 are bonded together. These substrates 200 to 400 are electrically connected to each other.

The substrate 200, which is a semiconductor substrate such as a silicon substrate, includes a plurality of photoelectric conversion elements 102. The photoelectric conversion elements 102 convert received light into an electrical signal corresponding to the amount of received light by photoelectric conversion. One photoelectric conversion element 102 corresponds to one pixel. The photoelectric conversion element 102 includes, for example, a PN junction photodiode. One photoelectric conversion element 102 may include a plurality of photodiodes. In the example of FIG. 24, the photoelectric conversion element 102 includes an N-type semiconductor region 201 of the substrate 200 and a P-type semiconductor region 202 formed so as to cover side surfaces thereof. Each photoelectric conversion element 102 is electrically separated by a pixel separation part 203 that separates pixels. The pixel separation part 203 includes a metal, an insulating film (for example, $SiO_2$), a combination thereof, or the like.

A lower end of the photoelectric conversion element 102, that is, a lower surface of the substrate 200 is covered with an insulating film 211. The insulating film 211 is formed by, for example, a film having a fixed charge, or the like. A flattening film 213, which is an insulating film or the like, may be further arranged on a lower end of the insulating film 211. The insulating film 211 is, for example, a metal oxide film of a hafnium oxide, a tantalum oxide, an aluminum oxide, or the like. The flattening film 213 is, for example, an insulating film of a silicon oxide, a silicon nitride, or the like. The insulating film 211 and the flattening film 213 may be each provided as a plurality of layers.

A color filter 212 is arranged below the insulating film 211. An on-chip lens 214 is arranged under the color filter 212. The on-chip lens 214 collects irradiated light. The collected light is guided to the photoelectric conversion element 102 via the color filter 212.

A P-type semiconductor region 204 (P well) is formed on the photoelectric conversion element 102. In the example of FIG. 24, the P-type semiconductor region 202 constituting the photoelectric conversion element 102 projects so as to cover a part of a side surface of the semiconductor region 204. However, the P-type semiconductor region 202 may have any depth. For example, an upper surface of the semiconductor region 202 and a lower surface of the semiconductor region 204 may be at the same height.

An N-type transfer transistor 103 is arranged above the photoelectric conversion element 102. Specifically, an N-type drain region 221 and an N-type source region 222 are formed near a surface of the semiconductor region 204. A gate electrode 223 is formed between the N-type drain region 221 and the N-type source region 222 on the semiconductor region 204. The drain region 221, the source region 222, and the gate electrode 223 form the transfer transistor 103.

In the example of FIG. 24, the gate electrode 223 is connected to the N-type semiconductor region 201 forming the photoelectric conversion element 102. As described above, one transfer transistor 103 is provided for one photoelectric conversion element 102. The transfer transistor 103 transfers an electrical signal output from the photoelectric conversion element 102 to a pixel transistor.

The source region 222 of the transfer transistor 103 functions as a floating diffusion (FD). The floating diffusion temporarily holds the electrical signal output from the photoelectric conversion element 102. The transfer transistor 103 including the source region 222 as the floating diffusion is covered with an insulating film 240. The substrate 300 is arranged on the insulating film 240.

The substrate 300, which is a semiconductor substrate such as a P-type silicon substrate, includes pixel transistors including a plurality of N-type amplification transistors 104. One pixel transistor such as the amplification transistor 104 is provided for one transfer transistor 103. The pixel transistor performs a process of reading an electrical signal corresponding to the amount of light received by the photoelectric conversion element 102. For example, the amplification transistor 104 amplifies and outputs an electrical signal transferred from the photoelectric conversion element 102 by the transfer transistor 103.

A wiring D1 is connected to a gate electrode 313 of the amplification transistor 104. The wiring D1 is connected to the source region 222 of the transfer transistor 103 as a floating diffusion via a contact Cfd.

In the example of FIG. 24, wirings D1 to D4 are formed over four layers in the substrate 300. The wiring D1 is a wiring formed at a lowest layer that is a first layer. The wiring D4 is a wiring formed at an uppermost layer that is a fourth layer. Note that the number of wiring layers is not limited to four, and can be changed to any number according to design conditions and the like. The amplification transistor 104 and the wirings D1 to D4 are covered with an insulating film 340.

The substrate 400, which is a semiconductor substrate such as a silicon substrate, is turned upside down and joined onto the wiring D4 of the substrate 300. In the example of FIG. 24, a junction point 503 between the wiring D4 and a wiring of the substrate 400 overlaps with a pixel region where the pixels are arranged. A plurality of logic transistors Tr is connected to the wiring of the substrate 400. The wiring of the substrate 400 and the logic transistor Tr are covered with an insulating film 440. A logic circuit as a signal processing circuit is formed by the wiring of the substrate 400 and the logic transistors Tr. The logic circuit corresponds to a peripheral circuit of the solid-state image sensor 100 that processes an electrical signal or the like generated by the photoelectric conversion element 102.

(Detailed Configuration Example of Solid-State Image Sensor)

Figure 25:
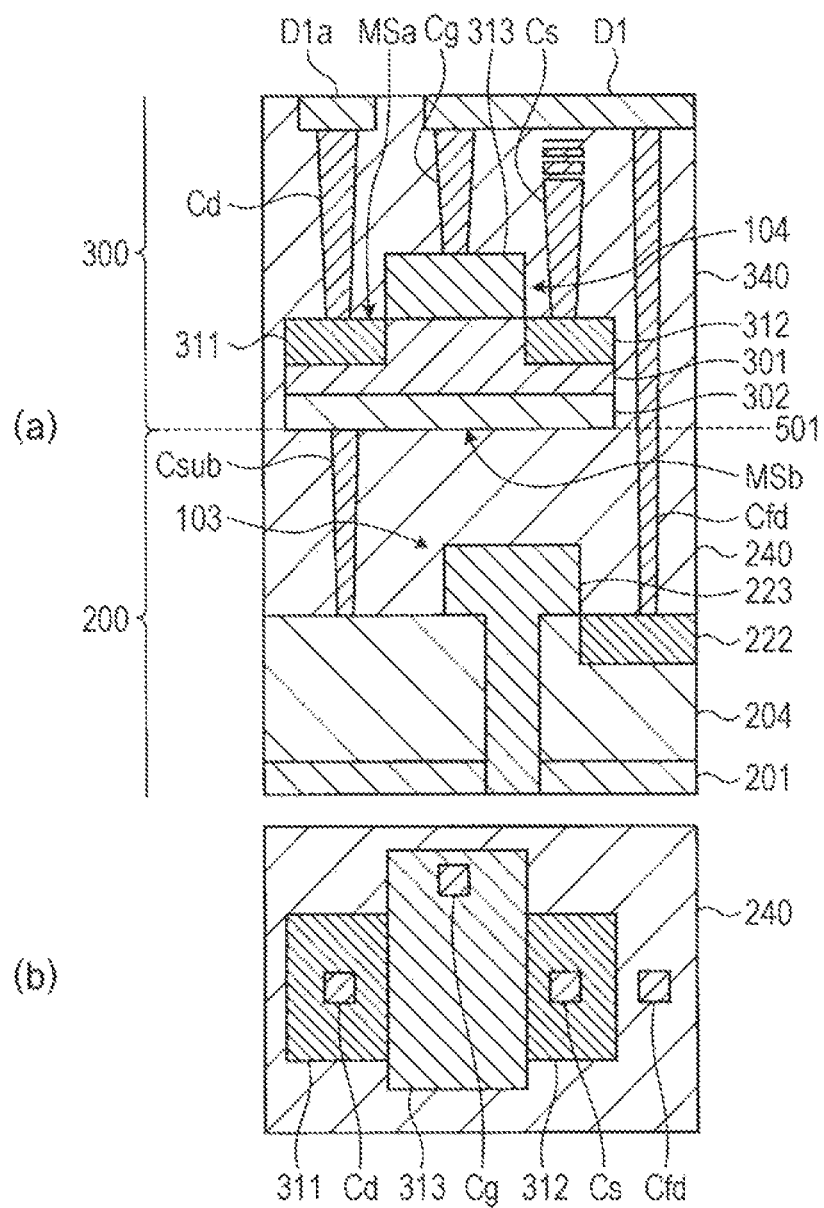
FIG. 25 is a schematic view illustrating the vicinity of bonding positions of substrates of the solid-state image sensor according to the first embodiment of the present disclosure.

Next, a detailed configuration example of the solid-state image sensor 100 of the first embodiment will be described with reference to FIG. 25. FIG. 25 is a schematic view illustrating the vicinity of bonding positions of the substrates 200 and 300 of the solid-state image sensor 100 according to the first embodiment of the present disclosure. FIG. 25(a) is a cross-sectional view illustrating the vicinity of the bonding positions of the substrates 200 and 300, and FIG. 25(b) is a top view of the substrate 300. However, in FIG. 25(a), the position of a contact Cg is displaced. Further, in FIG. 25(b), the insulating film 340 and the wiring D1 are omitted. Furthermore, in FIG. 25, the amplification transistor 104 is illustrated as an example of the pixel transistor.

As illustrated in FIG. 25, the solid-state image sensor 100 includes the substrate 200 as a first semiconductor substrate having a photoelectric conversion element 102 and the substrate 300 as a second semiconductor substrate facing the substrate 200 with the insulating film 240 interposed therebetween. The substrate 200 is grounded. That is, the potential of the substrate 200 is fixed at 0 V. The substrate 200 has the transfer transistor 103 with the gate electrode 223 and the N-type source region 222 as a floating diffusion. The transfer transistor 103 is formed as, for example, a metal oxide semiconductor (MOS) field effect transistor (MOSFET).

The substrate 300 has the amplification transistor 104 that amplifies an electrical signal output from the photoelectric conversion element 102 on a main surface MSa as a first main surface. The amplification transistor 104 is formed as, for example, a MOSFET. The amplification transistor 104 has an N-type source region 312 and an N-type drain region 311 provided in the substrate 300. The gate electrode 313 of the amplification transistor 104 is arranged on the substrate 300 between the source region 312 and the drain region 311. The source region 312 is provided with a contact Cs connected to an upper wiring that is not illustrated. The drain region 311 is provided with a contact Cd connected to a wiring D1a of Cu or the like. The gate electrode 313 is provided with a contact Cg connected to the wiring D1 of Cu or the like. The contact Cfd is connected to the wiring D1. The other end of the contact Cfd is connected to the source region 222 of the transfer transistor 103.

The substrate 300 has a substrate contact layer 302 as a region having a resistance lower than that of the substrate 300 on a main surface MSb as a second main surface opposite to the main surface MSa. Specifically, the substrate 300 has a certain conductive type, for example P type, and the substrate contact layer 302 contains a higher concentration of impurities than another region 301 of the substrate 300. The N-type source region 312 and the N-type drain region 311 of the amplification transistor 104 provided on the main surface MSa and the substrate contact layer 302 of P+ type provided on the main surface MSb are separated by the other region 301 of the substrate 300. Here, the substrate contact layer 302 does not necessarily have to have a lower resistance as a whole, and does not necessarily have to contain a high concentration of impurities. It is only required that at least a partial region of the substrate contact layer 302 has a lower resistance and a higher concentration of impurities than the other region 301 of the substrate 300. Therefore, the impurity concentration in the substrate contact layer 302 does not have to be uniform over the entire substrate contact layer 302.

The substrate 300 is grounded via the substrate contact layer 302. Specifically, the solid-state image sensor 100 includes a contact Csub extending from the substrate contact layer 302 of the substrate 300 toward the substrate 200 side. More specifically, the substrate 300 is arranged on the substrate 200 with a side of the main surface MSb facing the substrate 200, and the solid-state image sensor 100 includes the contact Csub that connects the substrate contact layer 302 of the substrate 300 and the substrate 200. Thus, the substrate 300 is grounded via the substrate contact layer 302 and the substrate 200. That is, the potential of the substrate 300 is fixed at 0 V.

[Example of Manufacturing Process of Solid-State Image Sensor]

Next, an example of a manufacturing process of the solid-state image sensor 100 of the first embodiment will be described with reference to FIGS. 26 to 28. FIGS. 26 to 28 are flow views illustrating an example of a procedure of the manufacturing process of the solid-state image sensor 100 according to the first embodiment of the present disclosure. Note that left views of FIGS. 26 to 28 are cross-sectional views in the manufacturing process of the solid-state image sensor 100. Furthermore, right views of FIGS. 26 to 28 excluding FIG. 26(a2) are top views in the manufacturing process of the solid-state image sensor 100.

As illustrated in FIG. 26(a1), the photoelectric conversion element 102 including the N-type semiconductor region 201, the P-type semiconductor region 204, the gate electrode 223 of the transfer transistor 103, and the source region 222 as a floating diffusion are formed on the substrate 200. The gate electrode 223 and the source region 222 are covered with the insulating film 240. The insulating film 240 is penetrated to form a through hole reaching the substrate 200, and a conductive material such as W is embedded in the through hole, thereby forming the contact Csub.

As illustrated in FIG. 26(a2), the substrate contact layer 302 is formed on the main surface MSb of the substrate 300, which is a P-type silicon substrate or the like. The substrate contact layer 302 can be formed by, for example, an ion implantation method, a solid phase diffusion method, a plasma doping method, or the like.

In a case where the ion implantation method is used, for example, boron is implanted into the main surface MSb of the substrate 300 with a dose amount of about $1\times10^{16}/\text{cm}^3$ to $1\times10^{20}/\text{cm}^3$, and heat treatment is performed at about 600° C. to 900° C., thereby forming the substrate contact layer 302.

In a case where the solid phase diffusion method is used, for example, a silicon oxide film such as a borosilicate glass (BSG) film is deposited by a low pressure chemical vapor deposition (LP-CVD) method using a $B_2H_6/SiH_4/O_2$ gas on the main surface MSb of the substrate 300. Then, heat treatment is performed at about 900° C. to cause diffusion of boron on the substrate 300 side. Thereafter, the BSG film is removed with hydrofluoric acid, thereby forming the substrate contact layer 302.

In a case where the plasma doping method is used, a $B_2H_6/He$ mixed gas is excited with plasma to cause diffusion of boron on the main surface MSb side of the substrate 300, thereby forming the substrate contact layer 302.

As illustrated in FIGS. 26(b1) and 26(b2), the substrate 300 on which the substrate contact layer 302 is formed is bonded to the substrate 200 of FIG. 26(a1) with the main surface MSb side facing the substrate 200. At this time, pressures of 0.1 MPa to several MPa are applied, and a heat treatment at about 350° C. to 600° C. is performed. Thus, the substrate 300 and the substrate 200 are joined with the insulating film 240 interposed therebetween. Note that before bonding the substrate 300 and the substrate 200, the bonding surface of the substrate 300 and the bonding surface of the substrate 200 may be each subjected to $O_2$ plasma treatment.

As illustrated in FIGS. 27(a1) and 27(a2), the substrate 300 is ground to a thickness of zero point several μm to a few μm by chemical mechanical polishing (CMP).

As illustrated in FIGS. 27(b1) and 27(b2), element isolation is performed on the substrate 300 while leaving a region where the pixel transistors such as the amplification transistor 104 are formed. Specifically, a resist pattern is formed on the region where the pixel transistor is formed by photolithography, and the other region is etched by dry etching. After ashing the resist pattern, the insulating film 340 such as a silicon oxide film is formed by a CVD method to back-fill the portion where the substrate 300 has been etched and removed. The excess insulating film 340 is removed by CMP to expose a surface of the substrate 300.

As illustrated in FIGS. 28(a1) and 28(a2), the amplification transistor 104 is formed on the main surface MSa of the substrate 300. Specifically, a gate oxide film (not illustrated) is formed on the surface of the substrate 300 by a thermal oxidation method. A polysilicon film or the like is formed by the CVD method, a resist pattern is formed by photolithography, the polysilicon film is etched, and the resist pattern is ashed to form the gate electrode 313. Phosphorus or arsenic is implanted into the substrate 300 on both sides of the gate electrode 313 by ion implantation, and a heat treatment is performed thereon by a high-temperature rapid thermal annealing (RTA) method to form the source region 312 and the drain region 311.

As illustrated in FIGS. 28(b1) and 28(b2), contacts Cg, Cs, Cd, and Cfd are formed. Specifically, the insulating film 340 that covers the amplification transistor 104 is further formed by the CVD method, and a surface of the insulating film 340 is flattened by CMP. A resist pattern is formed on the surface of the insulating film 340 by photolithography, and through holes reaching the gate electrode 313, the source region 312, the drain region 311, and the substrate 200 are formed by dry etching. After removing the resist pattern by ashing, a W film or the like is filled in each through hole by the CVD method, and the excess W film is removed by CMP.

Thereafter, the wirings D1 to D4 are formed, and the substrate 400 on which the logic transistor Tr and wirings are formed are joined, thereby finishing the manufacturing process of the solid-state image sensor 100.

Comparative Example

Next, with reference to FIG. 29, configurations of comparative examples 1 and 2 and the configuration of the first embodiment are compared. FIG. 29 is a diagram for comparing the solid-state image sensors according to the first embodiment of the present disclosure and comparative examples 1 and 2.

In the solid-state image sensor of Patent Document 1, a semiconductor substrate on which a pixel region is formed and a semiconductor substrate on which a logic circuit is formed are joined. That is, the photoelectric conversion element and the pixel transistors are formed on the same semiconductor substrate. However, in such a configuration, it is not possible to secure a sufficient space for arranging the pixel transistors. Among the pixel transistors, for example, if the amplification transistor has a small size, it is difficult to sufficiently reduce the noise level of random telegraph signal (RTS) noise or the like.

Therefore, for example, it is conceivable to separate the substrate on which the photoelectric conversion element is formed and the substrate on which the pixel transistors is formed and join them together. Such a configuration is illustrated in FIG. 29 as comparative example 1. Here, since the substrate on which the pixel transistors are formed is joined to the other substrate via the insulating film, it is a floating substrate in which a substrate potential is not fixed. If the substrate potential is indefinite, operation of the pixel transistor becomes unstable. In order to improve this, for example, as in comparative example 2 illustrated in FIG. 29, it is conceivable to provide a substrate contact layer 302' separated from the forming region of the amplification transistor by an element isolation region STI. The substrate potential can be fixed by connecting the substrate contact layer 302' to a ground wire of an upper layer. However, in the configuration of comparative example 2, by being pressed by the element isolation region STI and the substrate contact layer 302', the size of the amplification transistor has to be reduced, and the effect of separating the substrates is impaired.

In the solid-state image sensor 100 of the first embodiment, the substrate contact layer 302 that fixes the potential of the substrate 300 is arranged on the main surface MSb opposite to the side on which the amplification transistor 104 of the substrate 300 is formed. Thus, the area on the main surface MSa side is not reduced by the substrate contact layer 302. Furthermore, it is not necessary to separately provide an element isolation layer for separating the substrate contact layer 302. Therefore, the potential of the substrate 300 can be fixed while securing a space for arranging the amplification transistor 104.

When compared with the respective configurations, the sizes of the amplification transistors (AMP Tr size) are comparative example 1:comparative example 2:first embodiment=3:1:3, and a size equivalent to that of comparative example 1 is obtained in the first embodiment. Thus, the noise level of RTS noise is comparative example 1:comparative example 2:first embodiment=0.33:1:0.33, which is sufficiently reduced in the first embodiment.

With the above configuration, in the solid-state image sensor 100 of the first embodiment, the advantage of separating the photoelectric conversion element 102 and the pixel transistor between separate substrates 200 and 300 can be fully utilized. That is, the areas of both the photoelectric conversion element 102 and the pixel transistor can be expanded more than in a case where the photoelectric conversion element and the pixel transistor are arranged on the same substrate. Furthermore, the number of pixels per unit area can be increased.

Moreover, in the solid-state image sensor 100 of the first embodiment, the substrate 200 and the substrate 300 are connected via the contact Cfd. Furthermore, the substrate 300 and the substrate 400 are connected by the wiring D4 of the substrate 300 and the wiring of the substrate 400. With these configurations, the area required for inter-substrate connection can be made small as compared with cases where each substrate is connected by a through silicon via (TSV) provided in the peripheral region of the substrate, for example. Thus, the chip size of the solid-state image sensor 100 can be reduced. Alternatively, the pixel region can be expanded with the same chip size.

In addition, in the solid-state image sensor 100 of the first embodiment, the junction point 503 between the contact Cfd and the wiring D4 of the substrate 300 and the wiring of the substrate 400 is arranged in the pixel region. Thus, the chip size can be further reduced or the pixel region can be further expanded.

Here, FIG. 30 illustrates more detailed top views of the respective configurations.

FIG. 30 is a view illustrating arrangements of pixel transistors of the solid-state image sensor according to the first embodiment of the present disclosure and comparative example 2. FIG. 30(a) is a top view of the substrate on which the pixel transistor of comparative example 2 is formed, FIG. 30(b) is a top view of the substrate 300 of the first embodiment, and FIG. 30(c) is a top view of the substrate 200 of the first embodiment. However, a part of the insulating film is omitted in FIG. 30.

As illustrated in FIG. 30(c), the gate electrode 223 of the transfer transistor 103 is formed in a substantially U-shaped crank shape. By arranging both ends of the U-shaped gate electrode 223 respectively on two photoelectric conversion elements 102, the transfer transistor 103 can receive an electrical signal from the photoelectric conversion elements 102 and transfer the electrical signal to the amplification transistor 104. The gate electrode 223 of the transfer transistor 103 is connected to an upper layer wiring via contacts Ctga and Ctgb.

As illustrated in FIG. 30(b), the substrate 300 of the first embodiment includes the amplification transistor 104, a selection transistor 106, and a reset transistor 105. Only the amplification transistor 104 has been illustrated thus far as an example of the pixel transistors, but as described above, the pixel transistors also include the reset transistor 105, the selection transistor 106, and so on.

In order to process the electrical signal amplified by the amplification transistor 104, the selection transistor 106 selects whether or not to transmit the electrical signal to the wirings D1 to D4 of the upper layer. The selection transistor 106 has a gate electrode 323, a source region 322, and a drain region 321. The gate electrode 323 of the selection transistor 106 is arranged in parallel with the gate electrode 313 of the amplification transistor 104, and is connected to the wirings D1 to D4 of the upper layer via a contact Csg. The source region 322 of the selection transistor 106 is connected to the upper wirings D1 to D4 via a contact Css. The drain region 321 of the selection transistor 106 is connected to the source region 312 of the amplification transistor 104.

The reset transistor 105 resets (initializes) the potential of the gate of the amplification transistor 104 to the power supply potential. The reset transistor 105 is also a transistor that resets the potential of the floating diffusion. The reset transistor 105 has a gate electrode 333, a source region 332, and a drain region 331. The gate electrode 333 of the reset transistor 105 is arranged in series with the gate electrode 323 of the selection transistor 106, and is connected to the upper wirings D1 to D4 via a contact Crg. The source region 332 of the reset transistor 105 is connected to the gate electrode 313 of the amplification transistor 104 via contacts Crs and Cag and the wiring D1. The drain region 331 of the reset transistor 105 is connected to the upper wirings D1 to D4 via a contact Crd.

The gate electrode 313 of the amplification transistor 104 is connected to the floating diffusion which is the source region 222 of the transfer transistor 103 via the contacts Cag and Cfd and the wiring D1. The drain region 311 of the amplification transistor 104 is connected to the upper wirings D1 to D4 via a contact Cad.

As illustrated in FIG. 30(a), also in the configuration of comparative example 2, the amplification transistor 104' and the selection transistor 106' are arranged in parallel, and the selection transistor 106' and the reset transistor 105' are arranged in series. However, since a part of the region on the substrate is occupied by the substrate contact layer 302' and the element isolation region STI, the size of the amplification transistor 104' is limited.

As described above, even in the detailed diagram illustrating the pixel transistors other than the amplification transistor, it is clear that the configuration of the first embodiment has an advantage over the configuration of the comparative example 2.

Modification Example 1

Figure 31:
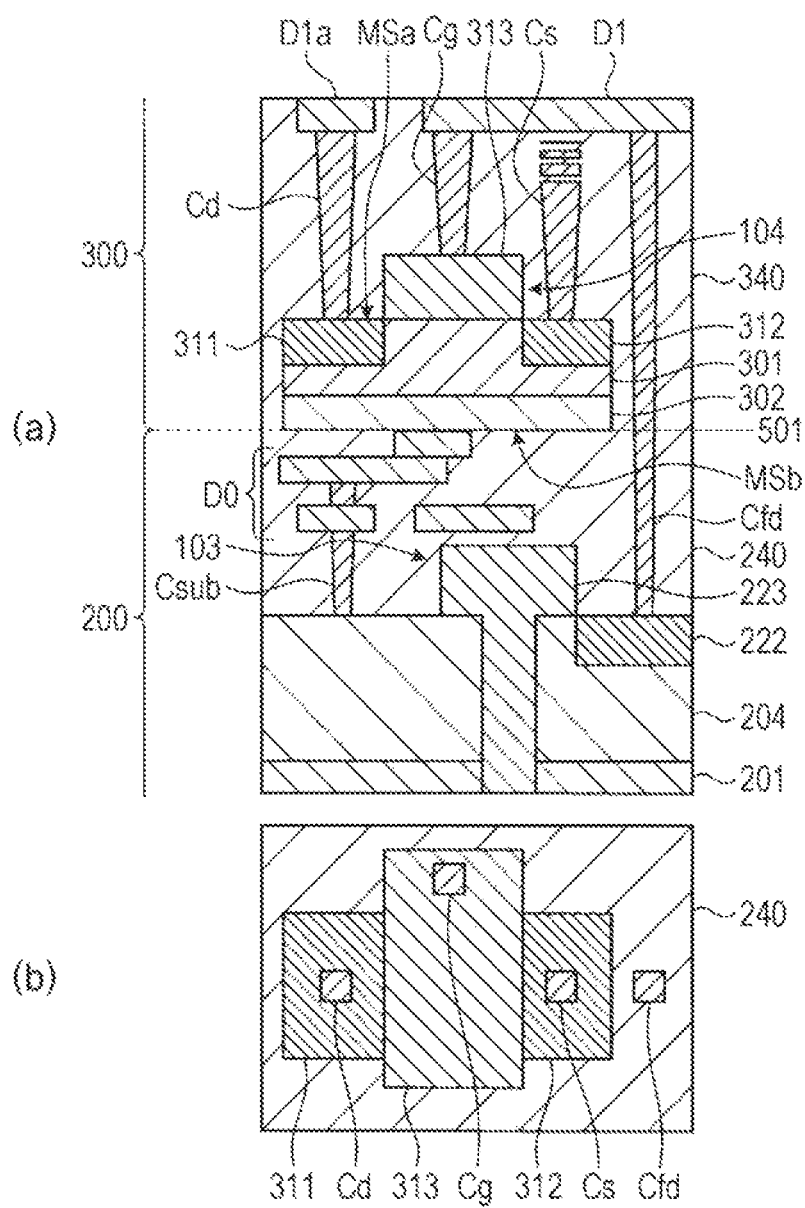
FIG. 31 is a schematic view illustrating the vicinity of bonding positions of substrates of the solid-state image sensor according to modification example 1 of the first embodiment of the present disclosure.

Next, a solid-state image sensor of modification example 1 of the first embodiment will be described with reference to FIG. 31. FIG. 31 is a schematic view illustrating the vicinity of bonding position of substrates 200, 300 of the solid-state image sensor according to modification example 1 of the first embodiment of the present disclosure.

As illustrated in FIG. 31, the solid-state image sensor of modification example 1 includes a contact Csub in which at least one or more wirings DO of W or the like are interposed. Thus, connection positions of the substrate 200 and the substrate contact layer 302 of the substrate 300 can be appropriately adjusted. That is, the connection positions of the substrate 200 and the substrate contact layer 302 of the substrate 300 do not have to overlap with in the vertical direction.

With such a configuration, the degree of freedom in relative positions between the substrate 200 and the substrate 300, arrangements of respective elements in the respective substrates 200 and 300, and the like is increased.

Modification Example 2

Figure 32:
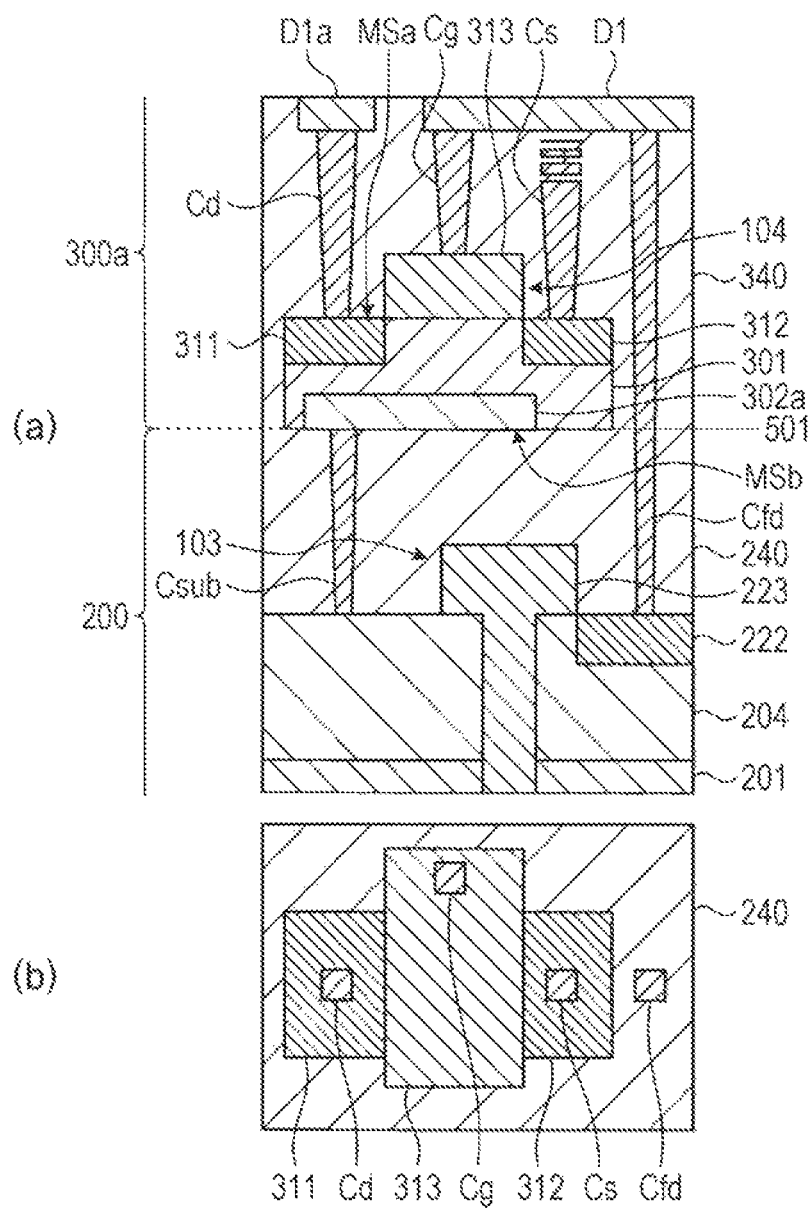
FIG. 32 is a schematic view illustrating the vicinity of bonding positions of substrates of the solid-state image sensor according to modification example 2 of the first embodiment of the present disclosure.

Next, a solid-state image sensor of modification example 2 of the first embodiment will be described with reference to FIG. 32. FIG. 32 is a schematic view illustrating the vicinity of bonding positions of substrates 200 and 300a of the solid-state image sensor according to modification example 2 of the first embodiment of the present disclosure.

As illustrated in FIG. 32, the solid-state image sensor of modification example 2 has a substrate contact layer 302a in a part of the main surface MSb of the substrate 300a. Thus, the substrate contact layer 302a does not have to cover the entire main surface MSb of the substrate 300a. In principle, the substrate contact layer 302a is only required to have an area in which the amount of displacement when the contact Csub is connected is added to a cross-sectional area required by the contact Csub.

Modification Example 3

Figure 33:
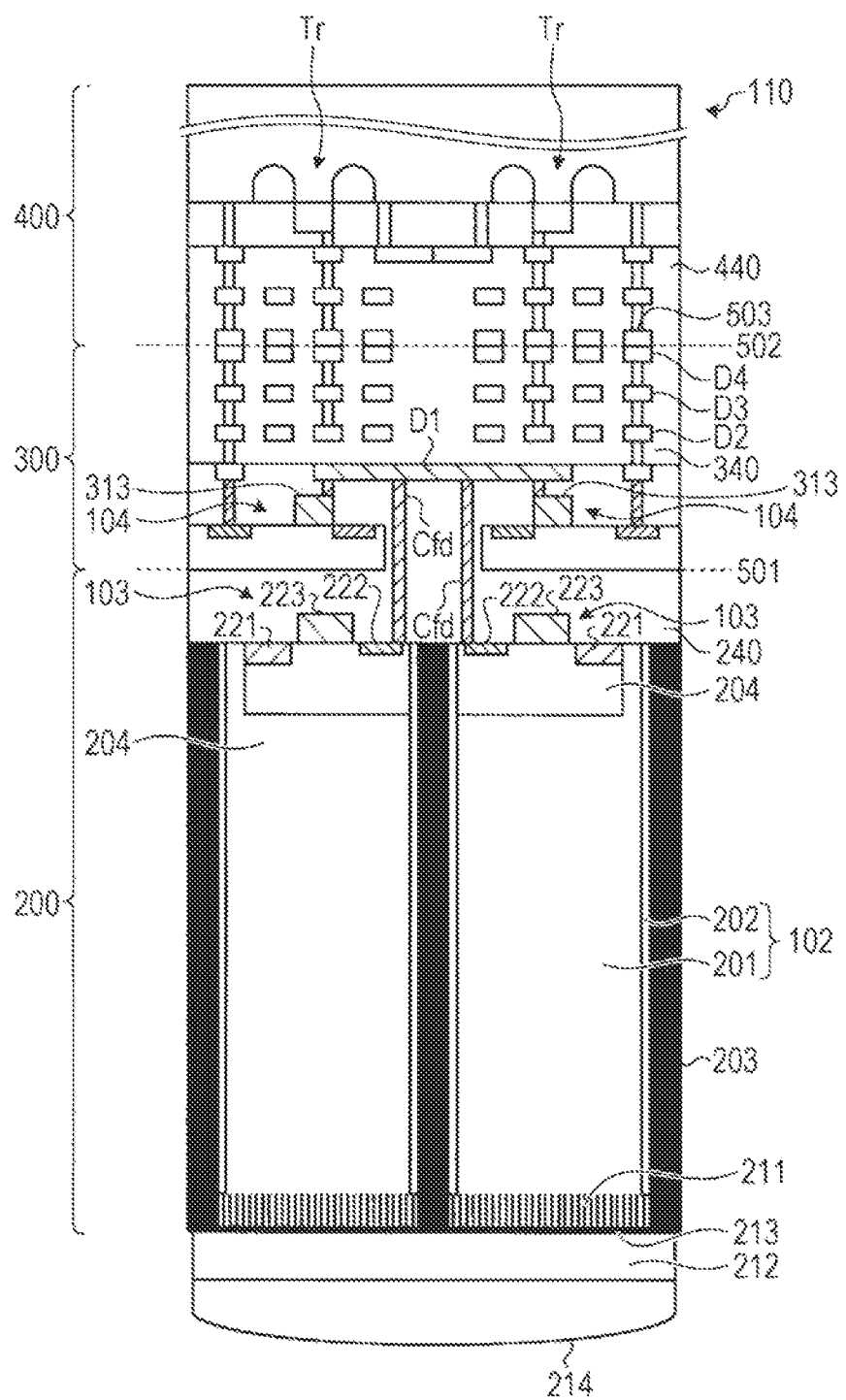
FIG. 33 is a diagram illustrating a part of a cross section of a solid-state image sensor according to modification example 3 of the first embodiment of the present disclosure.

Next, a solid-state image sensor 110 of modification example 3 of the first embodiment will be described with reference to FIG. 33. FIG. 33 is a diagram illustrating a part of a cross section of the solid-state image sensor 110 according to modification example 3 of the first embodiment of the present disclosure.

As illustrated in FIG. 33, in the solid-state image sensor 110 of modification example 2, the gate electrode 223 of the transfer transistor 103 is arranged on the semiconductor region 204 without being connected to the photoelectric conversion element 102. That is, the transfer transistor 103 has the gate electrode 223 as a planar transfer gate may be employed.

Modification Example 4

Figure 34:
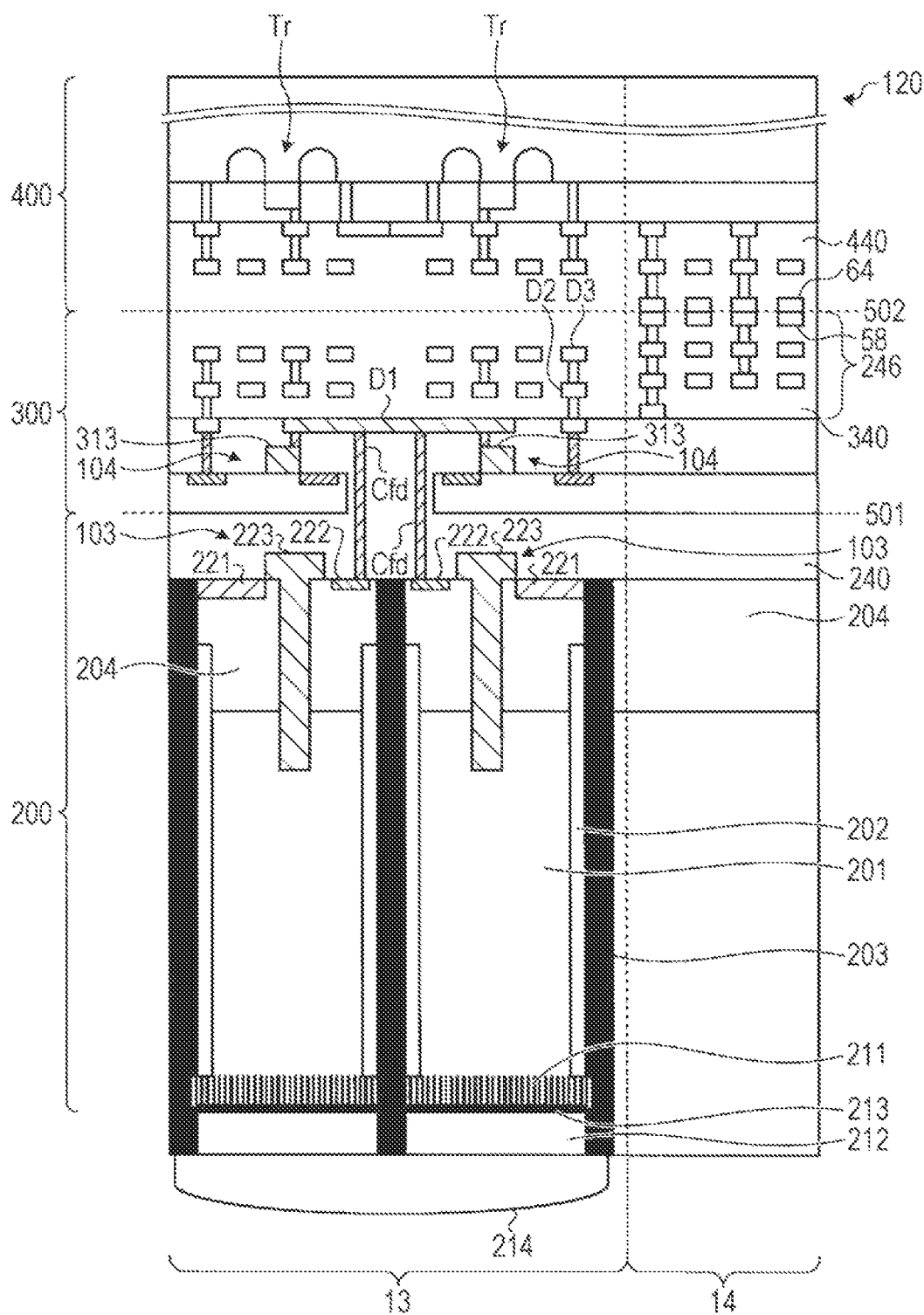
FIG. 34 is a diagram illustrating a part of a cross section of a solid-state image sensor according to modification example 4 of the first embodiment of the present disclosure.

Next, the solid-state image sensor 120 of the modification example 4 of the first embodiment will be described with reference to FIG. 34. FIG. 34 is a diagram illustrating a part of a cross section of a solid-state image sensor 120 according to modification example 4 of the first embodiment of the present disclosure.

As illustrated in FIG. 34, in the solid-state image sensor 120 of the modification example 4, the substrate 300 and the substrate 400 are electrically connected in a region facing a peripheral region 14 of the substrate 200. The peripheral region 14 corresponds to a frame region of the substrate 200, and is provided on a peripheral edge of the pixel region 13. The substrate 300 has a plurality of pad electrodes 58 in the region facing the peripheral region 14, and the substrate 400 has a plurality of pad electrodes 64 in the region facing the peripheral region 14. The substrate 300 and the substrate 400 are electrically connected to each other by joining the pad electrodes 58 and 64 provided in the region facing the peripheral region 14.

Thus, since the substrate 300 and the substrate 400 are connected by joining the pad electrodes 58 and 64 to each other, the chip size can be reduced as compared with the case where the respective substrates are connected by TSV provided in the peripheral region of the substrates, or the pixel region can be expanded, for example.

Second Embodiment

Next, a solid-state image sensor of a second embodiment will be described with reference to FIGS. 35 to 44. In the solid-state image sensor of the second embodiment, a shape of a substrate contact layer 302b is different from that of the first embodiment.

(Detailed Configuration Example of Solid-State Image Sensor)

Figure 35:
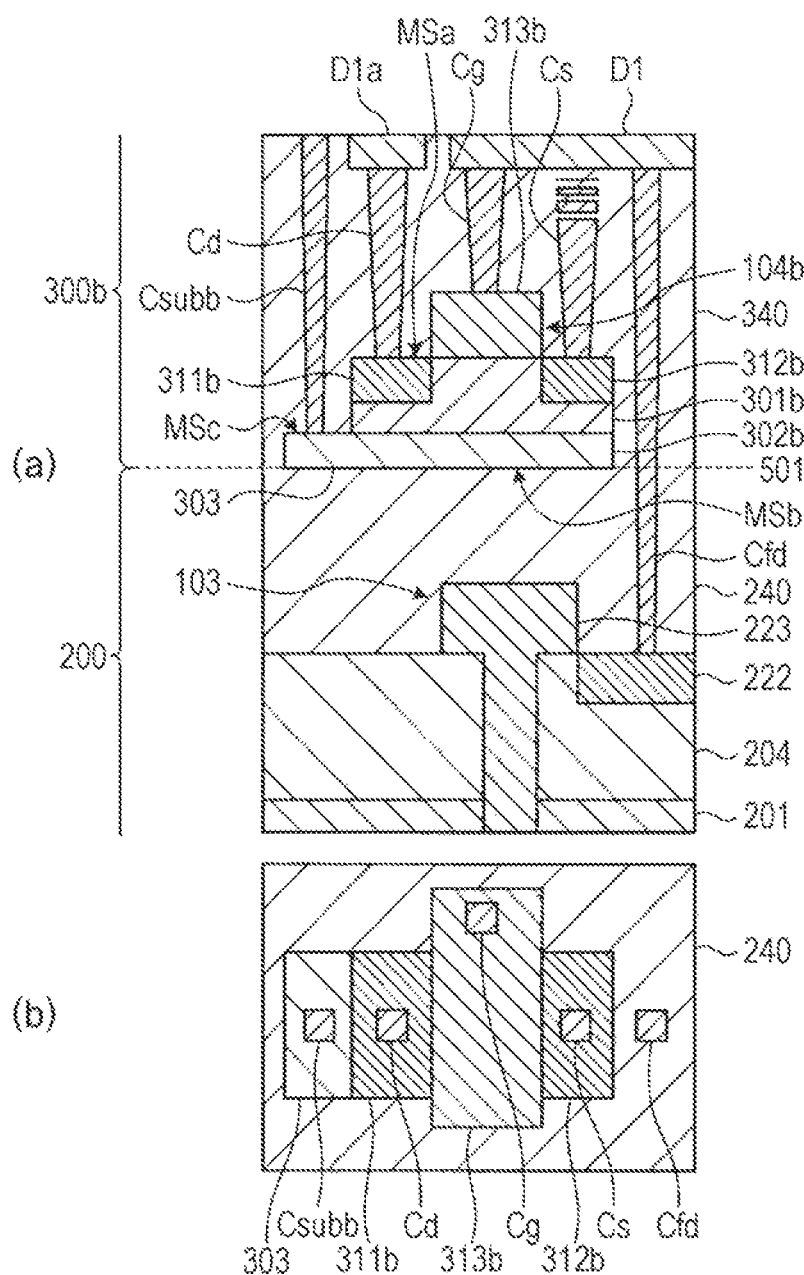
FIG. 35 is a schematic view illustrating the vicinity of bonding positions of substrates of a solid-state image sensor according to a second embodiment of the present disclosure.

FIG. 35 is a schematic view illustrating the vicinity of bonding positions of substrates 200 and 300b of the solid-state image sensor according to the second embodiment of the present disclosure. FIG. 35(a) is a cross-sectional view illustrating the vicinity of the bonding positions of the substrates 200 and 300b, and FIG. 35(b) is a top view of the substrate 300b. However, in FIG. 35(a), the position of the contact Cg is displaced. Further, in FIG. 35(b), the insulating film 340 and the wiring D1 are omitted. Furthermore, in FIG. 35, an amplification transistor 104b is illustrated as an example of the pixel transistor.

As illustrated in FIG. 35, the substrate 300b has a substrate contact layer 302b as a region having a resistance lower than that of the substrate 300b on the main surface MSb as the second main surface opposite to the main surface MSa as the first main surface. Specifically, the substrate 300b has a certain conductive type, for example P type, and the substrate contact layer 302b contains a higher concentration of impurities than another region 301b of the substrate 300b. That is, the substrate contact layer 302b is P+ type. Here, it is only required that at least a partial region of the substrate contact layer 302b has a lower resistance and a higher concentration of impurities than the other region 301b of the substrate 300b.

The substrate contact layer 302b of the substrate 300b has an extended portion 303 extending toward the outside of the substrate 300b in a direction along the substrate 300b. The direction along the substrate 300b includes a direction horizontal to the substrate 300b. That is, the extended portion 303 extends toward the outside of the substrate 300b in a horizontal direction or a substantially horizontal direction with respect to the substrate 300b. In other words, the extended portion 303 projects from a side surface of the substrate 300b.

The substrate 300b is grounded via the substrate contact layer 302b. Specifically, the solid-state image sensor of the second embodiment includes a contact Csubb extending from the substrate contact layer 302b of the substrate 300b to the side opposite to the substrate 200. More specifically, the extended portion 303 has a main surface MSc as a third main surface facing the same side as the main surface MSa of the substrate 300b, and there is provided the contact Csubb with one end being connected to the main surface MSc of the extended portion 303 and the other end being grounded. The other region 301b or the like of the substrate 300b does not exist on the main surface MSc of the extended portion 303. Therefore, the contact Csubb connected to the main surface MSc of the extended portion 303 can be extended to the upper layer and connected to the wiring D1 or the like. Thus, the substrate 300b can be grounded by connecting to the ground wire via the substrate contact layer 302b, the contact Csubb, and the wirings D1 to D4. That is, the potential of the substrate 300b is fixed at 0 V.

The substrate 300b has the amplification transistor 104b on the main surface MSa that amplifies an electrical signal output from the photoelectric conversion element 102. The amplification transistor 104b is formed as, for example, a MOSFET. The amplification transistor 104b has an N-type source region 312b and an N-type drain region 311b provided on the substrate 300b. A gate electrode 313b of the amplification transistor 104b is arranged on the substrate 300b between the source region 312b and the drain region 311b. The area of the main surface MSa of the substrate 300b is reduced by, for example, the area of the extended portion 303 of the substrate contact layer 302b. Accordingly, the size of the amplification transistor 104b is also slightly reduced. The size of the amplification transistor 104b is smaller than that of the amplification transistor 104 of the first embodiment and larger than that of the amplification transistor of comparative example 2.

[Example of Manufacturing Process of Solid-State Image Sensor]

Next, an example of a manufacturing process of the solid-state image sensor of the second embodiment will be described with reference to FIGS. 36 and 37. FIGS. 36 and 37 are flow views illustrating an example of a procedure of the manufacturing process of the solid-state image sensor according to the second embodiment of the present disclosure. Note that left views of FIGS. 36 and 37 are cross-sectional views in the manufacturing process of the solid-state image sensor. Furthermore, right views of FIGS. 36 and 37 are top views in the manufacturing process of the solid-state image sensor.

The solid-state image sensor of the second embodiment undergoes a manufacturing process similar to that in FIGS. 26 and 27 of the above-described first embodiment. Here, an example of the manufacturing process thereafter will be described.

As illustrated in FIGS. 36(a1) and 36(a2), the extended portion 303 is formed on the substrate contact layer 302b with respect to the substrate 300b on which element isolation have been performed. Specifically, a resist pattern having an opening at a position corresponding to the extended portion 303 of the substrate 300b is formed by photolithography, the substrate 300b at the opening is etched by dry etching, and the resist pattern is ashed. Thus, the main surface MSc of the extended portion 303 is exposed.

As illustrated in FIGS. 36(b1) and 36(b2), an insulating film 340 such as a silicon oxide film is formed on the main surface MSc of the extended portion 303 by the CVD method, and the portion where the substrate 300b is removed by etching is back-filled. The excess insulating film 340 is removed by CMP to expose the surface of the substrate 300b.

As illustrated in FIGS. 37(a1) and 37(a2), the amplification transistor 104b is formed on the main surface MSa of the substrate 300b by a similar method to that for the amplification transistor 104 of the first embodiment.

As illustrated in FIGS. 37(b1) and 37(b2), the contacts Cg, Cs, Cd, and Cfd are formed as in the first embodiment. Furthermore, the contact Csubb can also be formed by a similar method to that for the other contacts Cg, Cs, Cd, and Cfd.

Thereafter, the wirings D1 to D4 are formed, the substrate 400 on which the logic transistor Tr and the wiring is formed are joined, thereby finishing the manufacturing process of the solid-state image sensor of the second embodiment.

Comparative Example

Next, with reference to FIG. 38, configurations of comparative examples 1 and 2 described above and the configuration of the second embodiment are compared. FIG. 38 is a diagram for comparing the solid-state image sensors according to the second embodiment of the present disclosure and the comparative examples 1 and 2.

In the solid-state image sensor of the second embodiment, the contact Csubb is connected to the main surface MSc side, which faces the same side as the main surface MSa, of the substrate contact layer 302b arranged on the main surface MSb. Therefore, although the amplification transistor 104b is reduced by the amount that the substrate contact layer 302b has the extended portion 303, there is still an advantage as compared with the comparative examples 1 and 2.

The sizes of the amplification transistors (AMP Tr size) are comparative example 1:comparative example 2:second embodiment=3:1:2, and in the second embodiment, a size larger than that of comparative example 2 is obtained. Thus, the noise level of RTS noise is comparative example 1:comparative example 2:second embodiment=0.33:1:0.5, which is sufficiently reduced in the second embodiment as well.

Figure 39:
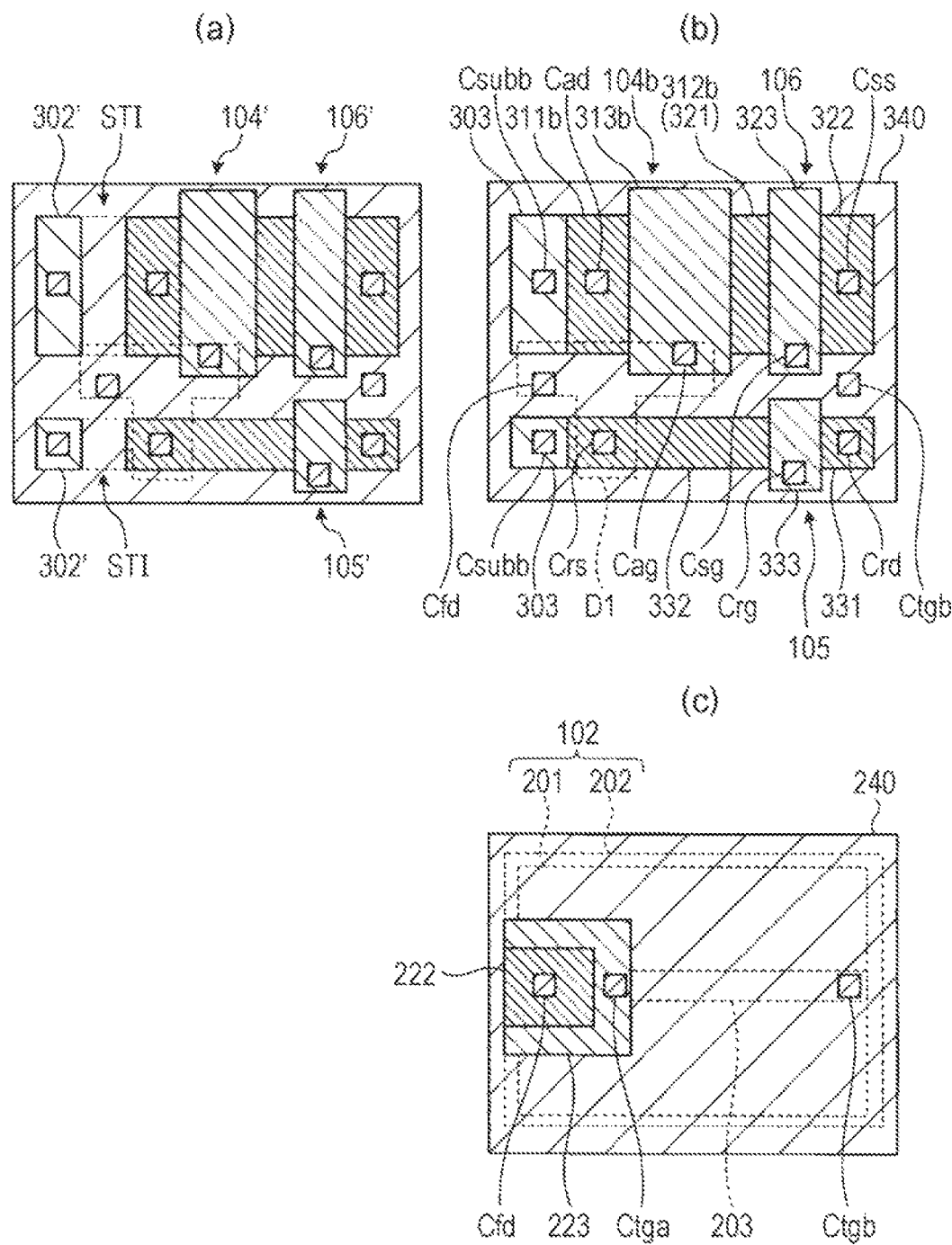
FIG. 39 is a view illustrating an arrangement of pixel transistors of the solid-state image sensors according to the second embodiment of the present disclosure and comparative example 2.

Here, FIG. 39 illustrates more detailed top views of respective configurations.

FIG. 39 is a view illustrating an arrangement of pixel transistors of the solid-state image sensors according to the second embodiment of the present disclosure and comparative example 2. FIG. 39(a) is a top view of the substrate on which a pixel transistor of comparative example 2 is formed, FIG. 39(b) is a top view of the substrate 300b of the second embodiment, and FIG. 39(c) is a top view of the substrate 200 of the second embodiment. However, a part of the insulating film is omitted in FIG. 39.

As illustrated in FIG. 39 (c), the solid-state image sensor of the second embodiment also includes the substrate 200 having a similar configuration to that of the first embodiment.

As illustrated in FIG. 39(b), the solid-state image sensor of the second embodiment also includes the amplification transistor 104b, a selection transistor 106, and a reset transistor 105, which are arranged substantially similarly to those in the first embodiment. The solid-state image sensor of the second embodiment is different from the first embodiment in that the extended portion 303 of the substrate contact layer 302b occupies a part of the region of the substrate 300b, and the amplification transistor 104b is reduced by that amount.

Figure 40:
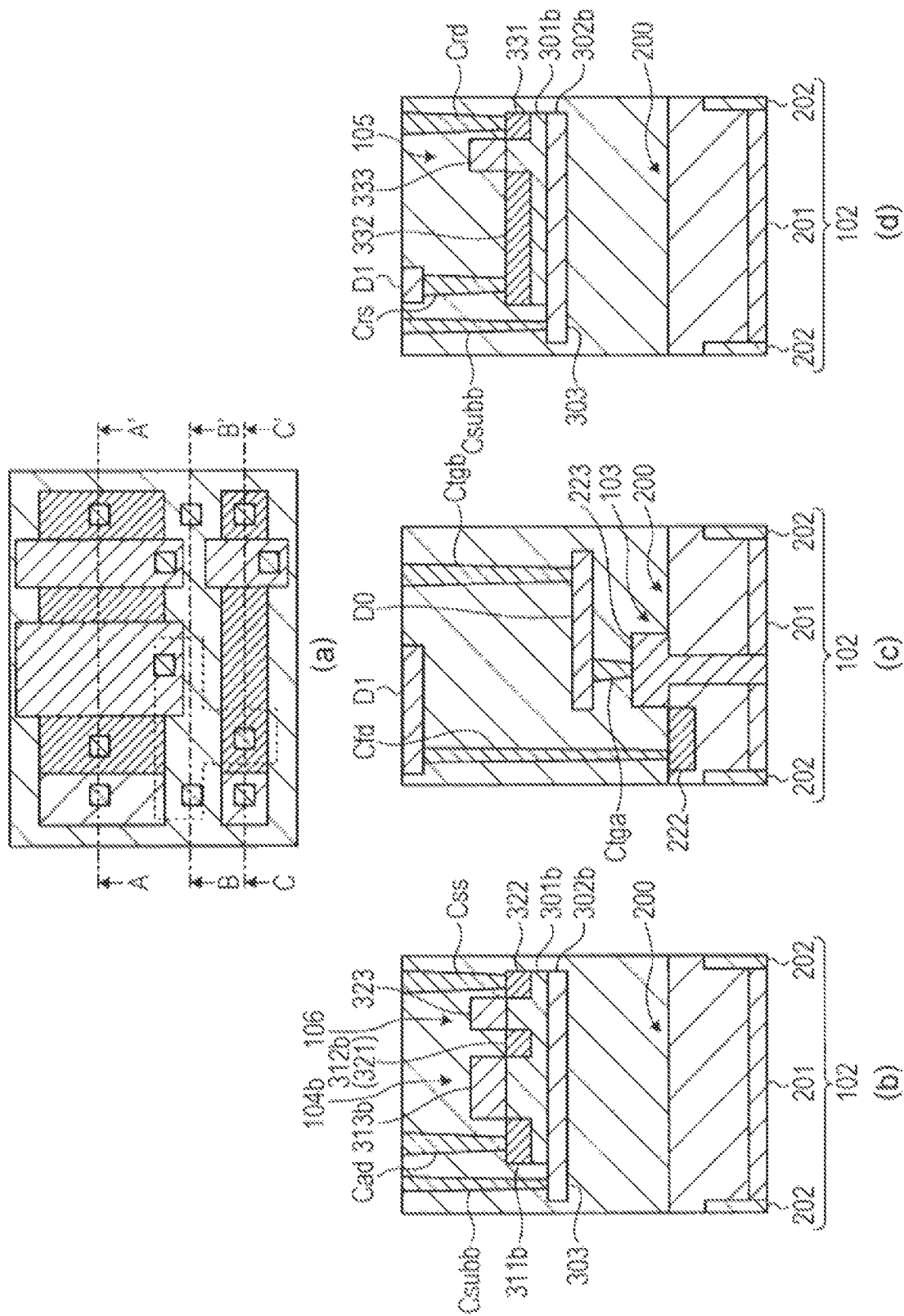
FIG. 40 is a view illustrating connections between respective elements of the solid-state image sensor according to the second embodiment of the present disclosure.

FIG. 40 illustrates cross-sectional views of respective parts of FIG. 39.

FIG. 40 is a view illustrating connections between respective elements of the solid-state image sensor according to the second embodiment of the present disclosure. FIG. 40(a) is a top view of the substrate 300b of the second embodiment, FIG. 40(b) is a cross-sectional view taken along a line A-A' of FIG. 40(a), FIG. 40(c) is a cross-sectional view taken along a line B-B' of FIG. 40(a), and FIG. 40(d) is a cross-sectional view taken along a line C-C' of FIG. 40(a).

As illustrated in FIG. 40(b), the substrate contact layer 302b is connected to the upper wirings D1 to D4 and grounded via the contact Csubb at the extended portion 303. The drain region 311b of the amplification transistor 104b is connected to the upper wirings D1 to D4 via a contact Cad. A source region 322 of the selection transistor 106 is connected to the upper wirings D1 to D4 via a contact Css.

As illustrated in FIG. 40(c), a source region 222 as a floating diffusion of a transfer transistor 103 is connected to the wiring D1 via the contact Cfd. Although not illustrated, the wiring D1 is connected to the gate electrode 313b of the amplification transistor 104b. A gate electrode 223 of the transfer transistor 103 is connected to a wiring DO of W or the like via a contact Ctga. The wiring DO is connected to the upper layer wiring via the contact Ctgb.

As illustrated in FIG. 40(d), a source region 332 of the reset transistor 105 is connected to the wiring D1 via a contact Crs. Although not illustrated, as described above, the wiring D1 is connected to the gate electrode 313b of the amplification transistor 104b. A drain region 331 of the reset transistor 105 is connected to the upper wirings D1 to D4 via a contact Crd.

Modification Example 1

Figure 41:
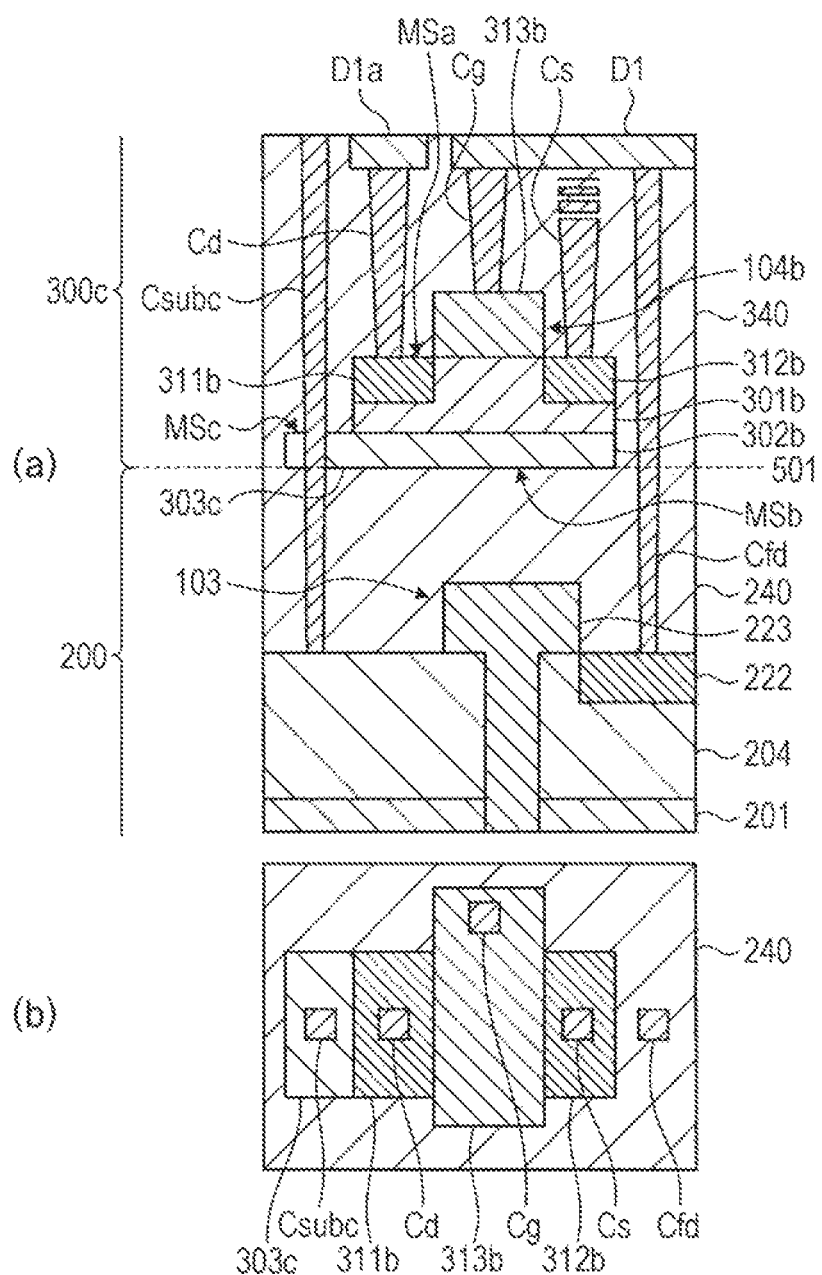
FIG. 41 is a schematic view illustrating the vicinity of bonding positions of substrates of the solid-state image sensor according to modification example 1 of the second embodiment of the present disclosure.

Next, a solid-state image sensor of modification example 1 of the second embodiment will be described with reference to FIG. 41. FIG. 41 is a schematic view illustrating the vicinity of bonding positions of substrates 200 and 300c of the solid-state image sensor according to modification example 1 of the second embodiment of the present disclosure.

As illustrated in FIG. 41, the solid-state image sensor of modification example 1 includes a contact Csubc that penetrates an extended portion 303c and has one end connected to the substrate 200 and the other end grounded. That is, the substrate contact layer 302c of the substrate 300c has an extended portion 303c through which the contact Csubc penetrates. The contact Csubc is connected to the ground wire via the upper wirings D1 to D4. The substrate 200 is grounded via the contact Csubc. The substrate 300c is grounded via the extended portion 303c of the substrate contact layer 302c and the contact Csubc.

With such a configuration, the substrate 200 and the substrate 300c can be grounded using a common configuration, and the wiring structure can be made simpler. Furthermore, the volume occupied by the configuration for grounding can be reduced.

Modification Example 2

Figure 42:
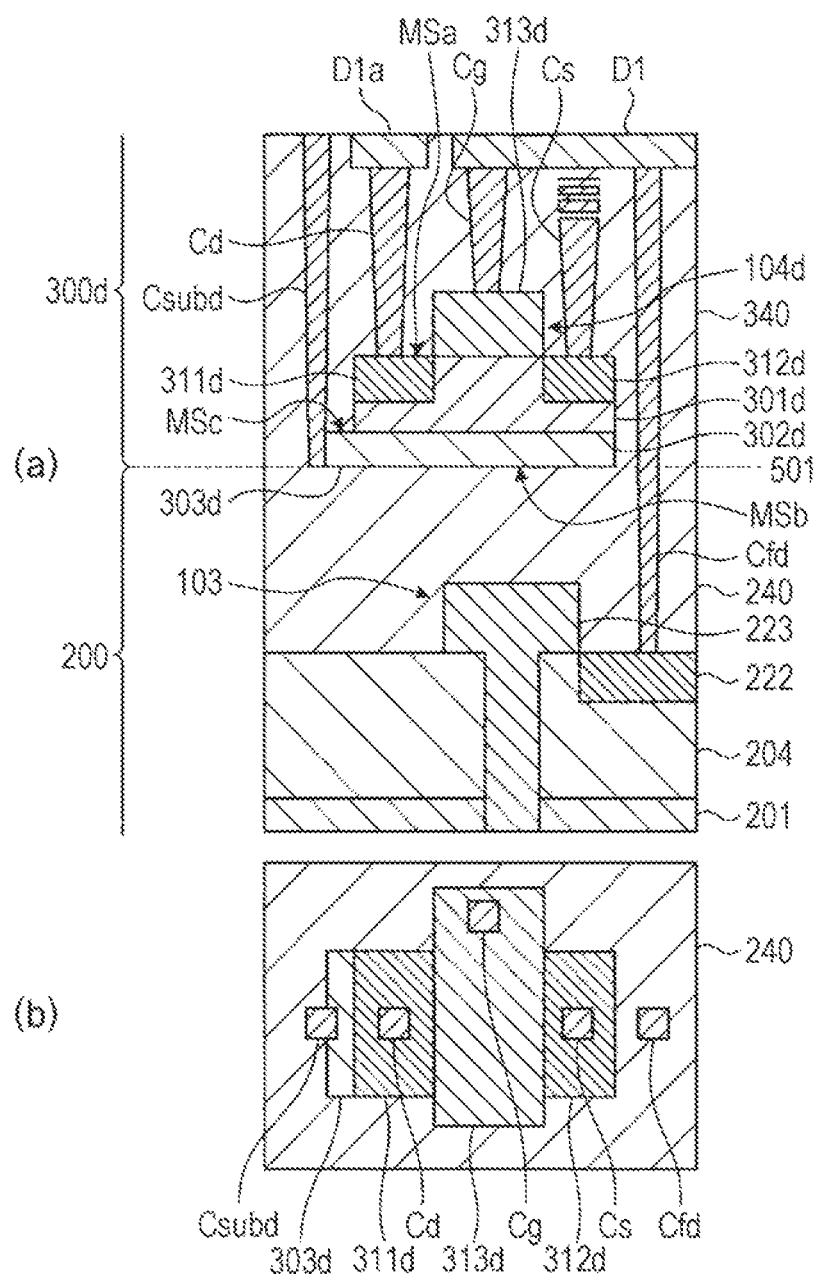
FIG. 42 is a schematic view illustrating the vicinity of bonding positions of substrates of the solid-state image sensor according to modification example 2 of the second embodiment of the present disclosure.

Next, a solid-state image sensor of modification example 2 of the second embodiment will be described with reference to FIGS. 42 and 43. FIG. 42 is a schematic view illustrating the vicinity of bonding positions of substrates 200 and 300d of the solid-state image sensor according to modification example 2 of the second embodiment of the present disclosure.

As illustrated in FIG. 42, the solid-state image sensor of modification example 2 includes a contact Csubd having one end connected to a side surface of the extended portion 303d and the other end grounded. That is, a substrate contact layer 302d of the substrate 300d has an extended portion 303d to which the contact Csubd is connected on a side surface. The contact Csubd is connected to the ground wire via the upper wirings D1 to D4. The substrate 300d is grounded via the extended portion 303d of the substrate contact layer 302d and the contact Csubd.

The substrate 300d has an amplification transistor 104d that amplifies an electrical signal output from the photoelectric conversion element 102 on the main surface MSa as the first main surface. The amplification transistor 104d is formed as, for example, a MOSFET. The amplification transistor 104d has an N-type source region 312d and an N-type drain region 311d provided on the substrate 300d. A gate electrode 313d of the amplification transistor 104d is arranged on the substrate 300d between the source region 312d and the drain region 311d.

With such a configuration, the extended portion 303d of the substrate contact layer 302d does not need to have an area in which the amount of displacement at the time of connection is added to the cross-sectional area for the contact Csubd, and the extended portion 303d can be formed smaller than the extended portion 303 in the second embodiment. Accompanying this, the size of the amplification transistor 104d can be slightly increased. The size of the amplification transistor 104d is smaller than that of the amplification transistor 104 of the first embodiment and larger than that of the amplification transistor 104b of the second embodiment.

Figure 43:
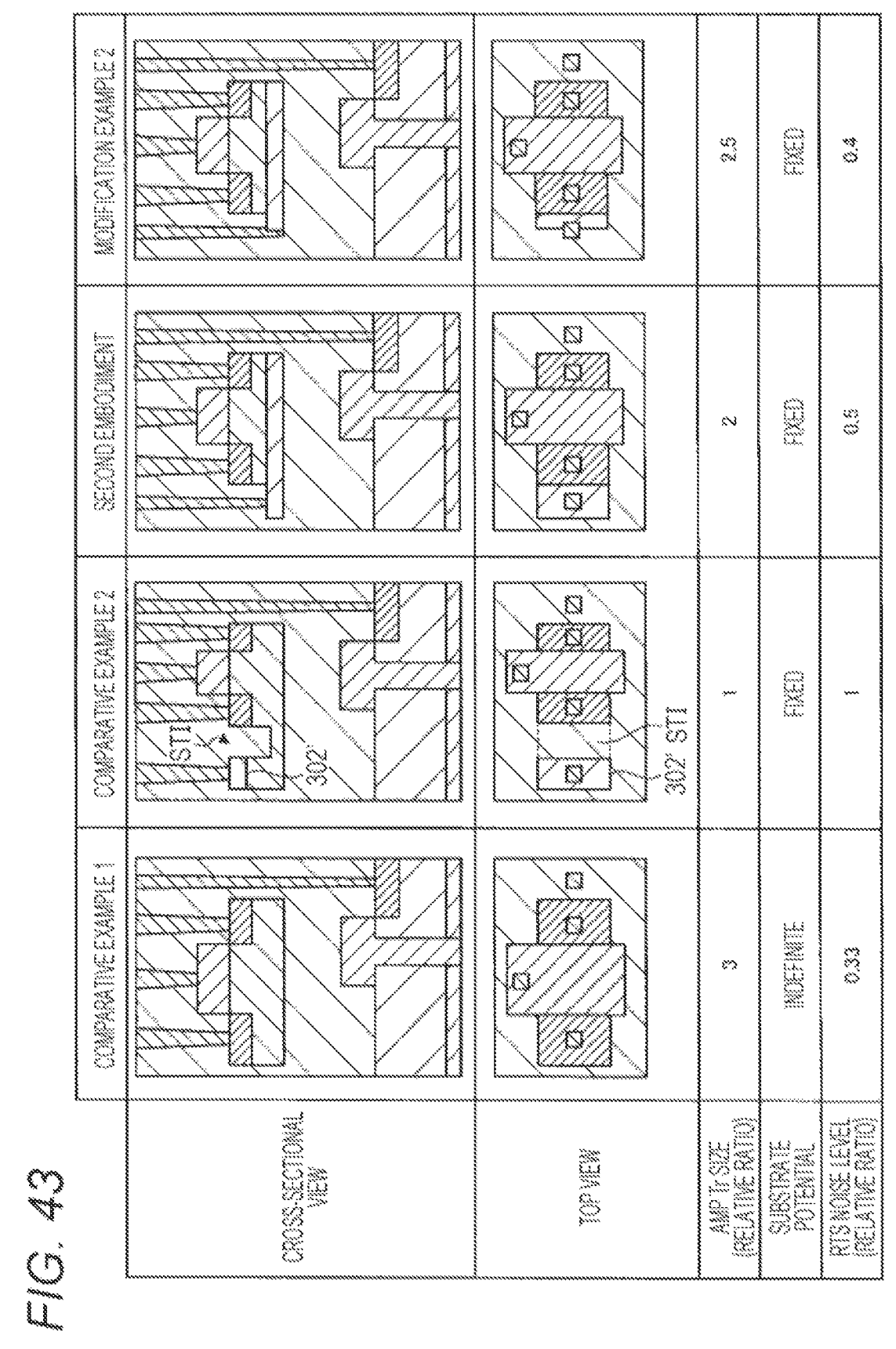

FIG. 43 is used to compare the configurations of comparative examples 1 and 2 described above and the configuration of modification example 2. FIG. 43 is a diagram for comparing the solid-state image sensors according to the second embodiment of the present disclosure, modification example 2 thereof, and comparative examples 1 and 2.

In the solid-state image sensor of modification example 2, the contact Csubd is connected to the side surface of the substrate contact layer 302d arranged on the main surface MSb.

Therefore, there is a further advantage over the solid-state image sensor of the second embodiment as compared with comparative examples 1 and 2.

The sizes of the amplification transistors (AMP Tr size) are comparative example 1:comparative example 2:second embodiment:modification example 2=3:1:2:2.5, and in modification example 2, a size larger than that of the second embodiment is obtained. Thus, the noise level of RTS noise is comparative example 1:comparative example 2:second embodiment:modification example 2=0.33:1.5:0.4, and modification example 2 has a better noise level than that of the second embodiment.

Modification Example 3

Figure 44:
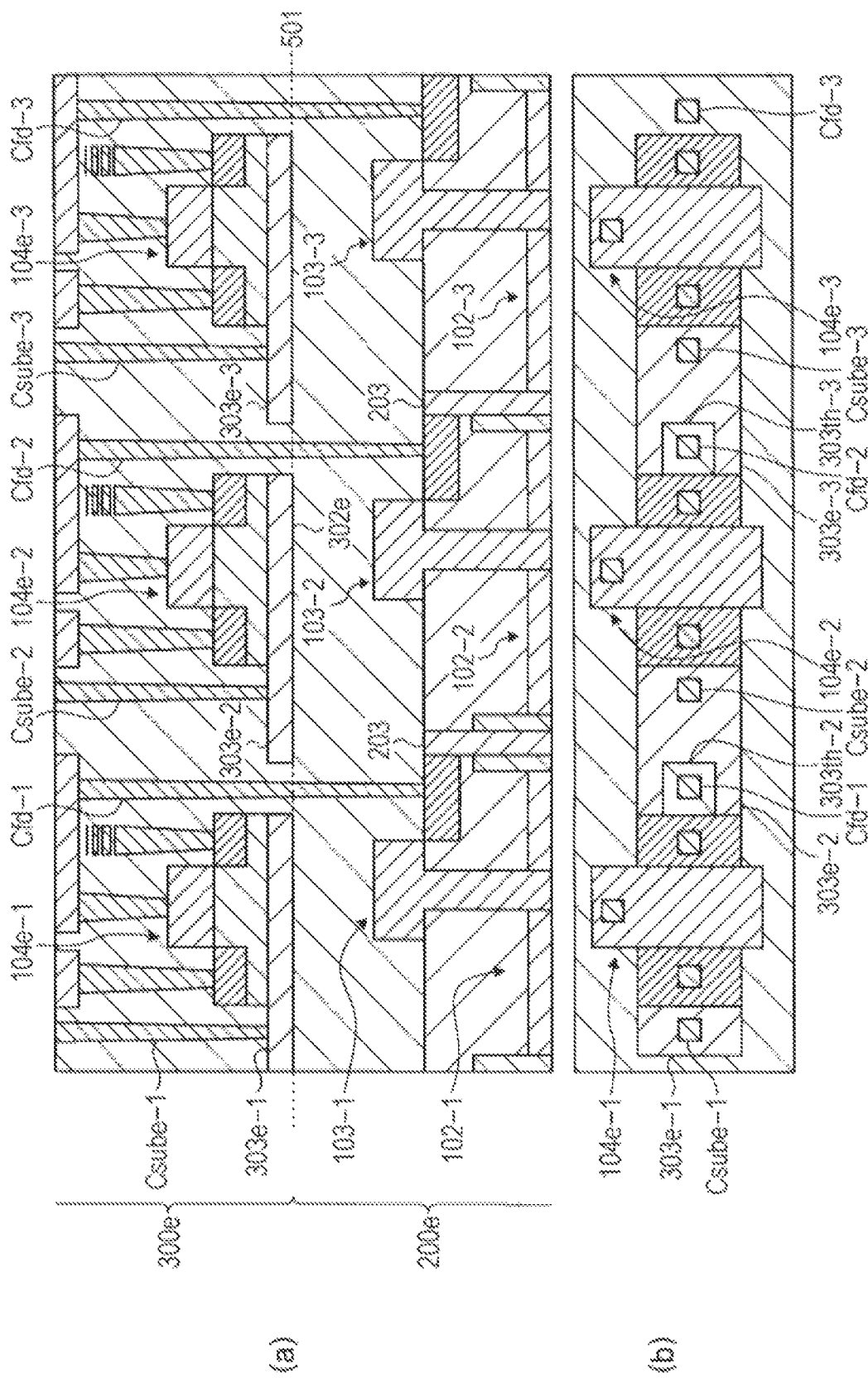
FIG. 44 is a schematic view illustrating the vicinity of bonding positions of substrates of the solid-state image sensor according to modification example 3 of the second embodiment of the present disclosure.

Next, a solid-state image sensor of modification example 3 of the second embodiment will be described with reference to FIG. 44. FIG. 44 is a schematic view illustrating the vicinity of bonding positions of substrates 200e and 300e of the solid-state image sensor according to modification example 3 of the second embodiment of the present disclosure.

As illustrated in a cross-sectional view of FIG. 44(a) and a top view of FIG. 44(b), in the solid-state image sensor of modification example 3, the number of amplification transistors 104e can be increased according to the numbers of photoelectric conversion elements 102 and corresponding transfer transistors 103.

Specifically, the substrate 200e includes a photoelectric conversion element 102-1 and a corresponding transfer transistor 103-1, a photoelectric conversion element 102-2 and a corresponding transfer transistor 103-2, and a photoelectric conversion element 102-3 and a corresponding transfer transistor 103-3.

The substrate 300e has an amplification transistor 104e-1 corresponding to the photoelectric conversion element 102-1 and the transfer transistor 103-1. Further, the substrate 300e has an amplification transistor 104e-2 corresponding to the photoelectric conversion element 102-2 and the transfer transistor 103-2. Furthermore, the substrate 300e has an amplification transistor 104e-3 corresponding to the photoelectric conversion element 102-3 and the transfer transistor 103-3.

Regions where the respective amplification transistors 104e-1 to 104e-3 are provided are connected by a substrate contact layer 302e of a bottom surface of the substrate 300e. The region where the amplification transistor 104e-1 is provided and the region where the amplification transistor 104e-2 is provided are connected by an extended portion 303e-2 of the substrate contact layer 302e. The region where the amplification transistor 104e-2 is provided and the region where the amplification transistor 104e-3 is provided are connected by an extended portion 303e-3 of the substrate contact layer 302e.

A contact Csube-1 for grounding the substrate 300e is connected to an extended portion 303e-1 near the amplification transistor 104e-1. A contact Csube-2 for grounding the substrate 300e is connected to the extended portion 303e-2 near the amplification transistor 104e-2. Furthermore, the extended portion 303e-2 is provided with a through hole 303th-2 through which Cfd-1 connecting a floating diffusion of the transfer transistor 103-1 and a gate electrode of the amplification transistor 104e-1 penetrates. A contact Csube-3 for grounding the substrate 300e is connected to the extended portion 303e-3 near the amplification transistor 104e-3. Furthermore, the extended portion 303e-3 is provided with a through hole 303th-3 through which Cfd-2 connecting a floating diffusion of the transfer transistor 103-2 and a gate electrode of the amplification transistor 104e-2 penetrates.

With such a configuration, even if the numbers of photoelectric conversion elements 102 and transfer transistors 103 increase, the number of amplification transistors 104e can be increased accordingly. In the example of FIG. 44, the three photoelectric conversion elements 102, the three transfer transistors 103, and the three amplification transistors 104e have a one-to-one correspondence, but the number of these elements is not limited to three. The number of these elements may be two or four or more.

Third Embodiment

Next, a solid-state image sensor 100f of a third embodiment will be described with reference to FIGS. 45 and 46. The solid-state image sensor 100f of the third embodiment is different from the first and second embodiments in that a plurality of photoelectric conversion elements 102 is integrated and handled as one.

Figure 45:
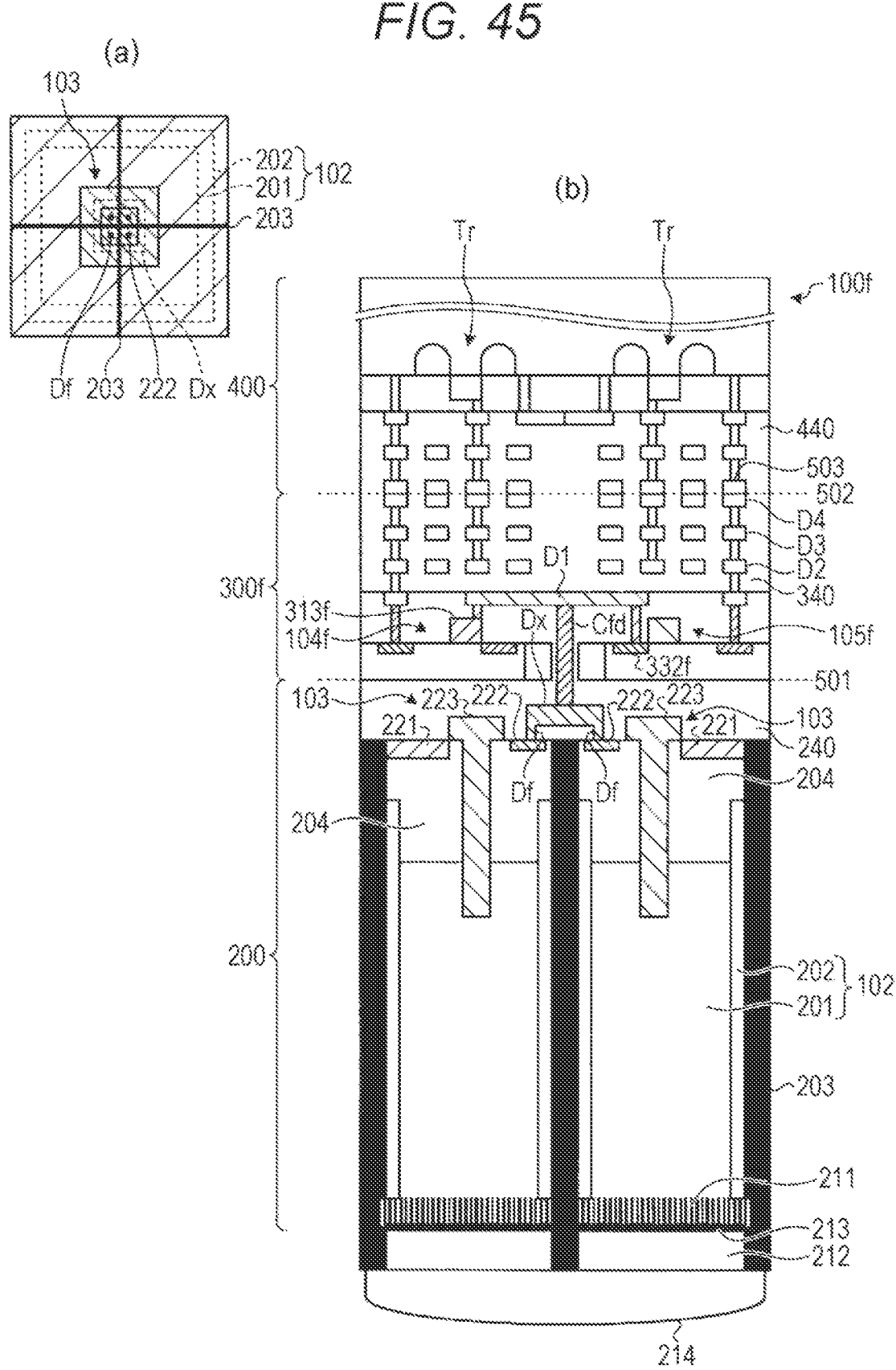
FIG. 45 is a view illustrating a part of a solid-state image sensor according to a third embodiment of the present disclosure.

FIG. 45 is a view illustrating a part of the solid-state image sensor 100f according to the third embodiment of the present disclosure. FIG. 45(a) is a view illustrating a part of an upper surface of a substrate 200, and FIG. 45(b) is a view illustrating a part of a cross section of the solid-state image sensor 100f.

As illustrated in FIG. 45(a), in the substrate 200, four transfer transistors 103 corresponding to four photoelectric conversion elements 102, respectively, are arranged near the center where the four photoelectric conversion elements 102 gather. Furthermore, source regions 222, which are floating diffusions of the four transfer transistors 103, are surrounded by the four transfer transistors 103 and are arranged close to each other.

As illustrated in FIGS. 45(a) and 45(b), these four source regions 222 are combined into one by a wiring Dx above the substrate 200. Specifically, the wiring Dx has four legs Df connected to the respective source regions 222. Furthermore, one contact Cfd is connected to an upper part of the wiring Dx. The other end of the contact Cfd is connected to the wiring D1.

A substrate 300f has one each of pixel transistors corresponding to the four photoelectric conversion elements 102 and the four transfer transistors 103. That is, the substrate 300f has one amplification transistor 104f, one reset transistor 105f, and one selection transistor that is not illustrated for the four photoelectric conversion elements 102 and the four transfer transistors 103.

The wiring D1 to which the contact Cfd is connected is connected to a gate electrode 313f of the amplification transistor 104f. Furthermore, the wiring D1 connects the gate electrode 313f of the amplification transistor 104f and a source region 332f of the reset transistor 105f.

The configurations of the above-described first and second embodiments or the like can be applied to such a solid-state image sensor 100f. FIG. 46 is a comparative diagram in a case where the configurations of the first and second embodiments of the present disclosure and comparative example 2 are applied to the solid-state image sensor 100f according to the third embodiment.

Figure 46:
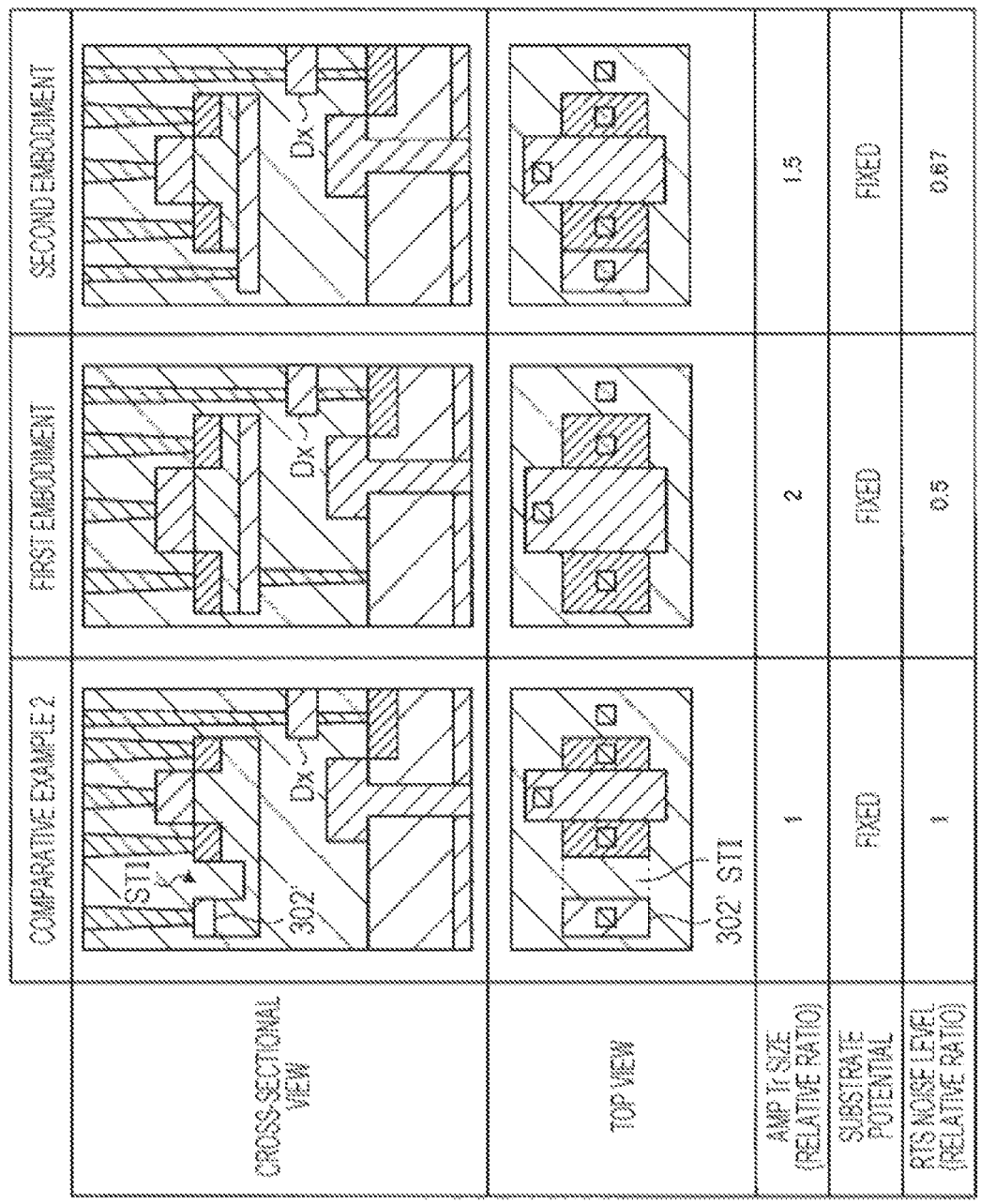
FIG. 46 is a comparative diagram in a case where the configurations of the first and second embodiments of the present disclosure and comparative example 2 are applied to the solid-state image sensor according to the third embodiment.

As illustrated in FIG. 46, the sizes of the amplification transistors (AMP Tr size) are comparative example 2:first embodiment:second embodiment=1:2:1.5, and the noise levels of RTS noise are comparative example 2:first embodiment:second embodiment=1:0.5:0.67.

As described above, the application example of the first embodiment to the third embodiment is more excellent in both the size of the amplification transistor and the noise level of RTS noise as compared with the application example of comparative example 2. The application example of the second embodiment to the third embodiment is more excellent in both the size of the amplification transistor and the noise level of RTS noise as compared with the application example of comparative example 2.

The application example of the first embodiment to the third embodiment is more excellent in both the size of the amplification transistor and the noise level of RTS noise than the application example of the second embodiment.

Fourth Embodiment

Figure 47:
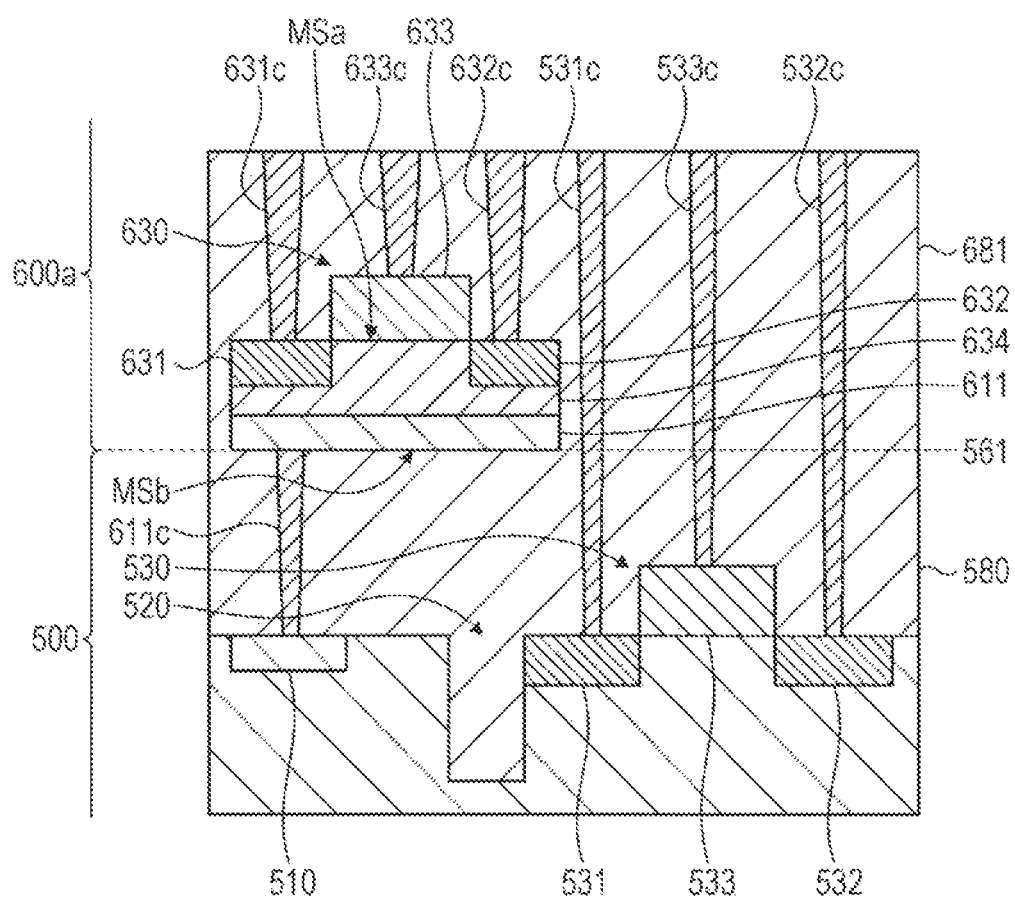
FIG. 47 is a schematic view illustrating the vicinity of bonding positions of substrates in a case where the configuration of the first embodiment of the present disclosure is applied to a semiconductor device according to the fourth embodiment.
Figure 48:
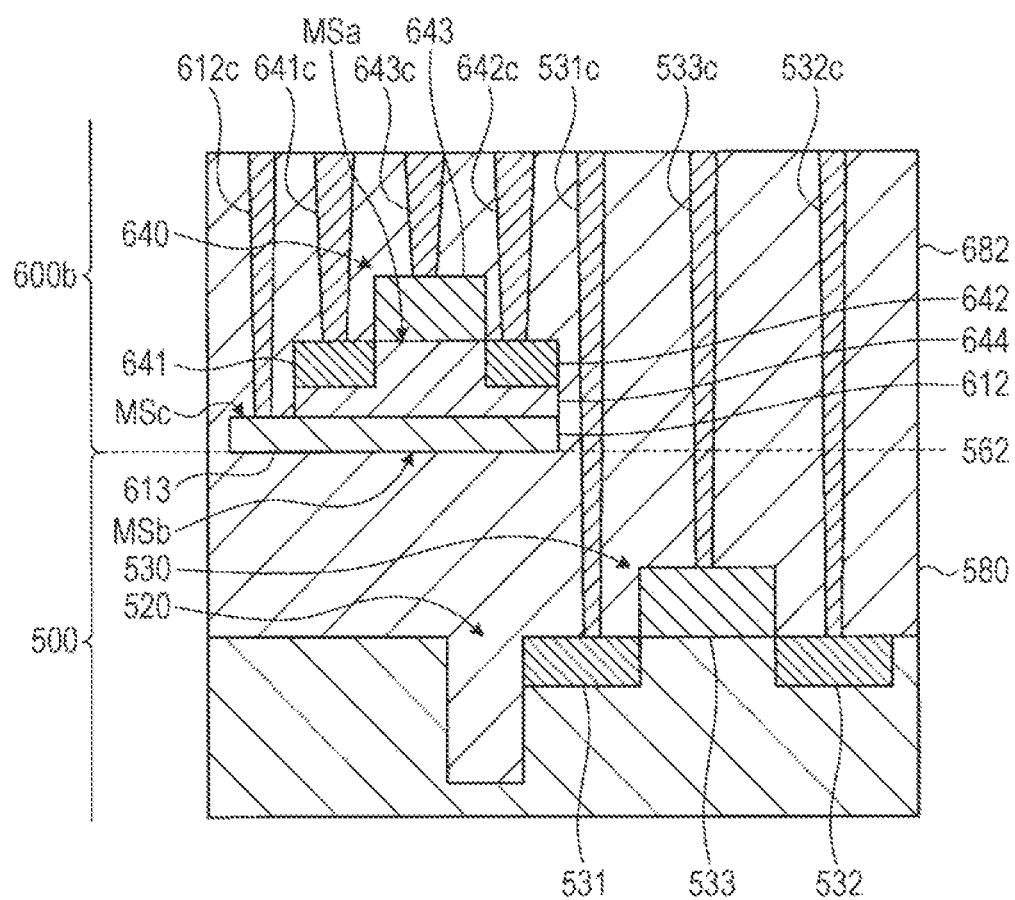
FIG. 48 is a schematic view illustrating the vicinity of bonding positions of substrates in a case where the configuration of the second embodiment of the present disclosure is applied to the semiconductor device according to the fourth embodiment.

The configurations of the first and second embodiments described above can also be applied to a semiconductor device having a transistor such as a MOSFET. FIG. 47 and FIG. 48 illustrate respective application examples.

FIG. 47 is a schematic view illustrating the vicinity of bonding positions of substrates 500 and 600a in a case where the configuration of the first embodiment of the present disclosure is applied to a semiconductor device according to a fourth embodiment.

As illustrated in FIG. 47, the semiconductor device of the fourth embodiment includes the substrate 500 as a first semiconductor substrate having a transistor 530 as a first transistor. The substrate 500, which is a silicon substrate or the like, is grounded. That is, the potential of the substrate 500 is fixed at 0 V. The transistor 530 is formed as, for example, a MOSFET. The transistor 530 includes a gate electrode 533, an N-type source region 532, and an N-type drain region 531. The gate electrode 533 is provided with a contact 533c connected to an upper layer wiring. The source region 532 is provided with a contact 532c connected to the upper layer wiring. The drain region 531 is provided with a contact 531c connected to the upper layer wiring. Furthermore, the substrate 500 has a P+ type substrate contact layer 510 separated from the region in which the transistor 530 is arranged by an element isolation region 520.

Furthermore, the semiconductor device of the fourth embodiment includes the substrate 600a as a second semiconductor substrate facing the substrate 500 with an insulating film 580 interposed therebetween. That is, the substrate 600a and the substrate 500 are joined. A surface 561 illustrated in FIG. 47 indicates a surface where the substrate 600a and the substrate 500 are joined.

The substrate 600a has a transistor 630 as a second transistor on a main surface MSa as a first main surface. The transistor 630 is formed as, for example, a MOSFET. The transistor 630 includes a gate electrode 633, an N-type source region 632, and an N-type drain region 631. The gate electrode 633 is provided with a contact 633c connected to the upper layer wiring. The source region 632 is provided with a contact 632c connected to the upper layer wiring. The drain region 631 is provided with a contact 631c connected to the upper layer wiring. The transistor 630 is covered with an insulating film 681.

The substrate 600a has a substrate contact layer 611 as a region having a resistance lower than that of the substrate 600a on a main surface MSb as a second main surface opposite to the main surface MSa. Specifically, the substrate 600a has a certain conductive type, for example P type, and the substrate contact layer 611 contains a higher concentration of impurities than another region 634 of the substrate 600a. That is, the N-type source region 632 and the N-type drain region 631 of the transistor 630 provided on the main surface MSa and the P+ type substrate contact layer 611 provided on the main surface MSb are separated by the other region 634 of the substrate 600a. Here, it is only required that at least a partial region of the substrate contact layer 611 has a lower resistance and a higher concentration of impurities than the other region 634 of the substrate 600a.

The substrate 600a is grounded via the substrate contact layer 611. Specifically, the semiconductor device of the fourth embodiment includes a contact 611c extending from the substrate contact layer 611 of the substrate 600a to the substrate 500 side. More specifically, the substrate 600a is arranged on the substrate 500 with a side of the main surface MSb facing the substrate 500, and the semiconductor device includes the contact 611c that connects the substrate contact layer 611 of the substrate 600a and the substrate contact layer 510 of the substrate 500. Thus, the substrate 600a is grounded via the substrate contact layer 611 and the substrate 500. That is, the potential of the substrate 600a is fixed at 0 V.

FIG. 48 is a schematic view illustrating the vicinity of bonding positions of substrates 500 and 600b in a case where the configuration of the second embodiment of the present disclosure is applied to the semiconductor device according to the fourth embodiment.

As illustrated in FIG. 48, the semiconductor device of the fourth embodiment includes a substrate 600b as a second semiconductor substrate facing the substrate 500 with the insulating film 580 interposed therebetween. That is, the substrate 600b and the substrate 500 are joined. The surface 562 illustrated in FIG. 48 indicates a surface where the substrate 600b and the substrate 500 are joined.

The substrate 600b has a transistor 640 as a second transistor on a main surface MSa as a first main surface. The transistor 640 is formed as, for example, a MOSFET. The transistor 640 includes a gate electrode 643, an N-type source region 642, and an N-type drain region 641. The gate electrode 643 is provided with a contact 643c connected to the upper layer wiring. The source region 642 is provided with a contact 642c connected to the upper layer wiring. The drain region 641 is provided with a contact 641c connected to the upper layer wiring. The transistor 640 is covered with an insulating film 682.

The substrate 600b has a substrate contact layer 612 as a region having a resistance lower than that of the substrate 600b on a main surface MSb as a second main surface opposite to the main surface MSa. Specifically, the substrate 600b has a certain conductive type, for example, P type, and the substrate contact layer 612 contains a higher concentration of impurities than another region 644 of the substrate 600b. That is, the N-type source region 642 and the N-type drain region 641 of the transistor 640 provided on the main surface MSa and the P+ type substrate contact layer 612 provided on the main surface MSb are separated by the other region 644 of the substrate 600b. Here, it is only required that at least a partial region of the substrate contact layer 612 has a lower resistance and a higher concentration of impurities than the other region 644 of the substrate 600b.

The substrate contact layer 612 of the substrate 600b has an extended portion 613 extending toward the outside of the substrate 600b in a direction along the substrate 600b.

The substrate 600b is grounded via the substrate contact layer 612. Specifically, the semiconductor device of the fourth embodiment includes a contact 612c extending from the substrate contact layer 612 of the substrate 600b to a side opposite to the substrate 500. More specifically, the extended portion 613 has a main surface MSc as a third main surface facing the same side as the main surface MSa of the substrate 600b, and is provided with the contact 612c having one end connected to the main surface MSc of the extended portion 613 and the other end grounded. Thus, the substrate 600b is grounded via the substrate contact layer 612, the contact 612c, the upper layer wiring, and so on. That is, the potential of the substrate 600b is fixed at 0 V.

In the semiconductor device of the fourth embodiment, applications of the transistor 530 of the substrate 500 and the transistors 630 and 640 of the substrates 600a and 600b can be different. The transistor 530 is suitable for applications that require high-speed processing. The transistors 630 and 640 have a slower operating speed than the transistor 530 of the substrate 500, but are suitable for applications that require low noise. Accordingly, for example, the transistor 530 can be used as a transistor constituting a logic circuit or the like.

Furthermore, the transistors 630 and 640 can be used as transistors constituting an analog circuit or the like.

Modification Example 1

Figure 49:
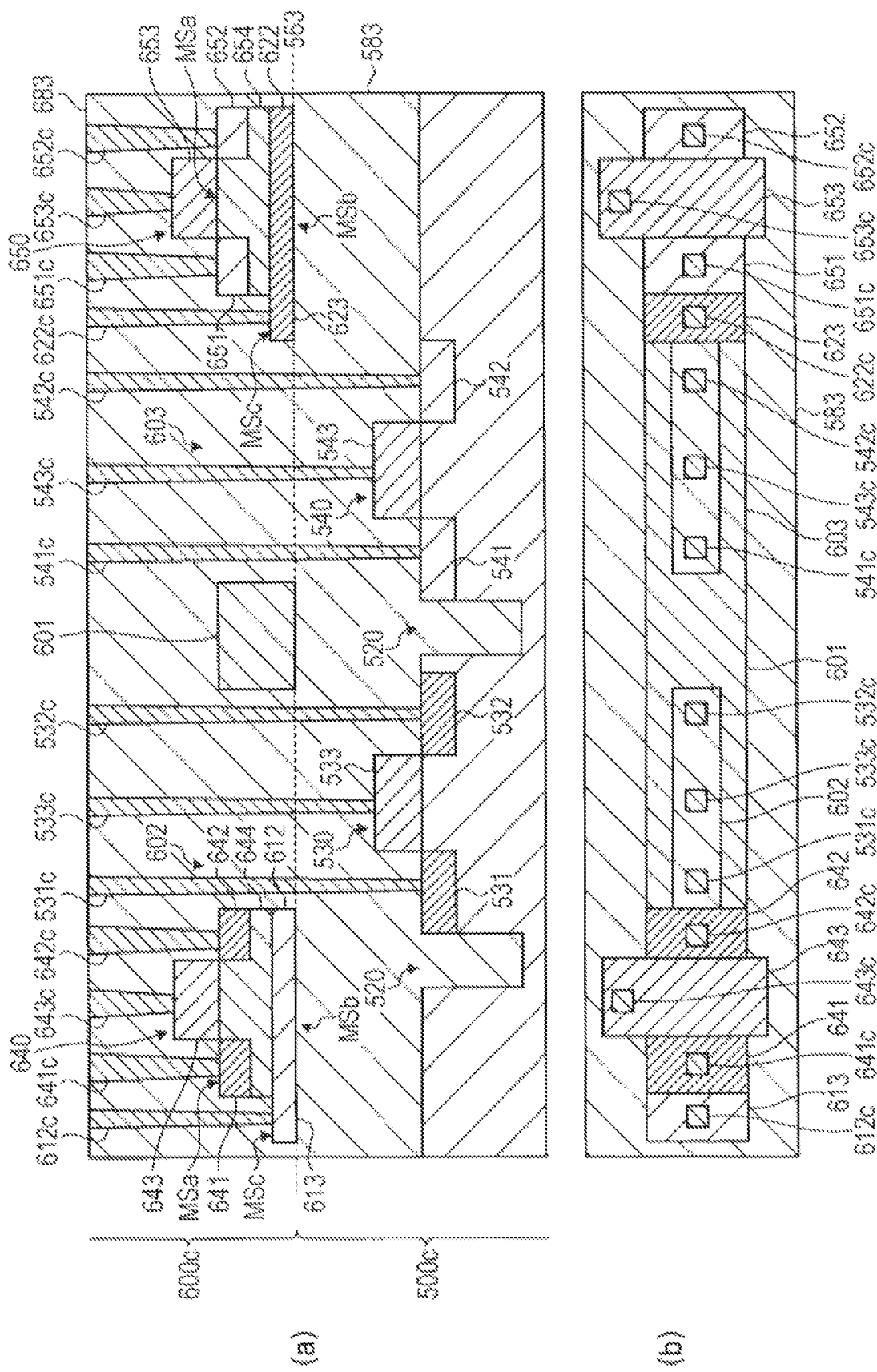
FIG. 49 is a schematic view illustrating the vicinity of bonding positions of substrates of a semiconductor device according to modification example 1 of the fourth embodiment of the present disclosure.

Next, a semiconductor device of modification example 1 of the fourth embodiment will be described with reference to FIG. 49. FIG. 49 is a schematic view illustrating the vicinity of bonding position of substrates 500c and 600c of the semiconductor device according to modification example 1 of the fourth embodiment of the present disclosure. The semiconductor device of modification example 1 is different from the above-described fourth embodiment in that the N-type transistors 530 and 640 and P-type transistors 540 and 650 are mixed.

As illustrated in a cross-sectional view of FIG. 49(a), the semiconductor device of modification example 1 includes the substrate 500c as a first semiconductor substrate having the transistor 530. The substrate 500c has the transistor 540 as a fourth transistor, which is separated from the transistor 530 by an element isolation region 520, of a conductive type different from that of the transistor 530, for example a P type. The transistor 540 is formed as, for example, a MOSFET. The transistor 540 includes a gate electrode 543, a P-type source region 542, and a P-type drain region 541. The gate electrode 543 is provided with a contact 543c connected to an upper layer wiring. The source region 542 is provided with a contact 542c connected to the upper layer wiring. The drain region 541 is provided with a contact 541c connected to the upper layer wiring.

The semiconductor device of modification example 1 includes the substrate 600c as a second semiconductor substrate facing the substrate 500c with an insulating film 583 interposed therebetween. That is, the substrate 600c and the substrate 500c are joined. The surface 563 illustrated in FIG. 49 indicates a surface where the substrate 600c and the substrate 500c are joined.

As illustrated in the cross-sectional view of FIG. 49(a) and a top view of FIG. 49(b), the substrate 600c has the transistor 640 on the main surface MSa. Furthermore, the substrate 600c has the transistor 650 as a fifth transistor, which is separated from the transistor 640 by element isolation regions 602 and 603, of a conductive type different from that of the transistor 640, for example a P type. The transistor 650 is formed as, for example, a MOSFET. The transistor 650 includes a gate electrode 653, a P-type source region 652, and a P-type drain region 651. The gate electrode 653 is provided with a contact 653c connected to the upper layer wiring. The source region 652 is provided with a contact 652c connected to the upper layer wiring. The drain region 651 is provided with a contact 651c connected to the upper layer wiring. The element isolation region 602 also functions as a through hole for passing the contacts 531c to 533c from the lower substrate 500c to the upper layer wiring side. The element isolation region 603 also functions as a through hole for passing the contacts 541c to 543c from the lower substrate 500c to the upper layer wiring side. The entire substrate 600c including the transistors 640 and 650 is covered with an insulating film 683.

The substrate 600c has a substrate contact layer 612 having a resistance lower than that of a region 644 near the transistor 640 of the substrate 600c at a position corresponding to the transistor 640 of the main surface MSb. That is, the region 644 of the substrate 600c is, for example, P type, and the substrate contact layer 612 is P+ type. The substrate contact layer 612 has an extended portion 613 extending toward the outside of the substrate 600c in a direction along the substrate 600c.

The substrate 600c has a substrate contact layer 622 having a resistance lower than that of a region 654 near the transistor 650 of the substrate 600c at a position corresponding to the transistor 650 of the main surface MSb. That is, the region 654 of the substrate 600c is, for example, N type, and the substrate contact layer 622 is N+ type. Here, it is only required that at least a partial region of the substrate contact layer 622 has a lower resistance and a higher concentration of impurities than the region 654 of the substrate 600c.

The substrate contact layer 622 has an extended portion 623 extending toward the outside of the substrate 600c in a direction along the substrate 600c. The extended portion 623 has a main surface MSc as a third main surface facing the same side as the main surface MSa of the substrate 600c, and is provided with a contact 622c having one end connected to the main surface MSc of the extended portion 623 and the other end grounded.

The substrate 600c is grounded via the substrate contact layers 612 and 622.

Modification Example 2

Figure 50:
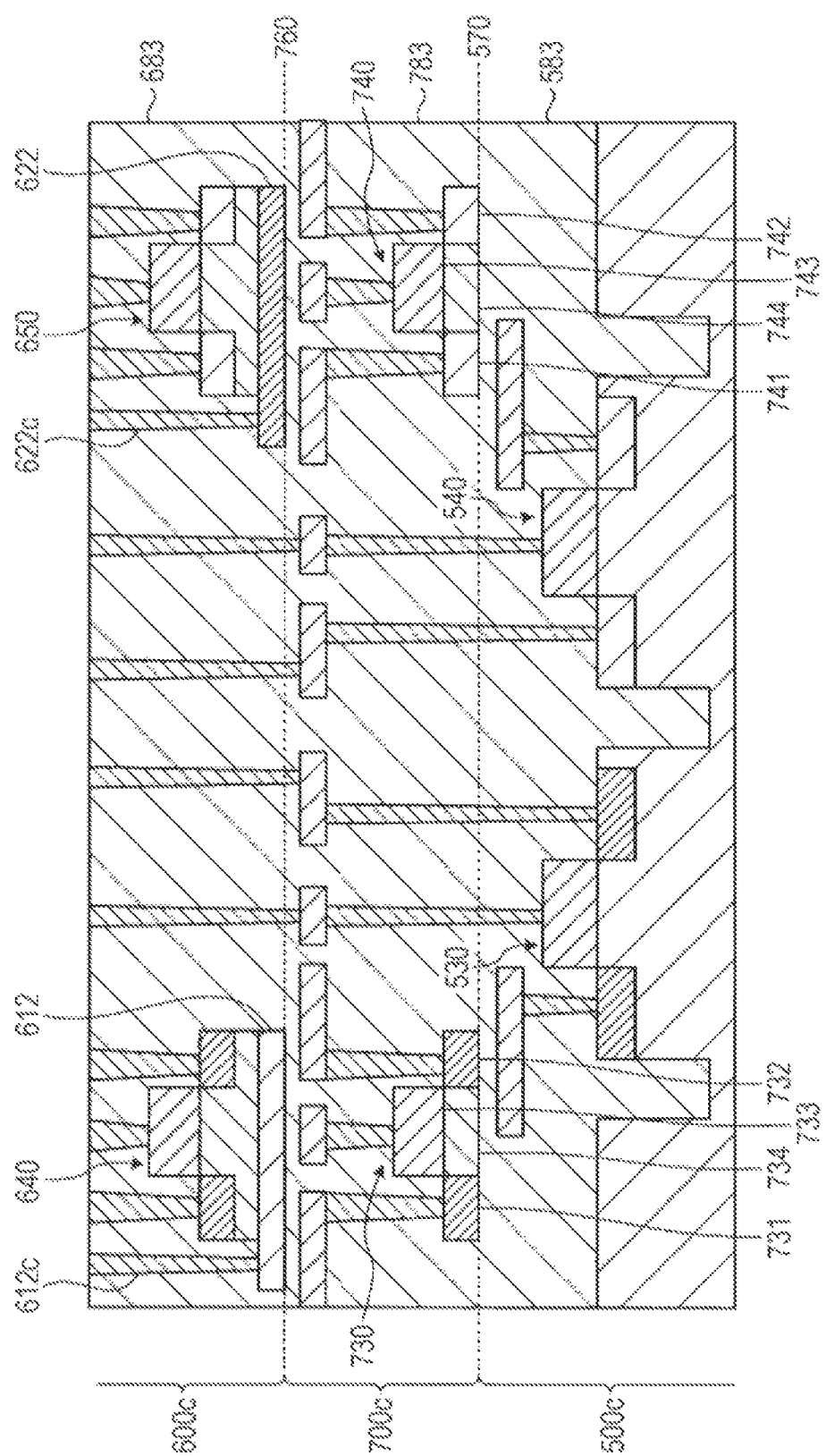
FIG. 50 is a schematic view illustrating the vicinity of bonding positions of substrates of a semiconductor device according to modification example 2 of the fourth embodiment of the present disclosure.

Next, a semiconductor device of modification example 2 of the fourth embodiment will be described with reference to FIG. 50. FIG. 50 is a schematic view illustrating the vicinity of bonding position of substrates 500c, 700c, and 600c of the semiconductor device according to modification example 2 of the fourth embodiment of the present disclosure. The semiconductor device of modification example 2 is different from the modification example 1 described above in that a substrate 700c is interposed between the substrates 500c and 600c.

As illustrated in FIG. 50, the semiconductor device of modification example 2 further includes the substrate 700c as a third semiconductor substrate which is a floating substrate facing the substrate 500c, in addition to the configuration of modification example 1. That is, the substrate 700c, which is a silicon substrate or the like, is joined to the substrate 500c. A surface 570 illustrated in FIG. 50 indicates a surface where the substrate 500c and the substrate 700c are joined. Furthermore, the substrate 600c is joined to the substrate 700c. A surface 760 illustrated in FIG. 50 indicates a surface where the substrate 700c and the substrate 600c are joined.

The substrate 500c is grounded and has a potential fixed at 0 V. The substrate 600c has substrate contact layers 612 and 622, is grounded via contacts 612c and 622c connected thereto, and has a potential fixed at 0 V. The substrate 700c does not have a substrate contact layer or the like and is not grounded. That is, the substrate 700c is a floating substrate having an indefinite substrate potential.

The substrate 700c has transistors 730 and 740 as third transistors. The transistors 730 and 740 are formed as, for example, MOSFETs. The transistor 730 has a gate electrode 733, an N-type source region 732, an N-type drain region 731, and a P-type region 734 interposed between these regions. The transistor 730 has a completely depleted silicon-on-insulator (FD-SOI) structure in which an insulating film 583 is arranged directly under the body of an NPN structure. The transistor 740 has a gate electrode 743, a P-type source region 742, a P-type drain region 741, and an N-type region 744 interposed between these regions. The transistor 740 has an FD-SOI structure in which the insulating film 583 is arranged directly under the body of a PNP structure.

By thus configuring the transistors 730 and 740 on the substrate 700c, the transistors 730 and 740 can be miniaturized, and the parasitic capacitance can be suppressed to obtain a high-speed transistor 730, 740.

Note that for the purpose of noise reduction effect, the substrate 700c may be provided with a substrate contact layer to fix the potential of the substrate 700c, similarly to the substrate 600c.

Furthermore, in modification examples 1 and 2 described above, the examples in which the configuration of the second embodiment as illustrated in FIG. 48 is applied have been described, but in modification examples 1 and 2, the configuration of the first embodiment illustrated in FIG. 47 may also be applied.

Fifth Embodiment

In a solid-state image sensor including a plurality of types of pixel transistors, how to suppress variations in threshold voltages of respective pixel transistors is also an issue.

In a fifth embodiment, a solid-state image sensor capable of adjusting the threshold voltages of the pixel transistors is proposed.

[Detailed Configuration Example of Solid-State Image Sensor]

Figure 51:
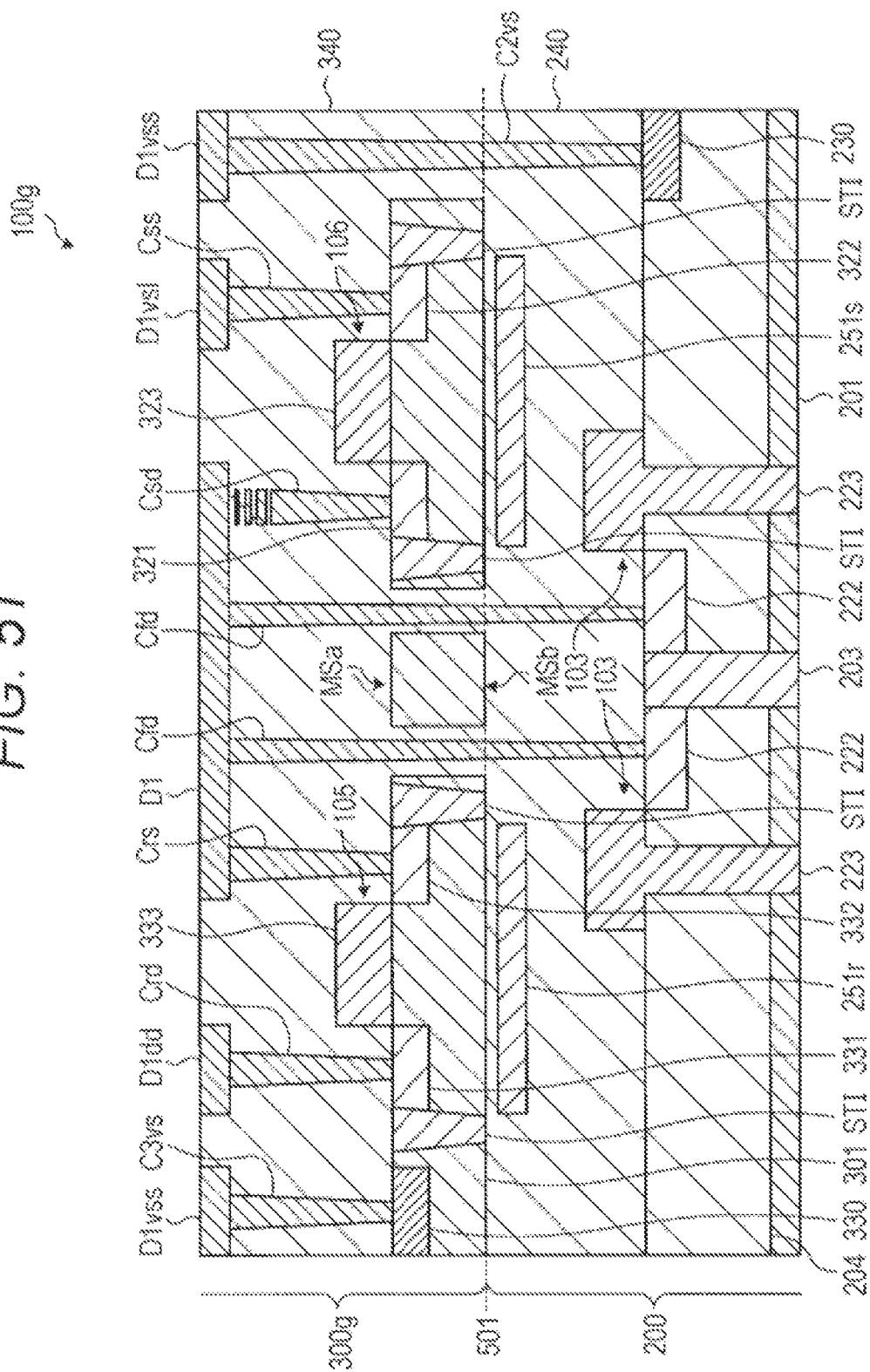
FIG. 51 is a vertical cross-sectional view illustrating the vicinity of bonding positions of substrates of a solid-state image sensor according to a fifth embodiment of the present disclosure.
Figure 52:
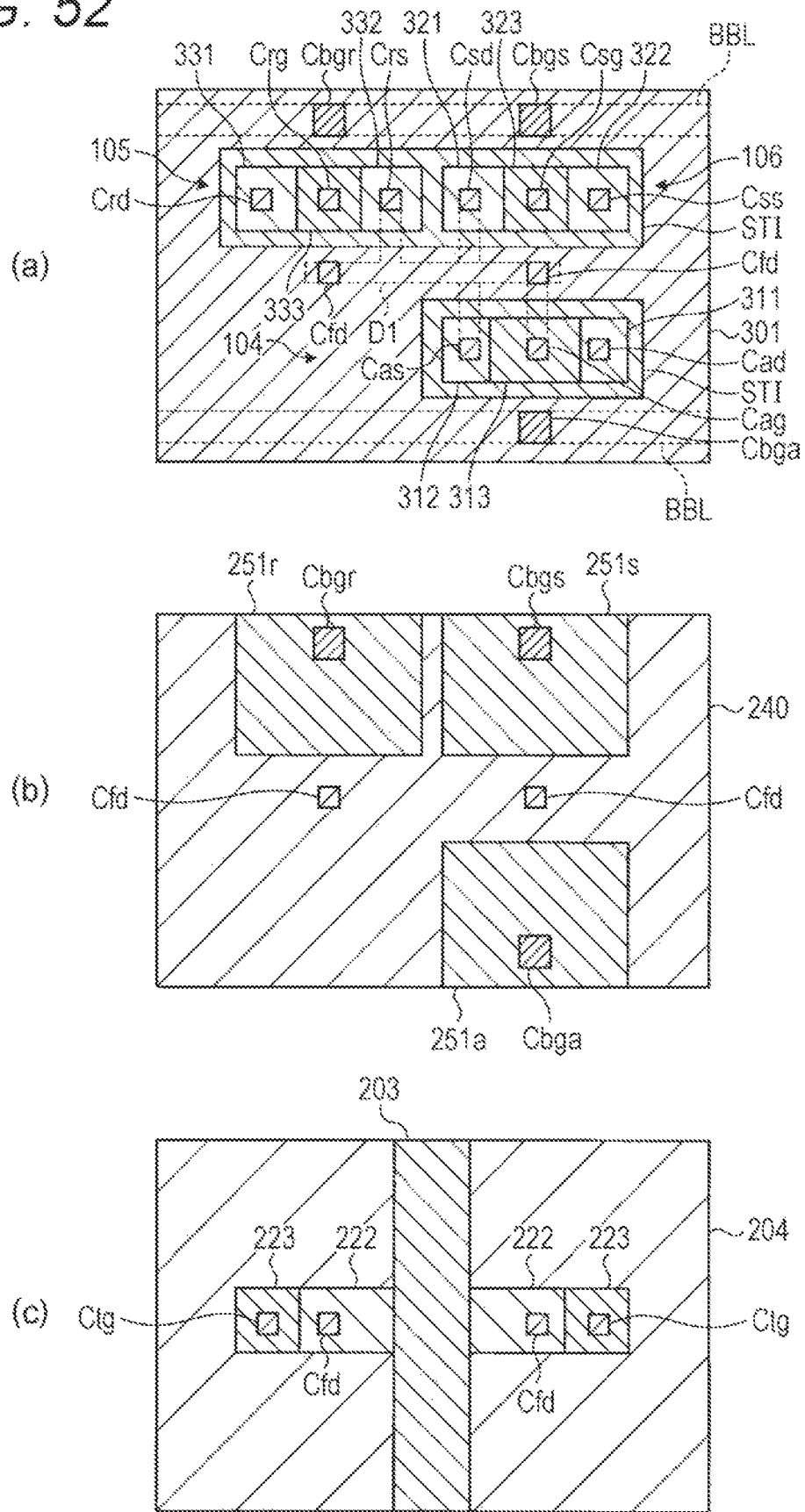
FIG. 52 is a horizontal cross-sectional view including the vicinity of the bonding positions of the substrates of the solid-state image sensor according to the fifth embodiment of the present disclosure.

FIG. 51 is a vertical cross-sectional view illustrating the vicinity of bonding positions of substrates 200 and 300g of a solid-state image sensor 100g according to the fifth embodiment of the present disclosure. FIG. 52 is a horizontal cross-sectional view including the vicinity of the bonding positions of the substrates 200 and 300g of the solid-state image sensor 100g according to the fifth embodiment of the present disclosure. FIG. 52(a) is a horizontal cross-sectional view of the substrate 300g in which an insulating film 340 is omitted. FIG. 52(b) is a horizontal cross-sectional view of an insulating film 240. FIG. 52(c) is a horizontal cross-sectional view of the substrate 200 in which the insulating film 240 is omitted.

As illustrated in FIG. 51, the solid-state image sensor 100g of the fifth embodiment has a configuration in which the substrate 200 and the substrate 300g are bonded together.

The substrate 200 as a first substrate has, for example, a similar configuration to that of the substrate 200 illustrated in the first embodiment described above. In FIG. 51, a cross section of a range different from the range illustrated in the first embodiment is illustrated. That is, the substrate 200 includes a plurality of transfer transistors 103 on a surface layer portion of a P-type semiconductor region 204 across a pixel separation part 203. A P-type diffusion region 230 is provided in a region that is a surface layer portion of the P-type semiconductor region 204 and is separated from regions where the transfer transistors 103 are formed. The diffusion region 230 is connected to, for example, a contact C2vs, and the contact C2vs is connected to a wiring D1vss. The semiconductor region 204 of the substrate 200 is grounded via the contact C2vs, the wiring D1vss, and so on.

As illustrated in FIGS. 51 and 52(c), a transfer transistor 103 includes a gate electrode 223 and an N-type source region 222 as a floating diffusion. The gate electrode 223 is connected to a contact Ctg. The source region 222 is connected to a contact Cfd.

As illustrated in FIG. 51, the substrate 300g as a second substrate has a P-type semiconductor region 301 including a main surface MSa as a first main surface and a main surface MSb as a second main surface. A distance between the main surfaces MSa and MSb, that is, the thickness of the semiconductor region 301 is, for example, 100 nm or less. The main surface MSb of the substrate 300g is bonded to the substrate 200 via the insulating film 240 that covers the entire transfer transistors 103 and so on of the substrate 200. The insulating film 240 has a thickness of, for example, about 350 nm.

The substrate 300g has pixel transistors on the main surface MSa side. The pixel transistors process an electrical signal output from a photoelectric conversion element including the N-type semiconductor region 201 included in the substrate 200. FIG. 51 illustrates a cross section including a selection transistor 106 and a reset transistor 105 as examples of the pixel transistors.

A P-type diffusion region 330 is provided in a region that is a surface layer portion of the P-type semiconductor region 301 and is separated from formation regions of the selection transistor 106, the reset transistor 105, and the like. The diffusion region 330 is connected to, for example, a contact C3vs, and the contact C3vs is connected to the wiring D1vss. The semiconductor region 301 of the substrate 300 is grounded via the contact C3vs, the wiring D1vss, and the like.

In the substrate 300g, the entire selection transistor 106, reset transistor 105, and so on are covered with the insulating film 340. The insulating film 340 has a thickness of, for example, about 350 nm.

As illustrated in FIGS. 51 and 52(a), the selection transistor 106 has a gate electrode 323, an N-type source region 322, and an N-type drain region 321. The gate electrode 323 is connected to a contact Csg. The source region 322 is connected to a contact Css, and the contact Css is connected to a source line (not illustrated) via a wiring D1vsl. The drain region 321 is connected to a contact Csd.

The reset transistor 105 has a gate electrode 333, an N-type source region 332, and an N-type drain region 331. The gate electrode 333 is connected to a contact Crg. The source region 332 is connected to a contact Crs, and the contact Crs is connected to the source region 222 of the transfer transistor 103 via a wiring D1 and the contact Cfd. The drain region 331 is connected to a contact Crd, and the contact Crd is connected to a power supply (not illustrated) via a wiring D1vdd.

As illustrated in FIG. 52(a), the amplification transistor 104 has a gate electrode 313, an N-type source region 312, and an N-type drain region 311. The gate electrode 313 is connected to a contact Cag, and the contact Cag is connected to the source region 222 of the transfer transistor 103 via the wiring D1 and the contact Cfd. The source region 312 is connected to a contact Cas. The contact Cas is connected to the contact Csd that connects to the drain region 321 of the selection transistor 106. The drain region 311 of the amplification transistor 104 is connected to the contact Cad.

As illustrated in FIGS. 51 and 52(a), the selection transistor 106, the reset transistor 105, and the amplification transistor 104 are separated from each other by an element isolation region STI formed around each of them.

As illustrated in FIGS. 51 and 52(b), back gate electrodes 251s, 251r, and 251a including polysilicon and the like are arranged near the main surface MSb side of the semiconductor region 301 of the substrate 300g at positions corresponding to the selection transistor 106, the reset transistor 105, and the amplification transistor 104, respectively.

That is, the back gate electrode 251s as a second electrode is arranged on a back surface of the selection transistor 106. At this time, the back gate electrode 251s is provided at a position overlapping with at least the gate electrode 323, the source region 322, and the drain region 321 of the selection transistor 106 in a top view, preferably, so as to completely cover these gate electrode 323, source region 322, and drain region 321.

Furthermore, the back gate electrode 251r as a third electrode is arranged on a back surface of the reset transistor 105. At this time, the back gate electrode 251r is provided at a position overlapping with at least the gate electrode 333, the source region 332, and the drain region 331 of the reset transistor 105 in a top view, preferably, so as to completely cover these gate electrode 333, source region 332, and drain region 331.

Furthermore, the back gate electrode 251a as a first electrode is arranged on a back surface of the amplification transistor 104. At this time, the back gate electrode 251a is provided at a position overlapping with at least the gate electrode 313, the source region 312, and the drain region 311 of the amplification transistor 104 in a top view, preferably, so as to completely cover these gate electrode 313, source region 312, and drain region 311.

Distances between these back gate electrodes 251s, 251r, and 251a and the main surface MSb of the semiconductor region 301 of the substrate 300g are, for example, 10 nm or less. For example, the insulating film 240 is interposed with a thickness of 10 nm or less between the back gate electrodes 251s, 251r, and 251a and the main surface MSb of the semiconductor region 301.

As illustrated in FIG. 52(b), the back gate electrodes 251s, 251r, and 251a are connected to contacts Cbgs, Cbgr, and Cbga, respectively. As illustrated in FIG. 52(a), these contacts Cbgs, Cbgr, and Cbga are each connected to a back bias line BBL.

The back bias line BBL is configured so that a voltage can be applied to the back gate electrodes 251s, 251r, and 251a via the contacts Cbgs, Cbgr, and Cbga. Thus, a back bias can be applied to the selection transistor 106, the reset transistor 105, and the amplification transistor 104 from the back gate electrodes 251s, 251r, and 251a. The back bias is a bias generated by the difference between the gate voltage of each of the back gate electrodes 251s, 251r, and 251a and the threshold voltage of each of the selection transistor 106, the reset transistor 105, and the amplification transistor 104.

[Operation Example of Solid-State Image Sensor]

Figure 53:
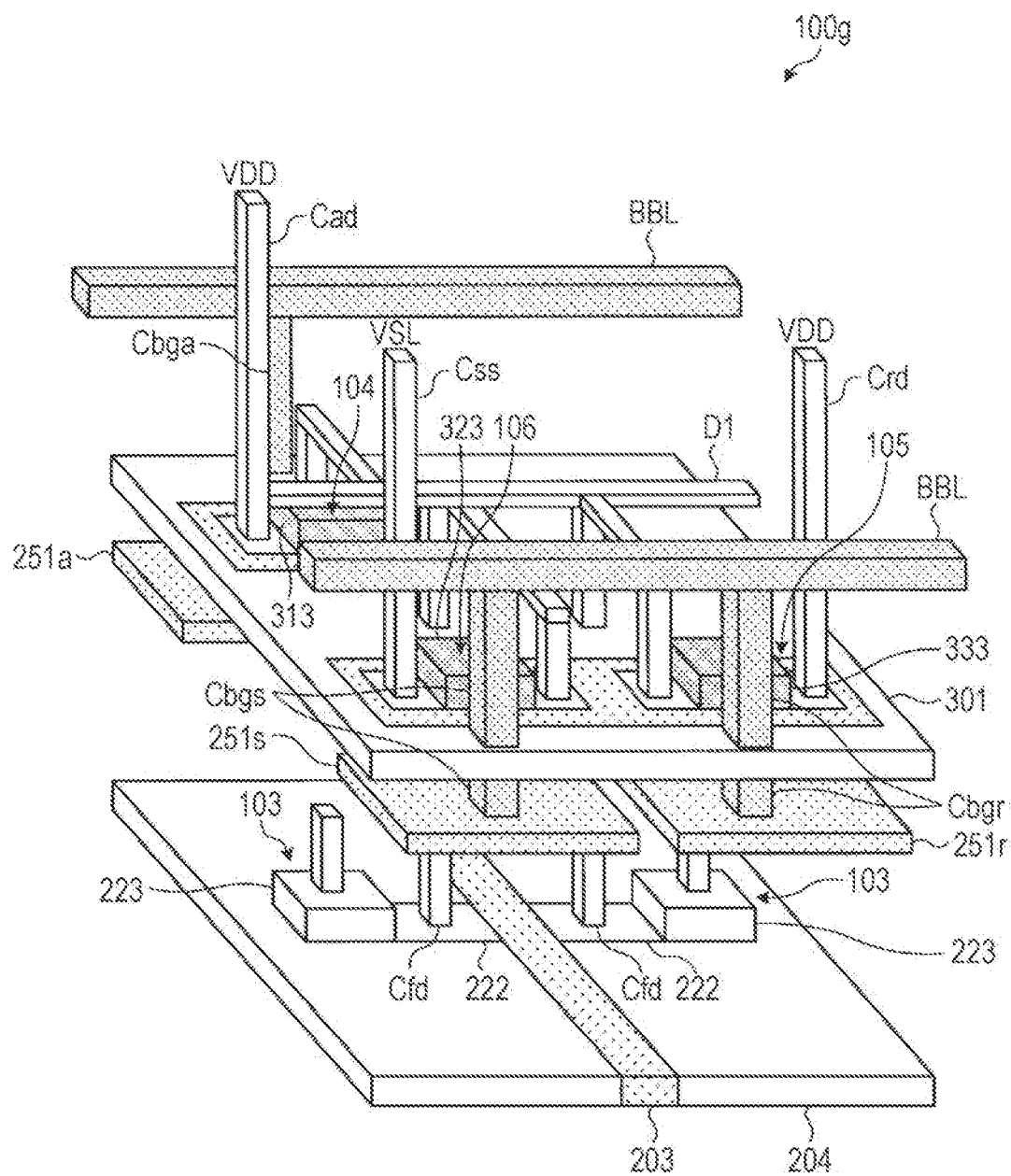
FIG. 53 is a perspective view illustrating a part of the solid-state image sensor according to the fifth embodiment of the present disclosure.
Figure 54:
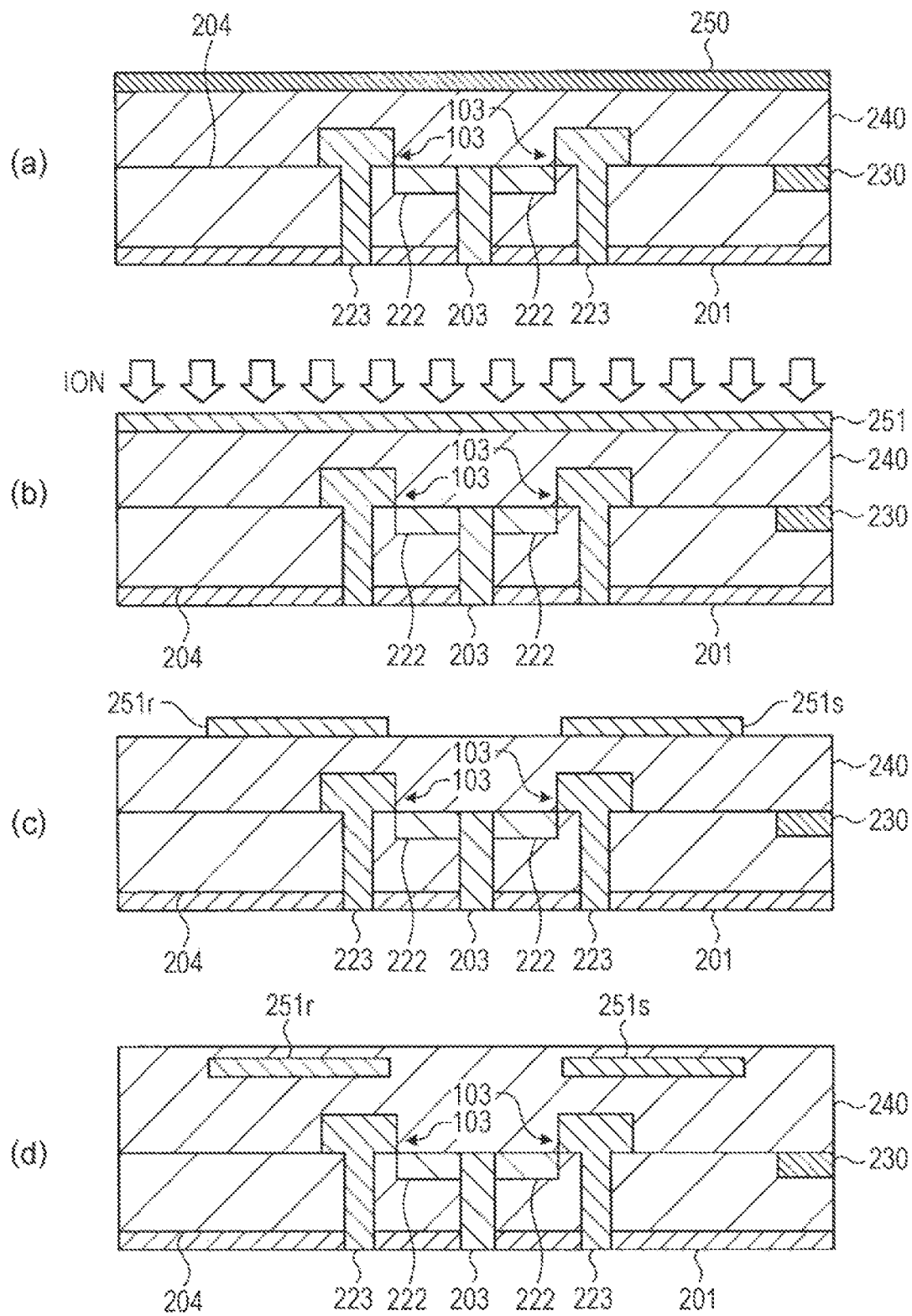
FIG. 54 is a flow view illustrating an example of a procedure of a manufacturing process of the solid-state image sensor according to the fifth embodiment of the present disclosure.

Next, an operation example of the solid-state image sensor 100g according to the fifth embodiment will be described with reference to FIG. 53. FIG. 53 is a perspective view illustrating a part of the solid-state image sensor 100g according to the fifth embodiment of the present disclosure. In FIG. 53, the insulating films 240 and 340 and so on are omitted.

An electrical signal from the photoelectric conversion element is transferred by the transfer transistor 103 to the amplification transistor 104 included in the solid-state image sensor 100g. A voltage corresponding to the magnitude of the electrical signal from the photoelectric conversion element is applied to the gate electrode 313 of the amplification transistor 104. At this time, a predetermined voltage is also applied to the back gate electrode 251a arranged on the back surface of the amplification transistor 104 via the contact Cbga, and the threshold voltage of the amplification transistor 104 is adjusted. Thus, the amplification transistor 104 can be turned on at a desired voltage value, and the electrical signal from the photoelectric conversion element is amplified.

In the selection transistor 106 included in the solid-state image sensor 100g, a voltage is applied to the gate electrode 323 via the contact Csg. At this time, a predetermined voltage is also applied to the back gate electrode 251s arranged on the back surface of the selection transistor 106 via the contact Cbgs, and the threshold voltage of the selection transistor 106 is adjusted. Thus, the selection transistor 106 can be turned on at a desired voltage value, and the electrical signal from the photoelectric conversion element amplified by the amplification transistor 104 is transferred via the wiring D1vsl.

Furthermore, in the selection transistor 106, the back gate electrode 251s can reduce channel resistance, that is, on-resistance of the selection transistor 106, and accelerate the timing at which the selection transistor 106 turns on. It takes time for a source line potential VSL to rise due to the resistance of the contact Css, the wiring D1vsl, and so on, and thus the time to wait for the source line potential VSL to rise can be shortened by advancing the timing to turn on the selection transistor 106.

In the reset transistor 105 included in the solid-state image sensor 100g, a voltage is applied to the gate electrode 333 via the contact Crg. At this time, a predetermined voltage is also applied to the back gate electrode 251r arranged on the back surface of the reset transistor 105 via the contact Cbgr, and the threshold voltage of the reset transistor 105 is adjusted. Thus, the reset transistor 105 can be turned on at a desired voltage value, and the potentials of the gate electrode 313 of the amplification transistor 104 and the source region 222 of the transfer transistor 103, which is a floating diffusion, are reset to the power supply potential VDD.

Note that in the examples of FIGS. 52 and 53, the back gate electrodes 251s and 251r corresponding to the selection transistor 106 and the reset transistor 105 are connected to the common back bias line BBL, but may be connected to separate back bias lines. Thus, for example, respective different voltages may be applied to the back gate electrodes 251s, 251r, and 251a to individually control the respective threshold voltages of the selection transistor 106, the reset transistor 105, and the amplification transistor 104.

[Example of Manufacturing Process of Solid-State Image Sensor]

Next, an example of a manufacturing process of the solid-state image sensor 100g of the fifth embodiment will be described with reference to FIGS. 54 to 57. FIGS. 54 to 57 are flow views illustrating an example of a procedure of the manufacturing process of the solid-state image sensor 100g according to the fifth embodiment of the present disclosure.

As illustrated in FIG. 54(a), the photoelectric conversion element including the N-type semiconductor region 201, the P-type semiconductor region 204, the gate electrodes 223 of the transfer transistors 103, and the source regions 222 as floating diffusions are formed on the substrate 200. A P-type diffusion region 230 is formed at a position away from the transfer transistor 103. The semiconductor region 204 including the gate electrodes 223 and the source regions 222 is covered with the insulating film 240. A polysilicon film 250 is formed on the insulating film 240 by, for example, a CVD method.

As illustrated in FIG. 54(b), the polysilicon film 250 is doped with N-type impurities (ion implantation) to form an N-type polysilicon film 251.

As illustrated in FIG. 54(c), a part of the polysilicon film 51 is etched to form the back gate electrode 251s at a position to correspond to the selection transistor 106 later, and form the back gate electrode 251r at a position to correspond to the reset transistor 105 later. At this time, the back gate electrode 251a that is not illustrated is also formed at a position to correspond to the amplification transistor 104 later.

As illustrated in FIG. 54(d), the insulating film 240 is further formed so as to cover the back gate electrodes 251s and 251r with a thickness of, for example, 10 nm or less.

As illustrated in FIG. 55(a), a thick film, that is, the substrate 300g before thinning is bonded onto the insulating film 240 with the main surface MSb facing the insulating film 240.

As illustrated in FIG. 55(b), the substrate 300g is ground with a grinder G or the like to shape the semiconductor region 301 so that the thickness of the semiconductor region 301 is, for example, 100 nm or less.

As illustrated in FIG. 56(a), the semiconductor region 301 of portions where the contacts Cfd and C2vs, and the like connected to the substrate 200 are arranged is removed.

As illustrated in FIG. 56(b), the selection transistor 106 and the reset transistor 105 are formed on the main surface MSa of the semiconductor region 301. Specifically, a gate oxide film (not illustrated) is formed on the main surface MSa of the semiconductor region 301 by a thermal oxidation method. A polysilicon film or the like is formed by the CVD method, and is partially etched to form the gate electrodes 323 and 333 of the selection transistor 106 and the reset transistor 105. N-type impurities are ion-implanted into the semiconductor region 301 on both sides of each of the gate electrodes 323 and 333 to form the source regions 322 and 332 and the drain regions 321 and 331. The amplification transistor 104 that is not illustrated is also formed similarly in parallel therewith.

Thereafter, the element isolation region STI is formed around the selection transistor 106, the reset transistor 105, and the like by a technique such as shallow trench isolation.

As illustrated in FIG. 57(a), the insulating film 340 is formed so as to cover the selection transistor 106, the reset transistor 105, and the like.

As illustrated in FIG. 57(b), the contacts Csg, Crg, Css, Crs, Csd, Crd, C3vs, C2vs, and Cfd are formed. Specifically, through holes reaching the gate electrodes 323 and 333, the source regions 322 and 332, the drain regions 321 and 33, and the substrate 200 are formed by dry etching, a W film or the like is added in the respective through holes by the CVD method, and the extra W film is removed by CMP. A contact connected to the amplification transistor 104 that is not illustrated is similarly formed in parallel with this.

Thereafter, the wirings D1, D1dd, D1vsl, D1vss, and so on to which the respective contacts Csg, Crg, Css, Crs, Csd, Crd, C3vs, C2vs, and Cfd are connected are formed.

Thereafter, an upper layer wiring that is not illustrated is further formed, and the substrate on which the logic transistor and wirings are formed are joined, thereby finishing the manufacturing process of the solid-state image sensor 100g.

Comparative Example

A solid-state image sensor includes a plurality of pixel transistors such as a selection transistor, a reset transistor, and an amplification transistor. These pixel transistors are manufactured and individualized in the state of a whole wafer. In the solid-state image sensor of the comparative example, it is possible that the threshold voltages of the respective pixel transistors vary due to variations in processing conditions within the wafer. That is, the threshold voltages of the pixel transistors vary in some cases among chips of the solid-state image sensor or within the chips.

In the solid-state image sensor 100g of the fifth embodiment, the back gate electrodes 251s, 251r, and 251a for applying the back bias are provided on the back surface of the selection transistor 106, the reset transistor 105, and the amplification transistor 104. Thus, the threshold voltages of the selection transistor 106, the reset transistor 105, and the amplification transistor 104 can be adjusted to suppress variations in the threshold voltages. Therefore, noise is reduced.

Note that the back bias line BBL that applies a voltage to each of the back gate electrodes 251s, 251r, and 251a can be separated to thereby apply respective different voltages to the back gate electrodes 251s, 251r, and 251a. Thus, controllability of the threshold voltages of the selection transistor 106, the reset transistor 105, and the amplification transistor 104 is further improved.

In the solid-state image sensor 100g of the fifth embodiment, when a voltage is applied to the gate electrodes 323, 333, and 313 of the selection transistor 106, the reset transistor 105, and the amplification transistor 104, the back bias is applied by the back gate electrodes 251s, 251r, and 251a. Thus, operating margins of the selection transistor 106, the reset transistor 105, and the amplification transistor 104 can be widened, and the reliability is improved.

In the solid-state image sensor 100g of the fifth embodiment, the back gate electrode 251s reduces the on-resistance of the selection transistor 106 so as to advance the timing at which the selection transistor 106 turns. Thus, the waiting time for rising of the source line potential VSL can be shortened.

In the solid-state image sensor 100g of the fifth embodiment, the distances between the back gate electrodes 251s, 251r, and 251a and the main surface MSb of the substrate 300g is, for example, 10 nm or less. Furthermore, the thickness of the semiconductor region 301 of the substrate 300g is, for example, 100 nm or less. As described above, since the back gate electrodes 251s, 251r, and 251a and the selection transistor 106, the reset transistor 105, and the amplification transistor 104 are at sufficiently close distances to each other, the back bias effect sufficient to adjust the threshold voltages can be obtained.

Modification Example 1

Next, a solid-state image sensor of modification example 1 of the fifth embodiment will be described with reference to FIGS. 58 and 59. The solid-state image sensor of modification example 1 is different from the above-described fifth embodiment in that it is manufactured by using an SOI substrate 300h.

FIGS. 58 and 59 are flow views illustrating an example of a procedure of a manufacturing process of the solid-state image sensor according to modification example 1 of the fifth embodiment of the present disclosure.

As illustrated in FIG. 58(a), a silicon-on-insulator (SOI) substrate 300h is prepared as a second substrate. The SOI substrate 300h includes, for example, a support substrate 301hdl that is a P-type silicon substrate or the like, a BOX layer 301box that is a silicon oxide layer or the like on the support substrate 301hdl, and an active layer 301act that is a P-type silicon layer or the like on the BOX layer 301box. The BOX layer 301box and the active layer 301act each have a thickness of, for example, about several tens of μm.

As illustrated in FIG. 58(b), the SOI substrate 300h is ground from the support substrate 301hdl side with the grinder G or the like so that the BOX layer 301box remains with a thickness of 10 nm or less.

As illustrated in FIG. 59(a), the active layer 301act having the BOX layer 301box with a thickness of 10 nm or less is bonded onto the insulating film 240 of the substrate 200 with the BOX layer 301box side facing the insulating film 240 side.

As illustrated in FIG. 59(b), the surface of the active layer 301act is ground with the grinder G or the like until the thickness becomes 100 nm or less.

Thereafter, the solid-state image sensor of modification example 1 is manufactured by performing similar processing to that in FIGS. 56 and 57 and the like of the above-described fifth embodiment.

In the solid-state image sensor of modification example 1, the SOI substrate 300h is used. Thus, distances between the back gate electrodes 251s, 251r, and 251a and the active layer 301act, which is a semiconductor region in which various pixel transistors are formed, can be accurately controlled.

Modification Example 2

Next, a solid-state image sensor of modification example 2 of the fifth embodiment will be described with reference to FIG. 60. In the solid-state image sensor of modification example 2, the back gate electrodes 252s and 252r and so on are formed by using materials different from those of the above-described fifth embodiment.

Figure 60:
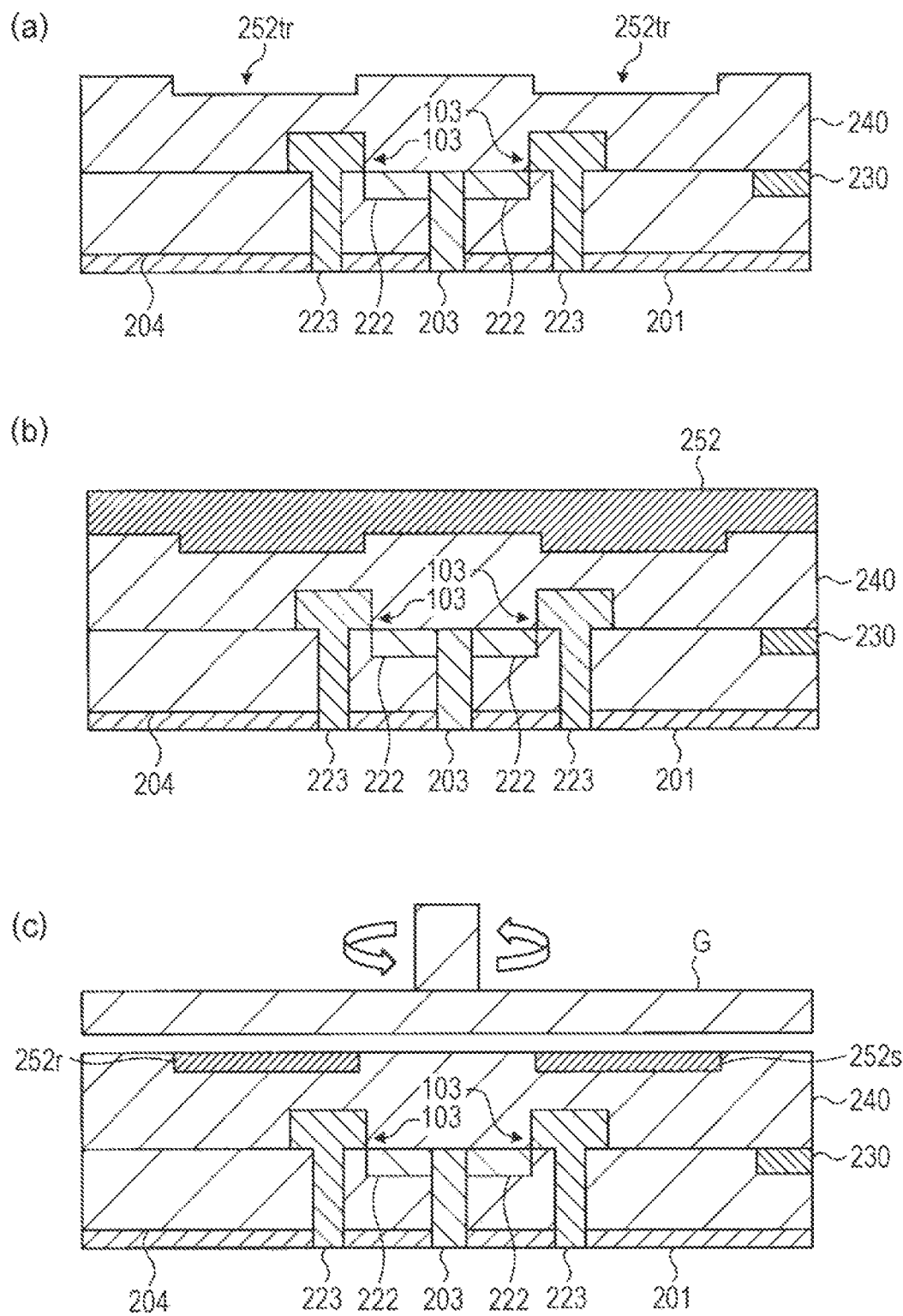
FIG. 60 is a flow view illustrating an example of a procedure of a manufacturing process of a solid-state image sensor according to modification example 2 of the fifth embodiment of the present disclosure.

FIG. 60 is a flow view illustrating an example of a procedure of a manufacturing process of the solid-state image sensor according to modification example 2 of the fifth embodiment of the present disclosure.

As illustrated in FIG. 60(a), trenches 252tr are formed in a surface layer of the insulating film 240 covering the semiconductor region 204 by etching or the like.

As illustrated in FIG. 60(b), for example, a metal film 252 such as a Cu film is formed on the insulating film 240 by, for example, a CVD method. At this time, the insides of the trenches 252tr are also filled with the metal film 252.

As illustrated in FIG. 60(c), the metal film 252 on the insulating film 240 is removed by, for example, a CMP method.

At this time, by leaving the metal film 252 in the trenches 252tr, the back gate electrode 252s is formed at a position to correspond to the selection transistor later, and the back gate electrode 252r is formed at a position to correspond to the reset transistor later. At this time, a back gate electrode that is not illustrated is also formed at a position to correspond to the amplification transistor later.

Thereafter, the solid-state image sensor of modification example 2 is manufactured by performing similar processing to that of the fifth embodiment or modification example 1 of the fifth embodiment described above.

In the solid-state image sensor of modification example 2, the back gate electrodes 252s, 252r, and the like are formed by using the metal film 252. Thus, the back gate electrodes 252s, 252r, and the like with lower resistance can be obtained.

Sixth Embodiment

Figure 61:
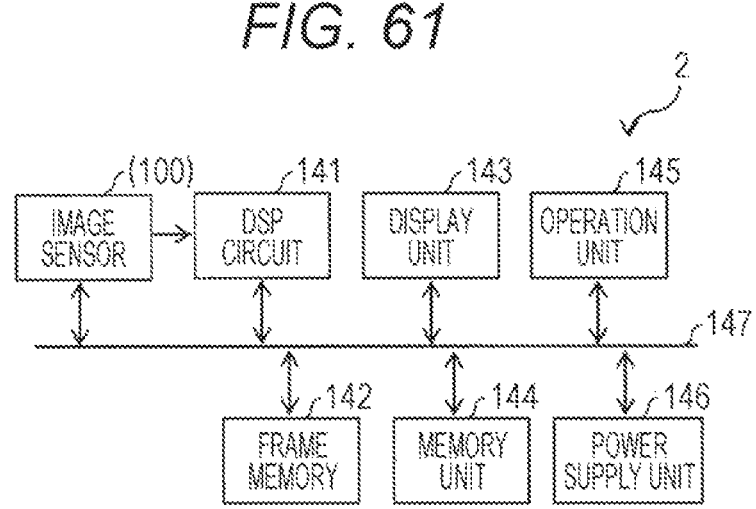
FIG. 61 is a diagram representing an example of a schematic configuration of an imaging system including the solid-state image sensor described above.

FIG. 61 is a diagram representing an example of a schematic configuration of an imaging system 2 including any of the solid-state image sensors of the first to third and fifth embodiments and modification examples thereof. That is, any of the solid-state image sensors of the first to third embodiments described above and modification examples thereof can be mounted in the imaging system 2. In the following description, the imaging system 2 equipped with the solid-state image sensor 100 of the first embodiment will be taken as an example.

The imaging system 2 is, for example, an imaging device such as a digital still camera or a video camera, or an electronic device such as a mobile terminal device such as a smartphone or a tablet terminal. The imaging system 2 includes, for example, the solid-state image sensor 100 of the first embodiment, a DSP circuit 141, a frame memory 142, a display unit 143, a storage unit 144, an operation unit 145, and a power supply unit 146. In the imaging system 2, the solid-state image sensor 100, the DSP circuit 141, the frame memory 142, the display unit 143, the storage unit 144, the operation unit 145, and the power supply unit 146 are connected to each other via a bus line 147.

The solid-state image sensor 100 outputs image data corresponding to incident light. The DSP circuit 141 is a signal processing circuit that processes image data, which is a signal output from the solid-state image sensor 100. The frame memory 142 temporarily holds the image data processed by the DSP circuit 141 in frame units. The display unit 143 includes, for example, a panel-type display device such as a liquid crystal panel or an organic electro-luminescence (EL) panel, and displays a moving image or a still image captured by the solid-state image sensor 100. The storage unit 144 records image data of a moving image or a still image captured by the solid-state image sensor 100 on a recording medium such as a semiconductor memory or a hard disk. The operation unit 145 issues operation commands for various functions of the imaging system 2 according to an operation by the user. The power supply unit 146 appropriately provides various power sources as operating power sources for the solid-state image sensor 100, the DSP circuit 141, the frame memory 142, the display unit 143, the storage unit 144, and the operation unit 145 to these supply targets.

Next, an imaging procedure in the imaging system 2 will be described.

Figure 62:
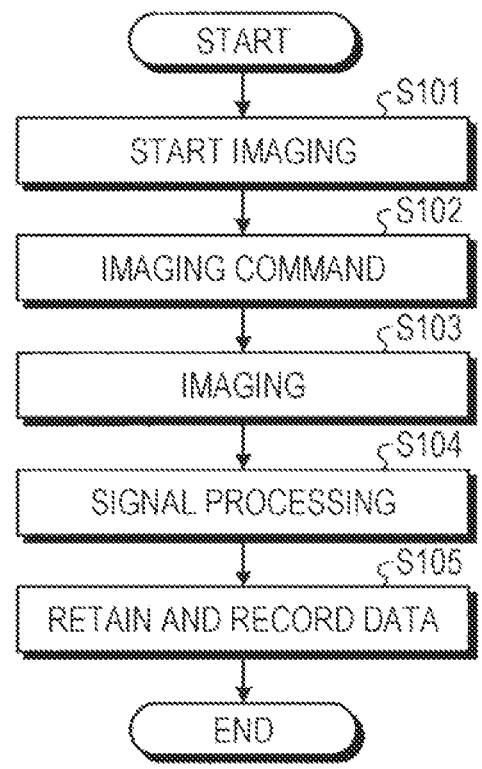
FIG. 62 is a diagram representing an example of an imaging procedure in the imaging system of FIG. 61.

FIG. 62 represents an example of a flowchart of an imaging operation in the imaging system 2. The imaging system 2 receives a start of imaging by an operation of the operation unit 145 by the user (step S101), or the like. Then, the operation unit 145 transmits an imaging command to the solid-state image sensor 100 (step S102). Upon receiving the imaging command, the system control circuit of the solid-state image sensor 100 (see the system control circuit 36 and so on in FIG. 1) executes imaging by a predetermined imaging method (step S103).

The solid-state image sensor 100 outputs image data obtained by imaging to the DSP circuit 141. Here, the image data is data for all pixels of the pixel signals generated on the basis of charges temporarily held in the floating diffusions FD. The DSP circuit 141 performs, for example, predetermined signal processing such as noise reduction processing on the basis of the image data input from the solid-state image sensor 100 (step S104). The DSP circuit 141 causes the image data subjected to the predetermined signal processing to be retained in the frame memory 142, and the frame memory 142 causes the image data to be stored in the storage unit 144 (step S105). Thus, the imaging in the imaging system 2 is performed.

Since the imaging system 2 is equipped with a miniaturized or high-definition solid-state image sensor 100, it is possible to provide a compact or high-definition imaging system 2.

Application Example 1

The technology according to the present disclosure can be applied to various products. For example, the technology according to the present disclosure may be achieved as a device mounted in any type of mobile object such as an automobile, an electric vehicle, a hybrid electric vehicle, a motorcycle, a bicycle, a personal mobility, an airplane, a drone, a ship, a robot, and the like.

Figure 63:
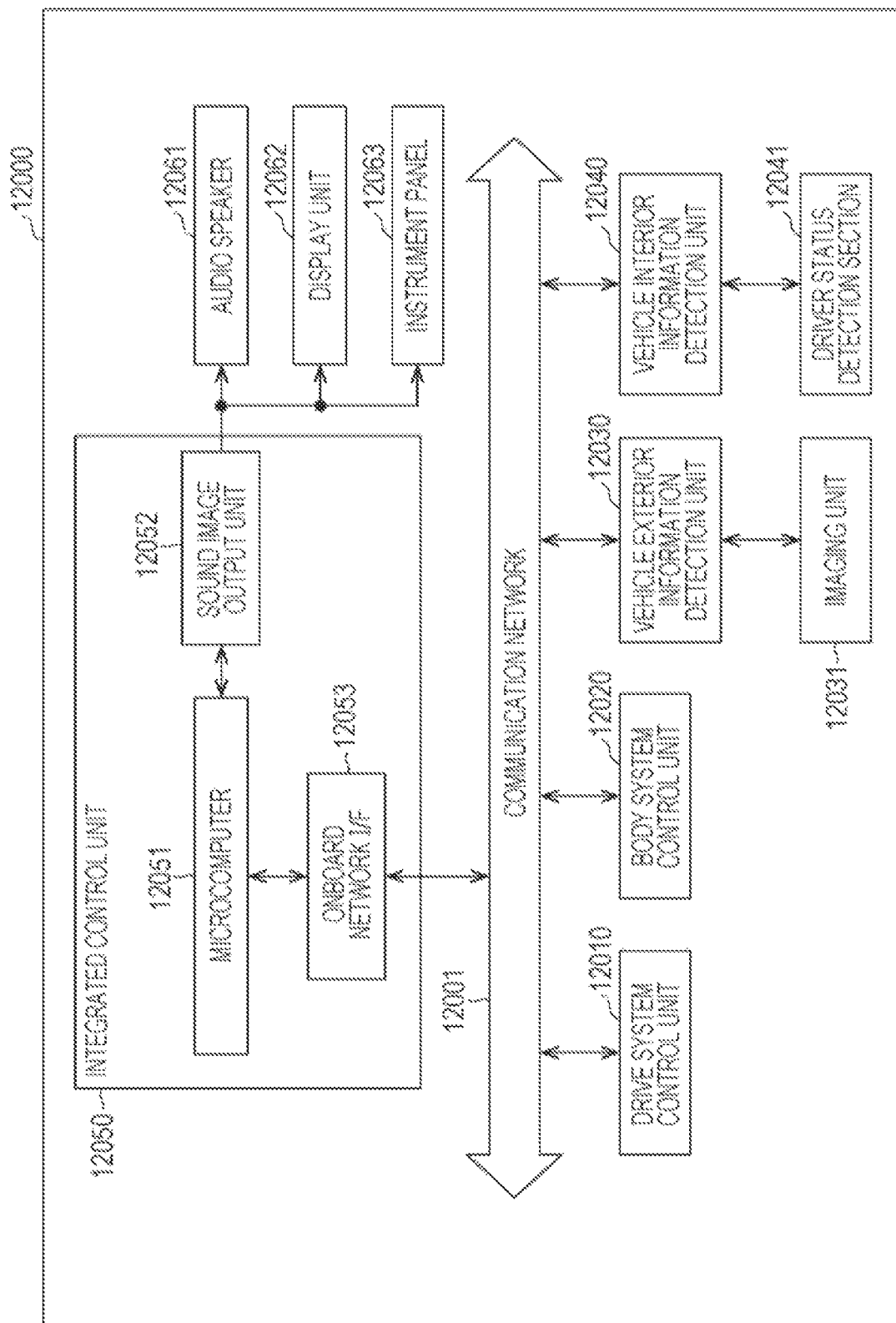
FIG. 63 is a block diagram illustrating an example of a schematic configuration of a vehicle control system.

FIG. 63 is a block diagram illustrating a schematic configuration example of a vehicle control system that is an example of a mobile object control system to which the technology according to the present disclosure can be applied.

A vehicle control system 12000 includes a plurality of electronic control units connected via a communication network 12001. In the example illustrated in FIG. 63, the vehicle control system 12000 includes a drive system control unit 12010, a body system control unit 12020, a vehicle exterior information detection unit 12030, a vehicle interior information detection unit 12040, and an integrated control unit 12050. Furthermore, as a functional configuration of the integrated control unit 12050, a microcomputer 12051, a sound image output unit 12052, and an onboard network interface (I/F) 12053 are illustrated.

The drive system control unit 12010 controls operation of devices related to the drive system of the vehicle according to various programs. For example, the drive system control unit 12010 functions as a control device for a driving force generation device for generating driving force of the vehicle such as an internal combustion engine or a driving motor, a driving force transmission mechanism for transmitting driving force to wheels, a steering mechanism for adjusting a steering angle of the vehicle, and a braking device for generating a braking force of the vehicle, and the like.

The body system control unit 12020 controls operation of various devices mounted on the vehicle body according to various programs. For example, the body system control unit 12020 functions as a control device for a keyless entry system, a smart key system, and a power window device, or various lamps such as a head lamp, a back lamp, a brake lamp, a blinker, or a fog lamp, and the like. In this case, radio waves transmitted from a portable device that substitutes for a key or signals from various switches can be input to the body system control unit 12020. The body system control unit 12020 receives input of these radio waves or signals, and controls a door lock device, a power window device, a lamp, and the like of the vehicle.

The vehicle exterior information detection unit 12030 detects information external to the vehicle on which the vehicle control system 12000 is mounted. For example, an imaging unit 12031 is connected to the vehicle exterior information detection unit 12030. The vehicle exterior information detection unit 12030 causes the imaging unit 12031 to capture an image outside the vehicle, and receives the captured image. The vehicle exterior information detection unit 12030 may perform an object detection process or a distance detection process of a person, a vehicle, an obstacle, a sign, or a character on a road surface, or the like on the basis of the received image.

The imaging unit 12031 is an optical sensor that receives light and outputs an electrical signal corresponding to the amount of received light. The imaging unit 12031 can output the electrical signal as an image or as distance measurement information. Furthermore, the light received by the imaging unit 12031 may be visible light or non-visible light such as infrared light.

The vehicle interior information detection unit 12040 detects information in the vehicle. The vehicle interior information detection unit 12040 is connected to, for example, a driver status detection section 12041 that detects the status of the driver. The driver status detection section 12041 includes, for example, a camera that captures an image of the driver, and the vehicle interior information detection unit 12040 may calculate the degree of fatigue or the degree of concentration of the driver, or judge whether or not the driver has fallen asleep on the basis of detection information input from the driver status detection section 12041.

The microcomputer 12051 can calculate a control target value of the driving force generation device, the steering mechanism, or the braking device on the basis of information of the inside and outside of the vehicle obtained by the vehicle exterior information detection unit 12030 or the vehicle interior information detection unit 12040, and outputs a control command to the drive system control unit 12010. For example, the microcomputer 12051 can perform cooperative control for the purpose of achieving functions of the advanced driver assistance system (ADAS) including vehicle collision avoidance or impact mitigation, following traveling based on an inter-vehicle distance, vehicle speed maintaining traveling, vehicle collision warning, or vehicle lane departure warning, and the like.

Furthermore, the microcomputer 12051 controls the driving force generation device, the steering mechanism, the braking device, or the like on the basis of information around the vehicle obtained by the vehicle exterior information detection unit 12030 or the vehicle interior information detection unit 12040, to thereby perform cooperative control for the purpose of autonomous driving or the like to travel autonomously without depending on operation by the driver.

Furthermore, the microcomputer 12051 can output a control command to the body system control unit 12020 on the basis of vehicle exterior information obtained by the vehicle exterior information detection unit 12030. For example, the microcomputer 12051 can perform cooperative control for the purpose of anti-glare, such as controlling headlamps according to the position of a preceding vehicle or oncoming vehicle detected by the vehicle exterior information detection unit 12030, and thereby switching a high beam to a low beam.

The sound image output unit 12052 transmits an output signal of at least one of sound or image to an output device capable of visually or audibly notifying a passenger of the vehicle or the outside of the vehicle of information. In the example of FIG. 63, an audio speaker 12061, a display unit 12062, and an instrument panel 12063 are exemplified as output devices. The display unit 12062 may include, for example, at least one of an on-board display or a head-up display.

Figure 64:
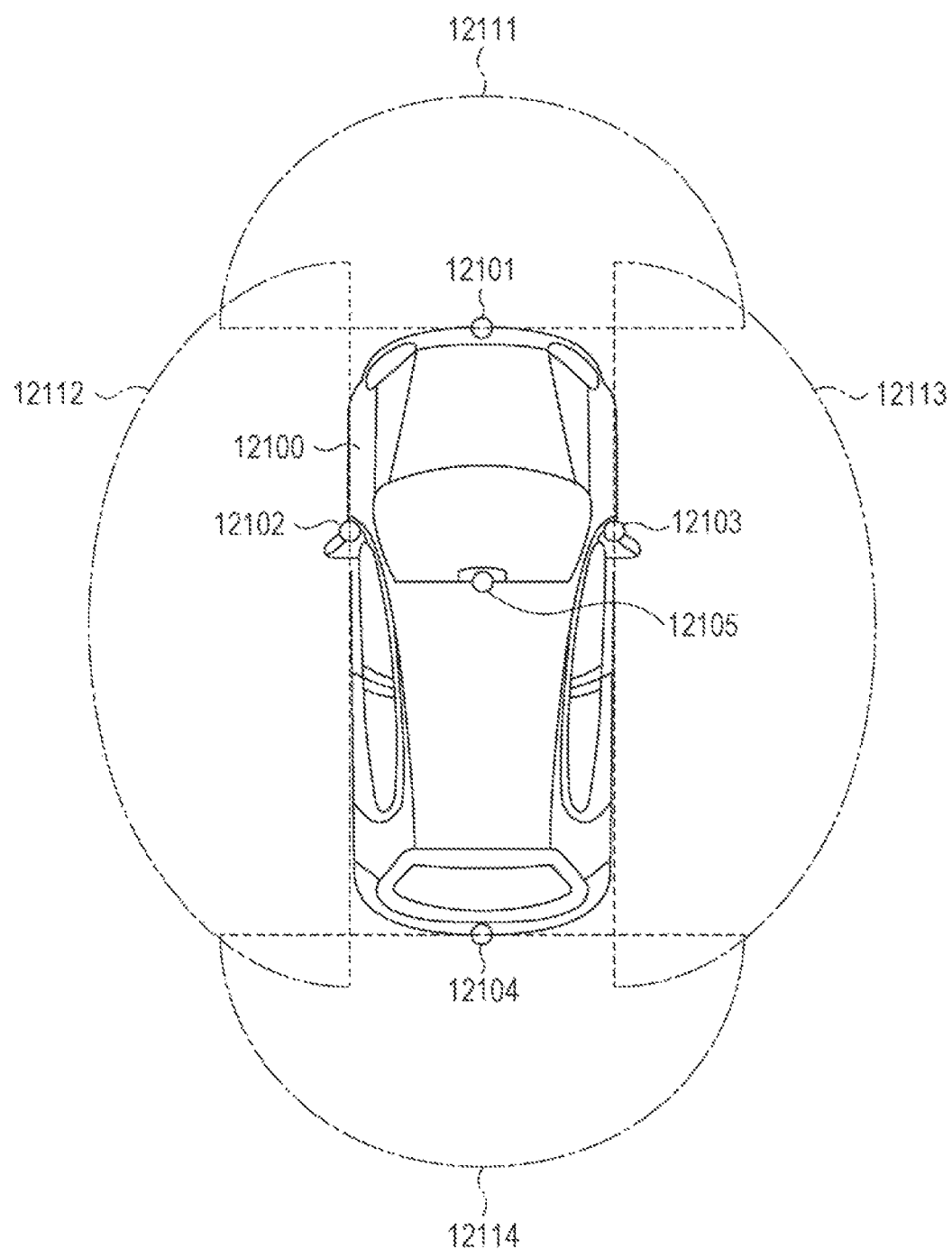
FIG. 64 is an explanatory diagram illustrating an example of installation positions of a vehicle exterior information detection section and an imaging unit.

FIG. 64 is a diagram illustrating an example of installation positions of the imaging unit 12031.

In FIG. 64, the vehicle 12100 has imaging units 12101, 12102, 12103, 12104, and 12105 as the imaging unit 12031.

The imaging units 12101 to 12105 are provided, for example, at positions such as a front nose, a side mirror, a rear bumper, a back door, and an upper part of a windshield in the cabin of the vehicle 12100. The imaging unit 12101 provided at the front nose and the imaging unit 12105 provided on the upper part of the windshield in the cabin mainly obtain a forward image of the vehicle 12100. The imaging units 12102 and 12103 provided in the side mirrors mainly obtain images of sides of the vehicle 12100. The imaging unit 12104 provided in a rear bumper or a back door mainly obtains an image behind the vehicle 12100. The forward image obtained by the imaging units 12101 and 12105 are mainly used for detecting a preceding vehicle, a pedestrian, an obstacle, a traffic light, a traffic sign, a lane, and the like.

Note that FIG. 64 illustrates an example of imaging ranges of the imaging units 12101 to 12104. An imaging range 12111 indicates the imaging range of the imaging unit 12101 provided on the front nose, imaging ranges 12112 and 12113 indicate imaging ranges of the imaging units 12102 and 12103 provided in the side mirrors, respectively, and an imaging range 12114 indicates an imaging range of an imaging unit 12104 provided in a rear bumper or a back door. For example, by overlaying image data captured by the imaging units 12101 to 12104, an overhead image of the vehicle 12100 viewed from above can be obtained.

At least one of the imaging units 12101 to 12104 may have a function of obtaining distance information. For example, at least one of the imaging units 12101 to 12104 may be a stereo camera including a plurality of solid-state image sensor or a solid-state image sensor having pixels for detecting a phase difference.

For example, on the basis of distance information obtained from the imaging units 12101 to 12104, the microcomputer 12051 can obtain a distance to each three-dimensional object in the imaging ranges 12111 to 12114, and a temporal change of this distance, that is, relative speed to the vehicle 12100, to thereby extract as a preceding vehicle a three-dimensional object that is closest particularly on the traveling path of the vehicle 12100 and travels at a predetermined speed, for example, 0 km/h or more in substantially the same direction as the vehicle 12100. Moreover, the microcomputer 12051 can set in advance an inter-vehicle distance to be secured before a preceding vehicle, and perform automatic brake control including follow-up stop control, automatic acceleration control including follow-up start control, and the like. In this way, it is possible to perform cooperative control for automatic driving or the like in which the vehicle travels autonomously without depending on operation of the driver.

For example, the microcomputer 12051 extracts, on the basis of distance information obtained from the imaging units 12101 to 12104, three-dimensional object data related to a three-dimensional object while categorizing into a two-wheeled vehicle, a normal vehicle, a large vehicle, a pedestrian, and other three-dimensional objects such as a telephone pole, and uses the extracted data for automatic avoidance of obstacles.

For example, the microcomputer 12051 distinguishes an obstacle around the vehicle 12100 into an obstacle that is visible to the driver of the vehicle 12100 and an obstacle that is difficult to see. Then, the microcomputer 12051 determines a collision risk indicating the risk of collision with each obstacle, and when the collision risk is equal to or higher than a set value and there is a possibility of collision, the microcomputer 12051 can output a warning to the driver via the audio speaker 12061 and the display unit 12062, or perform forced deceleration or avoidance steering via the drive system control unit 12010, to thereby perform assistance for collision avoidance.

At least one of the imaging units 12101 to 12104 may be an infrared camera that detects infrared light. For example, the microcomputer 12051 can recognize a pedestrian by determining whether or not a pedestrian exists in captured images of the imaging units 12101 to 12104. Recognition of such a pedestrian is performed by, for example, a procedure of extracting feature points in an image captured by the imaging units 12101 to 12104 as an infrared camera, and performing a pattern matching process on a series of feature points indicating the outline of an object to judge whether or not the object is a pedestrian. When the microcomputer 12051 determines that a pedestrian is present in the images captured by the imaging units 12101 to 12104 and recognizes the pedestrian, the sound image output unit 12052 controls the display unit 12062 so as to overlay a square contour line for emphasis on the recognized pedestrian.

Furthermore, the sound image output unit 12052 may cause the display unit 12062 to display an icon or the like indicating a pedestrian at a desired position.

The example of the mobile object vehicle control system to which the technology according to the present disclosure can be applied has been described above. The technology according to the present disclosure can be applied to the imaging unit 12031 among the configurations described above. Specifically, the solid-state image sensors according to the above-described first to third embodiments and modification examples thereof can be applied to the imaging unit 12031. By applying the technology according to the present disclosure to the imaging unit 12031, a high-definition captured image with less noise can be obtained, and thus highly accurate control using the captured image can be performed in the mobile object control system.

Application Example 2

Figure 65:
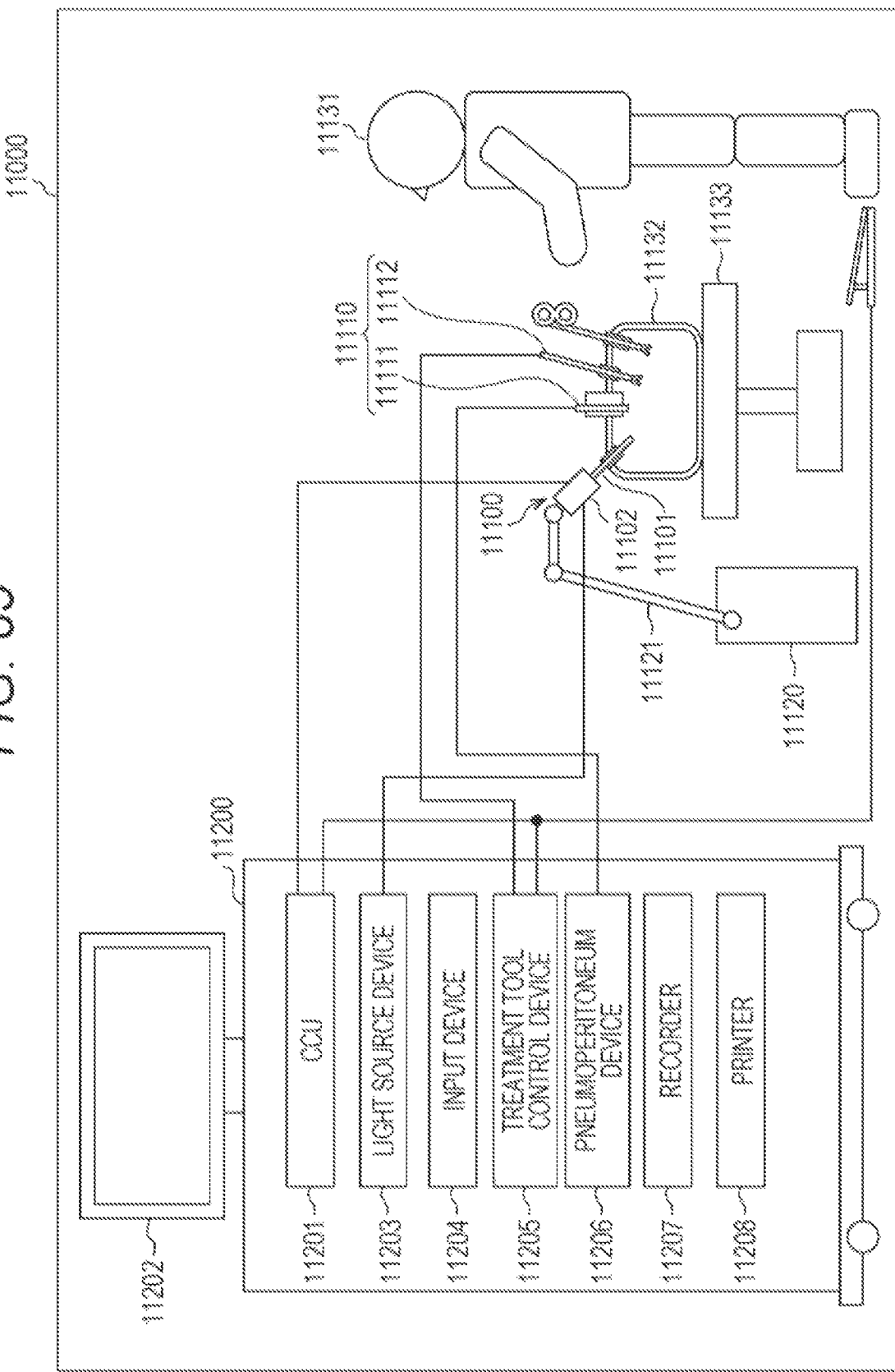
FIG. 65 is a diagram illustrating an example of a schematic configuration of an endoscopic surgery system.

FIG. 65 is a diagram illustrating an example of a schematic configuration of an endoscopic surgery system to which the technology according to the present disclosure can be applied.

FIG. 65 illustrates a surgeon 11131, such as a doctor, performing surgery on a patient 11132 on an examination table 11133 using an endoscopic surgery system 11000. As illustrated in the diagram, the endoscopic surgery system 11000 includes an endoscope 11100, other surgical tools 11110 such as a pneumoperitoneum tube 11111 and an energy treatment tool 11112, a support arm device 11120 that supports the endoscope 11100, and a cart 11200 on which various devices for endoscopic surgery are mounted.

The endoscope 11100 includes a lens barrel 11101 into which a region having a predetermined length from a distal end is inserted into the body cavity of the patient 11132, and a camera head 11102 connected to a base end of the lens barrel 11101. In the illustrated example, the endoscope 11100 formed as what is called a rigid mirror having the rigid lens barrel 11101 is illustrated, but the endoscope 11100 may also be formed as what is called a flexible mirror having a flexible lens barrel.

The distal end of the lens barrel 11101 is provided with an opening in which an objective lens is fitted. A light source device 11203 is connected to the endoscope 11100, and light generated by the light source device 11203 is guided to the distal end of the lens barrel 11101 by a light guide extending inside the lens barrel 11101, and is emitted through the objective lens toward the observation target in the body cavity of the patient 11132. Note that the endoscope 11100 may be a forward-viewing endoscope, an oblique-viewing endoscope, or a side-viewing endoscope.

An optical system and any one of the solid-state image sensors of the above-described first to third embodiments and modification examples thereof are provided inside the camera head 11102, and reflected light from the observation target, that is, observation light is focused on the solid-state image sensor by the optical system. The observation light is photoelectrically converted by the solid-state image sensor, and an electrical signal corresponding to the observation light, that is, an image signal corresponding to the observation image is generated. The image signal is transmitted as RAW data to a camera control unit (CCU) 11201.

The CCU 11201 includes a central processing unit (CPU), a graphics processing unit (GPU), or the like, and integrally controls operation of the endoscope 11100 and a display device 11202. Moreover, the CCU 11201 receives an image signal from the camera head 11102, and performs, for example, various image processing such as development processing (demosaic processing) on the image signal for displaying an image based on the image signal.

Under control of the CCU 11201, the display device 11202 displays an image based on the image signal on which the image processing is performed by the CCU 11201.

The light source device 11203 includes, for example, a light source such as a light emitting diode (LED), and supplies irradiation light for imaging a surgical site or the like to the endoscope 11100.

An input device 11204 is an input interface to the endoscopic surgery system 11000. The user can input various information and input instructions to the endoscopic surgery system 11000 via the input device 11204. For example, the user inputs an instruction to change imaging conditions such as the type, magnification, and focal length of the irradiation light emitted by the endoscope 11100.

A treatment tool control device 11205 controls driving of the energy treatment tool 11112 for cauterization, incision, or sealing of blood vessels of tissue, or the like. A pneumoperitoneum device 11206 delivers gas into the body cavity through the pneumoperitoneum tube 11111 in order to inflate the body cavity of the patient 11132 for the purpose of securing the field of view by the endoscope 11100 and the working space of the operator 11131. A recorder 11207 is a device that can record various information related to surgery. A printer 11208 is a device capable of printing various information related to surgery in various formats such as text, images, and graphs.

Note that the light source device 11203 that supplies the irradiation light to the endoscope 11100 when imaging the surgical site can include, for example, an LED, a laser light source, or a white light source including a combination thereof. In a case where a white light source is formed by a combination of RGB laser light sources, the output intensity and output timing of each wavelength in each color can be controlled with high accuracy, and thus the white balance of a captured image can be controlled in the light source device 11203. Furthermore, in this case, it is possible to irradiate the observation target with the laser light from each of the RGB laser light sources in a time-divided manner, and control driving of the solid-state image sensor of the camera head 11102 in synchronization with the irradiation timing, to thereby capture an image corresponding to each of RGB in a time-divided manner. According to this method, a color image can be obtained without providing a color filter on the solid-state image sensor.

Furthermore, driving of the light source device 11203 may be controlled so as to change the intensity of output light at every predetermined time interval. By controlling driving of the solid-state image sensor of the camera head 11102 in synchronization with timing of changing the intensity of light to obtain images in a time-divided manner and synthesizing the images, images with high dynamic ranges without what is called blackout and overexposure can be generated.

Furthermore, the light source device 11203 may be configured to be capable of supplying light in a predetermined wavelength band corresponding to special light observation. In the special light observation, for example, what is called narrow band light observation (narrow band imaging) is performed by utilizing the wavelength dependence of light absorption in body tissue and emitting light in a narrower band than white light, which is the irradiation light during normal observation, to thereby image a predetermined tissue such as blood vessels on a surface layer of a mucous membrane with high contrast. Alternatively, in the special light observation, fluorescence observation in which an image is obtained by fluorescence generated by emitting excitation light may be performed. In the fluorescence observation, it is possible to perform self-fluorescence observation by irradiating a body tissue with excitation light to observe fluorescence from the body tissue, or locally injecting a reagent such as indocyanine green (ICG) into a body tissue and irradiating the body tissue with excitation light corresponding to the fluorescent wavelength of the reagent to obtain a fluorescence image, or the like. The light source device 11203 may be configured to be capable of supplying at least one of narrow band light or excitation light corresponding to such special light observation.

Figure 66:
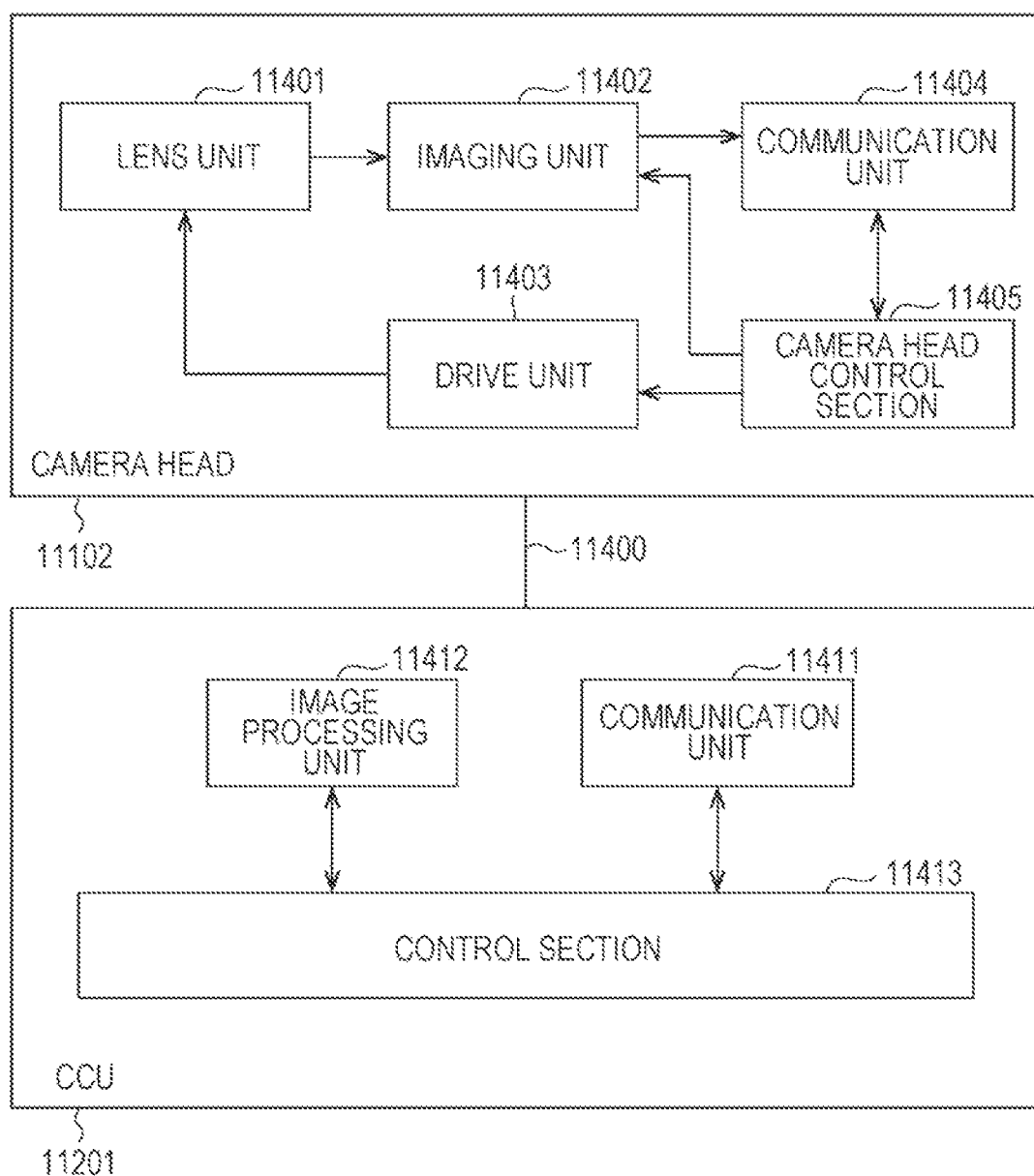
FIG. 66 is a block diagram illustrating an example of a functional configuration of a camera head and a CCU.

FIG. 66 is a block diagram illustrating an example of a functional configuration of the camera head 11102 and the CCU 11201 illustrated in FIG. 65.

The camera head 11102 has a lens unit 11401, an imaging unit 11402, a drive unit 11403, a communication unit 11404, and a camera head control section 11405. The CCU 11201 has a communication unit 11411, an image processing unit 11412, and a control section 11413. The camera head 11102 and the CCU 11201 are communicably connected to each other by a transmission cable 11400.

The lens unit 11401 is an optical system provided at a connection portion with the lens barrel 11101. The observation light taken in from the distal end of the lens barrel 11101 is guided to the camera head 11102 and incident on the lens unit 11401. The lens unit 11401 is configured by combining a plurality of lenses including a zoom lens and a focus lens.

The imaging unit 11402 includes a solid-state image sensor. The solid-state image sensor constituting the imaging unit 11402 may be one of what is called single-plate type, or may be a plurality of what is called multi-plate type. In a case where the imaging unit 11402 includes the multi-plate type, for example, respective solid-state image sensors may generate image signals corresponding to RGB, respectively, and the image signals may be combined to produce a color image. Alternatively, the imaging unit 11402 may be configured to have a pair of solid-state image sensors for obtaining respective image signals for the right eye and the left eye corresponding to three-dimensional (3D) display. Performing 3D display enables the surgeon 11131 to more accurately grasp the depth of living tissue at a surgical site. Note that in a case where the imaging unit 11402 includes the multi-plate type, multiple systems of lens units 11401 may be provided corresponding to the respective solid-state image sensors.

Furthermore, the imaging unit 11402 does not necessarily have to be provided on the camera head 11102. For example, the imaging unit 11402 may be provided inside the lens barrel 11101 immediately after the objective lens.

The drive unit 11403 includes an actuator, and the zoom lens and the focus lens of the lens unit 11401 are moved by a predetermined distance along the optical axis under the control of the camera head control section 11405. Thus, the magnification and focus of the image captured by the imaging unit 11402 can be adjusted as appropriate.

The communication unit 11404 includes a communication device for transmitting and receiving various information to and from the CCU 11201. The communication unit 11404 transmits an image signal obtained from the imaging unit 11402 as RAW data to the CCU 11201 via the transmission cable 11400.

Furthermore, the communication unit 11404 receives a control signal for controlling driving of the camera head 11102 from the CCU 11201 and supplies the control signal to the camera head control section 11405. Such a control signal include, for example, information regarding imaging conditions such as information specifying the frame rate of the captured image, information specifying the exposure value at the time of imaging, information specifying the magnification and focus of the captured image, and the like.

Note that the imaging conditions described above such as a frame rate, exposure value, magnification, and focus may be appropriately specified by the user, or may be automatically set by the control section 11413 of the CCU 11201 on the basis of the obtained image signal. In the latter case, what is called an auto exposure (AE) function, an auto focus (AF) function, and an auto white balance (AWB) function are installed in the endoscope 11100.

The camera head control section 11405 controls driving of the camera head 11102 on the basis of the control signal from the CCU 11201 received via the communication unit 11404.

The communication unit 11411 includes a communication device for transmitting and receiving various information to and from the camera head 11102. The communication unit 11411 receives the image signal transmitted from the camera head 11102 via the transmission cable 11400.

Furthermore, the communication unit 11411 transmits a control signal for controlling driving of the camera head 11102 to the camera head 11102. The image signal and control signals can be transmitted by electric communication, optical communication, or the like.

The image processing unit 11412 performs various image processing on the image signal which is the RAW data transmitted from the camera head 11102.

The control section 11413 performs various control regarding imaging of a surgical site or the like by the endoscope 11100 and displaying of a captured image obtained by imaging the surgical site or the like. For example, the control section 11413 generates a control signal for controlling driving of the camera head 11102.

Furthermore, the control section 11413 causes the display device 11202 to display a captured image reflecting a surgical site or the like on the basis of the image signal on which image processing is performed by the image processing unit 11412. At this time, the control section 11413 may recognize various objects in the captured image by using various image recognition techniques. For example, the control section 11413 can detect the shapes of edges, colors, and the like of an object included in the captured image, so as to recognize the surgical tool 11110 such as a forceps, a specific biological part, bleeding, mist when using the energy treatment tool 11112, or the like. When the control section 11413 causes the captured image to be displayed on the display device 11202, the control section 11413 may use the recognition result to superimpose various surgical support information on the image of the surgical site. By the surgery support information superimposed and presented to the operator 11131, a burden on the operator 11131 can be reduced, and the operator 11131 can reliably proceed with the operation.

The transmission cable 11400 that connects the camera head 11102 and the CCU 11201 is an electrical signal cable that supports electrical signal communication, an optical fiber that supports optical communication, or a composite cable thereof.

Here, although the communication is performed by wire using the transmission cable 11400 in the illustrated example, the communication between the camera head 11102 and the CCU 11201 may be performed wirelessly.

The example of the endoscopic surgery system to which the technology according to the present disclosure can be applied has been described above. In the configuration described above, the technology according to the present disclosure can be suitably applied to the imaging unit 11402 provided in the camera head 11102 of the endoscope 11100. By applying the technique according to the present disclosure to the imaging unit 11402, the imaging unit 11402 can be miniaturized or have high definition, so that a compact or high-definition endoscope 11100 can be provided.

Seventh Embodiment

Upon describing a seventh embodiment, terms are selected and reference signs are given again from a different viewpoint from that of each of the embodiments described above. Therefore, configurations referred to by the terms and reference signs below may differ from configurations referred to by similar terms and reference signs in each of the embodiments described above.
(Functional Configuration of Imaging Device 1)

Figure 67:
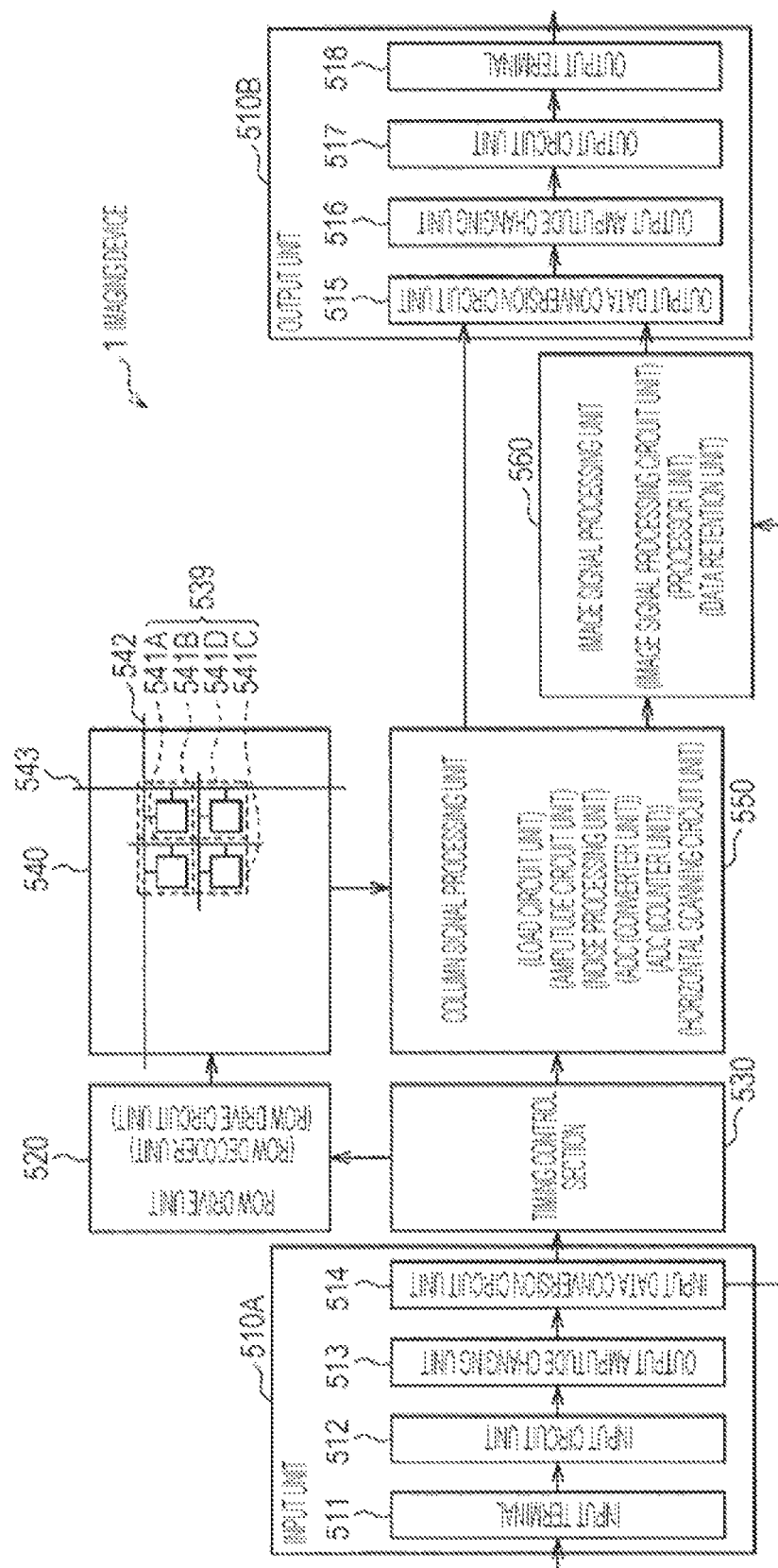
FIG. 67 is a block diagram representing an example of a functional configuration of an imaging device according to a seventh embodiment of the present disclosure.

FIG. 67 is a block diagram illustrating an example of a functional configuration of an imaging device (imaging device 1) according to the seventh embodiment of the present disclosure.

The imaging device 1 of FIG. 67 includes, for example, an input unit 510A, a row drive unit 520, a timing control section 530, a pixel array unit 540, a column signal processing unit 550, an image signal processing unit 560, and an output unit 510B.

Pixels 541 are repeatedly arranged in an array in the pixel array unit 540. More specifically, a pixel sharing unit 539 including a plurality of pixels forms a repeating unit, and such repeating units are repeatedly arranged in an array with a row direction and a column direction. Note that in this embodiment, for convenience, the row direction may be referred to as an H direction, and the column direction orthogonal to the row direction may be referred to as a V direction. In the example of FIG. 67, one pixel sharing unit 539 includes four pixels (pixels 541A, 541B, 541C, and 541D). The pixels 541A, 541B, 541C, and 541D each have a photodiode PD (illustrated in FIG. 72 and the like described later). The pixel sharing unit 539 is a unit that shares one pixel circuit (pixel circuit 210 in FIG. 69 described later). In other words, each of the four pixels (pixels 541A, 541B, 541C, and 541D) has one pixel circuit (pixel circuit 210 described later). By operating this pixel circuit in a time division manner, respective pixel signals of the pixels 541A, 541B, 541C, and 541D are sequentially read out. The pixels 541A, 541B, 541C, and 541D are arranged in, for example, two rows×two columns. The pixel array unit 540 is provided with a plurality of row drive signal lines 542 and a plurality of vertical signal lines (column readout lines) 543 together with the pixels 541A, 541B, 541C, and 541D. The row drive signal line 542 drives the pixels 541 included in each of a plurality of pixel sharing units 539 arranged to line up in the row direction in the pixel array unit 540. Among the pixel sharing units 539, each of pixels arranged to line up in the row direction is driven. As will be described in detail later with reference to FIG. 70, the pixel sharing unit 539 is provided with a plurality of transistors. In order to drive each of the plurality of transistors, a plurality of row drive signal lines 542 is connected to one pixel sharing unit 539. The pixel sharing unit 539 is connected to a vertical signal line (column readout line) 543. A pixel signal is read out from each of the pixels 541A, 541B, 541C, and 541D included in the pixel sharing unit 539 via the vertical signal line (column readout line) 543.

The row drive unit 520 includes, for example, a row address control section that determines a row position for pixel drive, in other words, a row decoder unit, and a row drive circuit unit that generates a signal for driving the pixels 541A, 541B, 541C, and 541D.

The column signal processing unit 550 includes, for example, a load circuit unit that is connected to the vertical signal line 543 and forms a source follower circuit with the pixels 541A, 541B, 541C, and 541D (pixel sharing unit 539). The column signal processing unit 550 may have an amplifier circuit unit that amplifies a signal read from the pixel sharing unit 539 via the vertical signal line 543. The column signal processing unit 550 may have a noise processing unit. In the noise processing unit, for example, the noise level of the system is removed from the signal read from the pixel sharing unit 539 as a result of photoelectric conversion.

The column signal processing unit 550 has, for example, an analog-to-digital converter (ADC). In the analog-to-digital converter, the signal read from the pixel sharing unit 539 or the noise-processed analog signal described above is converted into a digital signal. The ADC includes, for example, a comparator unit and a counter unit. In the comparator unit, the analog signal to be converted and a reference signal as a comparison target with this signal are compared. In the counter unit, the time until a comparison result in the comparator unit is inverted is measured. The column signal processing unit 550 may include a horizontal scanning circuit unit that performs control to scan a readout column.

The timing control section 530 supplies a signal for controlling timing to the row drive unit 520 and the column signal processing unit 550 on the basis of a reference clock signal and a timing control signal input to the device.

The image signal processing unit 560 is a circuit that performs various signal processing on data obtained as a result of photoelectric conversion, in other words, data obtained as a result of imaging operation in the imaging device 1. The image signal processing unit 560 includes, for example, an image signal processing circuit unit and a data retention unit. The image signal processing unit 560 may include a processor unit.

An example of signal processing executed by the image signal processing unit 560 is a tone curve correction process that increases gradations in a case where AD-converted imaging data is data obtained by imaging a dark subject, and decreases gradations in a case where it is data obtained by imaging a bright subject. In this case, it is desirable to store, in the data retention unit of the image signal processing unit 560 in advance, characteristic data of tone curve regarding the kind of the tone curve on the basis of which the gradations of imaging data are to be corrected.

The input unit 510A is for inputting, for example, the reference clock signal, the timing control signal, the characteristic data, and the like described above from the outside of the device to the imaging device 1. The timing control signal is, for example, a vertical synchronization signal and a horizontal synchronization signal, and the like. The characteristic data is, for example, for being stored in the data retention unit of the image signal processing unit 560. The input unit 510A includes, for example, an input terminal 511, an input circuit unit 512, an input amplitude changing unit 513, an input data conversion circuit unit 514, and a power supply unit (not illustrated).

The input terminal 511 is an external terminal for inputting data. The input circuit unit 512 is for taking a signal input to the input terminal 511 into the imaging device 1. In the input amplitude changing unit 513, the amplitude of the signal taken in by the input circuit unit 512 is changed to an amplitude that can be easily used inside the imaging device 1. In the input data conversion circuit unit 514, an arrangement of data strings of input data is changed. The input data conversion circuit unit 514 includes, for example, a serial-parallel conversion circuit. In this serial-parallel conversion circuit, a serial signal received as input data is converted into a parallel signal. Note that in the input unit 510A, the input amplitude changing unit 513 and the input data conversion circuit unit 514 may be omitted. The power supply unit provides power sources set to various voltages needed inside the imaging device 1 on the basis of the power source provided to the imaging device 1 from the outside.

When the imaging device 1 is connected to an external memory device, the input unit 510A may be provided with a memory interface circuit that receives data from the external memory device. The external memory device is, for example, flash memory, SRAM and DRAM, and the like.

The output unit 510B outputs image data to the outside of the device. The image data is, for example, image data of an image captured by the imaging device 1 and image data signal-processed by the image signal processing unit 560, and the like. The output unit 510B includes, for example, an output data conversion circuit unit 515, an output amplitude changing unit 516, an output circuit unit 517, and an output terminal 518.

The output data conversion circuit unit 515 includes, for example, a parallel-serial conversion circuit, and the output data conversion circuit unit 515 converts a parallel signal used inside the imaging device 1 into a serial signal. The output amplitude changing unit 516 changes the amplitude of a signal used inside the imaging device 1. The signal with a changed amplitude becomes readily available to an external device connected to the outside of the imaging device 1. The output circuit unit 517 is a circuit that outputs data from the inside of the imaging device 1 to the outside of the device, and the output circuit unit 517 drives wirings outside the imaging device 1 connected to the output terminal 518. At the output terminal 518, data is output from the imaging device 1 to the outside of the device. In the output unit 510B, the output data conversion circuit unit 515 and the output amplitude changing unit 516 may be omitted.

When the imaging device 1 is connected to an external memory device, the output unit 510B may be provided with a memory interface circuit that outputs data to the external memory device. The external memory device is, for example, flash memory, SRAM and DRAM, and the like.

(Schematic Configuration of Imaging Device 1)

Figure 68:
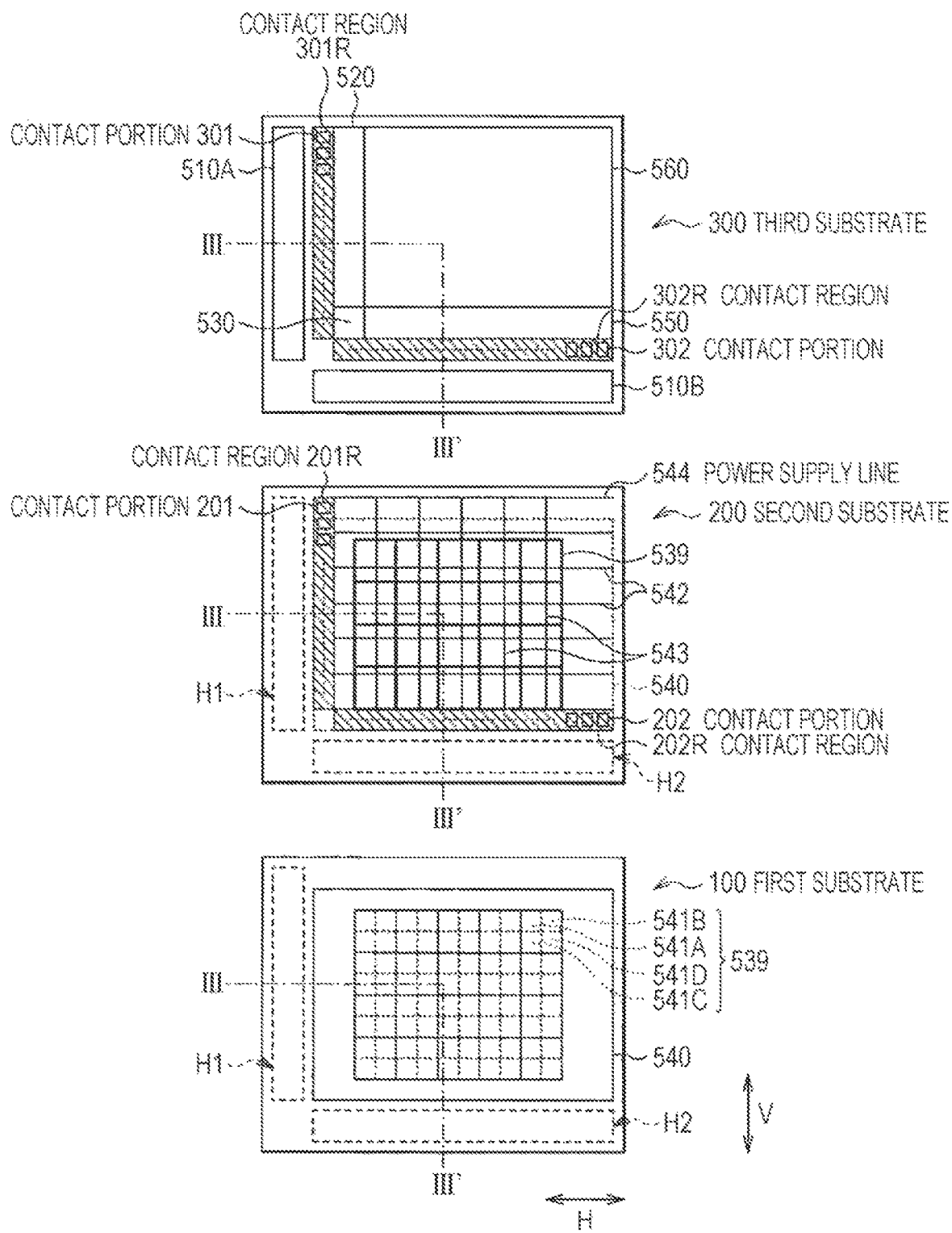
FIG. 68 is a schematic plan view representing a schematic configuration of the imaging device illustrated in FIG. 67.
Figure 69:
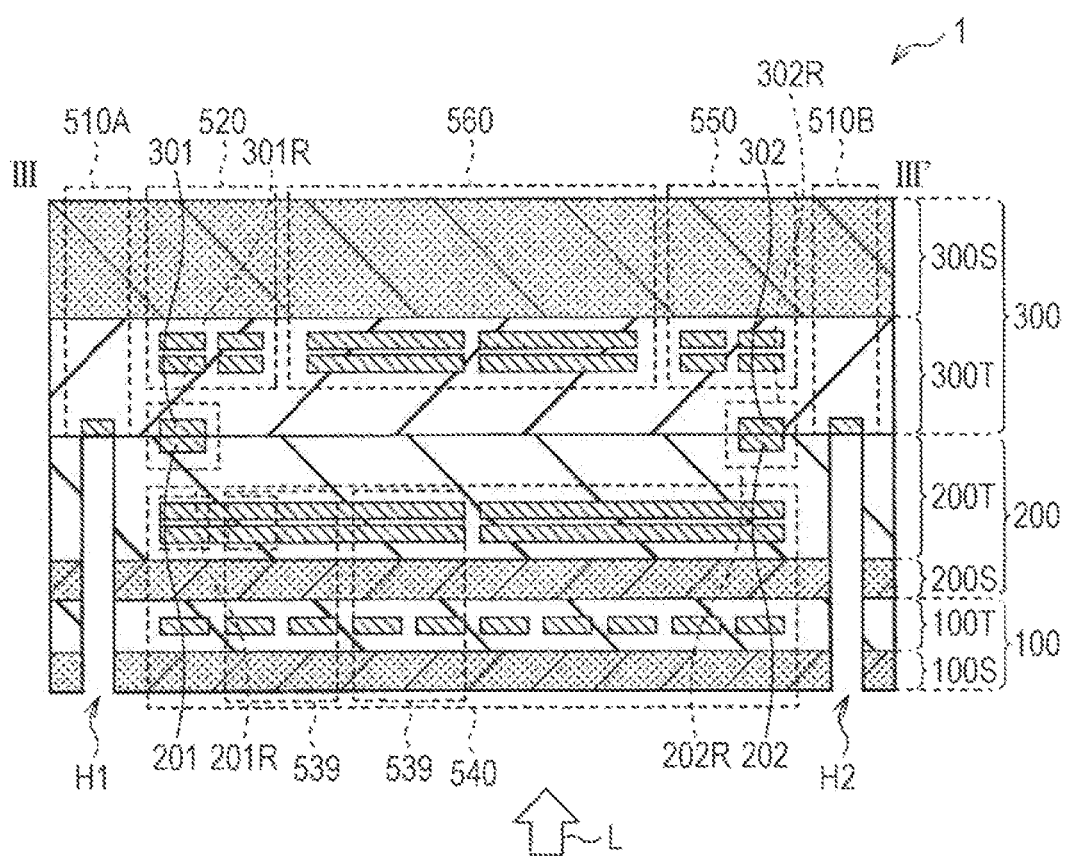
FIG. 69 is a schematic view representing a cross-sectional configuration taken along a line III-III' illustrated in FIG. 68.

FIGS. 68 and 69 illustrate an example of a schematic configuration of the imaging device 1. The imaging device 1 includes three substrates (a first substrate 100, a second substrate 200, and a third substrate 300). FIG. 68 schematically represents a planar configuration of each of the first substrate 100, the second substrate 200, and the third substrate 300, and FIG. 69 schematically represents cross-sectional configurations of the first substrate 100, the second substrate 200, and the third substrate 300 stacked on each other. FIG. 69 corresponds to a cross-sectional configuration taken along a line III-III' depicted in FIG. 68. The imaging device 1 is an imaging device having a three-dimensional structure formed by bonding three substrates (the first substrate 100, the second substrate 200, and the third substrate 300) together. The first substrate 100 includes a semiconductor layer 100S and a wiring layer 100T. The second substrate 200 includes a semiconductor layer 200S and a wiring layer 200T. The third substrate 300 includes a semiconductor layer 300S and a wiring layer 300T. Here, for convenience, a combination of wirings included in each of the first substrate 100, the second substrate 200, and the third substrate 300 and an interlayer insulating film around the substrate is called a wiring layer (100T, 200T, and 300T) that is provided on each of the substrates (the first substrate 100, the second substrate 200, and the third substrate 300). The first substrate 100, the second substrate 200, and the third substrate 300 are stacked in this order, and along the stacking direction, the semiconductor layer 100S, the wiring layer 100T, the semiconductor layer 200S, the wiring layer 200T, the wiring layer 300T, and the semiconductor layer 300S are arranged in this order. The specific configurations of the first substrate 100, the second substrate 200, and the third substrate 300 will be described later. An arrow illustrated in FIG. 69 indicates the direction of light L incident on the imaging device 1. In the present embodiment, for convenience, in the following cross-sectional views, the light incident side in the imaging device 1 may be referred to as "bottom", "lower side", and "below", and a side opposite to the light incident side will be referred to as "top", "upper side", and "above". Furthermore, in the present embodiment, for convenience, the side of the wiring layer may be referred to as a front surface and the side of the semiconductor layer may be referred to as a back surface, regarding the substrate provided with the semiconductor layer and the wiring layer. Note that the description of the specification is not limited to the terms described above. The imaging device 1 is, for example, a back-illuminated imaging device in which light is incident from the back surface side of the first substrate 100 having photodiodes.

Both the pixel array unit 540 and the pixel sharing units 539 included in the pixel array unit 540 are configured by using both the first substrate 100 and the second substrate 200. The first substrate 100 is provided with a plurality of pixels 541A, 541B, 541C, and 541D included in the pixel sharing units 539. Each of these pixels 541 has a photodiode (photodiode PD described later) and a transfer transistor (transfer transistor TR described later). The second substrate 200 is provided with a pixel circuit (pixel circuit 210 described later) included in the pixel sharing unit 539. The pixel circuit reads out a pixel signal transferred from the photodiode of each of the pixels 541A, 541B, 541C, and 541D via the transfer transistor, or resets the photodiode. In addition to such a pixel circuit, the second substrate 200 has a plurality of row drive signal lines 542 extending in the row direction and a plurality of vertical signal lines 543 extending in the column direction. The second substrate 200 further has a power supply line 544 extending in the row direction. The third substrate 300 has, for example, the input unit 510A, the row drive unit 520, the timing control section 530, the column signal processing unit 550, the image signal processing unit 560, and the output unit 510B. The row drive unit 520 is provided, for example, in a region partially overlapping with the pixel array unit 540 in the stacking direction of the first substrate 100, the second substrate 200, and the third substrate 300 (hereinafter, simply referred to as a stacking direction). More specifically, the row drive unit 520 is provided in a region overlapping with the vicinity of an end portion of the pixel array unit 540 in the H direction in the stacking direction (FIG. 68). The column signal processing unit 550 is provided, for example, in a region partially overlapping with the pixel array unit 540 in the stacking direction. More specifically, the column signal processing unit 550 is provided in a region overlapping with the vicinity of an end portion of the pixel array unit 540 in the V direction in the stacking direction (FIG. 68). Although not illustrated, the input unit 510A and the output unit 510B may be arranged in a portion other than the third substrate 300, and may be arranged in, for example, the second substrate 200. Alternatively, the input unit 510A and the output unit 510B may be provided on the back surface (light incident surface) side of the first substrate 100. Note that the pixel circuit provided on the second substrate 200 described above may also be referred to as a pixel transistor circuit, a pixel transistor group, a pixel transistor, a pixel readout circuit, or a readout circuit as another name. In the present embodiment, the term "pixel circuit" is used.

The first substrate 100 and the second substrate 200 are electrically connected by, for example, through electrodes (through electrodes 120E and 121E in FIG. 72 described later). The second substrate 200 and the third substrate 300 are electrically connected to each other via, for example, contact portions 201, 202, 301, and 302. The second substrate 200 is provided with the contact portions 201 and 202, and the third substrate 300 is provided with the contact portions 301 and 302. The contact portion 201 of the second substrate 200 is in contact with the contact portion 301 of the third substrate 300, and the contact portion 202 of the second substrate 200 is in contact with the contact portion 302 of the third substrate 300. The second substrate 200 has a contact region 201R provided with a plurality of contact portions 201, and a contact region 202R provided with a plurality of contact portions 202. The third substrate 300 has a contact region 301R provided with a plurality of contact portions 301, and a contact region 302R provided with a plurality of contact portions 302. The contact regions 201R and 301R are provided between the pixel array unit 540 and the row drive unit 520 in the stacking direction (FIG. 69). In other words, the contact regions 201R and 301R are provided in, for example, a region where the row drive unit 520 (third substrate 300) and the pixel array unit 540 (second substrate 200) overlap in the stacking direction, or provided near this region. The contact regions 201R and 301R are arranged, for example, at ends of such regions in the H direction (FIG. 68). In the third substrate 300, for example, the contact region 301R is provided at a position overlapping with a part of the row drive unit 520, specifically, an end portion of the row drive unit 520 in the H direction (FIGS. 68 and 69). The contact portions 201 and 301 connect, for example, the row drive unit 520 provided in the third substrate 300 and the row drive lines 542 provided in the second substrate 200. The contact portions 201 and 301 may, for example, connect the input unit 510A provided in the third substrate 300 and the power supply line 544 and a reference potential line (reference potential line VSS described later). The contact regions 202R and 302R are provided between the pixel array unit 540 and the column signal processing unit 550 in the stacking direction (FIG. 69). In other words, the contact regions 202R and 302R are provided in, for example, a region where the column signal processing unit 550 (third substrate 300) and the pixel array unit 540 (second substrate 200) overlap in the stacking direction, or provided near this region. The contact regions 202R and 302R are arranged, for example, at ends of such regions in the V direction (FIG. 68). In the third substrate 300, for example, the contact region 301R is provided at a position overlapping with a part of the column signal processing unit 550, specifically, an end portion of the column signal processing unit 550 in the V direction (FIGS. 68 and 69). For example, the contact portions 202 and 302 are for connecting pixel signals (signals corresponding to the amount of charges generated as a result of photoelectric conversion by the photodiodes) output from each of the plurality of pixel sharing units 539 included in the pixel array unit 540 to the column signal processing unit 550 provided in the third substrate 300. The pixel signals are sent from the second substrate 200 to the third substrate 300.

FIG. 69 is an example of a cross-sectional view of the imaging device 1 as described above. The first substrate 100, the second substrate 200, and the third substrate 300 are electrically connected via the wiring layers 100T, 200T, and 300T. For example, the imaging device 1 has an electrical connection portion that electrically connects the second substrate 200 and the third substrate 300. Specifically, the contact portions 201, 202, 301, and 302 are formed by electrodes formed by a conductive material. The conductive material is formed by, for example, a metal material such as copper (Cu), aluminum (Al), or gold (Au). The contact regions 201R, 202R, 301R, and 302R, for example, electrically connect the second substrate and the third substrate by directly joining wirings formed as electrodes to each other, enabling input and/or output of signals to and/or from the second substrate 200 and the third substrate 300.

The electrical connection portion that electrically connects the second substrate 200 and the third substrate 300 can be provided at a desired location. For example, as described as the contact regions 201R, 202R, 301R, and 302R in FIG. 69, they may be provided in regions that overlap the pixel array unit 540 in the stacking direction. Furthermore, the electrical connection portion may be provided in a region that does not overlap the pixel array unit 540 in the stacking direction. Specifically, the electrical connection portion may be provided in a region that overlaps a peripheral portion arranged outside the pixel array unit 540 in the stacking direction.

The first substrate 100 and the second substrate 200 are provided with connection holes H1 and H2, for example. The connection holes H1 and H2 penetrate the first substrate 100 and the second substrate 200 (FIG. 69). The connection holes H1 and H2 are provided outside the pixel array unit 540 (or a portion overlapping with the pixel array unit 540) (FIG. 68). For example, the connection hole H1 is arranged outside the pixel array unit 540 in the H direction, and the connection hole H2 is arranged outside the pixel array unit 540 in the V direction. For example, the connection hole H1 reaches the input unit 510A provided in the third substrate 300, and the connection hole H2 reaches the output unit 510B provided in the third substrate 300. The connection holes H1 and H2 may be hollow, and at least a part thereof may contain a conductive material. For example, there is a configuration in which a bonding wire is connected to an electrode formed as the input unit 510A and/or the output unit 510B. Alternatively, there is a configuration in which electrodes formed as the input unit 510A and/or the output unit 510B are connected to conductive materials provided in the connection holes H1 and H2. The conductive material provided in the connection holes H1 and H2 may be embedded in a part or all of the connection holes H1 and H2, or the conductive material may be formed on side walls of the connection holes H1 and H2.

Note that in FIG. 69, in the structure, the third substrate 300 is provided with the input unit 510A and the output unit 510B, but it is not limited to this. For example, the input unit 510A and/or the output unit 510B can be provided in the second substrate 200 by sending signals of the third substrate 300 to the second substrate 200 via the wiring layers 200T and 300T. Similarly, the input unit 510A and/or the output unit 510B can be provided in the first substrate 100 by sending signals of the second substrate 200 to the first substrate 1000 via the wiring layers 100T and 200T.

Figure 70:
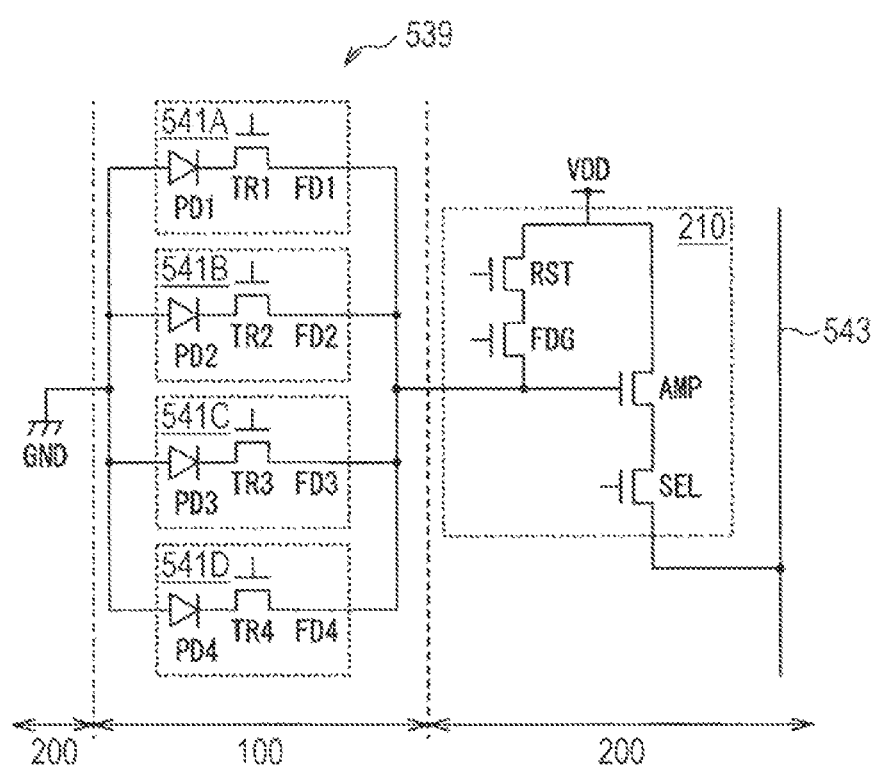
FIG. 70 is an equivalent circuit diagram of a pixel sharing unit illustrated in FIG. 67.

FIG. 70 is an equivalent circuit diagram representing an example of a configuration of the pixel sharing unit 539. The pixel sharing unit 539 includes a plurality of pixels 541 (four pixels 541 of pixels 541A, 541B, 541C, and 541D are represented in FIG. 70), one pixel circuit 210 connected to the plurality of pixels 541, and a vertical signal line 5433 connected to the pixel circuit 210. The pixel circuit 210 includes, for example, four transistors, specifically, an amplification transistor AMP, a selection transistor SEL, a reset transistor RST, and an FD conversion gain switching transistor FD. As described above, by operating one pixel circuit 210 in a time division manner, the pixel sharing unit 539 sequentially outputs respective pixel signals of the four pixels 541 (pixels 541A, 541B, 541C, and 541D) included in the pixel sharing unit 539 to the vertical signal line 543. The mode that one pixel circuit 210 is connected to the plurality of pixels 541 and the pixel signals of the plurality of pixels 541 are output in a time division manner by the one pixel circuit 210 is described as "a plurality of pixels 541 share one pixel circuit 210."

The pixels 541A, 541B, 541C, and 541D have components in common with each other. Hereinafter, in order to distinguish components of the pixels 541A, 541B, 541C, and 541D from each other, an identification number 1 is added to the ends of the reference signs of components of the pixel 541A, an identification number 2 is added to the ends of the reference signs of components of the pixel 541B, an identification number 3 is added to the ends of the reference signs of components of the pixel 541C, and an identification number 4 is added to the ends of the reference signs of components of pixel 541D. In a case where it is not necessary to distinguish the components of the pixels 541A, 541B, 541C, and 541D from each other, the identification numbers at the ends of the reference signs of components of the pixels 541A, 541B, 541C, and 541D are omitted.

The pixels 541A, 541B, 541C, and 541D each have, for example, a photodiode PD, a transfer transistor TR electrically connected to the photodiode PD, and a floating diffusion FD electrically connected to the transfer transistor TR. In the photodiode PD (PD1, PD2, PD3, PD4), a cathode is electrically connected to a source of the transfer transistor TR, and an anode is electrically connected to a reference potential line (for example, ground). The photodiode PD photoelectrically converts incident light and generates a charge corresponding to the amount of received light. The transfer transistor TR (transfer transistor TR1, TR2, TR3, TR4) is, for example, an n-type complementary metal oxide semiconductor (CMOS) transistor. In the transfer transistor TR, a drain is electrically connected to the floating diffusion FD and a gate is electrically connected to the drive signal line. This drive signal line is a part of the plurality of row drive signal lines 542 (see FIG. 67) connected to one pixel sharing unit 539. The transfer transistor TR transfers the charge generated by the photodiode PD to the floating diffusion FD. The floating diffusion FD (floating diffusion FD1, FD2, FD3, FD4) is an n-type diffusion layer region formed in a p-type semiconductor layer. The floating diffusion FD is a charge holding means that temporarily holds the charge transferred from the photodiode PD and is a charge-voltage conversion means that generates a voltage corresponding to the amount of the charge.

The four floating diffusions FD (floating diffusions FD1, FD2, FD3, and FD4) included in one pixel sharing unit 539 are electrically connected to each other, and electrically connected to a gate of the amplification transistor AMP and a source of the FD conversion gain switching transistor FDG. A drain of the FD conversion gain switching transistor FDG is connected to a source of the reset transistor RST, and a gate of the FD conversion gain switching transistor FDG is connected to the drive signal line. This drive signal line is a part of the plurality of row drive signal lines 542 connected to one pixel sharing unit 539. A drain of the reset transistor RST is connected to the power supply line VDD, and a gate of the reset transistor RST is connected to the drive signal line. This drive signal line is a part of the plurality of row drive signal lines 542 connected to one pixel sharing unit 539. The gate of the amplification transistor AMP is connected to the floating diffusion FD, a drain of the amplification transistor AMP is connected to the power supply line VDD, and a source of the amplification transistor AMP is connected to a drain of the selection transistor SEL. A source of the selection transistor SEL is connected to the vertical signal line 543, and a gate of the selection transistor SEL is connected to the drive signal line. This drive signal line is a part of the plurality of row drive signal lines 542 connected to one pixel sharing unit 539.

When the transfer transistor TR is turned on, the transfer transistor TR transfers the charge of the photodiode PD to the floating diffusion FD. A gate of the transfer transistor TR (transfer gate TG) includes, for example, what is called a vertical electrode, and is provided to extend to a depth reaching the PD from a surface of the semiconductor layer (semiconductor layer 100S in FIG. 72 described later) as illustrated in FIG. 72 described later. The reset transistor RST resets the potential of the floating diffusion FD to a predetermined potential. When the reset transistor RST is turned on, the potential of the floating diffusion FD is reset to the potential of the power supply line VDD. The selection transistor SEL controls the output timing of a pixel signal from the pixel circuit 210. The amplification transistor AMP generates as a pixel signal a signal with a voltage corresponding to the level of a charge held in the floating diffusion FD. The amplification transistor AMP is connected to the vertical signal line 543 via the selection transistor SEL. This amplification transistor AMP forms a source follower together with the load circuit unit (see FIG. 67) connected to the vertical signal line 543 in the column signal processing unit 550. When the selection transistor SEL is turned on, the amplification transistor AMP outputs the voltage of the floating diffusion FD to the column signal processing unit 550 via the vertical signal line 543. The reset transistor RST, the amplification transistor AMP, and the selection transistor SEL are, for example, n-type CMOS transistors.

The FD conversion gain switching transistor FDG is used to change the gain of charge-voltage conversion in a floating diffusion FD. Generally, the pixel signal is small when capturing an image in a dark place. If capacitance of the floating diffusion FD (FD capacitance C) is large when performing charge-voltage conversion based on Q=CV, V when converted to voltage by the amplification transistor AMP becomes small. On the other hand, in a bright place, the pixel signal becomes large, and thus unless the FD capacitance C is large, the floating diffusion FD cannot receive the charge of the photodiode PD. Moreover, the FD capacitance C needs to be large so that V when converted to voltage by the amplification transistor AMP does not become too large (in other words, so that it becomes small). Based on these factors, when the FD conversion gain switching transistor FDG is turned on, the gate capacitance for the amount of the FD conversion gain switching transistor FDG increases, and thus the overall FD capacitance C increases. On the other hand, when the FD conversion gain switching transistor FDG is turned off, the overall FD capacitance C decreases. In this manner, by switching the FD conversion gain switching transistor FDG on and off, the FD capacitance C can be made variable and the conversion efficiency can be switched. The FD conversion gain switching transistor FDG is, for example, an n-type CMOS transistor.

Note that a configuration without providing the FD conversion gain switching transistor FDG is also possible. At this time, for example, the pixel circuit 210 includes three transistors, for example, the amplification transistor AMP, the selection transistor SEL, and the reset transistor RST. The pixel circuit 210 has at least one of pixel transistors such as, for example, the amplification transistor AMP, the selection transistor SEL, the reset transistor RST, and the FD conversion gain switching transistor FDG.

The selection transistor SEL may be provided between the power supply line VDD and the amplification transistor AMP. In this case, the drain of the reset transistor RST is electrically connected to the power supply line VDD and the drain of the selection transistor SEL. The source of the selection transistor SEL is electrically connected to the drain of the amplification transistor AMP, and the gate of the selection transistor SEL is electrically connected to the row drive signal line 542 (see FIG. 67). The source of the amplification transistor AMP (output end of the pixel circuit 210) is electrically connected to the vertical signal line 543, and the gate of the amplification transistor AMP is electrically connected to a source of the reset transistor RST. Note that although not illustrated, the number of pixels 541 sharing one pixel circuit 210 may be other than four. For example, two or eight pixels 541 may share one pixel circuit 210.

Figure 71:
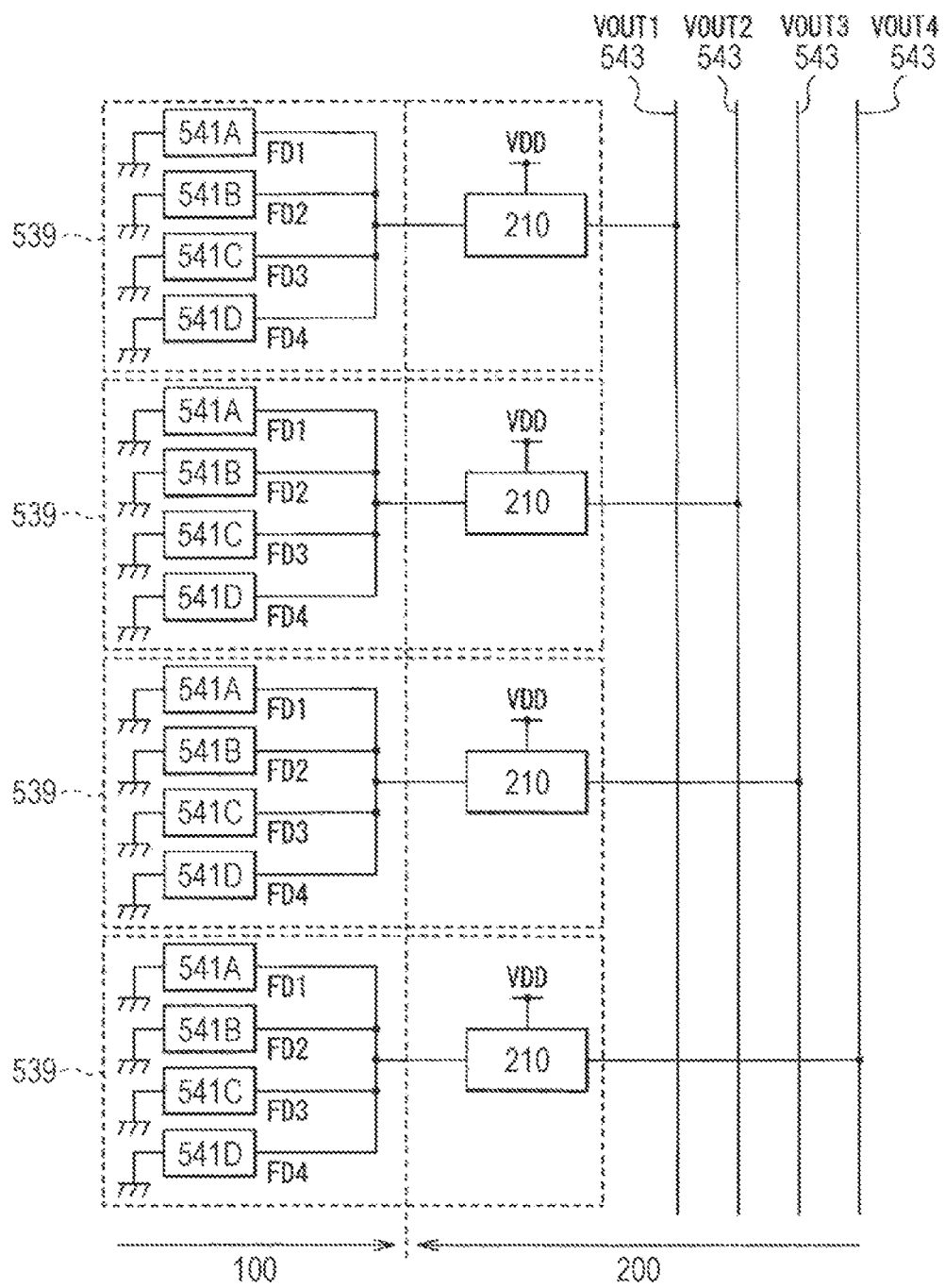
FIG. 71 is a diagram representing an example of a connection mode of a plurality of pixel sharing units and a plurality of vertical signal lines.

FIG. 71 represents an example of a connection mode of the plurality of pixel sharing units 539 and the vertical signal line 543. For example, four pixel sharing units 539 arranged in a column direction are divided into four groups, and the vertical signal line 543 is connected to each of the four groups. FIG. 71 illustrates an example in which each of the four groups has one pixel sharing unit 539 for simplicity of description, but each of the four groups may include a plurality of pixel sharing units 539. As described above, in the imaging device 1, the plurality of pixel sharing units 539 lined up in the column direction may be divided into groups including one or more pixel sharing units 539. For example, the vertical signal line 543 and the column signal processing circuit 550 are connected to each of these groups, and pixel signals can be read out from the respective groups at the same time. Alternatively, in the imaging device 1, one vertical signal line 543 may be connected to a plurality of pixel sharing units 539 lined up in the column direction. At this time, pixel signals are sequentially read out in a time-division manner from the plurality of pixel sharing units 539 connected to one vertical signal line 543.

(Specific Configuration of Imaging Device 1)

Figure 72:
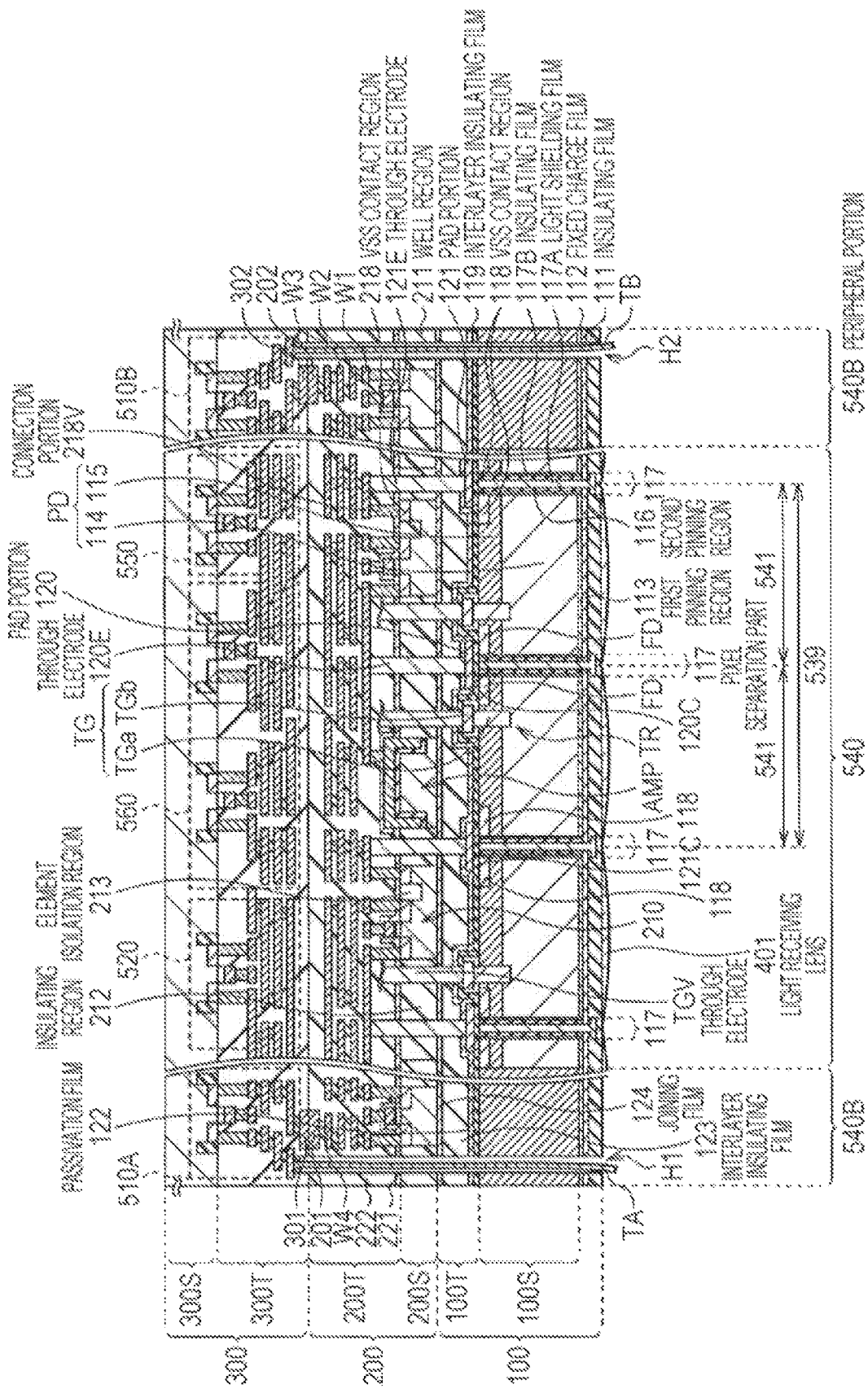
FIG. 72 is a schematic cross-sectional view representing an example of a specific configuration of the imaging device illustrated in FIG. 69.

FIG. 72 represents an example of a cross-sectional configuration in a direction perpendicular to main surfaces of the first substrate 100, the second substrate 100, and the third substrate 300 of the imaging device 1. FIG. 72 is a schematic representation for making it easier to understand a positional relationship of components, and may differ from an actual cross section. In the imaging device 1, the first substrate 100, the second substrate 200, and the third substrate 300 are stacked in this order. The imaging device 1 further has a light receiving lens 401 on the back surface side (light incident surface side) of the first substrate 100. A color filter layer (not illustrated) may be provided between the light receiving lens 401 and the first substrate 100. The light receiving lens 401 is provided for each of the pixels 541A, 541B, 541C, and 541D, for example. The imaging device 1 is, for example, a back-illuminated imaging device. The imaging device 1 has the pixel array unit 540 arranged in a central portion and a peripheral portion 540B arranged outside the pixel array unit 540.

The first substrate 100 has an insulating film 111, a fixed charge film 112, a semiconductor layer 100S, and a wiring layer 100T in this order from the light receiving lens 401 side. The semiconductor layer 100S includes, for example, a silicon substrate. The semiconductor layer 100S has, for example, a p-well layer 115 in a part of a surface (a surface on the wiring layer 100T side) and a vicinity thereof, and has an n-type semiconductor region 114 in another region (a region deeper than the p-well layer 115). For example, the n-type semiconductor region 114 and the p-well layer 115 constitute a pn junction type photodiode PD. The p-well layer 115 is a p-type semiconductor region.

Figure 73A:
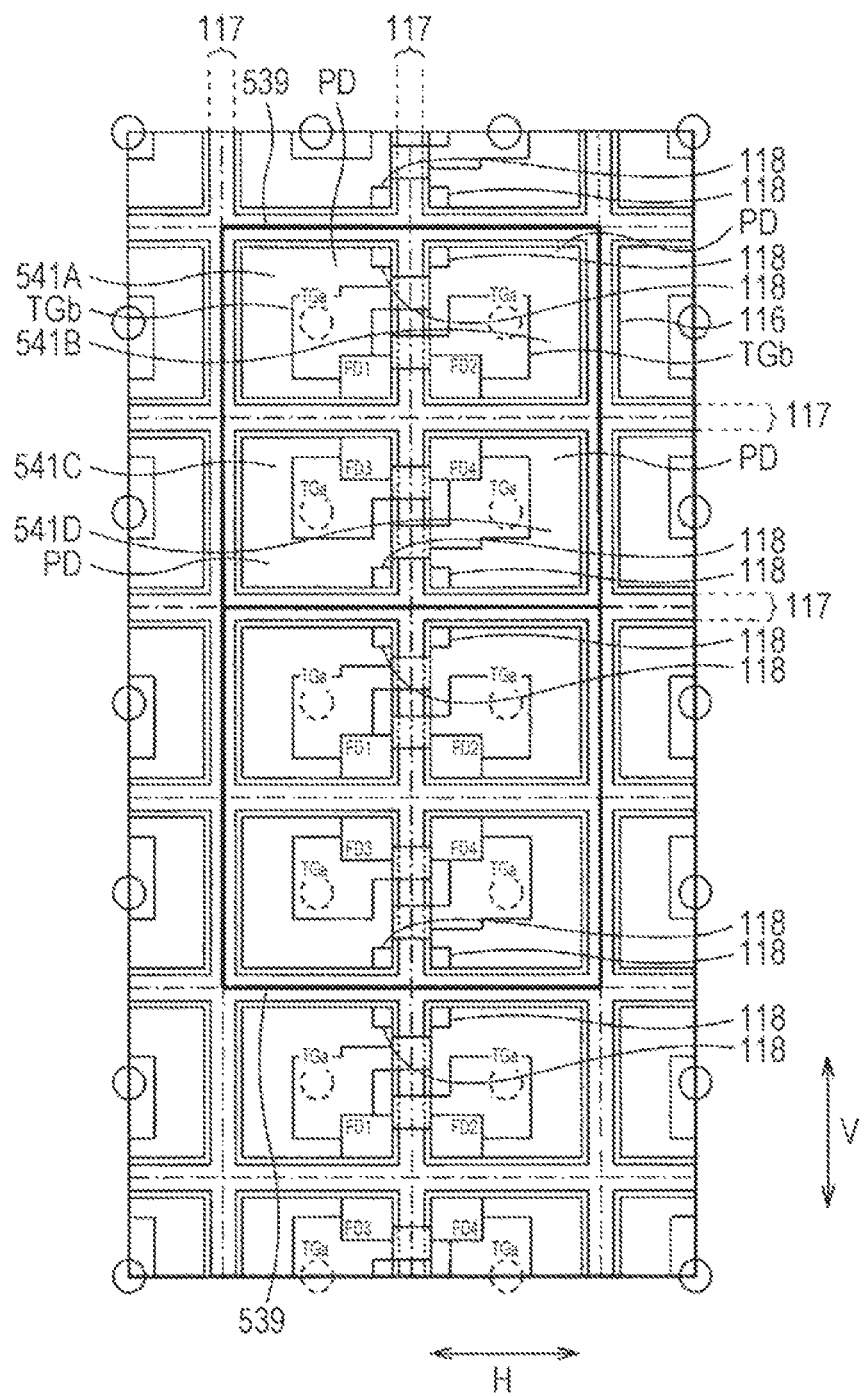
FIG. 73A is a schematic view representing an example of a planar configuration of a main part of a first substrate illustrated in FIG. 72.

FIG. 73A illustrates an example of a planar configuration of the first substrate 100. FIG. 73A mainly represents planar configurations of a pixel separation part 117, the photodiode PD, the floating diffusion FD, a VSS contact region 118, and the transfer transistor TR of the first substrate 100. The configuration of the first substrate 100 will be described using FIG. 73A together with FIG. 72.

The floating diffusion FD and the VSS contact region 118 are provided near the surface of the semiconductor layer 100S. The floating diffusion FD includes an n-type semiconductor region provided in the p-well layer 115. The respective floating diffusions FD (floating diffusions FD1, FD2, FD3, and FD4) of the pixels 541A, 541B, 541C, and 541D are provided close to each other, for example, in a central portion of the pixel sharing unit 539 (FIG. 73A). Although details will be described later, the four floating diffusions (floating diffusions FD1, FD2, FD3, and FD4) included in this sharing unit 539 are electrically connected to each other via an electrical connection means (pad portion 120 described later) in the first substrate 100 (more specifically, in the wiring layer 100T). Moreover, the floating diffusions FD are connected from the first substrate 100 to the second substrate 200 (more specifically, from the wiring layer 100T to the wiring layer 200T) via electrical means (through electrodes 120E described later). In the second substrate 200 (more specifically, inside the wiring layer 200T), the electrical means electrically connect the floating diffusion FD to the gate of the amplification transistor AMP and the source of the FD conversion gain switching transistor FDG.

The VSS contact region 118 is a region electrically connected to the reference potential line VSS, and is arranged apart from the floating diffusion FD. For example, in pixels 541A, 541B, 541C, and 541D, the floating diffusion FD is arranged at one end in the V direction of each pixel, and the VSS contact region 118 is arranged at the other end (FIG. 73A). The VSS contact region 118 includes, for example, a p-type semiconductor region. The VSS contact region 118 is connected to, for example, a ground potential or a fixed potential. Thus, the reference potential is supplied to the semiconductor layer 100S.

The first substrate 100 is provided with the transfer transistor TR together with the photodiode PD, the floating diffusion FD, and the VSS contact region 118. These photodiode PD, floating diffusion FD, VSS contact region 118, and transfer transistor TR are provided in each of the pixels 541A, 541B, 541C, and 541D. The transfer transistor TR is provided on the front surface side of the semiconductor layer 100S (side opposite to the light incident surface side, the second substrate 200 side). The transfer transistor TR has a transfer gate TG. The transfer gate TG includes, for example, a horizontal portion TGb facing the front surface of the semiconductor layer 100S and a vertical portion TGa provided in the semiconductor layer 100S. The vertical portion TGa extends in a thickness direction of the semiconductor layer 100S. One end of the vertical portion TGa is in contact with the horizontal portion TGb, and the other end is provided in the n-type semiconductor region 114. By forming the transfer transistor TR by such a vertical transistor, it is possible to reduce the occurrence of transfer failure of pixel signal and improve the pixel signal reading efficiency.

The horizontal portion TGb of the transfer gate TG extends from a position facing the vertical portion TGa, for example, toward the central portion of the pixel sharing unit 539 in the H direction (FIG. 73A). Thus, the position of the through electrode (through electrode TGV described later) reaching the transfer gate TG in the H direction can be made close to the position of the H direction of the through electrodes (through electrodes 120E and 121E described later) connected to the floating diffusion FD and VSS contact region 118. For example, the plurality of pixel sharing units 539 provided on the first substrate 100 have the same configuration as each other (FIG. 73A).

Figure 73B:
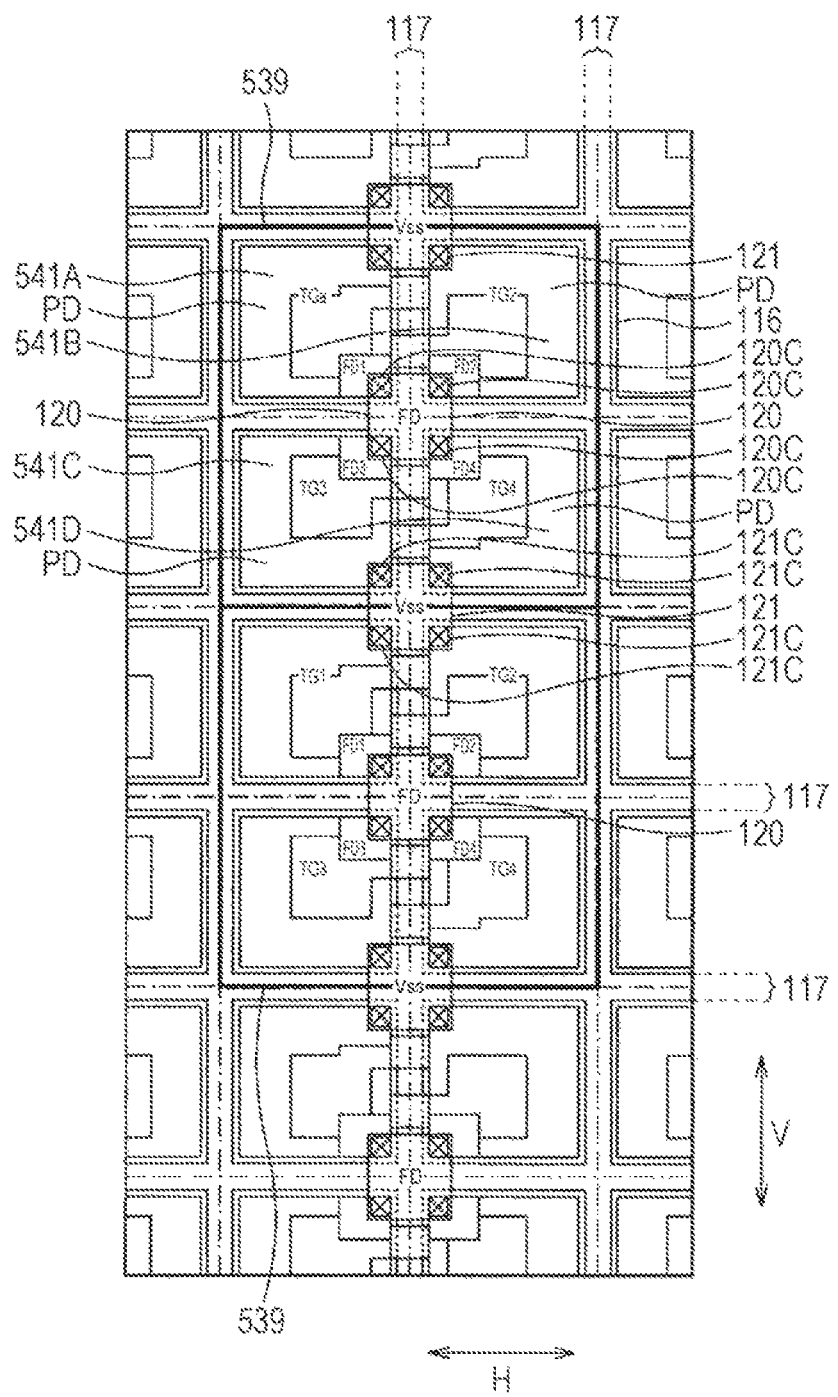
FIG. 73B is a schematic view representing a planar configuration of a pad portion together with the main part of the first substrate illustrated in FIG. 73A.

The semiconductor layer 100S is provided with the pixel separation part 117 that separates pixels 541A, 541B, 541C, and 541D from each other. The pixel separation part 117 is formed so as to extend in a normal direction of the semiconductor layer 100S (direction perpendicular to the surface of the semiconductor layer 100S). The pixel separation part 117 is provided so as to partition the pixels 541A, 541B, 541C, and 541D from each other, and has, for example, a grid-like planar shape (FIGS. 73A and 73B). The pixel separation part 117 electrically and optically separates the pixels 541A, 541B, 541C, and 541D from each other, for example. The pixel separation part 117 includes, for example, a light shielding film 117A and an insulating film 117B. For the light shielding film 117A, for example, tungsten (W) or the like is used. The insulating film 117B is provided between the light shielding film 117A and the p-well layer 115 or the n-type semiconductor region 114. The insulating film 117B includes, for example, a silicon oxide (SiO). The pixel separation part 117 has, for example, a full trench isolation (FTI) structure and penetrates the semiconductor layer 100S. Although not illustrated, the pixel separation part 117 is not limited to the FTI structure penetrating the semiconductor layer 100S. For example, it may have a deep trench isolation (DTI) structure that does not penetrate the semiconductor layer 100S. The pixel separation part 117 extends in the normal direction of the semiconductor layer 100S and is formed in a part of the semiconductor layer 100S.

The semiconductor layer 100S is provided with, for example, a first pinning region 113 and a second pinning region 116. The first pinning region 113 is provided near the back surface of the semiconductor layer 100S, and is arranged between the n-type semiconductor region 114 and the fixed charge film 112. The second pinning region 116 is provided on a side surface of the pixel separation part 117, specifically, between the pixel separation part 117 and the p-well layer 115 or the n-type semiconductor region 114. The first pinning region 113 and the second pinning region 116 include, for example, a p-type semiconductor region.

The fixed charge film 112 having a negative fixed charge is provided between the semiconductor layer 100S and the insulating film 111. An electric field induced by the fixed charge film 112 forms the first pinning region 113 of a hole storage layer at an interface on the light receiving surface (back surface) side of the semiconductor layer 100S. Thus, generation of dark current due to an interface state on the light receiving surface side of the semiconductor layer 100S is suppressed. The fixed charge film 112 is formed by, for example, an insulating film having a negative fixed charge. Examples of the material of the insulating film having a negative fixed charge include hafnium oxide, zircon oxide, aluminum oxide, titanium oxide, and tantalum oxide.

A light shielding film 117A is provided between the fixed charge film 112 and the insulating film 111. The light shielding film 117A may be provided continuously with the light shielding film 117A forming the pixel separation part 117. The light shielding film 117A between the fixed charge film 112 and the insulating film 111 is selectively provided at a position facing the pixel separation part 117 in the semiconductor layer 100S, for example. The insulating film 111 is provided so as to cover the light shielding film 117A. The insulating film 111 includes, for example, a silicon oxide.

The wiring layer 100T provided between the semiconductor layer 100S and the second substrate 200 has an interlayer insulating film 119, pad portions 120 and 121, a passivation film 122, an interlayer insulating film 123, and a joining film 124 in this order from the semiconductor layer 100S side. The horizontal portion TGb of the transfer gate TG is provided in this wiring layer 100T, for example. The interlayer insulating film 119 is provided over the entire surface of the semiconductor layer 100S and is in contact with the semiconductor layer 100S. The interlayer insulating film 119 is formed by, for example, a silicon oxide film. Note that the configuration of the wiring layer 100T is not limited to the above, and is only required to be a configuration having a wiring and an insulating film.

FIG. 73B represents configurations of the pad portions 120 and 121 together with the planar configuration illustrated in FIG. 73A. The pad portions 120 and 121 are provided in a selective region on the interlayer insulating film 119. The pad portion 120 is for connecting the floating diffusions FD (floating diffusions FD1, FD2, FD3, and FD4) of the pixels 541A, 541B, 541C, and 541D to each other. For every pixel sharing unit 539, the pad portion 120 is arranged, for example, at the central portion of the pixel sharing unit 539 in a plan view (FIG. 73B). The pad portion 120 is provided so as to straddle the pixel separation part 117, and is arranged so as to overlap with at least a part of each of the floating diffusions FD1, FD2, FD3, and FD4 (FIGS. 72 and 73B). Specifically, the pad portion 120 is formed in a region that overlaps, in a direction perpendicular to the surface of the semiconductor layer 100S, at least a part of each of the plurality of floating diffusions FD (floating diffusions FD1, FD2, FD3, and FD4) sharing the pixel circuit 210, and at least a part of the pixel separation part 117 formed among the plurality of photodiodes PDs (photodiodes PD1, PD2, PD3, and PD4) sharing the pixel circuit 210. The interlayer insulating film 119 is provided with a connection via 120C for electrically connecting the pad portion 120 and the floating diffusions FD1, FD2, FD3, and FD4. The connection via 120C is provided for each of the pixels 541A, 541B, 541C, and 541D. For example, by embedding a part of the pad portion 120 in the connection via 120C, the pad portion 120 and the floating diffusion FD1, FD2, FD3, and FD4 are electrically connected.

The pad portion 121 is for connecting a plurality of VSS contact regions 118 to each other. For example, the VSS contact regions 118 provided in the pixels 541C and 541D of one pixel sharing unit 539 adjacent in the V direction and the VSS contact regions 118 provided in the pixels 541A and 541B of the other pixel sharing unit 539 are electrically connected by the pad portion 121. The pad portion 121 is provided so as to straddle the pixel separation part 117, for example, and is arranged so as to overlap with at least a part of each of these four VSS contact regions 118. Specifically, the pad portion 121 is formed in a region that overlaps, in the direction perpendicular to the surface of the semiconductor layer 100S, at least a part of each of the plurality of VSS contact regions 118 and at least a part of the pixel separation part 117 formed among the plurality of VSS contact regions 118. The interlayer insulating film 119 is provided with a connection via 121C for electrically connecting the pad portion 121 and the VSS contact region 118. The connection via 121C is provided for each of the pixels 541A, 541B, 541C, and 541D. For example, by embedding a part of the pad portion 121 in the connection via 121C, the pad portion 121 and the VSS contact region 118 are electrically connected. For example, the pad portions 120 and the pad portions 121 of each of the plurality of pixel sharing units 539 lined up in the V direction are arranged at substantially the same positions in the H direction (FIG. 73B).

By providing the pad portions 120, it is possible to reduce the wirings for connecting each floating diffusion FD to the pixel circuit 210 (for example, the gate electrode of the amplification transistor AMP) in the entire chip. Similarly, by providing the pad portions 121, it is possible to reduce the wirings that supply the potential to each VSS contact region 118 in the entire chip. Thus, reducing the area of the entire chip, suppressing electrical interference between wirings in miniaturized pixels, and/or reducing costs by reducing the number of parts, and the like are possible.

The pad portions 120 and 121 can be provided at desired positions on the first substrate 100 and the second substrate 200. Specifically, the pad portions 120 and 121 can be provided in either the wiring layer 100T or the insulating region 212 of the semiconductor layer 200S. In a case of providing in the wiring layer 100T, the pad portions 120 and 121 may be brought into direct contact with the semiconductor layer 100S. Specifically, a configuration may be employed in which the pad portions 120 and 121 are directly connected to at least a part of each of the floating diffusions FD and/or the VSS contact regions 118. Furthermore, a configuration may be employed in which the connection vias 120C and 121C are provided from each of the floating diffusions FD and/or the VSS contact regions 118 connected to the pad portions 120 and 121, and the pad portions 120 and 121 are provided at desired positions in the wiring layer 100T and the insulating region 2112 of the semiconductor layer 200S.

In particular, in a case where the pad portions 120 and 121 are provided in the wiring layer 100T, wirings connected to the floating diffusions FD and/or the VSS contact regions 118 in the insulating region 212 of the semiconductor layer 200S can be reduced. Thus, in the second substrate 200 for forming the pixel circuit 210, the area of the insulating region 212 for forming the through wirings for connecting the floating diffusions FD to the pixel circuit 210 can be reduced. Therefore, a large area of the second substrate 200 for forming the pixel circuits 210 can be secured. By securing the area for the pixel circuits 210, large pixel transistors can be formed, which can contribute to improvement of image quality by reducing noise and the like.

In particular, in a case where the FTI structure is used for the pixel separation part 117, it is preferable that the floating diffusions FD and/or the VSS contact regions 118 are provided in each pixel 541. Thus, by using the configuration of the pad portions 120 and 121, the wirings connecting the first substrate 100 and the second substrate 200 can be significantly reduced.

Further, as illustrated in FIG. 73B, for example, the pad portion 120 to which the plurality of floating diffusions FD is connected and the pad portion 121 to which the plurality of VSS contacts 118 is connected are alternately arranged linearly in the V direction. Furthermore, the pad portions 120 and 121 are formed at positions surrounded by the plurality of photodiode PDs, the plurality of transfer gates TGs, and the plurality of floating diffusions FD. Thus, in the first substrate 100 for forming a plurality of elements, elements other than the floating diffusions FD and the VSS contact regions 118 can be freely arranged, and layout efficiency of the entire chip can be improved. Furthermore, the symmetry in layout of the elements formed in each pixel sharing unit 539 is ensured, and variations in characteristics of each pixel 541 can be suppressed.

The pad portions 120 and 121 include, for example, polysilicon (Poly Si), more specifically, doped polysilicon to which impurities are added. It is preferable that the pad portions 120 and 121 are formed by a conductive material having high heat resistance such as polysilicon, tungsten (W), titanium (Ti), and titanium nitride (TiN). Thus, the pixel circuit 210 can be formed after the semiconductor layer 200S of the second substrate 200 is bonded to the first substrate 100. The reason for this will be described below. Note that in the following description, a method of forming the pixel circuit 210 after bonding the first substrate 100 and the semiconductor layer 200S of the second substrate 200 together will be referred to as a first manufacturing method.

Here, it is also conceivable that the pixel circuit 210 is formed on the second substrate 200 and then the second substrate 200 is bonded to the first substrate 100 (hereinafter referred to as a second manufacturing method). In this second manufacturing method, electrodes for electrical connection are formed in advance on each of a surface of the first substrate 100 (surface of the wiring layer 100T) and a surface of the second substrate 200 (surface of the wiring layer 200T). When the first substrate 100 and the second substrate 200 are bonded together, at the same time, the electrodes for electrical connection formed on each of the surface of the first substrate 100 and the surface of the second substrate 200 come into contact with each other. Thus, electrical connection is formed between the wirings included in the first substrate 100 and the wirings included in the second substrate 200. Therefore, with the configuration of the imaging device 1 using the second manufacturing method, for example, it is possible to manufacture by using an appropriate process according to the respective configurations of the first substrate 100 and the second substrate 200, and thus it is possible to manufacture high-quality, high-performance imaging devices.

In such a second manufacturing method, when the first substrate 100 and the second substrate 200 are bonded together, an alignment error may occur due to the manufacturing apparatus for bonding. Furthermore, the first substrate 100 and the second substrate 200 have a size of, for example, about several tens of cm in diameter, and when the first substrate 100 and the second substrate 200 are bonded together, expansion and contraction of the substrates may occur in microscopic regions of respective parts of the first substrate 100 and the second substrate 200. The expansion and contraction of the substrates are caused by a slight shift in the timing of contact between the substrates. Due to such expansion and contraction of the first substrate 100 and the second substrate 200, it is possible that an error occurs in the positions of the electrodes for electrical connection formed on each of the surface of the first substrate 100 and the surface of the second substrate 200. In the second manufacturing method, it is preferable to take measures so that the respective electrodes of the first substrate 100 and the second substrate 200 are in contact with each other even if such an error occurs. Specifically, at least one of the electrodes of the first substrate 100 and the second substrate 200 is, or preferably both are, increased in consideration of the error described above. Therefore, when the second manufacturing method is used, for example, the sizes of the electrodes formed on the surface of the first substrate 100 or the second substrate 200 (sizes in a plane direction of the substrate) become larger than the sizes of the internal electrodes extending from the inside of the first substrate 100 or the second substrate 200 to the surface in the thickness direction.

On the other hand, by forming the pad portions 120 and 121 with a heat-resistant conductive material, the first manufacturing method described above can be used. In the first manufacturing method, after forming the first substrate 100 including the photodiodes PD and the transfer transistors TR, and so on, the first substrate 100 and the second substrate 200 (semiconductor layer 2000S) are bonded together. At this time, the second substrate 200 is in a state in which a pattern of active elements and wiring layers and so on constituting the pixel circuit 210 are not formed. Since the second substrate 200 is in a state before forming the pattern, even if an error occurs in the bonding positions when the first substrate 100 and the second substrate 200 are bonded, the bonding error will not cause an error in the alignment between the pattern of the first substrate 100 and the pattern of the second substrate 200. This is because the pattern of the second substrate 200 is formed after the first substrate 100 and the second substrate 200 are bonded together. Note that when the pattern is formed on the second substrate, for example, the pattern is formed while taking the pattern formed on the first substrate as a target for alignment in an exposure apparatus for pattern formation. For the reason described above, the error in the bonding positions between the first substrate 100 and the second substrate 200 does not pose a problem in manufacturing the imaging device 1 by the first manufacturing method. For a similar reason, the error caused by the expansion and contraction of the substrate caused by the second manufacturing method does not pose a problem in manufacturing the imaging device 1 by the first manufacturing method.

In the first manufacturing method, after the first substrate 100 and the second substrate 200 (semiconductor layer 200S) are bonded together in this way, active elements are formed on the second substrate 200. Thereafter, through electrodes 120E and 121E and through electrodes TGV (FIG. 72) are formed. In formation of the through electrodes 120E, 121E, and TGV, for example, a pattern of the through electrodes is formed from above the second substrate 200 by using reduced projection exposure by an exposure apparatus. Since the reduced exposure projection is used, even if an error occurs in alignment between the second substrate 200 and the exposure apparatus, the magnitude of the error is only a fraction (the reciprocal of the reduced exposure projection magnification) of the error in the second manufacturing method described above in the second substrate 200. Thus, by forming the imaging device 1 using the first manufacturing method, it is easy to align the respective elements formed on the first substrate 100 and the second substrate 200, and it is possible to manufacture imaging devices with high quality and high performance.

The imaging device 1 manufactured by using such a first manufacturing method has different characteristics from the imaging device manufactured by the second manufacturing method. Specifically, in the imaging device 1 manufactured by the first manufacturing method, for example, the through electrodes 120E, 121E, and TGV have substantially constant thicknesses (sizes in the substrate plane direction) from the second substrate 200 to the first substrate 100). Alternatively, when the through electrodes 120E, 121E, and TGV have a tapered shape, they have a tapered shape with a constant inclination. In the imaging device 1 having such through electrodes 120E, 121E, and TGV, the pixels 541 can be easily miniaturized.

Here, when the imaging device 1 is manufactured by the first manufacturing method, since the active elements are formed on the second substrate 200 after the first substrate 100 and the second substrate 200 (semiconductor layer 200S) are bonded together, the first substrate 100 is also affected by a heat treatment required for forming the active elements. Therefore, as described above, it is preferable to use a conductive material having high heat resistance for the pad portions 120 and 121 provided on the first substrate 100. For example, for the pad portions 120 and 121, it is preferable to use a material having a higher melting point (that is, higher heat resistance) than at least a part of the wiring material contained in the wiring layer 200T of the second substrate 200. For example, a conductive material having high heat resistance such as doped polysilicon, tungsten, titanium, or titanium nitride is used for the pad portions 120 and 121. Thus, it is possible to manufacture the imaging device 1 by using the first manufacturing method described above.

The passivation film 122 is provided over the entire surface of the semiconductor layer 100S so as to cover, for example, the pad portions 120 and 121 (FIG. 72). The passivation film 122 is formed by, for example, a silicon nitride (SiN) film. The interlayer insulating film 123 covers the pad portions 120 and 121 with the passivation film 122 in between. The interlayer insulating film 123 is provided over the entire surface of the semiconductor layer 100S, for example. The interlayer insulating film 123 is formed by, for example, a silicon oxide (SiO) film. The joining film 124 is provided on joining surfaces of the first substrate 100 (specifically, the wiring layer 100T) and the second substrate 200. That is, the joining film 124 is in contact with the second substrate 200. This joining film 124 is provided over the entire main surface of the first substrate 100. The joining film 124 is formed by, for example, a silicon nitride film.

The light receiving lens 401 faces the semiconductor layer 100S with the fixed charge film 112 and the insulating film 111 in between, for example (FIG. 72). The light receiving lens 401 is provided at a position facing each of the photodiodes PD of the pixels 541A, 541B, 541C, and 541D, for example.

The second substrate 200 has the semiconductor layer 200S and the wiring layer 200T in this order from the first substrate 100 side. The semiconductor layer 200S is formed by a silicon substrate. In the semiconductor layer 200S, the well region 211 is provided over the thickness direction. The well region 211 is, for example, a p-type semiconductor region. The second substrate 20 is provided with pixel circuits 210 arranged for every pixel sharing unit 539. The pixel circuit 210 is provided, for example, on a front surface side (wiring layer 200T side) of the semiconductor layer 200S. In the imaging device 1, the second substrate 200 is bonded to the first substrate 100 so that a back surface side (semiconductor layer 200S side) of the second substrate 200 faces the front surface side (wiring layer 100T side) of the first substrate 100. That is, the second substrate 200 is bonded to the first substrate 100 face-to-back.

Figure 74:
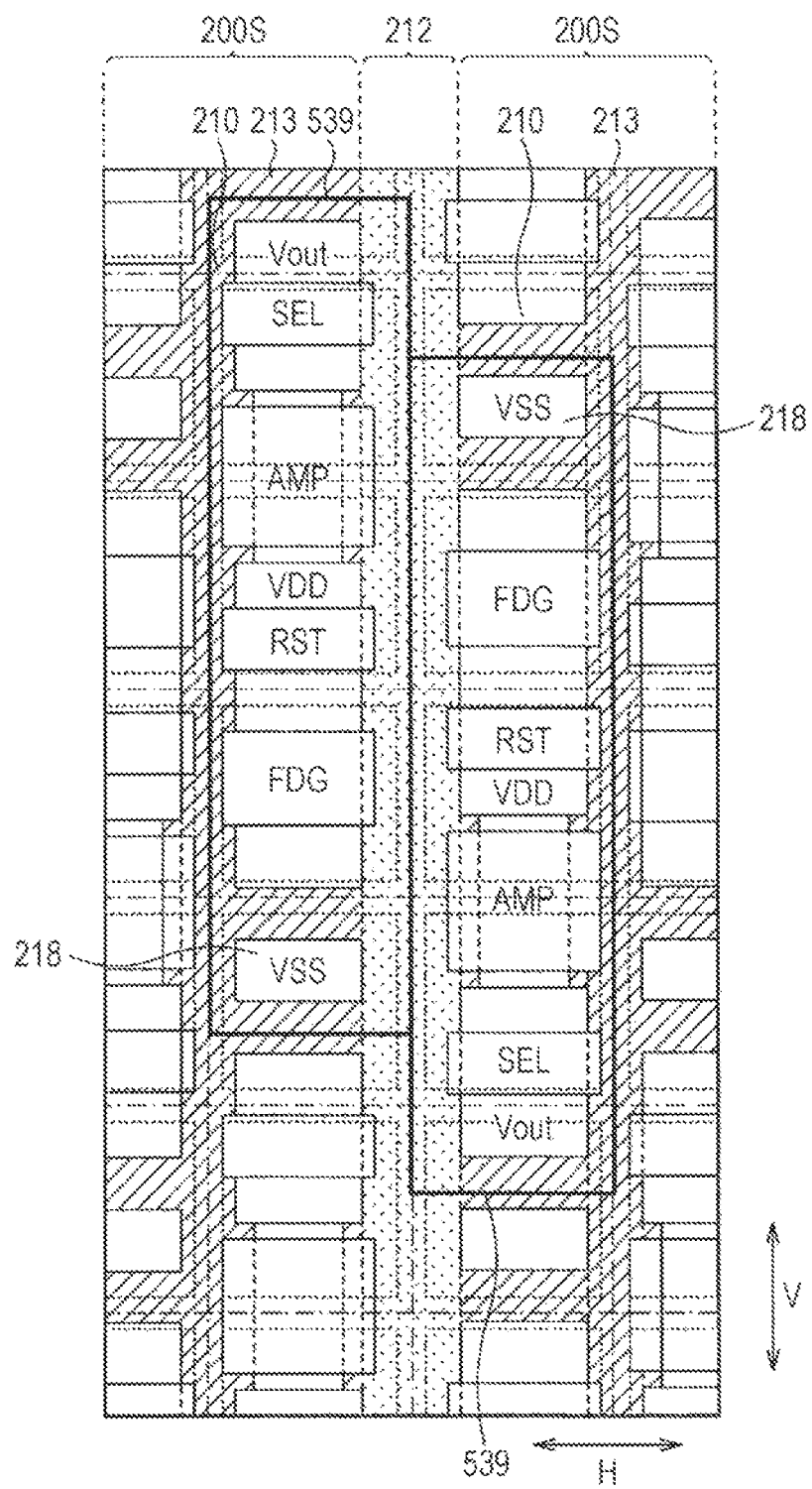
FIG. 74 is a schematic view representing an example of a planar configuration of a second substrate (semiconductor layer) illustrated in FIG. 72.
Figure 75:
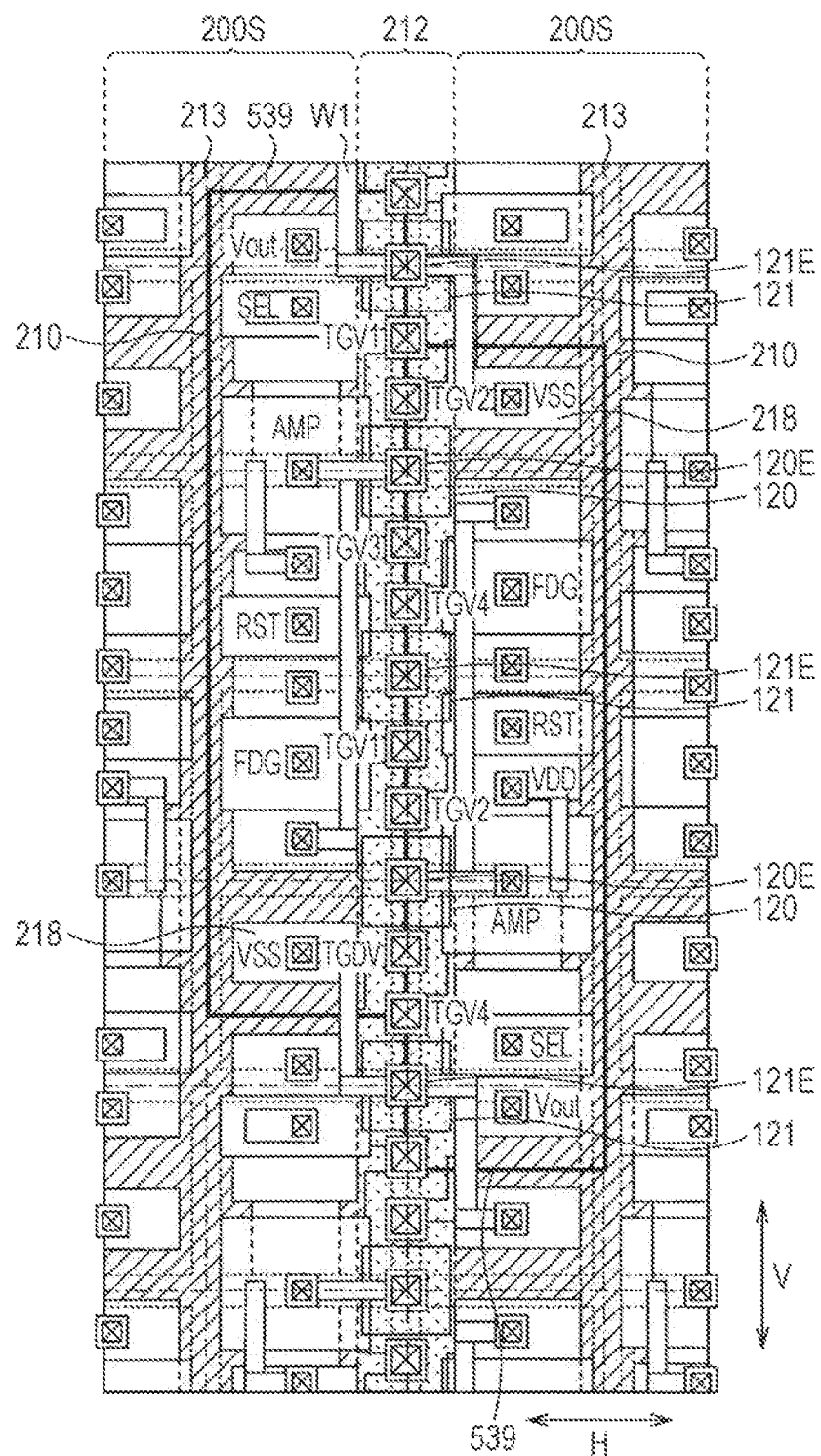
FIG. 75 is a schematic view representing an example of a planar configuration of a pixel circuit and the main part of the first substrate together with a first wiring layer illustrated in FIG. 72.
Figure 76:
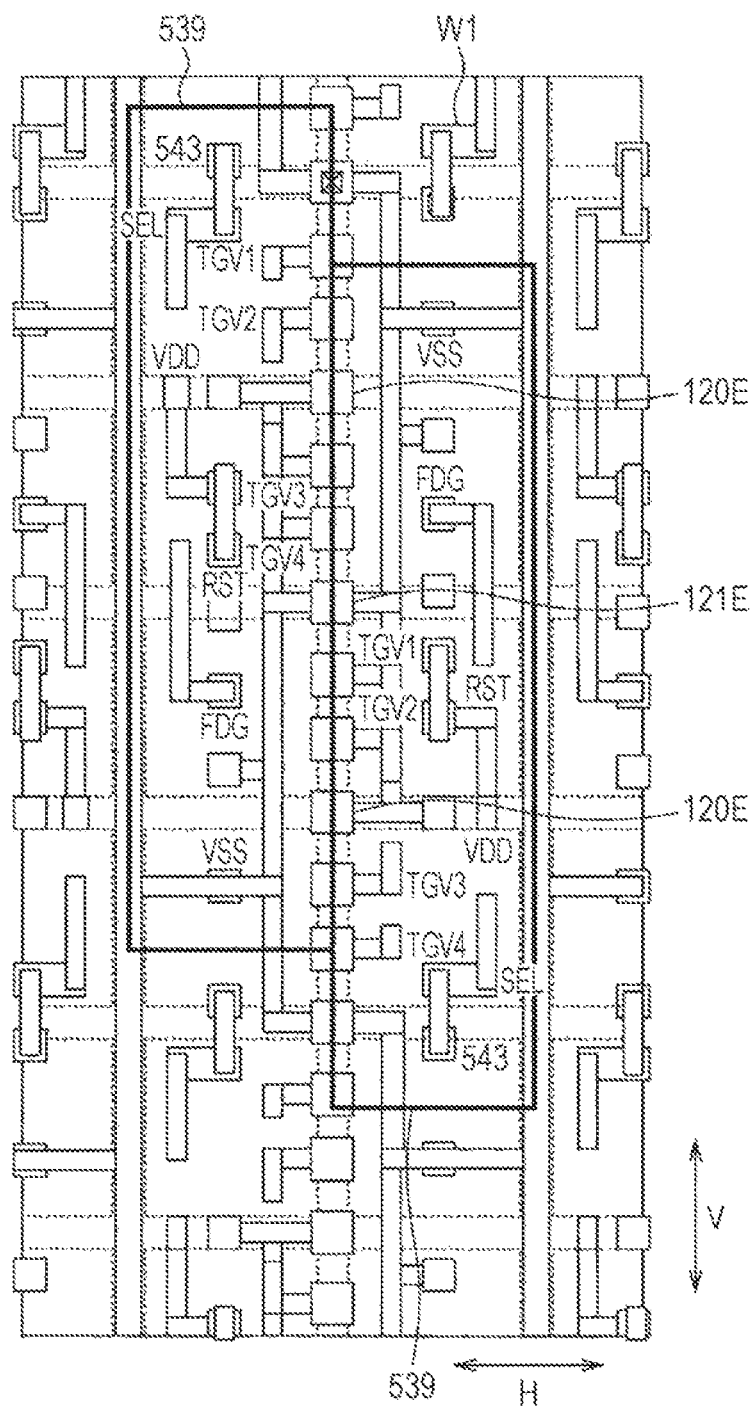
FIG. 76 is a schematic view representing an example of planar configurations of the first wiring layer and a second wiring layer illustrated in FIG. 72.
Figure 77:
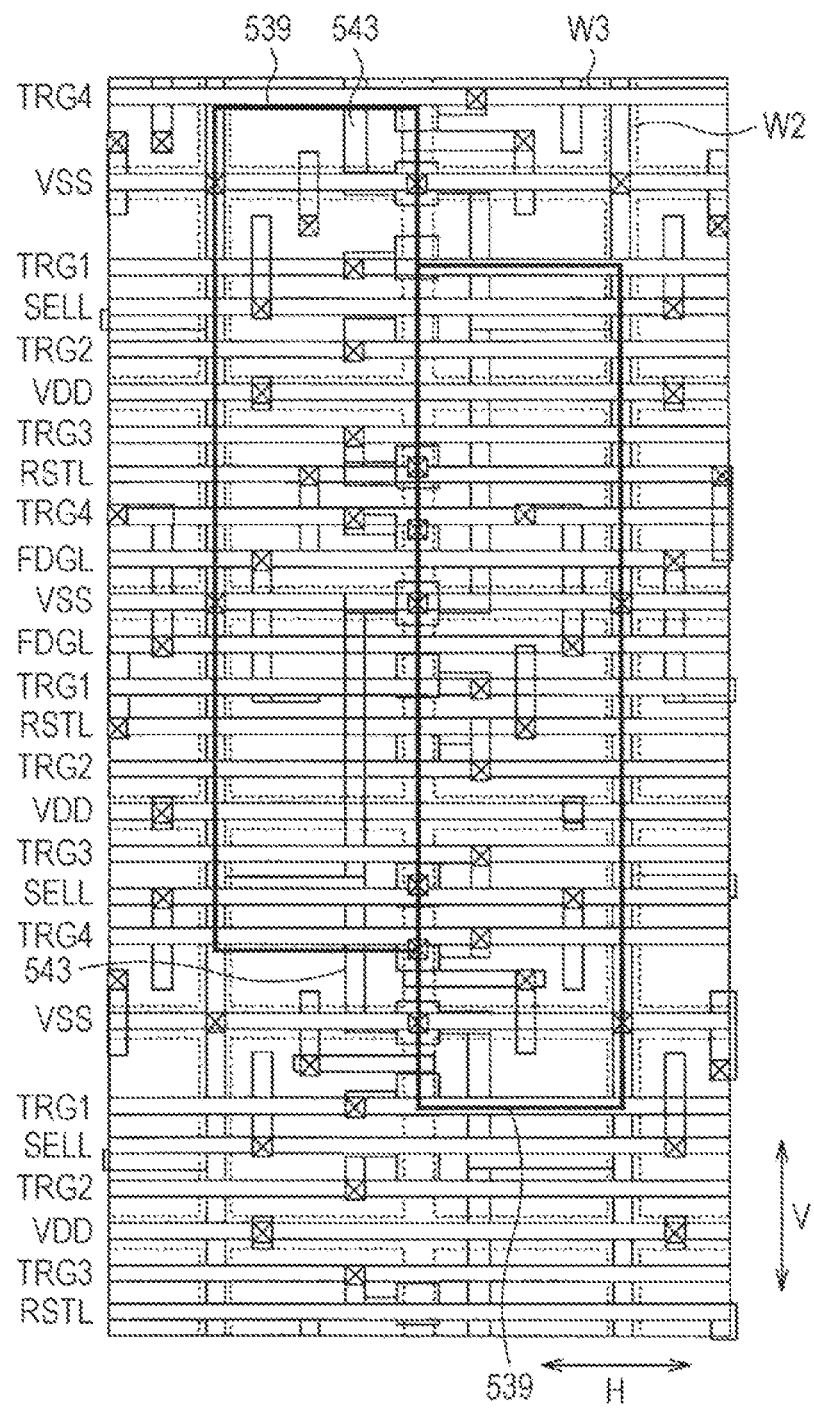
FIG. 77 is a schematic view representing an example of planar configurations of the second wiring layer and a third wiring layer illustrated in FIG. 72.
Figure 78:
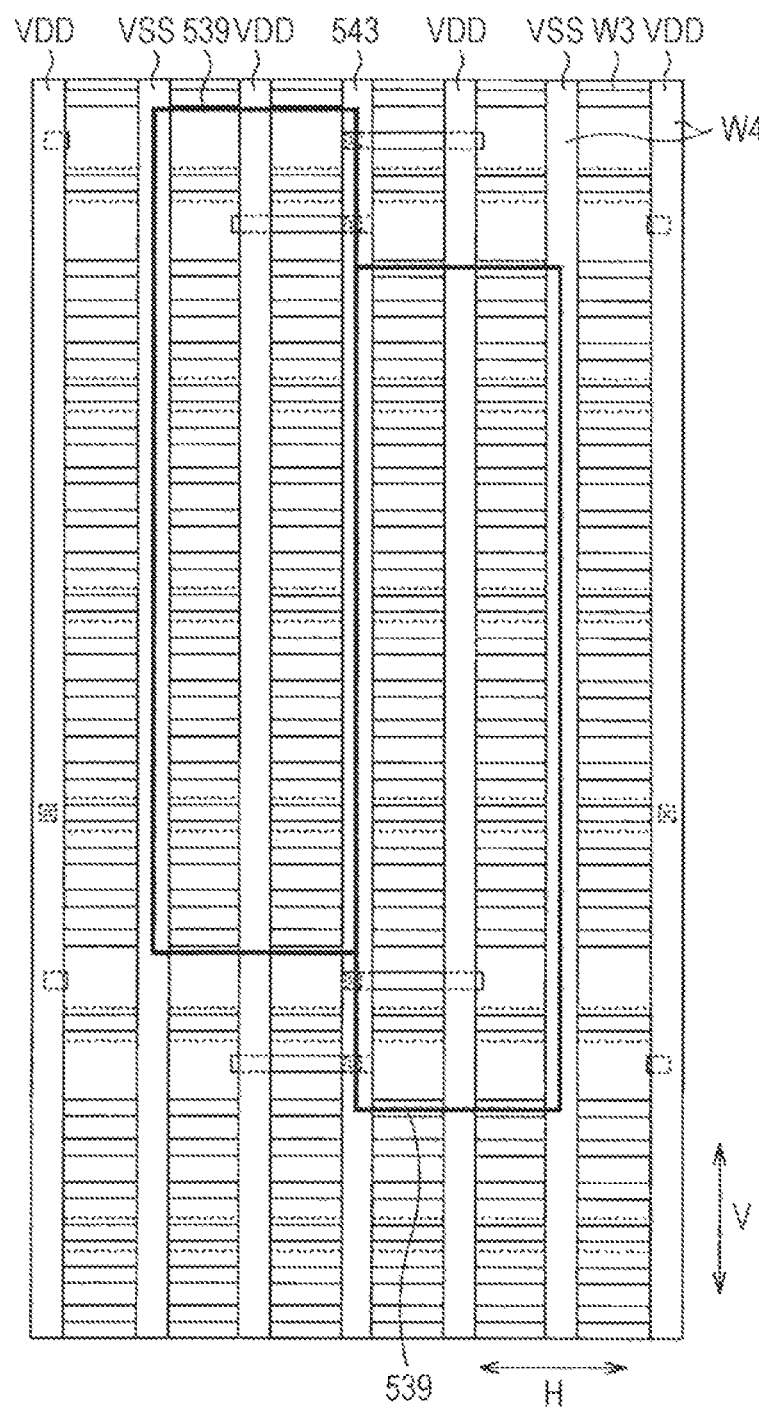
FIG. 78 is a schematic view representing an example of planar configurations of the third wiring layer and a fourth wiring layer illustrated in FIG. 72.

FIGS. 74 to 78 schematically represent examples of planar configurations of the second substrate 200. FIG. 74 illustrates the configuration of the pixel circuit 210 provided near a surface of the semiconductor layer 200S. FIG. 75 schematically illustrates configurations of respective parts of the wiring layer 200T (specifically, a first wiring layer W1 described later), the semiconductor layer 200S connected to the wiring layer 200T, and the first substrate 100. FIGS. 76 to 78 represent examples of planar configurations of the wiring layer 200T. Hereinafter, the configuration of the second substrate 200 will be described with reference to FIGS. 74 to 78 together with FIG. 72. In FIGS. 74 and 75, an outer shape of a photodiode PD (boundary between the pixel separation part 117 and the photodiode PD) is represented by a dashed line, and the boundary between the semiconductor layer 200S at a portion overlapping with the gate electrode of each transistor constituting the pixel circuit 210 and the element isolation region 213 or the insulating region 214 is represented by a dotted line. In a portion overlapping with the gate electrode of the amplification transistor AMP, the boundary between the semiconductor layer 200S and the element isolation region 213 and the boundary between the element isolation region 213 and the insulating region 213 are provided on one side in a channel width direction.

The second substrate 200 is provided with the insulating region 212 for dividing the semiconductor layer 200S and the element isolation region 213 provided in a part of the semiconductor layer 200S in the thickness direction (FIG. 72). For example, in the insulating region 212 provided between two pixel circuits 210 adjacent to each other in the H direction, the through electrodes 120E and 121E and the through electrodes TGV (through electrodes TGV1, TGV2, TGV3, and TGV4) of the two pixel sharing units 539 connected to these two pixel circuits 210 are arranged (FIG. 75).

The insulating region 212 has substantially the same thickness as the thickness of the semiconductor layer 200S (FIG. 72). The semiconductor layer 200S is divided by this insulating region 212. The through electrodes 120E and 121E and the through electrodes TGV are arranged in this insulating region 212. The insulating region 212 includes, for example, a silicon oxide.

The through electrodes 120E and 121E are provided so as to penetrate the insulating region 212 in the thickness direction. The upper ends of the through electrodes 120E and 121E are connected to wirings of the wiring layer 200T (first wiring W1, second wiring W2, third wiring W3, and fourth wiring W4, which will be described later). The through electrodes 120E and 121E are provided so as to penetrate the insulating region 212, the joining film 124, the interlayer insulating film 123, and the passivation film 122, and their lower ends are connected to the pad portions 120, 121 (FIG. 72). The through electrode 120E is for electrically connecting the pad portion 120 and the pixel circuit 210.

That is, the through electrode 120E electrically connects the floating diffusion FD of the first substrate 100 to the pixel circuit 210 of the second substrate 200. The through electrode 121E is for electrically connecting the pad portion 121 and the reference potential line VSS of the wiring layer 200T. That is, the through electrode 121E electrically connects the VSS contact region 118 of the first substrate 100 to the reference potential line VSS of the second substrate 200.

The through electrode TGV is provided so as to penetrate the insulating region 212 in the thickness direction. An upper end of the through electrode TGV is connected to the wiring of the wiring 200T. The through electrode TGV is provided so as to penetrate the insulating region 212, the joining film 124, the interlayer insulating film 123, the passivation film 122, and the interlayer insulating film 119, and a lower end thereof is connected to the transfer gate TG (FIG. 72). Such a through electrode TGV is for electrically connecting the transfer gate TG (transfer gate TG1, TG2, TG3, TG4) of each of the pixels 541A, 541B, 541C, and 541D and a wiring of the wiring layer 200T (a part of the row drive signal line 542, specifically, wiring TRG1, TRG2, TRG3, TRG4 of FIG. 77, which will be described later). That is, the transfer gate TG of the first substrate 100 is electrically connected to the wiring TRG of the second substrate 200 by the through electrode TGV, and a drive signal is sent to each of the transfer transistors TR (transfer transistors TR1, TR2, TR3, and TR4).

The insulating region 212 is a region for providing the through electrodes 120E and 121E and the through electrodes TGV for electrically connecting the first substrate 100 and the second substrate 200, by insulating from the semiconductor layer 200S. For example, in the insulating region 212 provided between two pixel circuits 210 (sharing unit 539) adjacent to each other in the H direction, the through electrodes 120E, 121E and through electrodes TGV (through electrodes TGV1, TGV2, TGV3, and TGV4) connected to these two pixel circuits 210 are arranged. The insulating region 212 is provided, for example, extending in the V direction (FIGS. 74 and 75). Here, by devising the arrangement of the horizontal portion TGb of the transfer gate TG, the positions of the through electrodes TGV in the H direction are arranged closer to the positions of the through electrodes 120E and 121E in the H direction as compared with the positions of the vertical portions TGa (FIG. 73A and FIG. 75). For example, the through electrodes TGV are arranged at substantially the same positions as the through electrodes 120E and 120E in the H direction. Thus, the through electrodes 120E and 121E and the through electrodes TGV can be provided together in the insulating region 212 extending in the V direction. As another arrangement example, it is conceivable to provide the horizontal portions TGb only in the region overlapping with the vertical portions TGa. In this case, the through electrode TGV is formed substantially directly above the vertical portion TGa, and for example, the through electrode TGV is arranged in a substantially central portion of each pixel 541 in the H direction and the V direction. At this time, the position of the through electrode TGV in the H direction and the positions of the through electrodes 120E and 121E in the H direction deviate largely. For example, the insulating region 212 is provided around the through electrode TGV and the through electrodes 120E and 121E in order to electrically insulate them from the adjacent semiconductor layer 200S. In a case where the position of the through electrode TGV in the H direction and the positions of the through electrodes 120E and 121E in the H direction are largely separated, it is necessary to independently provide the insulating region 212 around each of the through electrodes 120E, 121E, and TGV. Thus, the semiconductor layer 200S is minutely divided. On the other hand, in the layout in which the through electrodes 120E and 121E and the through electrodes TGV are arranged together in the insulating region 212 extending in the V direction, the size of the semiconductor layer 200S in the H direction can be increased. Therefore, a large area of the semiconductor element forming region in the semiconductor layer 200S can be secured. Thus, it becomes possible, for example, to increase the size of the amplification transistor AMP and suppress noise.

As described with reference to FIG. 70, the pixel sharing unit 539 has a structure in which the respective floating diffusions FD provided in the plurality of pixels 541 are electrically connected, and the plurality of pixels 541 shares one pixel circuit 210. Then, the electrical connection among the floating diffusions FD is made by the pad portion 120 provided on the first substrate 100 (FIGS. 72 and 73B). The electrical connection portion (pad portion 120) provided on the first substrate 100 and the pixel circuit 210 provided on the second substrate 200 are electrically connected via one through electrode 120E. As another structural example, it is conceivable to provide the electrical connection portion among the floating diffusions FD on the second substrate 200. In this case, the pixel sharing unit 539 is provided with four through electrodes connected to the floating diffusions FD1, FD2, FD3, and FD4, respectively. Therefore, in the second substrate 200, the number of through electrodes penetrating the semiconductor layer 200S increases, and the insulating region 212 that insulates the periphery of these through electrodes becomes large. On the other hand, in the structure in which the pad portion 120 is provided on the first substrate 100 (FIGS. 72 and 73B), the number of through electrodes can be reduced and the insulating region 212 can be reduced. Therefore, a large area of the semiconductor element forming region in the semiconductor layer 200S can be secured. Thus, it becomes possible, for example, to increase the size of the amplification transistor AMP and suppress noise.

The element isolation region 213 is provided on the front surface side of the semiconductor layer 200S. The element isolation region 213 has an STI (Shallow Trench Isolation) structure. In this element isolation region 213, the semiconductor layer 200S is dug in the thickness direction (perpendicular to the main surface of the second substrate 200), and an insulating film is embedded in this digging. This insulating film includes, for example, a silicon oxide. The element isolation region 213 provides an element isolation among the plurality of transistors constituting the pixel circuit 210 according to the layout of the pixel circuit 210. The semiconductor layer 200S (specifically, the well region 211) extends below the element isolation region 213 (deep portion of the semiconductor layer 200S).

Here, with reference to FIGS. 73A, 73B, and 74, the difference between an outer shape of the pixel sharing unit 539 in the first substrate 100 (outer shape in the plane direction of the substrate) and an outer shape of the pixel sharing unit 539 in the second substrate 200 will be described.

In the imaging device 1, the pixel sharing units 539 are provided over both the first substrate 100 and the second substrate 200. For example, the outer shape of the pixel sharing unit 539 provided on the first substrate 100 and the outer shape of the pixel sharing unit 539 provided on the second substrate 200 are different from each other.

In FIGS. 73A and 73B, outlines of the pixels 541A, 541B, 541C, and 541D are represented by alternate long and short dash lines, and an outer shape of the pixel sharing unit 539 is represented by a bold line. For example, the pixel sharing unit 539 of the first substrate 100 includes two pixels 541 (pixels 541A and 541B) arranged adjacent to each other in the H direction and two pixels 541 (pixels 541C and 541D) arranged adjacent thereto in the V direction. That is, the pixel sharing unit 539 of the first substrate 100 includes four pixels 541 of adjacent two rows×two columns, and the pixel sharing unit 539 of the first substrate 100 has a substantially square outer shape. In the pixel array unit 540, such pixel sharing units 539 are arranged adjacent to each other with two-pixel pitches in the H direction (each pitch corresponding to two pixels 541) and two-pixel pitches in the V direction (each pitch corresponding to two pixels 541).

In FIGS. 74 and 75, the outlines of the pixels 541A, 541B, 541C, and 541D are represented by alternate long and short dash lines, and the outer shape of the pixel sharing unit 539 is represented by a bold line. For example, the outer shape of the pixel sharing unit 539 of the second substrate 200 is smaller than the pixel sharing unit 539 of the first substrate 100 in the H direction and larger than the pixel sharing unit 539 of the first substrate 100 in the V direction. For example, the pixel sharing unit 539 of the second substrate 200 is formed with a size (region) corresponding to one pixel in the H direction and a size corresponding to four pixels in the V direction. That is, the pixel sharing unit 539 of the second substrate 200 is formed in a size corresponding to the pixels arranged in adjacent one row×four columns, and the pixel sharing unit 539 of the second substrate 200 has a substantially rectangular outer shape.

For example, in each pixel circuit 210, the selection transistor SEL, the amplification transistor AMP, the reset transistor RST, and the FD conversion gain switching transistor FDG are arranged to line up in this order in the V direction (FIG. 74). By providing the outer shape of each pixel circuit 210 in a substantially rectangular shape as described above, the four transistors (selection transistor SEL, amplification transistor AMP, reset transistor RST, and FD conversion gain switching transistor FDG) can be arranged to line up in one direction (V direction in FIG. 74). Thus, the drain of the amplification transistor AMP and the drain of the reset transistor RST can be shared by one diffusion region (diffusion region connected to the power supply line VDD). For example, the formation region of each pixel circuit 210 can also be provided in a substantially square shape (see FIG. 87 described later). In this case, two transistors are arranged along one direction, and it is difficult to share the drain of the amplification transistor AMP and the drain of the reset transistor RST in one diffusion region. Therefore, by providing the formation region of the pixel circuit 210 in a substantially rectangular shape, it is easy to arrange the four transistors in close proximity to each other, and the formation region of the pixel circuit 210 can be reduced. That is, the pixels can be miniaturized. Furthermore, when it is not necessary to reduce the formation region of the pixel circuit 210, it is possible to increase the formation region of the amplification transistor AMP and suppress noise.

For example, near the surface of the semiconductor layer 200S, the VSS contact region 218 connected to the reference potential line VSS is provided in addition to the selection transistor SEL, the amplification transistor AMP, the reset transistor RST, and the FD conversion gain switching transistor FDG. The VSS contact region 218 is formed by, for example, a p-type semiconductor region. The VSS contact region 218 is electrically connected to the VSS contact region 118 of the first substrate 100 (semiconductor layer 100S) via the wiring of the wiring layer 200T and the through electrode 121E. The VSS contact region 218 is provided at a position adjacent to the source of the FD conversion gain switching transistor FDG, for example, with the element isolation region 213 in between (FIG. 74).

Next, a positional relationship between the pixel sharing unit 539 provided in the first substrate 100 and the pixel sharing unit 539 provided in the second substrate 200 will be described with reference to FIGS. 73B and 74. For example, one pixel sharing unit 539 (for example, on the upper side of the paper plane in FIG. 73B) of the two pixel sharing units 539 lined up in the V direction of the first substrate 100 is connected to one pixel sharing unit 539 (for example, on the left side of the paper plane in FIG. 74) of the two pixel sharing units 539 lined up in the H direction of the second substrate 200. For example, the other pixel sharing unit 539 (for example, on the lower side of the paper plane in FIG. 73B) of the two pixel sharing units 539 lined up in the V direction of the first substrate 100 is connected to the other pixel sharing unit 539 (for example, on the right side of the paper plane in FIG. 74) of the two pixel sharing units 539 lined up in the H direction of the second substrate 200.

For example, in the two pixel sharing units 539 lined up in the H direction of the second substrate 200, an internal layout of one pixel sharing unit 539 (arrangement of transistors, and so on) is substantially equal to the layout in which an internal layout of the other pixel sharing unit 539 is inverted in the V direction and the H direction. Effects obtained by this layout will be described below.

In the two pixel sharing units 539 lined up in the V direction of the first substrate 100, each pad portion 120 is arranged in the central portion of the outer shape of the pixel sharing unit 539, that is, the central portion in the V direction and the H direction of the pixel sharing unit 539 (FIG. 73B). On the other hand, since the pixel sharing unit 539 of the second substrate 200 has a substantially rectangular outer shape that is long in the V direction as described above, for example, the amplification transistor AMP connected to the pad portion 120 is arranged at a position displaced upward on the paper plane from the center of the V direction of the pixel sharing unit 539. For example, when the internal layouts of the two pixel sharing units 539 lined up in the H direction of the second substrate 200 are the same, the distance between the amplification transistor AMP of one pixel sharing unit 539 and the pad portion 120 (for example, the pad portion 120 of the pixel sharing unit 539 on the upper side of the paper plane in FIG. 73B) is relatively short. However, the distance between the amplification transistor AMP of the other pixel sharing unit 539 and the pad portion 120 (for example, the pad portion 120 of the pixel sharing unit 539 on the lower side of the paper plane in FIG. 73B) is long. Therefore, the area of a wiring needed for connecting the amplification transistor AMP and the pad portion 120 is large, and it is possible that the wiring layout of the pixel sharing unit 539 is complicated. This factor may affect the miniaturization of the imaging device 1.

On the other hand, in the two pixel sharing units 539 lined up in the H direction of the second substrate 200, by inverting the internal layouts of each other at least in the V direction, the distance between the amplification transistors AMP of both of these two pixel sharing units 539 and the pad portion 120 can be shortened. Therefore, the imaging device 1 can be easily miniaturized as compared with the configuration in which the internal layouts of the two pixel sharing units 539 lined up in the H direction of the second substrate 200 are the same. Note that although the plane layout of each of the plurality of pixel sharing units 539 of the second substrate 200 is symmetrical in the range illustrated in FIG. 74, when the layout of the first wiring layer W1 illustrated in FIG. 75, which will be described later, is included, the plane layout is asymmetrical.

Furthermore, it is preferable that the internal layouts of the two pixel sharing units 539 lined up in the H direction of the second substrate 200 are inverted with each other in the H direction. The reason for this will be described below. As illustrated in FIG. 75, the two pixel sharing units 539 lined up in the H direction of the second substrate 200 are each connected to the pad portions 120 and 121 of the first substrate 100. For example, the pad portions 120 and 121 are arranged in the central portion in the H direction of the two pixel sharing units 539 lined up in the H direction of the second substrate 200 (between the two pixel sharing units 539 lined up in the H direction). Therefore, by inverting the internal layouts of the two pixel sharing units 539 lined up in the H direction of the second substrate 200 also in the H direction from each other, the distance between each of the plurality of pixel sharing units 539 of the second substrate 200 and the pad portions 120 and 121 can be reduced. That is, the imaging device 1 can be more easily miniaturized.

Furthermore, the positions of the outlines of the pixel sharing units 539 of the second substrate 200 do not have to be aligned with the positions of any of the outlines of the pixel sharing units 539 of the first substrate 100. For example, in one pixel sharing unit 539 (for example, on the left side of the paper plane in FIG. 75) of the two pixel sharing units 539 lined up in the H direction of the second substrate 200, an outline of one side in the V direction (for example, the upper side of the paper plane in FIG. 75) is arranged outside an outline of one side in the V direction of the corresponding pixel sharing unit 539 (for example, the upper side of the paper plane in FIG. 73B) of the first substrate 100. Furthermore, in the other pixel sharing unit 539 (for example, on the right side of the paper plane in FIG. 75) of the two pixel sharing units 539 lined up in the H direction of the second substrate 200, an outline of the other side in the V direction (for example, the lower side of the paper plane in FIG. 75) is arranged outside an outline of the other side in the V direction of the corresponding pixel sharing unit 539 (for example, the lower side of the paper plane in FIG. 73B) of the first substrate 100. By thus arranging the pixel sharing unit 539 of the second substrate 200 and the pixel sharing unit 539 of the first substrate 100 with each other, it is possible to shorten the distance between the amplification transistor AMP and the pad portion 120. Therefore, the imaging device 1 can be easily miniaturized.

Furthermore, the positions of outlines of the plurality of pixel sharing units 539 of the second substrate 200 do not have to be aligned with each other. For example, the two pixel sharing units 539 lined up in the H direction of the second substrate 200 are arranged so that the positions of outlines thereof in the V direction are displaced. Thus, it is possible to shorten the distance between the amplification transistor AMP and the pad portion 120. Therefore, the imaging device 1 can be easily miniaturized.

The repetitive arrangement of the pixel sharing units 539 in the pixel array unit 540 will be described with reference to FIGS. 73B and 75. The pixel sharing unit 539 of the first substrate 100 has the size of two pixels 541 in the H direction and the size of two pixels 541 in the V direction (FIG. 73B). For example, in the pixel array unit 540 of the first substrate 100, the pixel sharing units 539 having a size corresponding to these four pixels 541 are arranged adjacently and repeatedly with two-pixel pitches in the H direction (each pitch corresponding to two pixels 541) and two-pixel pitches in the V direction (each pitch corresponding to two pixels 541). Alternatively, the pixel array unit 540 of the first substrate 100 may be provided with pairs of pixel sharing units 539 in each of which two pixel sharing units 539 are arranged adjacent to each other in the V direction. In the pixel array unit 540 of the first substrate 100, for example, the pairs of pixel sharing units 539 are arranged adjacently and repeatedly with two-pixel pitches in the H direction (each pitch corresponding to two pixels 541) and four-pixel pitches in the V direction (each pitch corresponding to four pixels 541). The pixel sharing unit 539 of the second substrate 200 has the size of one pixel 541 in the H direction and the size of four pixels 541 in the V direction (FIG. 75). For example, the pixel array unit 540 of the second substrate 200 is provided with a pair of pixel sharing units 539 that includes two pixel sharing units 539 having a size corresponding to four pixels 541. The pixel sharing units 539 are arranged adjacent to each other in the H direction and arranged to be displaced in the V direction. In the pixel array unit 540 of the second substrate 200, for example, such pairs of pixel sharing units 539 are arranged adjacently and without any gaps with two-pixel pitches in the H direction (each pitch corresponding to two pixels 541) and four-pixel pitches in the V direction (each pitch corresponding to four pixels 541). Thus, by such repetitive arrangement of the pixel sharing units 539, the pixel sharing unit 539 can be arranged without any gaps. Therefore, the imaging device 1 can be easily miniaturized.

The amplification transistor AMP preferably has, for example, a three-dimensional structure of Fin type or the like (FIG. 72). Thus, the size of the effective gate width becomes large, and noise can be suppressed. The selection transistor SEL, the reset transistor RST, and the FD conversion gain switching transistor FDG have, for example, a planar structure. The amplification transistor AMP may have a planar structure. Alternatively, the selection transistor SEL, the reset transistor RST, or the FD conversion gain switching transistor FDG may have a three-dimensional structure. The wiring layer 200T includes, for example, the passivation film 221, the interlayer insulating film 222, and the plurality of wirings (first wiring layer W1, second wiring layer W2, third wiring layer W3, and fourth wiring layer W4).

The passivation film 221 is in contact with the surface of the semiconductor layer 200S, for example, and covers the entire surface of the semiconductor layer 200S. The passivation film 221 covers the respective gate electrodes of the selection transistor SEL, the amplification transistor AMP, the reset transistor RST, and the FD conversion gain switching transistor FDG. The interlayer insulating film 222 is provided between the passivation film 221 and the third substrate 300. The plurality of wirings (first wiring layer W1, second wiring layer W2, third wiring layer W3, and fourth wiring layer W4) is separated by the interlayer insulating film 222. The interlayer insulating film 222 includes, for example, a silicon oxide.

The wiring layer 200T is provided with, for example, the first wiring layer W1, the second wiring layer W2, the third wiring layer W3, the fourth wiring layer W4, and the contact portions 201 and 202 in this order from the semiconductor layer 200S side, and these are insulated by the interlayer insulating film 222. The interlayer insulating film 222 is provided with a plurality of connection portions for connecting the first wiring layer W1, the second wiring layer W2, the third wiring layer W3, or the fourth wiring layer W4, and their lower layers. A connection portion is a portion in which a conductive material is embedded in a connection hole provided in the interlayer insulating film 222. For example, the interlayer insulating film 222 is provided with a connection portion 218V that connects the first wiring layer W1 and the VSS contact region 218 of the semiconductor layer 200S. For example, the hole diameters of the connection portions connecting such elements of the second substrate 200 are different from hole diameters of the through electrodes 120E and 121E and the through electrodes TGV. Specifically, it is preferable that the hole diameters of the connection holes that connect the elements of the second substrate 200 with each other are smaller than the hole diameters of the through electrodes 120E and 121E and the through electrodes TGV. The reason for this will be described below. The depths of the connection portions (connection portion 218V and so on) provided in the wiring layer 200T are smaller than the depths of the through electrodes 120E and 121E and the through electrode TGV. Therefore, the connection portions allow easily filling a connection hole with the conductive material as compared with the through electrodes 120E and 121E and the through electrodes TGV. By making the hole diameters of this connection portions smaller than the hole diameters of the through electrodes 120E and 121E and the through electrodes TGV, the imaging device 1 can be easily miniaturized.

For example, the first wiring layer W1 connects the through electrode 120E, the gate of the amplification transistor AMP, and the source of the FD conversion gain switching transistor FDG (specifically, the connection hole reaching the source of the FD conversion gain switching transistor FDG). The first wiring layer W1 connects, for example, the through electrode 121E and the connection portion 218V, thereby electrically connecting the VSS contact region 218 of the semiconductor layer 200S and the VSS contact region 118 of the semiconductor layer 100S.

Next, the planar configurations of the wiring layer 200T will be described with reference to FIGS. 76 to 78. FIG. 76 illustrates an example of planar configurations of the first wiring layer W1 and the second wiring layer W2. FIG. 77 illustrates an example of planar configurations of the second wiring layer W2 and the third wiring layer W3. FIG. 78 illustrates an example of planar configurations of the third wiring layer W3 and the fourth wiring layer W4.

For example, the third wiring layer W3 includes wirings TRG1, TRG2, TRG3, TRG4, SELL, RSTL, and FDGL extending in the H direction (row direction) (FIG. 77). These wirings correspond to the plurality of row drive signal lines 542 described with reference to FIG. 70. The wirings TRG1, TRG2, TRG3, and TRG4 are for sending drive signals to the transfer gates TG1, TG2, TG3, and TG4, respectively. The wirings TRG1, TRG2, TRG3, and TRG4 are connected to the transfer gates TG1, TG2, TG3, and TG4, respectively, via the second wiring layer W2, the first wiring layer W1, and the through electrode 120E. The wiring SELL is for sending a drive signal to the gate of the selection transistor SEL, the wiring RSTL is for sending a drive signal to the gate of the reset transistor RST, and the wiring FDGL is for sending a drive signal to the gate of the FD conversion gain switching transistor FDG. The wirings SELL, RSTL, and FDGL are connected to the gates of the selection transistor SEL, the reset transistor RST, and the FD conversion gain switching transistor FDG, respectively, via the second wiring layer W2, the first wiring layer W1, and the connection portion.

For example, the fourth wiring layer W4 includes the power supply line VDD, the reference potential line VSS, and the vertical signal line 543 extending in the V direction (column direction) (FIG. 78). The power supply line VDD is connected to the drain of the amplification transistor AMP and the drain of the reset transistor RST via the third wiring layer W3, the second wiring layer W2, the first wiring layer W1, and the connection portion. The reference potential line VSS is connected to the VSS contact region 218 via the third wiring layer W3, the second wiring layer W2, the first wiring layer W1, and the connection portion 218V. Furthermore, the reference potential line VSS is connected to the VSS contact region 118 of the first substrate 100 via the third wiring layer W3, the second wiring layer W2, the first wiring layer W1, the through electrode 121E, and the pad portion 121. The vertical signal line 543 is connected to the source (Vout) of the selection transistor SEL via the third wiring layer W3, the second wiring layer W2, the first wiring layer W1, and the connection portion.

The contact portions 201 and 202 may be provided at positions overlapping with the pixel array unit 540 in a plan view (for example, FIG. 69), or may be provided on the peripheral portion 540B on the outside of the pixel array unit 540 (for example, FIG. 72). The contact portions 201 and 202 are provided on the surface of the second substrate 200 (the surface on the wiring layer 200T side). The contact portions 201 and 202 are formed by, for example, metals such as Cu (copper) and Al (aluminum). The contact portions 201 and 202 are exposed on the surface of the wiring layer 200T (the surface on the third substrate 300 side). The contact portions 201 and 202 are used for electrical connection between the second substrate 200 and the third substrate 300 and for bonding the second substrate 200 and the third substrate 300 with each other.

FIG. 72 illustrates an example in which a peripheral circuit is provided in the peripheral portion 540B of the second substrate 200. This peripheral circuit may include a part of the row drive unit 520, or a part of the column signal processing unit 550 and the like. Furthermore, as illustrated in FIG. 69, the connection holes H1 and H2 may be arranged near the pixel array unit 540 without arranging the peripheral circuit in the peripheral portion 540B of the second substrate 200.

The third substrate 300 has, for example, the wiring layer 300T and the semiconductor layer 300S in this order from the second substrate 200 side. For example, the surface of the semiconductor layer 300S is provided on the second substrate 200 side. The semiconductor layer 300S is formed by a silicon substrate. A circuit is provided in a portion of the front surface side of the semiconductor layer 300S. Specifically, on the portion of the front surface side of the semiconductor layer 300S, for example, at least a part of the input unit 510A, the row drive unit 520, the timing control section 530, the column signal processing unit 550, the image signal processing unit 560, or the output unit 510B is provided. The wiring layer 300T provided between the semiconductor layer 300S and the second substrate 200 includes, for example, an interlayer insulating film, a plurality of wiring layers separated by the interlayer insulating film, and contact portions 301 and 302. The contact portions 301 and 302 are exposed on a surface of the wiring layer 300T (a surface on the second substrate 200 side), the contact portion 301 is in contact with the contact portion 201 of the second substrate 200, and the contact portion 302 is in contact with the contact portion 202 of the second substrate 200. The contact portions 301 and 302 are electrically connected to a circuit formed in the semiconductor layer 300S (for example, at least one of the input unit 510A, the row drive unit 520, the timing control section 530, the column signal processing unit 550, the image signal processing unit 560, or the output unit 510B). The contact portions 301 and 302 are formed by, for example, metals such as Cu (copper) and aluminum (Al). For example, an external terminal TA is connected to the input unit 510A via the connection hole H1, and an external terminal TB is connected to the output unit 510B via the connection hole H2.

Here, characteristics of the imaging device 1 will be described.

In general, an imaging device mainly includes a photodiode and a pixel circuit. Here, if the area of the photodiode is increased, the charge generated as a result of photoelectric conversion increases, and consequently, the signal/noise ratio (S/N ratio) of the pixel signal is improved and the imaging device can output better image data (image information). On the other hand, if the size of the transistors contained in the pixel circuit (particularly the size of the amplification transistor) is increased, noise generated in the pixel circuit decreases, and consequently, the S/N ratio of the imaging signal is improved and the imaging device can output better image data (image information).

However, in an imaging device in which a photodiode and a pixel circuit are provided on the same semiconductor substrate, if the area of the photodiode is increased within the limited area of the semiconductor substrate, it is conceivable that the sizes of the transistors provided in the pixel circuit become small. Furthermore, if the size of the transistor provided in the pixel circuit is increased, it is conceivable that the area of the photodiode becomes smaller.

In order to solve these problems, for example, the imaging device 1 of the present embodiment uses a structure in which a plurality of pixels 541 shares one pixel circuit 210, and the shared pixel circuit 210 is arranged by overlapping with the photodiode PD. Consequently, it is possible to achieve that the area of the photodiode PD is made as large as possible, and the size of the transistor provided in the pixel circuit 210 is made as large as possible within the limited area of the semiconductor substrate. Thus, the S/N ratio of the pixel signal can be improved, and the imaging device 1 can output better image data (image information).

When achieving a structure in which a plurality of pixels 541 shares one pixel circuit 210 and arranging the pixel circuit 210 by overlapping with the photodiode PD, a plurality of wirings extends from the respective floating diffusions FD of the plurality of pixels 541 to be connected to the one pixel circuit 210. In order to secure a large area of the semiconductor substrate 200 for forming the pixel circuit 210, for example, it is possible to form a connection wiring that interconnects the plurality of extending wires and integrates them into one. Similarly, for a plurality of wirings extending from the VSS contact region 118, it is possible to form a connection wiring that interconnects the plurality of extending wires and integrates them into one.

For example, if the connection wiring for interconnecting the plurality of wirings extending from the respective floating diffusions FD of the plurality of pixels 541 is formed on the semiconductor substrate 200 in which the pixel circuit 210 is formed, it is conceivable that the area for forming the transistors included in the pixel circuit 210 becomes small.

Similarly, if the connection wiring that interconnects the plurality of wirings extending from respective VSS contact regions 118 of the plurality of pixels 541 and integrates them into one is formed on the semiconductor substrate 200 in which the pixel circuit 210 is formed, it is conceivable that the area for forming the transistors included in the pixel circuit 210 becomes small.

In order to solve these problems, for example, in the imaging device 1 of the present embodiment, it is possible to provide a structure in which a plurality of pixels 541 shares one pixel circuit 210, and the shared pixel circuit 210 is arranged by overlapping with the photodiode PD, in which a connection wiring that interconnects respective floating diffusions FD of the plurality of pixels 541 and integrates them into one, and a connection wiring that interconnects respective VSS contact regions 118 provided in the plurality of pixels 541 and integrates them into one, are provided on the first substrate 100.

Here, if the second manufacturing method described above is used as a manufacturing method for providing the connection wiring that interconnects respective floating diffusions FD of the plurality of pixels 541 and integrates them into one, and the connection wiring that interconnects respective VSS contact regions 118 of the plurality of pixels 541 and integrates them into one in the first substrate 100, for example, the manufacturing can be performed using an appropriate process according to the configuration of each of the first substrate 100 and the second substrate 200, and it is possible to manufacture a high-quality, high-performance imaging device. Furthermore, the connection wirings of the first substrate 100 and the second substrate 200 can be formed by a simple process. Specifically, in a case where the second manufacturing method described above is used, the electrodes that connect to the floating diffusions FD and the electrodes that connect to the VSS contact regions 118 are provided on the surface of the first substrate 100 and the surface of the second substrate 200, respectively, which become the bonding interface between the first substrate 100 and the second substrate 200. Moreover, it is preferable to enlarge the electrodes formed on the surfaces of the first substrate 100 and the second substrate 200 so that when these two substrates are bonded together, even if the electrodes provided on the surfaces of the two substrates are displaced, the electrodes formed on the surfaces of the two substrates are in contact with each other. In this case, it is conceivable that it may be difficult to arrange the electrodes described above in the limited areas of the respective pixels provided in the imaging device 1.

In order to solve the problem that a large electrode is required on the bonding interface between the first substrate 100 and the second substrate 200, for example, as a manufacturing method for the imaging device 1 of the present embodiment in which the plurality of pixels 541 shares one pixel circuit 210 and the shared pixel circuit 210 is arranged by overlapping with the photodiode PD, the first manufacturing method described above can be used. Thus, the elements formed on the first substrate 100 and the second substrate 200 can be easily aligned with each other, and an imaging device with high quality and high performance can be manufactured. Moreover, it is possible to provide a unique structure generated by using this manufacturing method. That is, a structure is provided in which the semiconductor layer 100S and the wiring layer 100T of the first substrate 100 and the semiconductor layer 200S and the wiring layer 200T of the second substrate 200 are stacked in this order, in other words, the first substrate 100 and the second substrate 200 are stacked face-to-face, and the through electrodes 120E and 121E are provided that penetrate the semiconductor layer 200S and the wiring layer 100T of the first substrate 100 from the front surface side of the semiconductor layer 200S of the second substrate 200 to reach the front surface of the semiconductor layer 100S of the first substrate 100.

In the structure in which the connection wiring that interconnects the respective floating diffusions FD of the plurality of pixels 541 and integrate them into one, and the connection wiring that interconnects the respective VSS contact regions 118 of the plurality of pixels 541 and integrate them into one are provided in the first substrate 100, if this structure and the second substrate 200 are stacked using the first manufacturing method and the pixel circuit 210 is formed on the second substrate 200, there is a possibility that the heat treatment needed for forming the active elements provided on the pixel circuit 210 affects the connection wirings described above formed on the first substrate 100.

Therefore, in order to solve the above-described problem that the heat treatment when the active elements are formed affects the connection wiring, in the imaging device 1 of the present embodiment, it is desirable to use a conductive material with high heat resistance for the connection wiring that interconnects the respective floating diffusions FD of the plurality of pixels 541 and integrates them into one, and the connection wiring that interconnects the respective VSS contact regions 118 of the plurality of pixels 541 and integrates them into one. Specifically, as the conductive material with high heat resistance, it is possible to use a material having a higher melting point than that for at least a part of wiring materials contained in the wiring layer 200T of the second substrate 200.

As described above, for example, the imaging device 1 of the present embodiment has (1) the structure in which the first substrate 100 and the second substrate 200 are stacked face-to-back (specifically, the semiconductor layer 100S and the wiring layer 100T of the first substrate 100 and the semiconductor layer 200S and the wiring layer 200T of the second substrate 200 are stacked in this order), (2) the structure provided with the through electrodes 120E, 121E that penetrate the semiconductor layer 200S and the wiring layer 100T of the first substrate 100 and reach the front surface of the semiconductor layer 100S of the first substrate 100 from the front surface side of the semiconductor layer 200S of the second substrate 200, and (3) the structure in which the connection wiring that interconnects the respective floating diffusions FD provided in the plurality of pixels 541 and integrates them into one, and the connection wiring that interconnects the respective VSS contact regions 118 provided in the plurality of pixels 541 and integrates them into one, are formed by a conductive material with high heat resistance. It is thereby possible to provide the first substrate 100 with the connection wiring that interconnects the respective floating diffusions FD provided in the plurality of pixels 541 and integrates them into one, and the connection wiring that interconnects the respective VSS contact regions 118 provided in the plurality of pixels 541 and integrates them into one, without providing large electrodes at the interface between the first substrate 100 and the second substrate 200.

(Operation of Imaging Device 1)

Figure 79:
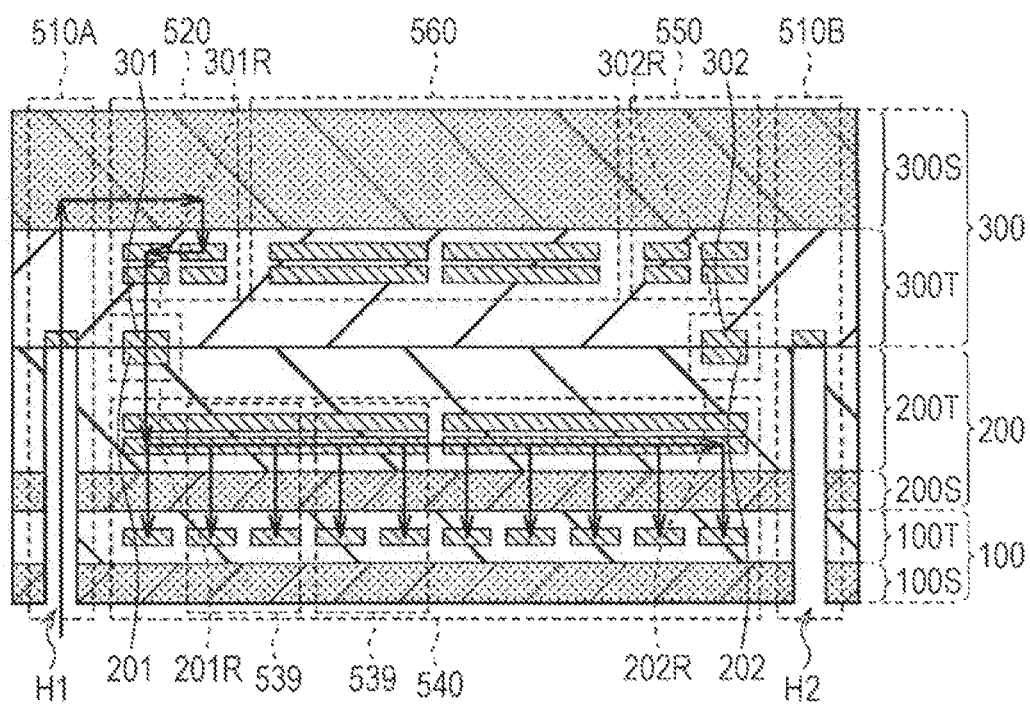
FIG. 79 is a schematic view for explaining a path of an input signal to the imaging device illustrated in FIG. 69.
Figure 80:
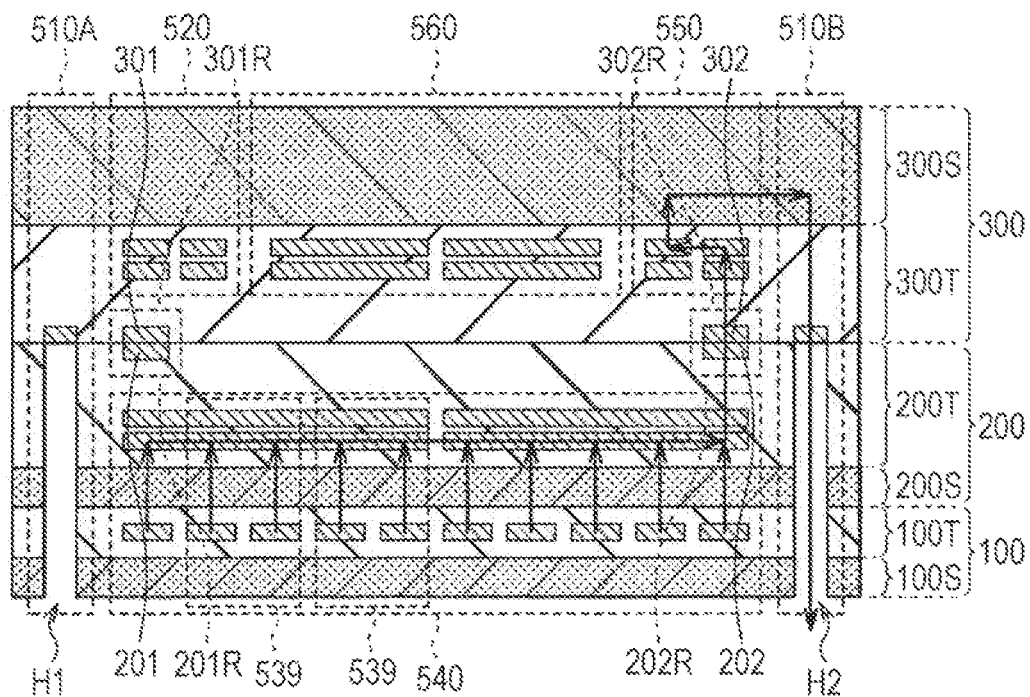
FIG. 80 is a schematic view for explaining a signal path of a pixel signal of the imaging device illustrated in FIG. 69.

Next, operation of the imaging device 1 will be described with reference to FIGS. 79 and 80. FIGS. 79 and 80 are made by adding arrows representing paths of respective signals to FIG. 69. In FIG. 79, paths of an input signal input to the imaging device 1 from the outside and a power supply potential and a reference potential are represented by arrows. In FIG. 80, a signal path of a pixel signal output from the imaging device 1 to the outside is represented by an arrow. For example, the input signal (for example, a pixel clock and a synchronization signal) input to the imaging device 1 via the input unit 510A is transmitted to the row drive unit 520 of the third substrate 300, and a row drive signal is created in the row drive unit 520. This row drive signal is sent to the second substrate 200 via the contact portions 301 and 201. Moreover, the row drive signal reaches each of the pixel sharing units 539 of the pixel array unit 540 via the row drive signal line 542 in the wiring layer 200T. Of the row drive signals that have reached the pixel sharing units 539 of the second substrate 200, a drive signal other than the transfer gate TG is input to the pixel circuit 210, and each transistor included in the pixel circuit 210 is driven. A drive signal for the transfer gate TG is input to the transfer gates TG1, TG2, TG3, and TG4 of the first substrate 100 via the through electrodes TGV, and the pixels 541A, 541B, 541C, and 541D are driven (FIG. 79). Furthermore, the power supply potential and the reference potential supplied from the outside of the imaging device 1 to the input unit 510A (input terminal 511) of the third substrate 300 are sent to the second substrate 200 via the contact portions 301 and 201, and are supplied to the respective pixel circuits 210 of the pixel sharing units 539 via the wirings in the wiring layer 200T. The reference potential is further supplied to the pixels 541A, 541B, 541C, and 541D of the first substrate 100 via the through electrodes 121E. On the other hand, pixel signals photoelectrically converted by the pixels 541A, 541B, 541C, and 541D of the first substrate 100 are sent to the pixel circuit 210 of the second substrate 200 in every pixel sharing unit 539 via the through electrodes 120E. A pixel signal based on the pixel signals is sent from the pixel circuit 210 to the third substrate 300 via the vertical signal line 543 and the contact portions 202 and 302. This pixel signal is processed by the column signal processing unit 550 and the image signal processing unit 560 of the third substrate 300, and then output to the outside via the output unit 510B.

Effects

In the present embodiment, the pixels 541A, 541B, 541C, and 541D (pixel sharing unit 539) and the pixel circuit 210 are provided on different substrates (first substrate 100 and second substrate 200). Thus, the areas of the pixels 541A, 541B, 541C, and 541D and the pixel circuit 210 can be expanded as compared with the case where the pixels 541A, 541B, 541C, and 541D and the pixel circuit 210 are formed on the same substrate. Consequently, it is possible to increase the amount of pixel signals obtained by photoelectric conversion and reduce transistor noise of the pixel circuit 210. Thus, the signal/noise ratio of the pixel signal is improved, and the imaging device 1 can output better pixel data (image information). Furthermore, the imaging device 1 can be miniaturized (in other words, the pixel size can be reduced and the imaging device 1 can be downsized). The imaging device 1 can increase the number of pixels per unit area by reducing the pixel size, and can output a high-quality image.

Furthermore, in the imaging device 1, the first substrate 100 and the second substrate 200 are electrically connected to each other by the through electrodes 120E and 121E provided in the insulating region 212. For example, a method of connecting the first substrate 100 and the second substrate 200 by joining pad electrodes to each other, or a method of connecting by through wiring (for example, thorough Si via (TSV)) penetrating the semiconductor layer are also conceivable. Compared with such methods, by providing the through electrodes 120E and 121E in the insulating region 212, the area required for connecting the first substrate 100 and the second substrate 200 can be reduced. Thus, the pixel size can be reduced and the imaging device 1 can be further downsized. Furthermore, the resolution can be further increased by further miniaturizing the area per pixel. When it is not necessary to reduce the chip size, the formation region of the pixels 541A, 541B, 541C, and 541D and the pixel circuit 210 can be expanded. Consequently, it is possible to increase the amount of pixel signals obtained by photoelectric conversion and reduce the noise of the transistor provided in the pixel circuit 210. Thus, the signal/noise ratio of the pixel signal is improved, and the imaging device 1 can output better pixel data (image information).

Furthermore, in the imaging device 1, the pixel circuit 210, the column signal processing unit 550, and the image signal processing unit 560 are provided on different substrates from each other (second substrate 200 and third substrate 300). Thus, as compared with a case where the pixel circuit 210 and the column signal processing unit 550 and the image signal processing unit 560 are formed in the same substrate, the area of the pixel circuit 210 and the areas of the column signal processing unit 550 and the image signal processing unit 560 can be expanded. Thus, it is possible to reduce the noise generated in the column signal processing unit 550 and to mount an advanced image processing circuit in the image signal processing unit 560. Therefore, the signal/noise ratio of the pixel signal is improved, and the imaging device 1 can output better pixel data (image information).

Further, in the imaging device 1, the pixel array unit 540 is provided on the first substrate 100 and the second substrate 200, and the column signal processing unit 550 and the image signal processing unit 560 are provided on the third substrate 300. Furthermore, the contact portions 201, 202, 301, and 302 connecting the second substrate 200 and the third substrate 300 are formed above the pixel array unit 540. Thus, the contact portions 201, 202, 301, and 302 can be freely laid out without intervention on layout by various wirings provided in the pixel array. Thus, it is possible to use the contact portions 201, 202, 301, and 302 for the electrical connection between the second substrate 200 and the third substrate 300. By using the contact portions 201, 202, 301, and 302, for example, the column signal processing unit 550 and the image signal processing unit 560 have a high degree of freedom in layout. Thus, it is possible to reduce the noise generated in the column signal processing unit 550 and to mount an advanced image processing circuit in the image signal processing unit 560. Therefore, the signal/noise ratio of the pixel signal is improved, and the imaging device 1 can output better pixel data (image information).

Furthermore, in the imaging device 1, the pixel separation part 117 penetrates the semiconductor layer 100S. Thus, even in a case where the distance between adjacent pixels (pixels 541A, 541B, 541C, and 541D) is reduced due to miniaturization of the area per pixel, color mixing between the pixels 541A, 541B, 541C, and 541D can be suppressed. Thus, the signal/noise ratio of the pixel signal is improved, and the imaging device 1 can output better pixel data (image information).

Furthermore, in the imaging device 1, the pixel circuit 210 is provided for every pixel sharing unit 539. Thus, the formation region for the transistors (amplification transistor AMP, reset transistor RST, selection transistor SEL, FD conversion gain switching transistor FDG) constituting the pixel circuit 210 can be increased as compared with a case where the pixel circuit 210 is provided for each of the pixels 541A, 541B, 541C, and 541D. For example, noise can be suppressed by increasing the formation region of the amplification transistor AMP. Thus, the signal/noise ratio of the pixel signal is improved, and the imaging device 1 can output better pixel data (image information).

Moreover, in the imaging device 1, the pad portion 120 for electrically connecting the floating diffusions FD (floating diffusion FD1, FD2, FD3, and FD4) of four pixels (pixels 541A, 541B, 541C, and 541D) is provided in the first substrate 100. Thus, the number of through electrodes (through electrodes 120E) connecting the first substrate 100 and the second substrate 200 can be reduced as compared with the case where such a pad portion 120 is provided on the second substrate 200. Therefore, the insulating region 212 can be made small, and the formation region for the transistors (semiconductor layer 200S) constituting the pixel circuit 210 can be secured with a sufficient size. Thus, it is possible to reduce the noise of the transistors provided in the pixel circuit 210 and improve the signal/noise ratio of the pixel signal, and the imaging device 1 can output better pixel data (image information).

Hereinafter, a modification example of the imaging device 1 according to the seventh embodiment described above will be described. In the following modification example, components common to the seventh embodiment described above will be described with the same reference numerals.

Modification Example 1

Figure 81:
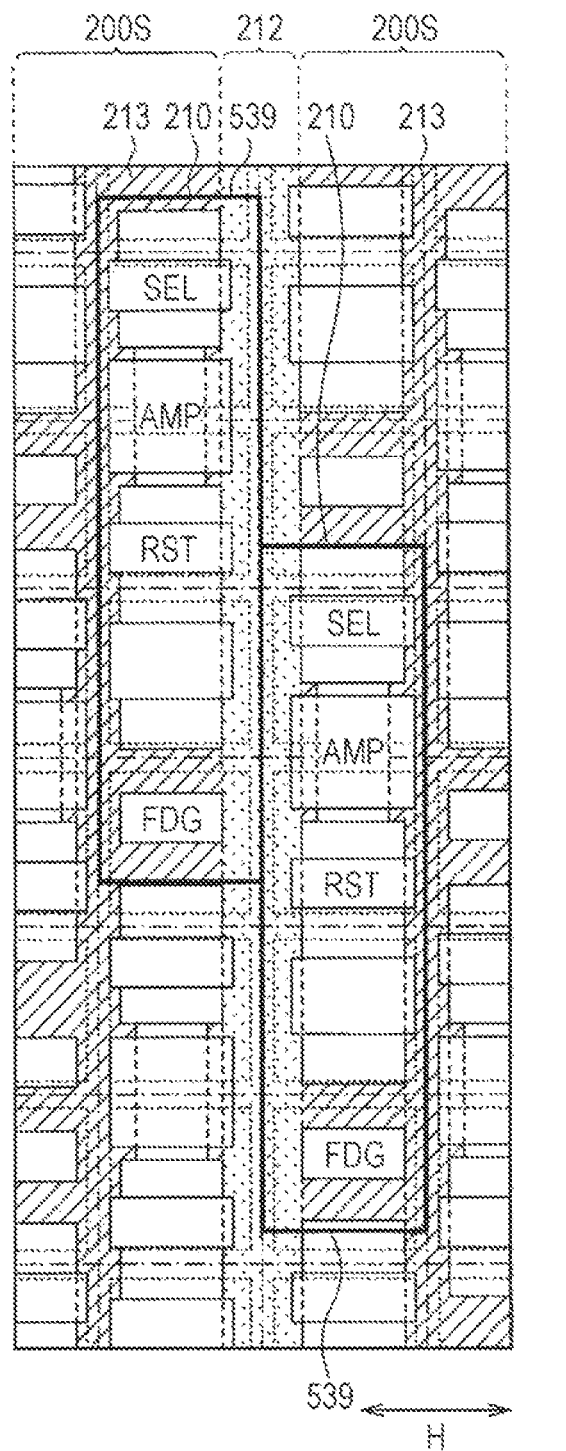
FIG. 81 is a schematic view representing a modification example of the planar configuration of the second substrate (semiconductor layer) illustrated in FIG. 74.
Figure 82:
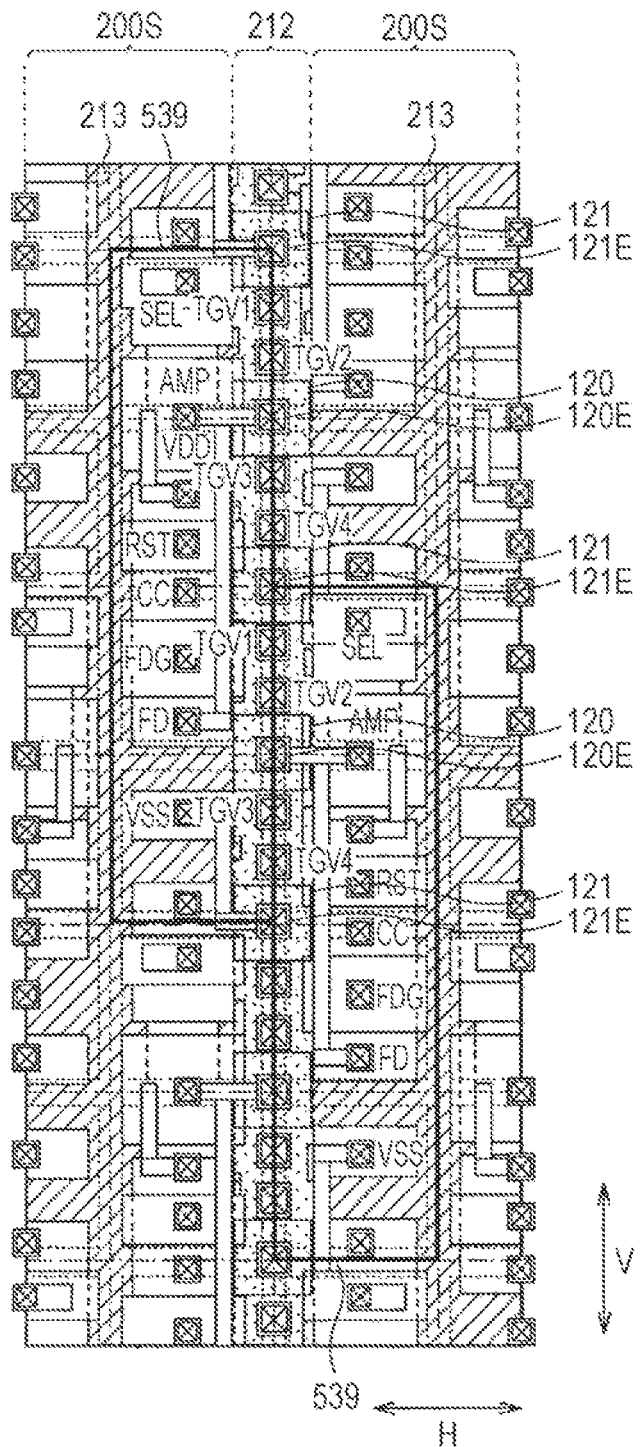
FIG. 82 is a schematic view representing the planar configuration of the first wiring layer and the main part of the first substrate together with a pixel circuit illustrated in FIG. 81.
Figure 83:
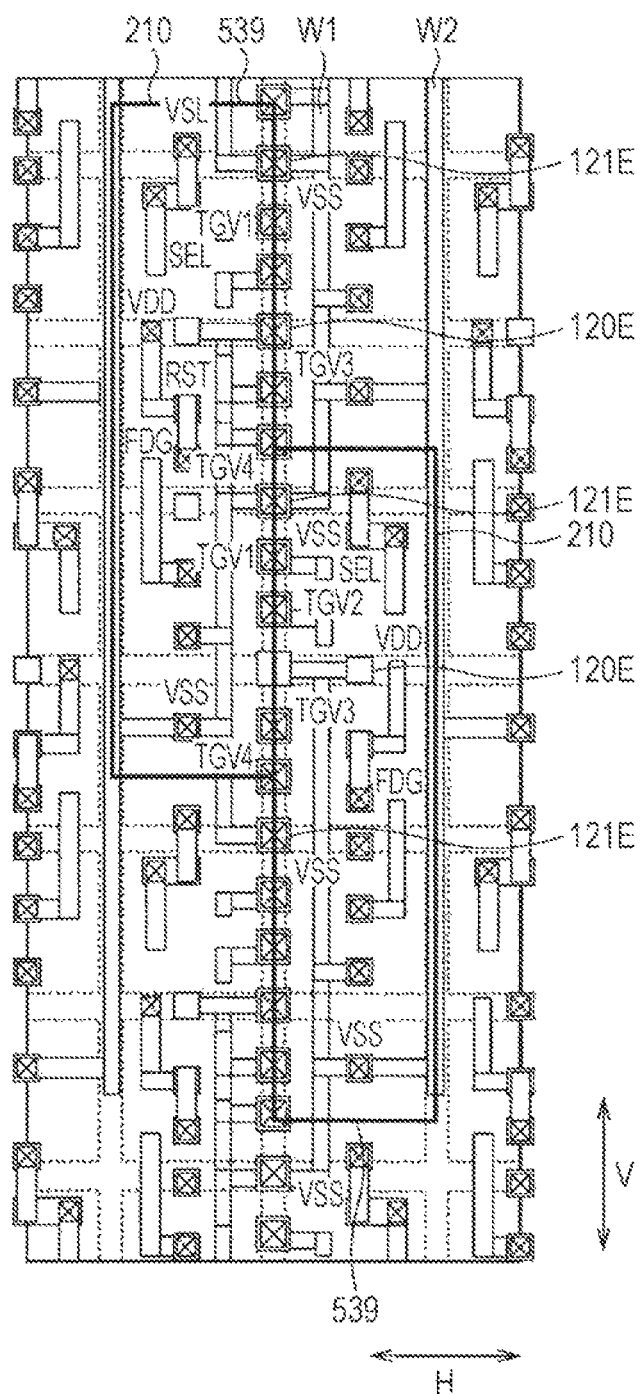
FIG. 83 is a schematic view representing an example of the planar configuration of the second wiring layer together with the first wiring layer illustrated in FIG. 82.
Figure 84:
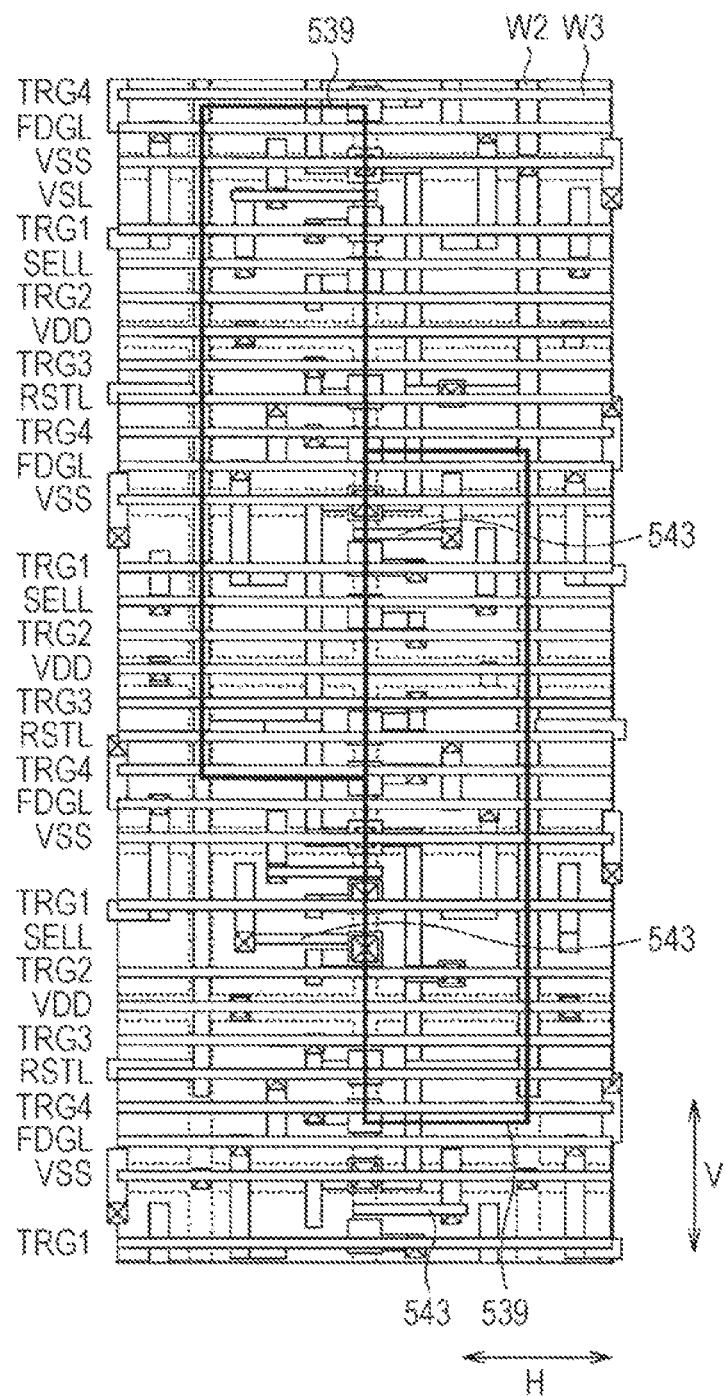
FIG. 84 is a schematic view representing an example of the planar configuration of the third wiring layer together with the second wiring layer illustrated in FIG. 83.
Figure 85:
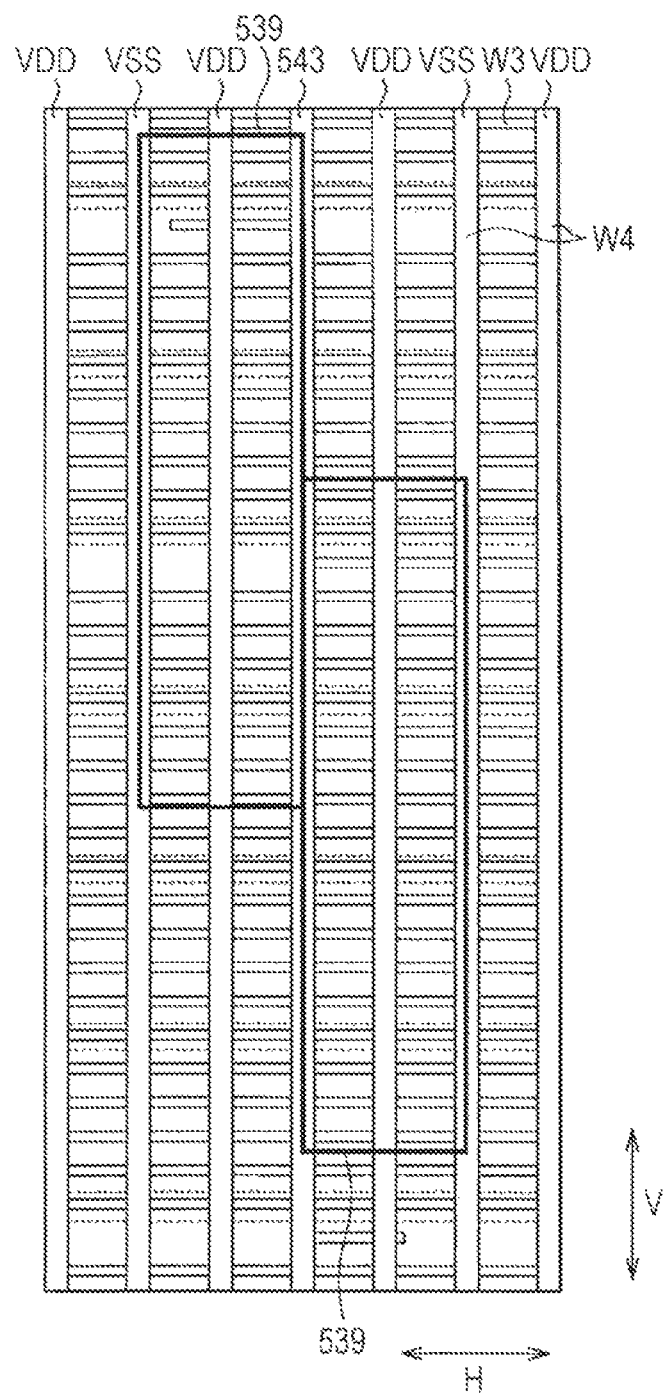
FIG. 85 is a schematic view representing an example of the planar configuration of the fourth wiring layer together with the third wiring layer illustrated in FIG. 84.

FIGS. 81 to 85 represent a modification example of the planar configuration of the imaging device 1 according to the seventh embodiment described above. FIG. 81 schematically represents a planar configuration near the front surface of the semiconductor layer 200S of the second substrate 200 and corresponds to FIG. 74 described in the seventh embodiment described above. FIG. 82 schematically represents configurations of the first wiring layer W1 and respective parts of the semiconductor layer 200S and the first substrate 100 connected to the first wiring layer W1, and corresponds to FIG. 75 described in the seventh embodiment described above described above. FIG. 83 represents an example of planar configurations of the first wiring layer W1 and the second wiring layer W2, and corresponds to FIG. 76 described in the seventh embodiment described above. FIG. 84 represents an example of planar configurations of the second wiring layer W2 and the third wiring layer W3, and corresponds to FIG. 77 described in the seventh embodiment described above. FIG. 85 represents an example of planar configurations of the third wiring layer W3 and the fourth wiring layer W4, and corresponds to FIG. 78 described in the seventh embodiment described above.

In this modification example, as illustrated in FIG. 82, of the two pixel sharing units 539 lined up in the H direction of the second substrate 200, the internal layout of one pixel sharing unit 539 (for example, on the right side of the paper plane) is formed by inverting the internal layout of the other pixel sharing unit 539 (for example, the left side of the paper plane) only in the H direction. Furthermore, the displacement in the V direction between the outline of one pixel sharing unit 539 and the outline of the other pixel sharing unit 539 is larger than the displacement described in the seventh embodiment described above (FIG. 75). Thus, by increasing the displacement in the V direction, the distance between the amplification transistor AMP of the other pixel sharing unit 539 and the pad portion 120 (the pad portion 120 of the other (lower side on the paper plane) of the two pixel sharing units 539 lined up in the V direction illustrated in FIGS. 73A and 73B) connected thereto can be reduced. With such a layout, in modification example 1 of the imaging device 1 illustrated in FIGS. 81 to 85, without inverting plane layouts of the two pixel sharing units 539 lined up in the H direction in the V direction from each other, the areas thereof can be made the same as the areas of the pixel sharing units 539 of the second substrate 200 described in the seventh embodiment described above. Note that the plane layout of the pixel sharing units 539 of the first substrate 100 is the same as the plane layout (FIGS. 73A and 73B) described in the seventh embodiment described above. Therefore, the imaging device 1 of this modification example can obtain similar effects to those of the imaging device 1 described in the seventh embodiment described above. The arrangement of the pixel sharing units 539 of the second substrate 200 is not limited to the arrangement described in the seventh embodiment described above and this modification example.

Modification Example 2

Figure 86:
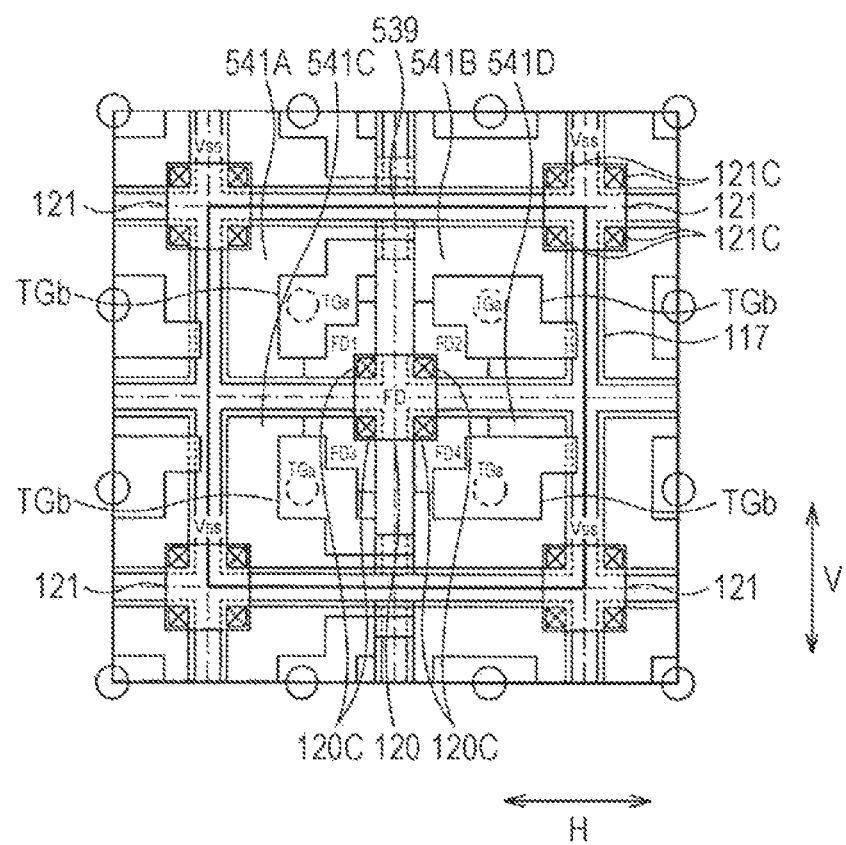
FIG. 86 is a schematic view representing a modification example of the planar configuration of the first substrate illustrated in FIG. 73A.
Figure 87:
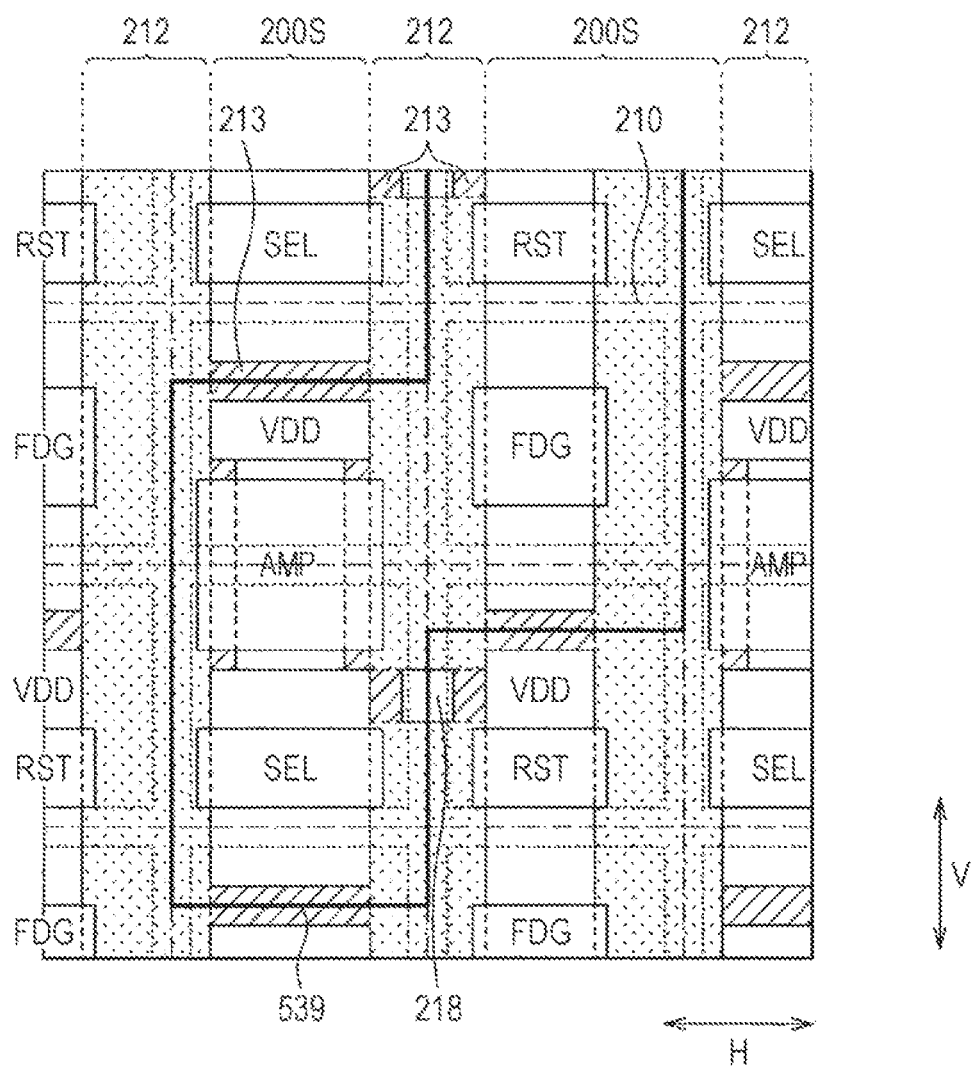
FIG. 87 is a schematic view representing an example of a planar configuration of the second substrate (semiconductor layer) stacked on the first substrate illustrated in FIG. 86.
Figure 88:
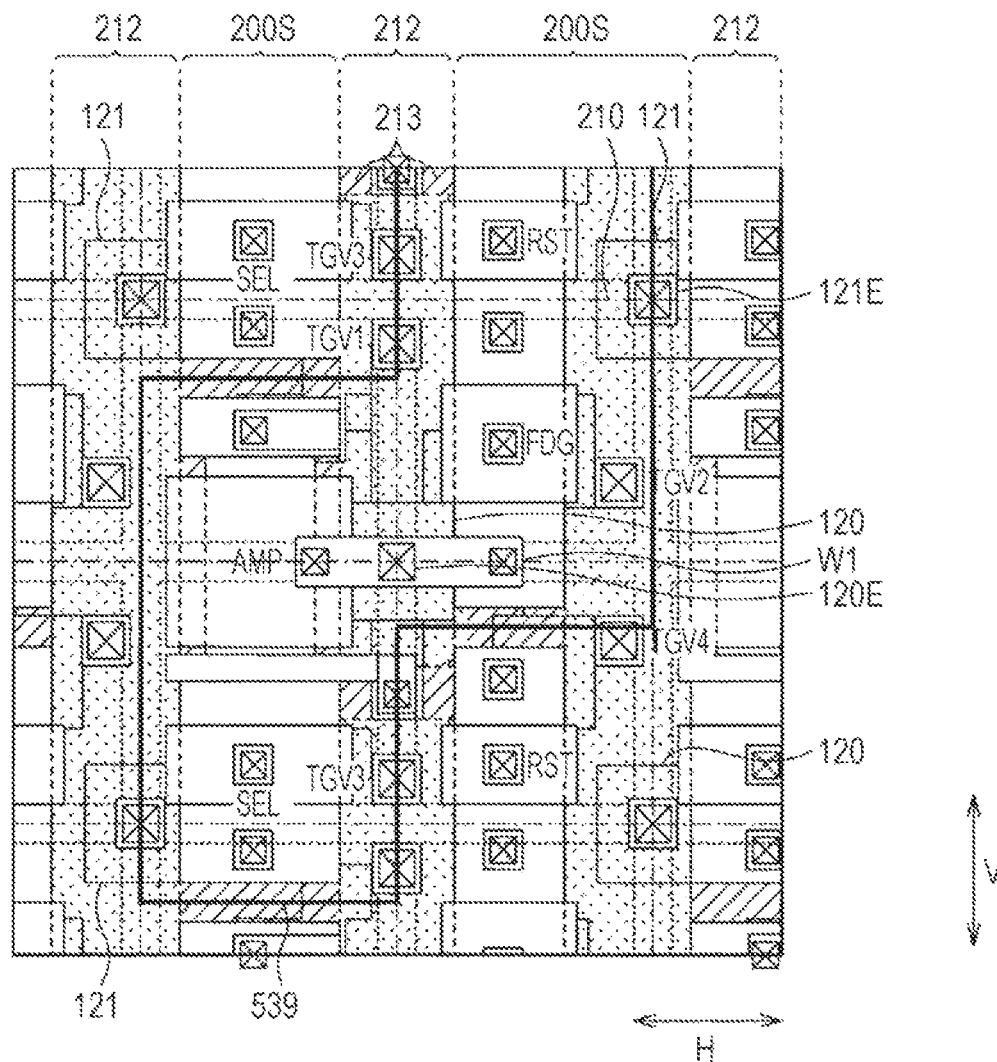
FIG. 88 is a schematic view representing an example of a planar configuration of the first wiring layer together with a pixel circuit illustrated in FIG. 87.
Figure 89:
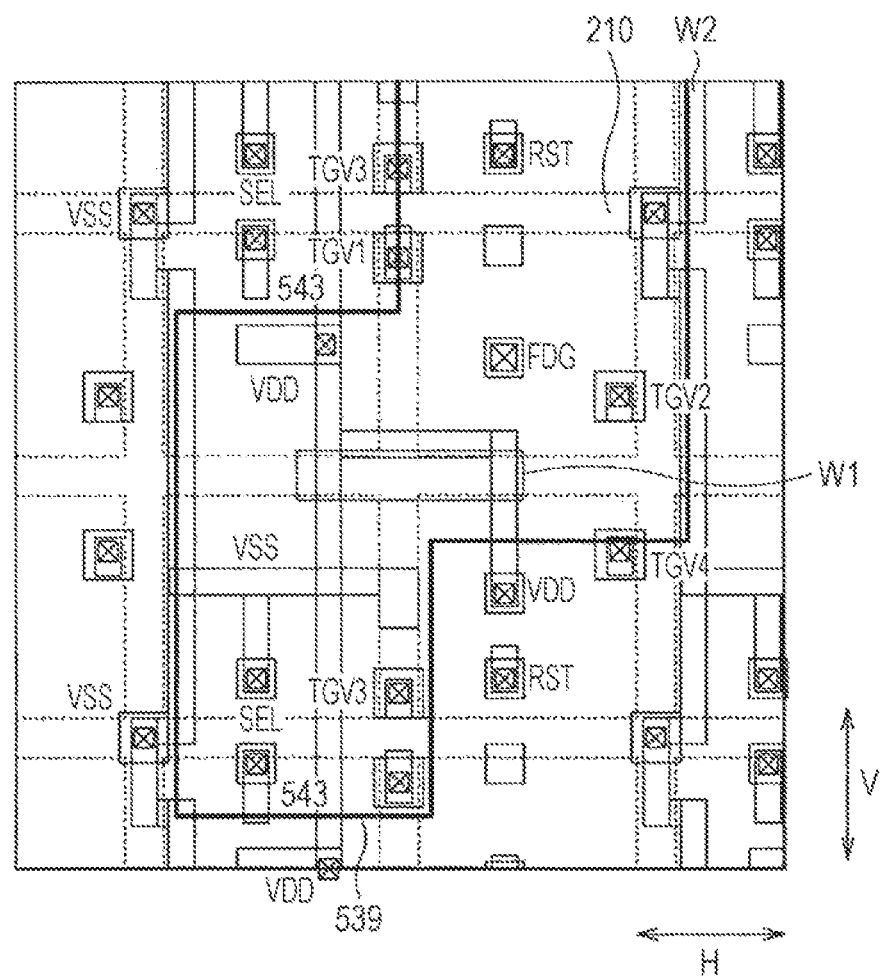
FIG. 89 is a schematic view representing an example of a planar configuration of the second wiring layer together with the first wiring layer illustrated in FIG. 88.
Figure 90:
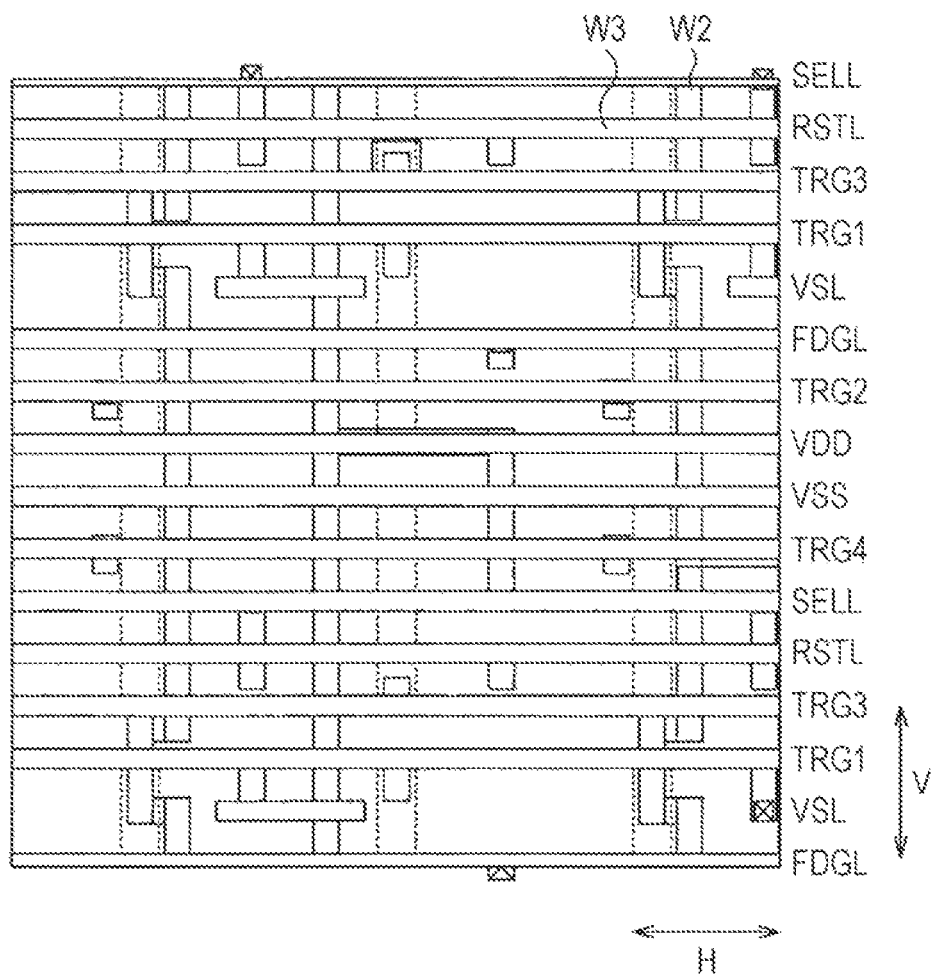
FIG. 90 is a schematic view representing an example of a planar configuration of the third wiring layer together with the second wiring layer illustrated in FIG. 89.
Figure 91:
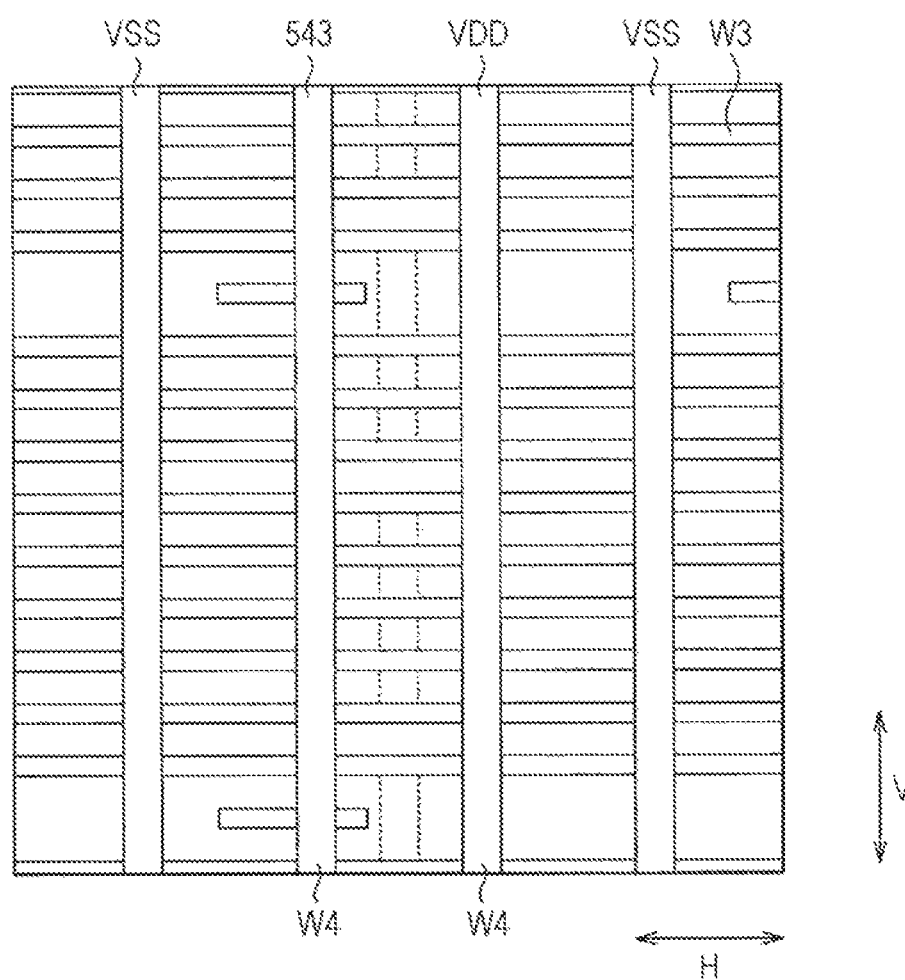
FIG. 91 is a schematic view representing an example of a planar configuration of the fourth wiring layer together with the third wiring layer illustrated in FIG. 90.

FIGS. 86 to 91 represent a modification example of the planar configuration of the imaging device 1 according to the seventh embodiment described above. FIG. 86 schematically represents a planar configuration of the first substrate 100 and corresponds to FIG. 73A described in the seventh embodiment described above. FIG. 87 schematically represents a planar configuration near the front surface of the semiconductor layer 200S of the second substrate 200, and corresponds to FIG. 74 described in the seventh embodiment described above. FIG. 88 schematically represents configurations of the first wiring layer W1 and respective parts of the semiconductor layer 200S and the first substrate 100 connected to the first wiring layer W1, and corresponds to FIG. 75 described in the seventh embodiment described above. FIG. 89 represents an example of planar configurations of the first wiring layer W1 and the second wiring layer W2, and corresponds to FIG. 76 described in the seventh embodiment described above. FIG. 90 represents an example of planar configurations of the second wiring layer W2 and the third wiring layer W3, and corresponds to FIG. 77 described in the seventh embodiment described above. FIG. 91 represents an example of planar configurations of the third wiring layer W3 and the fourth wiring layer W4, and corresponds to FIG. 78 described in the seventh embodiment described above.

In this modification example, the outer shape of each pixel circuit 210 has a substantially square planar shape (FIG. 87 and the like). In this respect, the planar configuration of the imaging device 1 of this modification example is different from the planar configuration of the imaging device 1 described in the seventh embodiment described above.

For example, the pixel sharing unit 539 of the first substrate 100 is formed over a pixel region of two rows×two columns and has a substantially square planar shape, as described in the seventh embodiment described above (FIG. 86).

For example, in each of the pixel sharing units 539, the horizontal portions TGb of the transfer gates TG1, TG3 of the pixel 541A and the pixel 541C of one pixel column extend in a direction toward the central portion of the pixel sharing unit 539 in the H direction from the position where it overlaps with the vertical portion TGa (more specifically, a direction toward outer edges of the pixels 541A, 541C and a direction toward the central portion of the pixel sharing unit 539), and the horizontal portion TGb of the transfer gates TG2 and TG4 of the pixel 541B and the pixel 541D of the other pixel column extend in a direction toward the outside of the pixel sharing unit 539 in the H direction from the position where it overlaps with the vertical portion TGa (more specifically, a direction toward outer edges of the pixels 541B and 541D and a direction toward the outside of the pixel sharing unit 539). The pad portion 120 connected to the floating diffusions FD is provided in the central portion of the pixel sharing unit 539 (the central portion in the H direction and the V direction of the pixel sharing unit 539), and the pad portion 121 connected to the VSS contact regions 118 is provided at an end of the pixel sharing unit 539 at least in the H direction (in the H direction and V direction in FIG. 86).

As another arrangement example, it is conceivable to provide the horizontal portions TGb of the transfer gates TG1, TG2, TG3, and TG4 only in a region facing the vertical portion TGa. At this time, the semiconductor layer 200S is easily divided minutely, as described in the seventh embodiment described above. Therefore, it becomes difficult to form a large transistor of the pixel circuit 210. On the other hand, if the horizontal portions TGb of the transfer gates TG1, TG2, TG3, and TG4 extend in the H direction from the position where they overlap with the vertical portion TGa similarly to that in the above modification example, the width of the semiconductor layer 200S can be increased similarly as described in the seventh embodiment described above. Specifically, the positions in the H direction of the through electrodes TGV1 and TGV3 connected to the transfer gates TG1 and TG3 can be arranged close to the positions of the through electrodes 120E in the H direction, and the positions in the H direction of the through electrodes TGV2 and TGV4 connected to the transfer gates TG2 and TG4 can be arranged close to the positions of the through electrodes 121E in the H direction (FIG. 88). Thus, the width (size in the H direction) of the semiconductor layer 200S extending in the V direction can be increased as described in the seventh embodiment described above. Therefore, it is possible to increase the size of the transistors of the pixel circuit 210, particularly the size of the amplification transistor AMP. Consequently, the signal/noise ratio of the pixel signal is improved, and the imaging device 1 can output better pixel data (image information).

The pixel sharing unit 539 of the second substrate 200 has, for example, substantially the same size as the size in the H direction and the V direction of the pixel sharing unit 539 of the first substrate 100, and is provided over the region corresponding to, for example, a pixel region of approximately two rows×two columns. For example, in each pixel circuit 210, the selection transistor SEL and the amplification transistor AMP are arranged to line up in the V direction on one semiconductor layer 200S extending in the V direction, and the FD conversion gain switching transistor FDG and the reset transistor RST are arranged to line up in the V direction on one semiconductor layer 200S extending in the V direction. This one semiconductor layer 200S provided with the selection transistor SEL and the amplification transistor AMP and the one semiconductor layer 200S provided with the FD conversion gain switching transistor FDG and the reset transistor RST line up in the H direction via the insulating region 212. This insulating region 212 extends in the V direction (FIG. 87).

Here, an outer shape of the pixel sharing unit 539 of the second substrate 200 will be described with reference to FIGS. 87 and 88. For example, the pixel sharing unit 539 of the first substrate 100 illustrated in FIG. 86 is connected to the amplification transistor AMP and the selection transistor SEL provided on one side of the pad portion 120 in the H direction (left side of the paper plane in FIG. 88), and the FD conversion gain switching transistor FDG and the reset transistor RST provided on the other side of the pad portion 120 in the H direction (right side of the paper plane in FIG. 88). An outer shape of the sharing unit 541 of the second substrate 200 including the amplification transistor AMP, the selection transistor SEL, the FD conversion gain switching transistor FDG, and the reset transistor RST is determined by four outer edges as follows.

A first outer edge is an outer edge of the semiconductor layer 200S at one end in the V direction (end on the upper side of the paper plane in FIG. 88) including the selection transistor SEL and the amplification transistor AMP. This first outer edge is provided between the amplification transistor AMP included in the pixel sharing unit 539 and the selection transistor SEL included in a pixel sharing unit 539 adjacent to one side of the pixel sharing unit 539 in the V direction (upper side of the paper plane in FIG. 88). More specifically, the first outer edge is provided in a central portion of the element isolation region 213 in the V direction between the amplification transistor AMP and the selection transistor SEL.

A second outer edge is an outer edge of the semiconductor layer 200S at the other end in the V direction (end on the lower side of the paper plane in FIG. 88) including the selection transistor SEL and the amplification transistor AMP. This second outer edge is provided between the selection transistor SEL included in the pixel sharing unit 539 and the amplification transistor AMP included in a pixel sharing unit 539 adjacent to the other side of the pixel sharing unit 539 in the V direction (lower side of the paper plane in FIG. 88). More specifically, the second outer edge is provided the in a central portion of the element isolation region 213 in the V direction between the selection transistor SEL and the amplification transistor AMP.

A third outer edge is an outer edge of the semiconductor layer 200S at the other end in the V direction (end on the lower side of the paper plane in FIG. 88) including the reset transistor RST and the FD conversion gain switching transistor FDG. This third outer edge is provided between the FD conversion gain switching transistor FDG included in the pixel sharing unit 539 and the reset transistor RST included in the pixel sharing unit 539 adjacent to the other side of the pixel sharing unit 539 in the V direction (lower side of the paper plane in FIG. 88).

More specifically, the third outer edge is provided in a central portion of the element isolation region 213 in the V direction between the FD conversion gain switching transistor FDG and the reset transistor RST. A fourth outer edge is an outer edge of the semiconductor layer 200S at one end in the V direction (end on the upper side of the paper plane in FIG. 88) including the reset transistor RST and the FD conversion gain switching transistor FDG. This fourth outer edge is provided between the reset transistor RST included in the pixel sharing unit 539 and the FD conversion gain switching transistor FDG (not illustrated) included in the pixel sharing unit 539 adjacent to one side of the pixel sharing unit 539 in the V direction (upper side of the paper plane in FIG. 88). More specifically, the fourth outer edge is provided in a central portion of the element isolation region 213 (not illustrated) in the V direction between the reset transistor RST and the FD conversion gain switching transistor FDG.

In the outer shape of the pixel sharing unit 539 of the second substrate 200 including such first, second, third, and fourth outer edges, the third and fourth outer edges are arranged to be displaced to one side in the V direction with respect to the first and second outer edges (in other words, it is offset to one side in the V direction). By using such a layout, both the gate of the amplification transistor AMP and the source of the FD conversion gain switching transistor FDG can be arranged as close as possible to the pad portion 120. Therefore, the area of the wiring connecting these is reduced, and the imaging device 1 can be easily miniaturized. Note that the VSS contact region 218 is provided between the semiconductor layer 200S including the selection transistor SEL and the amplification transistor AMP and the semiconductor layer 200S including the reset transistor RST and the FD conversion gain switching transistor FDG. For example, the plurality of pixel circuits 210 has the same arrangement as each other.

The imaging device 1 having such a second substrate 200 can also obtain similar effects to those described in the seventh embodiment described above. The arrangement of the pixel sharing units 539 of the second substrate 200 is not limited to the arrangement described in the seventh embodiment described above and this modification example.

Modification Example 3

Figure 92:
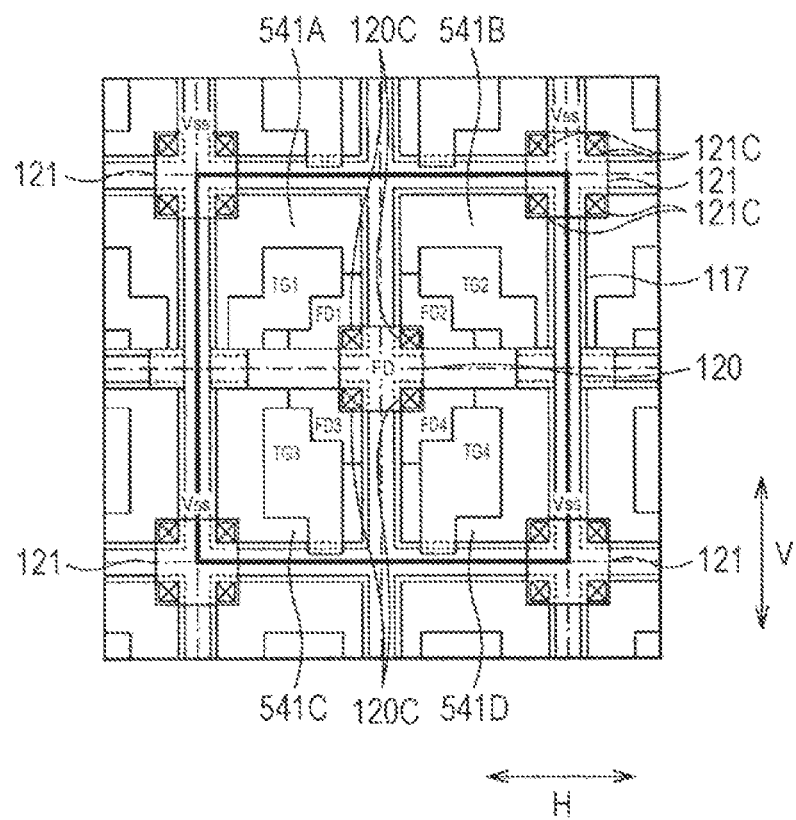
FIG. 92 is a schematic view representing another example of the planar configuration of the first substrate illustrated in FIG. 86.
Figure 93:
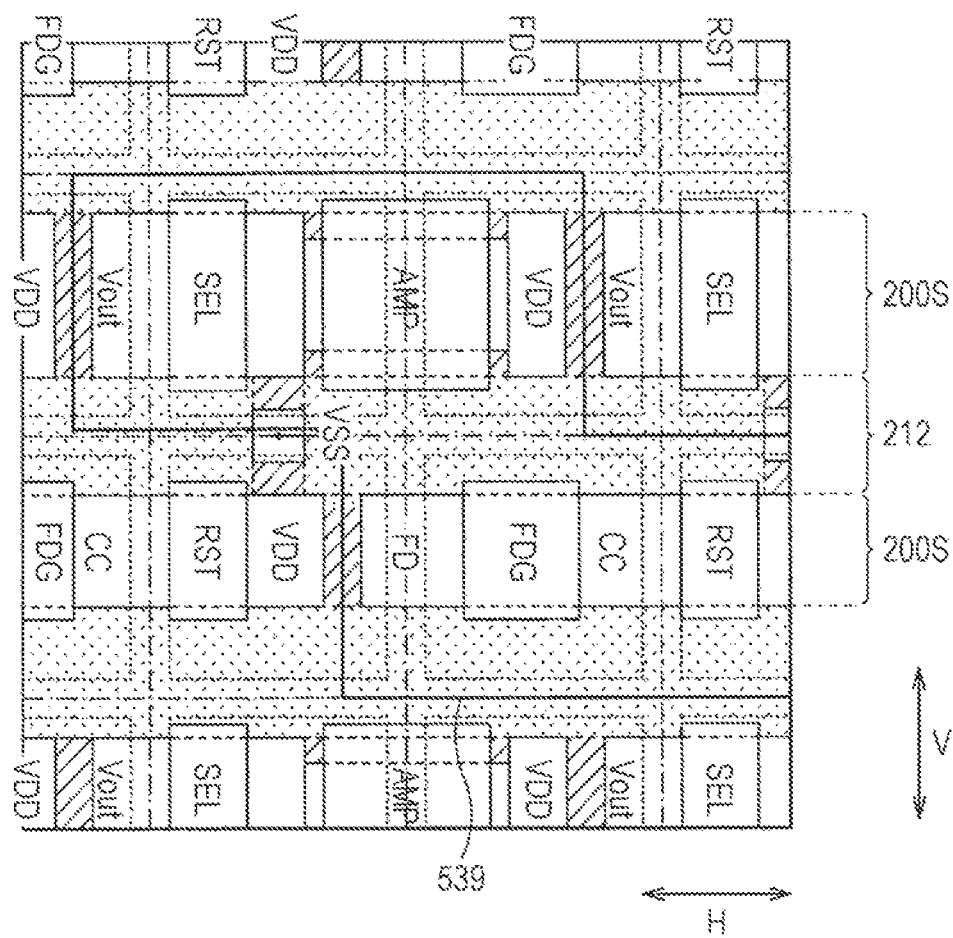
FIG. 93 is a schematic view representing an example of a planar configuration of the second substrate (semiconductor layer) stacked on the first substrate illustrated in FIG. 92.
Figure 94:
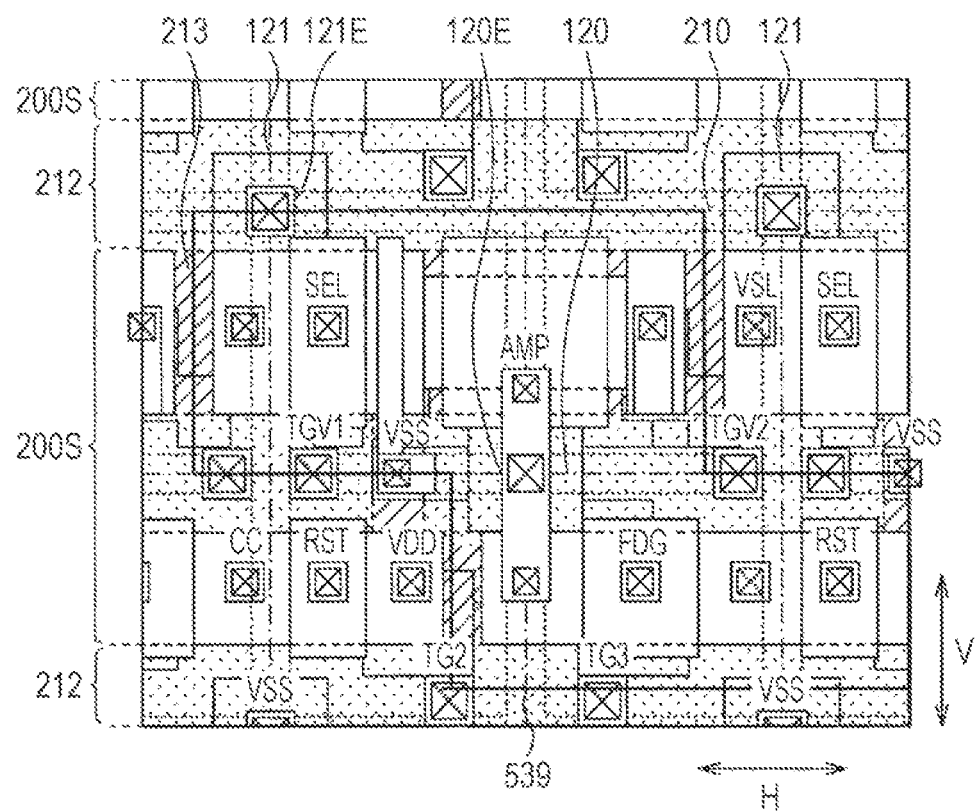
FIG. 94 is a schematic view representing an example of a planar configuration of the first wiring layer together with the pixel circuit illustrated in FIG. 93.
Figure 95:
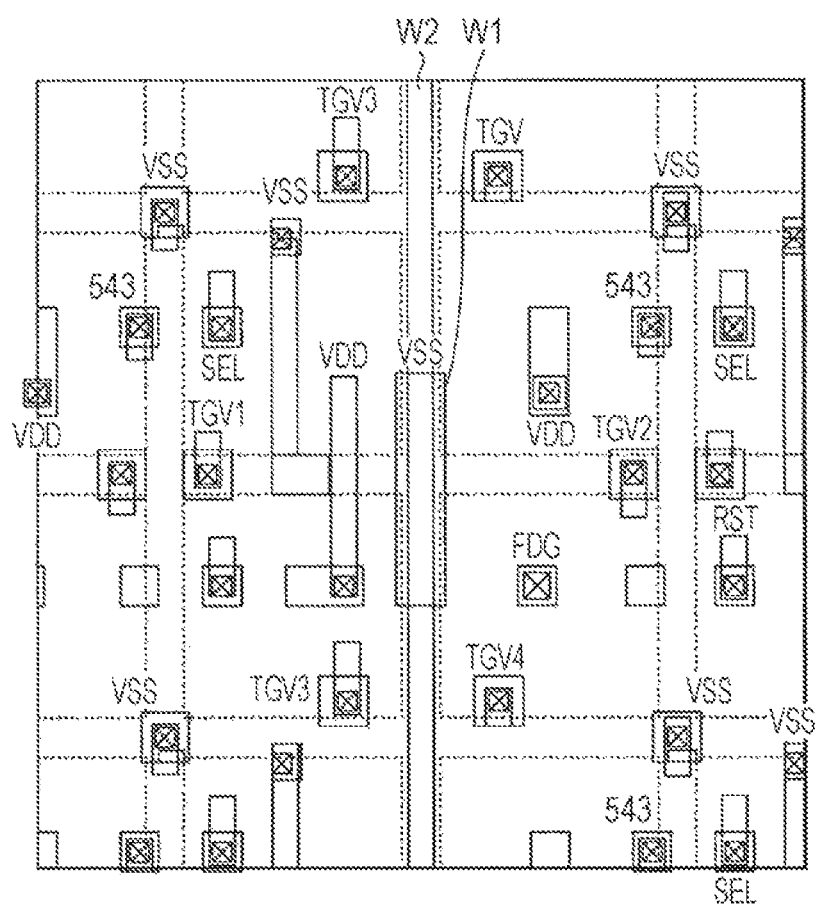
FIG. 95 is a schematic view representing an example of a planar configuration of the second wiring layer together with the first wiring layer illustrated in FIG. 94.
Figure 96:
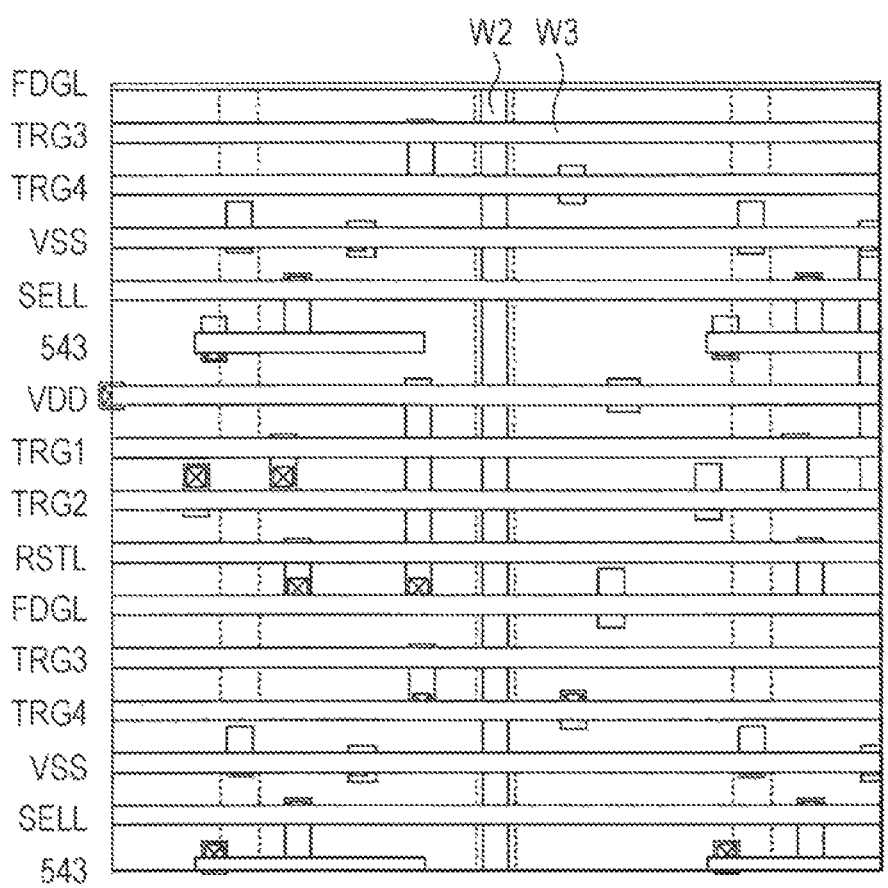
FIG. 96 is a schematic view representing an example of a planar configuration of the third wiring layer together with the second wiring layer illustrated in FIG. 95.
Figure 97:
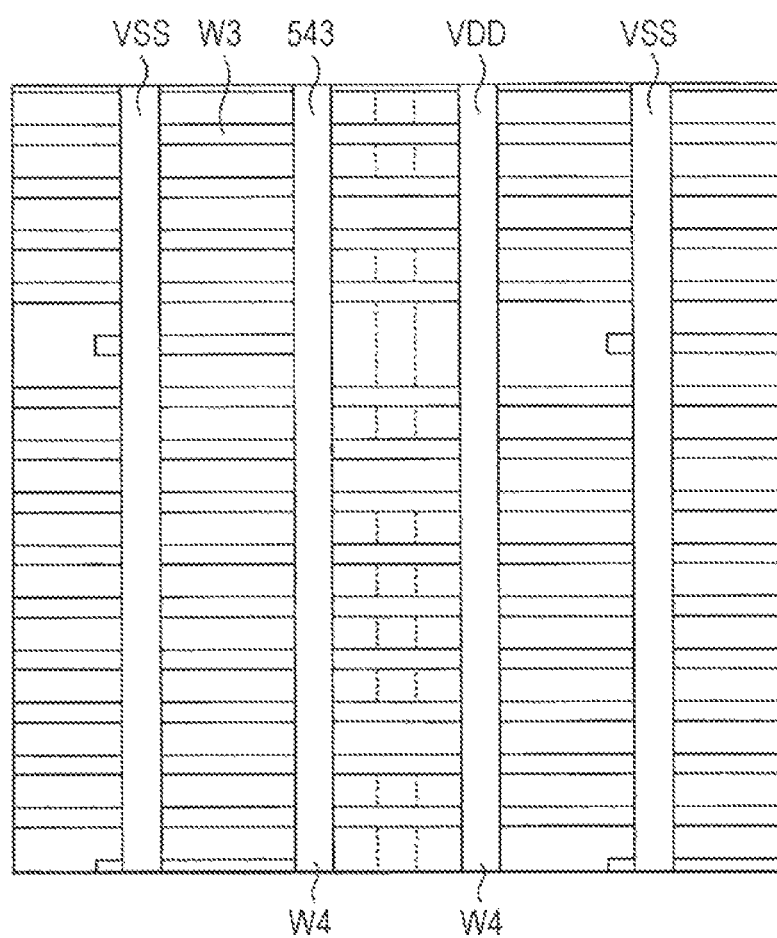
FIG. 97 is a schematic view representing an example of a planar configuration of the fourth wiring layer together with the third wiring layer illustrated in FIG. 96.

FIGS. 92 to 97 represent a modification example of the planar configuration of the imaging device 1 according to the seventh embodiment described above. FIG. 92 schematically represents a planar configuration of the first substrate 100 and corresponds to FIG. 73B described in the seventh embodiment described above. FIG. 93 schematically represents a planar configuration near the front surface of the semiconductor layer 200S of the second substrate 200 and corresponds to FIG. 74 described in the seventh embodiment described above. FIG. 94 schematically represents configurations of the first wiring layer W1 and respective parts of the semiconductor layer 200S and the first substrate 100 connected to the first wiring layer W1, and corresponds to FIG. 75 described in the seventh embodiment described above. FIG. 95 represents an example of planar configurations of the first wiring layer W1 and the second wiring layer W2, and corresponds to FIG. 76 described in the seventh embodiment described above. FIG. 96 represents an example of planar configurations of the second wiring layer W2 and the third wiring layer W3, and corresponds to FIG. 77 described in the seventh embodiment described above. FIG. 97 represents an example of planar configurations of the third wiring layer W3 and the fourth wiring layer W4, and corresponds to FIG. 78 described in the seventh embodiment described above.

In this modification example, the semiconductor layer 200S of the second substrate 200 extends in the H direction (FIG. 94). That is, it substantially corresponds to a configuration in which the planar configuration of the imaging device 1 illustrated in FIG. 87 described above and the like is rotated by 90 degrees.

For example, the pixel sharing unit 539 of the first substrate 100 is formed over a pixel region of two rows×two columns and has a substantially square planar shape, as described in the seventh embodiment described above (FIG. 92). For example, in each pixel sharing unit 539, the transfer gates TG1 and TG2 of the pixel 541A and the pixel 541B in one pixel row extend toward the central portion of the pixel sharing unit 539 in the V direction, and the transfer gates TG3 and TG4 of the pixel 541C and the pixel 541D in the other pixel row extend in a direction toward the outside of the pixel sharing unit 539 in the V direction. The pad portion 120 connected to the floating diffusions FD is provided in the central portion of the pixel sharing unit 539, and the pad portion 121 connected to the VSS contact regions 118 is provided at an end of the pixel sharing unit 539 at least in the V direction (in the V direction and the H direction in FIG. 92). At this time, the positions of the through electrodes TGV1 and TGV2 of the transfer gates TG1 and TG2 in the V direction approach the positions of the through electrodes 120E in the V direction, and the positions of the through electrodes TGV3 and TGV4 of the transfer gates TG3 and TG4 in the V direction approach the position of the through electrodes 121E in the V direction (FIG. 94). Therefore, for a similar reason to that described in the seventh embodiment described above, the width (size in the V direction) of the semiconductor layer 200S extending in the H direction can be increased. Therefore, it is possible to increase the size of the amplification transistor AMP and suppress noise.

In each of the pixel circuits 210, the selection transistor SEL and the amplification transistor AMP are arranged to line up in the H direction, and the reset transistor RST is arranged at an adjacent position in the V direction with the selection transistor SEL and the insulating region 212 in between (FIG. 93). The FD conversion gain switching transistor FDG is arranged to line up with the reset transistor RST in the H direction. The VSS contact region 218 is provided in an island shape in the insulating region 212. For example, the third wiring layer W3 extends in the H direction (FIG. 96), and the fourth wiring layer W4 extends in the V direction (FIG. 97). The imaging device 1 having such a second substrate 200 can also obtain similar effects to those described in the seventh embodiment described above. The arrangement of the pixel sharing units 539 of the second substrate 200 is not limited to the arrangement described in the seventh embodiment described above and this modification example. For example, the semiconductor layer 200S described in the seventh embodiment described above and modification example 1 may extend in the H direction.

Modification Example 4

Figure 98:
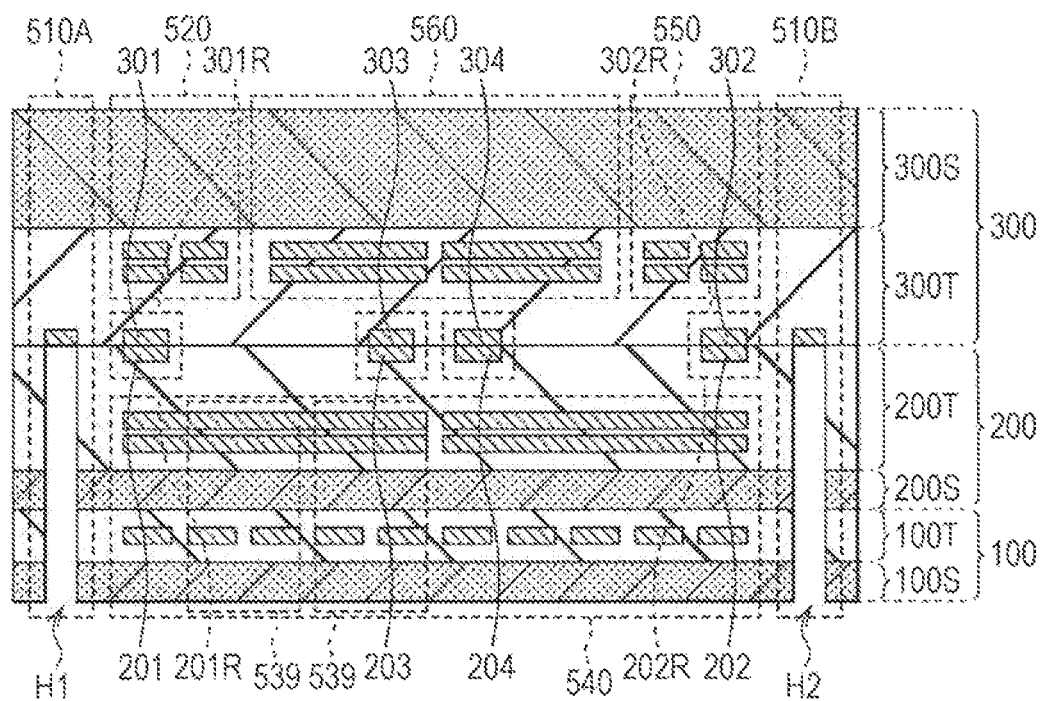
FIG. 98 is a schematic cross-sectional view representing another example of the imaging device illustrated in FIG. 69.

FIG. 98 schematically represents a modification example of the cross-sectional configuration of the imaging device 1 according to the seventh embodiment described above. FIG. 98 corresponds to FIG. 69 described in the seventh embodiment described above. In this modification example, the imaging device 1 has contact portions 203, 204, 303, and 304 at positions facing a central portion of the pixel array unit 540 in addition to the contact portions 201, 202, 301, and 302. In this respect, the imaging device 1 of this modification example is different from the imaging device 1 described in the seventh embodiment described above.

The contact portions 203 and 204 are provided on the second substrate 200, and exposed on the joining surface with the third substrate 300. The contact portions 303 and 304 are provided on the third substrate 300 and are exposed on the joining surface with the second substrate 200. The contact portion 203 is in contact with the contact portion 303, and the contact portion 204 is in contact with the contact portion 304. That is, in this imaging device 1, the second substrate 200 and the third substrate 300 are connected by the contact portions 203, 204, 303, and 304 in addition to the contact portions 201, 202, 301, and 302.

Figure 99:
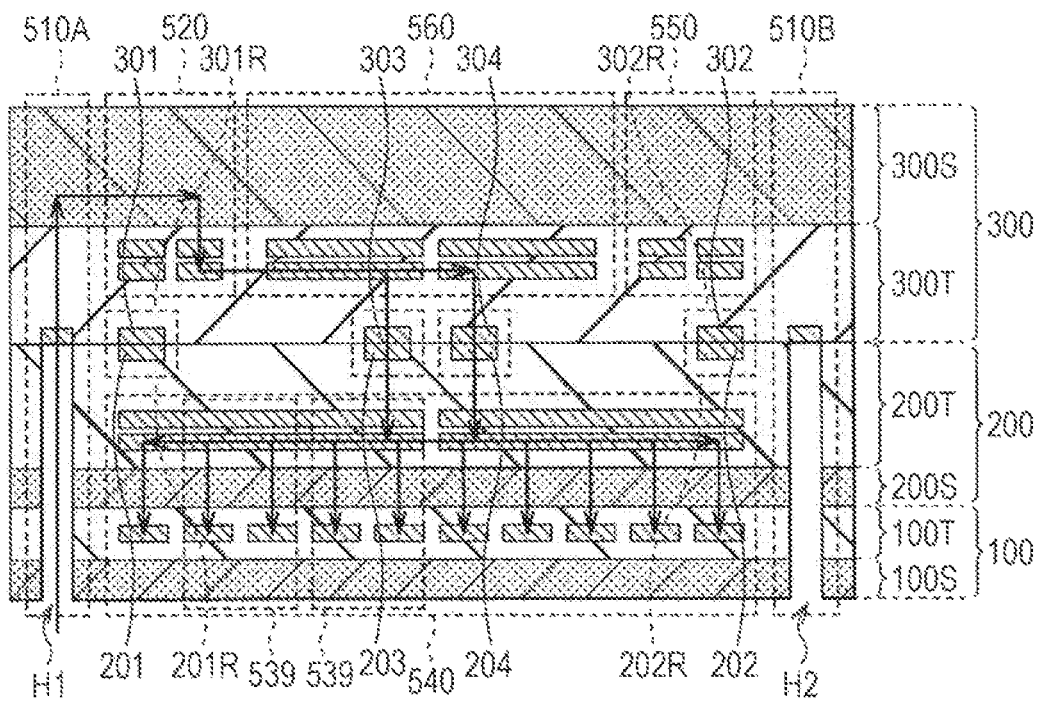
FIG. 99 is a schematic view for explaining a path of an input signal to the imaging device illustrated in FIG. 98.
Figure 100:
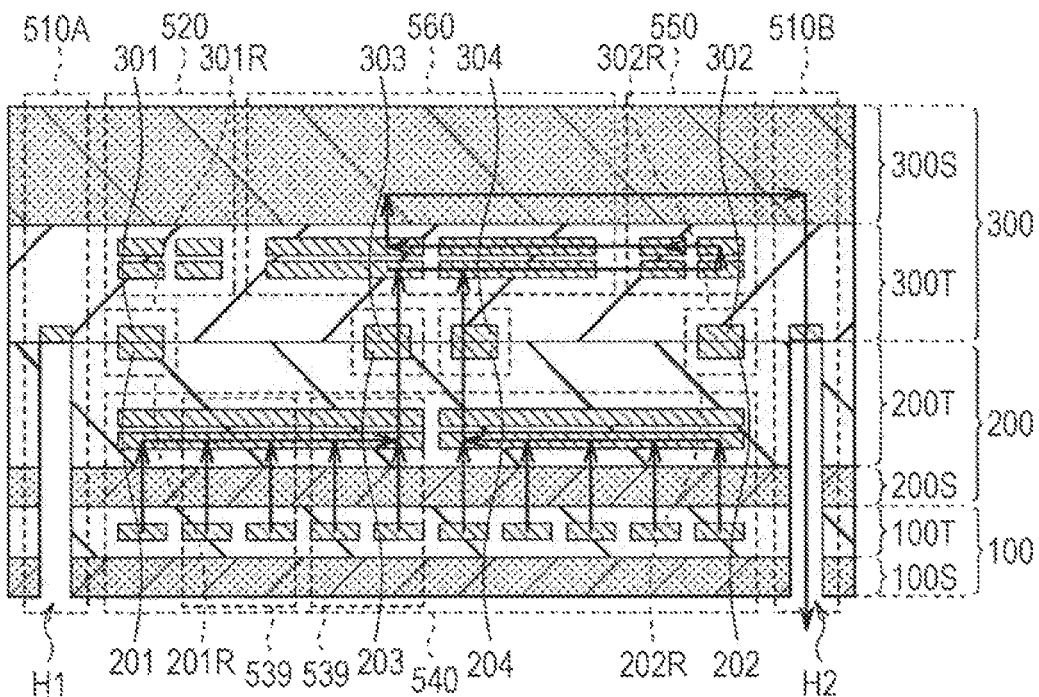
FIG. 100 is a schematic view for explaining a signal path of a pixel signal of the imaging device illustrated in FIG. 98.

Next, operation of the imaging device 1 will be described with reference to FIGS. 99 and 100. In FIG. 99, paths of an input signal input to the imaging device 1 from the outside and a power supply potential and a reference potential are represented by arrows. In FIG. 100, a signal path of a pixel signal output from the imaging device 1 to the outside is represented by an arrow. For example, the input signal input to the imaging device 1 via the input unit 510A is transmitted to the row drive unit 520 of the third substrate 300, and a row drive signal is created in the row drive unit 520. This row drive signal is sent to the second substrate 200 via the contact portions 303 and 203. Moreover, the row drive signal reaches each of the pixel sharing units 539 of the pixel array unit 540 via the row drive signal line 542 in the wiring layer 200T. Of the row drive signals that have reached the pixel sharing units 539 of the second substrate 200, a drive signal other than the transfer gate TG is input to the pixel circuit 210, and each transistor included in the pixel circuit 210 is driven. A drive signal for the transfer gate TG is input to the transfer gates TG1, TG2, TG3, and TG4 of the first substrate 100 via the through electrodes TGV, and the pixels 541A, 541B, 541C, and 541D are driven. Furthermore, the power supply potential and the reference potential supplied from the outside of the imaging device 1 to the input unit 510A (input terminal 511) of the third substrate 300 are sent to the second substrate 200 via the contact portions 303 and 203, and are supplied to the respective pixel circuits 210 of the pixel sharing units 539 via the wirings in the wiring layer 200T. The reference potential is further supplied to the pixels 541A, 541B, 541C, and 541D of the first substrate 100 via the through electrodes 121E. On the other hand, pixel signals photoelectrically converted by the pixels 541A, 541B, 541C, and 541D of the first substrate 100 are sent to the pixel circuit 210 of the second substrate 200 in every pixel sharing unit 539. A pixel signal based on the pixel signals is sent from the pixel circuit 210 to the third substrate 300 via the vertical signal line 543 and the contact portions 204 and 304. This pixel signal is processed by the column signal processing unit 550 and the image signal processing unit 560 of the third substrate 300, and then output to the outside via the output unit 510B.

The imaging device 1 having such contact portions 203, 204, 303, and 304 can also obtain similar effects to those described in the seventh embodiment described above. The positions and number and the like of contact portions can be changed according to the design of the circuit and the like of the third substrate 300, which is the connection destination of the wirings via the contact portions 303 and 304.

Modification Example 5

Figure 101:
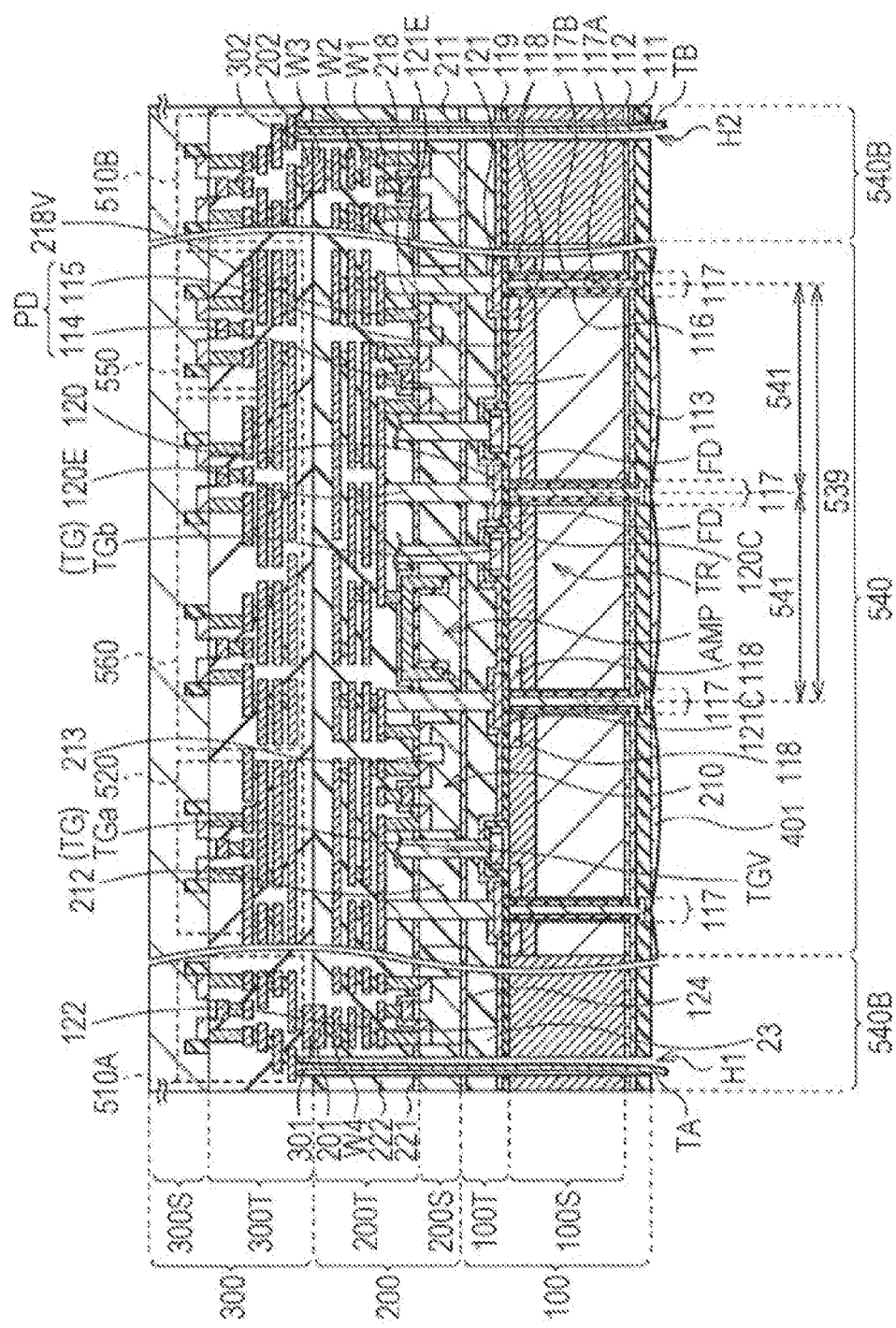
FIG. 101 is a schematic cross-sectional view representing another example of the imaging device illustrated in FIG. 72.

FIG. 101 represents a modification example of the cross-sectional configuration of the imaging device 1 according to the seventh embodiment described above. FIG. 101 corresponds to FIG. 72 described in the seventh embodiment described above. In this modification example, a transfer transistor TR having a planar structure is provided on the first substrate 100. In this respect, the imaging device 1 of this modification example is different from the imaging device 1 described in the seventh embodiment described above.

In this transfer transistor TR, the transfer gate TG includes only a horizontal portion TGb. In other words, the transfer gate TG does not have the vertical portion TGa and is provided so as to face the semiconductor layer 100S.

The imaging device 1 having the transfer transistor TR with such a planar structure can also obtain similar effects to those described in the seventh embodiment described above. Moreover, by providing the planar type transfer gate TG on the first substrate 100, it is conceivable to form a photodiode PD closer to the front surface of the semiconductor layer 100S as compared with the case where the vertical transfer gate TG is provided on the first substrate 100, thereby increasing a saturation signal amount (Qs). Furthermore, a method of forming the planar type transfer gate TG on the first substrate 100 has a smaller number of manufacturing steps than the method of forming the vertical transfer gate TG on the first substrate 100, and it is also conceivable that adverse effects on the photodiodes PD caused by the manufacturing process are unlikely to occur.

Modification Example 6

Figure 102:
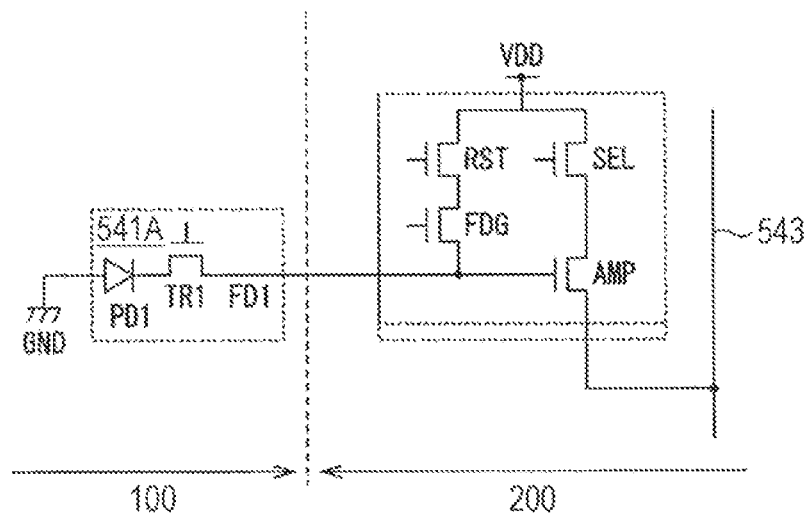
FIG. 102 is a diagram representing another example of an equivalent circuit illustrated in FIG. 70.

FIG. 102 represents a modification example of the pixel circuit of the imaging device 1 according to the seventh embodiment described above. FIG. 102 corresponds to FIG. 70 described in the seventh embodiment described above. In this modification example, a pixel circuit 210 is provided for every pixel (pixel 541A). That is, the pixel circuit 210 is not shared by a plurality of pixels. In this respect, the imaging device 1 of this modification example is different from the imaging device 1 described in the seventh embodiment described above.

The imaging device 1 of this modification example is the same as the imaging device 1 described in the seventh embodiment described above in that the pixels 541A and the pixel circuits 210 are provided on different substrates (first substrate 100 and second substrate 200). Accordingly, the imaging device 1 according to this modification example can also obtain similar effects to those described in the seventh embodiment described above.

Modification Example 7

Figure 103:
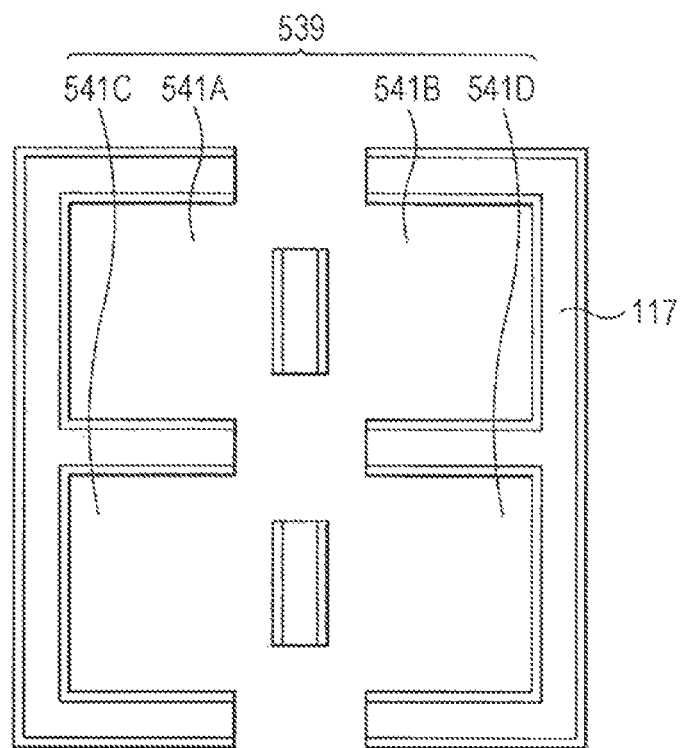

FIG. 103 represents a modification example of the planar configuration of the pixel separation part 117 described in the seventh embodiment described above. A gap may be provided in the pixel separation part 117 surrounding each of the pixels 541A, 541B, 541C, and 541D. That is, it is not required that the entire circumference of the pixels 541A, 541B, 541C, and 541D are surrounded by the pixel separation part 117. For example, the gap of the pixel separation part 117 is provided near the pad portions 120 and 121 (see FIG. 73B).

In the seventh embodiment described above, the example in which the pixel separation part 117 has the FTI structure penetrating the semiconductor layer 100S (see FIG. 72) has been described, but the pixel separation part 117 may have a configuration other than the FTI structure. For example, the pixel separation part 117 is not required to be provided so as to completely penetrate the semiconductor layer 100S, and may have what is called a deep trench isolation (DTI) structure.

OTHER EMBODIMENTS

The above-described first to fifth embodiments and the like have a configuration such that the side of the main surface MSb of the second semiconductor substrate faces the first semiconductor substrate, but is not limited to this. The main surface MSa on the side where the transistors of the second semiconductor substrate are formed may face the first semiconductor substrate. In that case, in the configuration of the first embodiment, the substrate contact layer of the second semiconductor substrate may be grounded by connecting to the upper layer wirings. Furthermore, in the configuration of the second embodiment, the substrate contact layer of the second semiconductor substrate may be grounded by connecting to the first semiconductor substrate.

In addition to the above, the first to fifth embodiments and their modification examples can be combined with each other as appropriate.

Furthermore, the effects described herein are merely examples and are not limited, and other effects may be provided.

Note that the present technology can have configurations as follows.

(1)

A solid-state image sensor including:
a first semiconductor substrate having a photoelectric conversion element; and
a second semiconductor substrate facing the first semiconductor substrate with an insulating film interposed therebetween,
in which the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region.

(2)

The solid-state image sensor according to (1) above, in which
the second semiconductor substrate has a certain conductive type, and
the region with a lower resistance includes a higher concentration of impurities than other regions of the second semiconductor substrate.

(3)

The solid-state image sensor according to (1) or (2) above, further including
a contact extending from the region of the second semiconductor substrate to the first semiconductor substrate side.

(4)

The solid-state image sensor according to (1) or (2) above, further including
a contact extending from the region of the second semiconductor substrate to an opposite side of the first semiconductor substrate.

(5)

The solid-state image sensor according to any one of (1) to (4) above, in which
the second semiconductor substrate is arranged on the first semiconductor substrate with a side of the second main surface facing the first semiconductor substrate.

(6)

The solid-state image sensor according to (5) above, further including
a contact that connects the region of the second semiconductor substrate and the first semiconductor substrate.

(7)

The solid-state image sensor according to (5) above, in which
the region of the second semiconductor substrate has an extended portion that extends toward an outside of the second semiconductor substrate in a direction along the second semiconductor substrate.

(8)

The solid-state image sensor according to (7) above, in which
the extended portion has a third main surface that faces on a same side as the first main surface of the second semiconductor substrate, and
the solid-state image sensor further includes a contact having one end connected to the third main surface of the extended portion and the other end grounded.

(9)

The solid-state image sensor according to (7) above, further including
a contact that penetrates the extended portion and has one end connected to the first semiconductor substrate and the other end grounded.

(10)

The solid-state image sensor according to (7) above, further including
a contact that has one end connected to a side surface of the extended portion and the other end grounded.

(11)

The solid-state image sensor according to any one of (1) to (10) above, in which
the first semiconductor substrate has a transfer transistor that transfers the electrical signal output from the photoelectric conversion element to the amplification transistor.

(12)

The solid-state image sensor according to (11) above, in which
the transfer transistor has a floating diffusion that temporarily holds the electrical signal output from the photoelectric conversion element.

(13)

The solid-state image sensor according to any one of (1) to (12) above, in which
the second semiconductor substrate has:
a reset transistor that resets a potential of a gate of the amplification transistor to a power supply potential; and
a selection transistor that selects whether or not to transmit the electrical signal amplified by the amplification transistor to a signal processing circuit.

(14)

The solid-state image sensor according to (12) above, in which
a gate of the amplification transistor is connected to the floating diffusion.

(15)

The solid-state image sensor according to (13) above, in which
a gate of the amplification transistor is connected to a source of the reset transistor.

(16)

A semiconductor device including:
a first semiconductor substrate having a first transistor; and
a second semiconductor substrate facing the first semiconductor substrate with an insulating film interposed therebetween,
in which the second semiconductor substrate has a second transistor on a first main surface, has a region having a resistance lower than a resistance of the second semiconductor substrate on a second main surface opposite to the first main surface, and is grounded via the region.

(17)

The semiconductor device according to (16) above, in which
the region of the second semiconductor substrate has an extended portion that extends toward an outside of the second semiconductor substrate in a direction along the second semiconductor substrate.

(18)

The semiconductor device according to (16) or (17) above, further including
a third semiconductor substrate that is a floating substrate facing the first semiconductor substrate,
in which the third semiconductor substrate has a third transistor.

(19)
The semiconductor device according to any one of (16) to (18) above, in which
the first semiconductor substrate has a fourth transistor, which is separated from the first transistor by an element isolation region, of a conductive type different from a conductive type of the first transistor.

(20)
The semiconductor device according to any one of (16) to (19) above, in which
the second semiconductor substrate has a fifth transistor, which is separated from the second transistor by an element isolation region, of a conductive type different from a conductive type of the second transistor.

(21)
A solid-state image sensor including:
a first semiconductor substrate having a photoelectric conversion element; and
a second semiconductor substrate facing the first semiconductor substrate with an insulating film interposed therebetween,
in which the second semiconductor substrate includes:
a pixel transistor that processes an electrical signal output from the photoelectric conversion element on a first main surface; and
an electrode to which a predetermined voltage is applied, the electrode being provided at a position that is near a second main surface opposite to the first main surface and corresponds to a gate electrode of the pixel transistor.

(22)
The solid-state image sensor according to (21) above, further including
a wiring that applies the predetermined voltage to the electrode.

(23)
The solid-state image sensor according to (21) or (22) above, in which
the electrode is a back gate electrode that applies a back bias to the pixel transistor by the predetermined voltage being applied.

(24)
The solid-state image sensor according to any one of (21) to (23) above, in which
the pixel transistor includes:
an amplification transistor that amplifies an electrical signal output from the photoelectric conversion element;
a selection transistor that controls transmission of the electrical signal amplified by the amplification transistor; and
a reset transistor that resets a gate potential of the amplification transistor to a power supply potential, and
the electrode includes:
a first electrode arranged at a position corresponding to a gate electrode of the amplification transistor;
a second electrode arranged at a position corresponding to a gate electrode of the selection transistor; and
a third electrode arranged at a position corresponding to a gate electrode of the reset transistor.

(25)
The solid-state image sensor according to (24) above, in which
the first electrode, by the predetermined voltage different from a threshold voltage of the amplification transistor being applied, applies a back bias to the amplification transistor to control the threshold voltage of the amplification transistor,
the second electrode, by the predetermined voltage different from a threshold voltage of the selection transistor being applied, applies a back bias to the selection transistor to control the threshold voltage of the selection transistor, and
the third electrode, by the predetermined voltage different from a threshold voltage of the reset transistor being applied, applies a back bias to the reset transistor to control the threshold voltage of the reset transistor.

(26)
The solid-state image sensor according to (25) above, in which
the first to third electrodes apply back biases of different values to the amplification transistor, the selection transistor, and the reset transistor, respectively, to individually control the respective threshold voltages of the amplification transistor, the selection transistor, and the reset transistor.

(27)
The solid-state image sensor according to any one of (21) to (23) above, in which
the pixel transistor is a selection transistor.

(28)
The solid-state image sensor according to (27) above, in which
the electrode applies a back bias to the selection transistor to make on-resistance of the selection transistor different.

(29)
The solid-state image sensor according to any one of (21) to (28) above, in which
a distance from the second main surface of the second semiconductor substrate to the electrode is ten nanometers or less.

(30)
The solid-state image sensor according to any one of (21) to (29) above, in which
a distance between the first main surface and the second main surface of the second semiconductor substrate is one hundred nanometers or less.

REFERENCE SIGNS LIST

100 Solid-state image sensor
200, 300, 300b, 400 Substrate
102 Photoelectric conversion element
103 Transfer transistor
104, 104b Amplification transistor
105 Reset transistor
106 Selection transistor
251a, 251r, 251s, 252r, 252s Back gate electrode
302, 302b Substrate contact layer
303 Extended portion
BBL Back bias line
Cbga, Cbgr, Cbgs, Csub, CsubbContact
MSa, MSb, MSc Main surface

What is claimed is:
1. A solid-state image sensor, comprising:
a first semiconductor substrate having a photoelectric conversion element; and
a second semiconductor substrate facing the first semiconductor substrate with an insulating film interposed therebetween, wherein the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region, wherein the second semiconductor substrate has a certain conductive type, and wherein the region with a lower resistance includes a higher concentration of impurities than other regions of the second semiconductor substrate.

2. A solid-state image sensor, comprising:

a first semiconductor substrate having a photoelectric conversion element; and a second semiconductor substrate facing the first semiconductor substrate with an insulating film interposed therebetween, wherein the second semiconductor substrate includes:

a pixel transistor that processes an electrical signal output from the photoelectric conversion element on a first main surface; and an electrode to which a predetermined voltage is applied, the electrode being provided at a position that is near a second main surface opposite to the first main surface and corresponds to a gate electrode of the pixel transistor, wherein a distance from the second main surface of the second semiconductor substrate to the electrode is ten nanometers or less.

3. The solid-state image sensor according to claim 1, further comprising a contact extending from the region of the second semiconductor substrate to the first semiconductor substrate side.

4. The solid-state image sensor according to claim 1, further comprising a contact extending from the region of the second semiconductor substrate to an opposite side of the first semiconductor substrate.

5. The solid-state image sensor according to claim 1, wherein the second semiconductor substrate is arranged on the first semiconductor substrate with a side of the second main surface facing the first semiconductor substrate.

6. The solid-state image sensor according to claim 5, further comprising a contact that connects the region of the second semiconductor substrate and the first semiconductor substrate.

7. The solid-state image sensor according to claim 5, wherein the region of the second semiconductor substrate has an extended portion that extends toward an outside of the second semiconductor substrate in a direction along the second semiconductor substrate.

8. A solid-state image sensor, comprising:

a first semiconductor substrate having a photoelectric conversion element;

a second semiconductor substrate facing the first semiconductor substrate with an insulating film interposed therebetween, wherein the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region, wherein the second semiconductor substrate is arranged on the first semiconductor substrate with a side of the second main surface facing the first semiconductor substrate;

a contact that connects the region of the second semiconductor substrate and the first semiconductor substrate, wherein the region of the second semiconductor substrate has an extended portion that extends toward an outside of the second semiconductor substrate in a direction along the second semiconductor substrate, wherein the extended portion has a third main surface that faces on a same side as the first main surface of the second semiconductor substrate; and a contact having one end connected to the third main surface of the extended portion and another end grounded.

9. A solid-state image sensor, comprising:

a first semiconductor substrate having a photoelectric conversion element;

a second semiconductor substrate facing the first semiconductor substrate with an insulating film interposed therebetween, wherein the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region, wherein the second semiconductor substrate is arranged on the first semiconductor substrate with a side of the second main surface facing the first semiconductor substrate;

a contact that connects the region of the second semiconductor substrate and the first semiconductor substrate, wherein the region of the second semiconductor substrate has an extended portion that extends toward an outside of the second semiconductor substrate in a direction along the second semiconductor substrate; and a contact that penetrates the extended portion and has one end connected to the first semiconductor substrate and another end grounded.

10. A solid-state image sensor, comprising:

a first semiconductor substrate having a photoelectric conversion element;

a second semiconductor substrate facing the first semiconductor substrate with an insulating film interposed therebetween, wherein the second semiconductor substrate has an amplification transistor that amplifies an electrical signal output from the photoelectric conversion element on a first main surface, has a region having a resistance lower than a resistance of the second semiconductor substrate on a second main surface opposite to the first main surface, and is grounded via the region, wherein the second semiconductor substrate is arranged on the first semiconductor substrate with a side of the second main surface facing the first semiconductor substrate;

a contact that connects the region of the second semiconductor substrate and the first semiconductor substrate, wherein the region of the second semiconductor substrate has an extended portion that extends toward an outside of the second semiconductor substrate in a direction along the second semiconductor substrate; and a contact that has one end connected to a side surface of the extended portion and another end grounded.

11. The solid-state image sensor according to claim 8, wherein
the second semiconductor substrate has a certain conductive type, and
the region with a lower resistance includes a higher concentration of impurities than other regions of the second semiconductor substrate.

12. The solid-state image sensor according to claim 2, further comprising
a wiring that applies the predetermined voltage to the electrode.

13. The solid-state image sensor according to claim 2, wherein
the electrode is a back gate electrode that applies a back bias to the pixel transistor by the predetermined voltage being applied.

14. The solid-state image sensor according to claim 2, wherein
the pixel transistor includes:
an amplification transistor that amplifies an electrical signal output from the photoelectric conversion element;
a selection transistor that controls transmission of the electrical signal amplified by the amplification transistor; and
a reset transistor that resets a gate potential of the amplification transistor to a power supply potential, and
the electrode includes:
a first electrode arranged at a position corresponding to a gate electrode of the amplification transistor;
a second electrode arranged at a position corresponding to a gate electrode of the selection transistor; and
a third electrode arranged at a position corresponding to a gate electrode of the reset transistor.

15. A solid-state image sensor, comprising:
a first semiconductor substrate having a photoelectric conversion element; and
a second semiconductor substrate facing the first semiconductor substrate with an insulating film interposed therebetween,
wherein the second semiconductor substrate includes:
a pixel transistor that processes an electrical signal output from the photoelectric conversion element on a first main surface; and
an electrode to which a predetermined voltage is applied, the electrode being provided at a position that is near a second main surface opposite to the first main surface and corresponds to a gate electrode of the pixel transistor, wherein
the pixel transistor includes:
an amplification transistor that amplifies an electrical signal output from the photoelectric conversion element;
a selection transistor that controls transmission of the electrical signal amplified by the amplification transistor; and
a reset transistor that resets a gate potential of the amplification transistor to a power supply potential, and
the electrode includes:
a first electrode arranged at a position corresponding to a gate electrode of the amplification transistor;
a second electrode arranged at a position corresponding to a gate electrode of the selection transistor; and
a third electrode arranged at a position corresponding to a gate electrode of the reset transistor,
wherein the first electrode, by the predetermined voltage different from a threshold voltage of the amplification transistor being applied, applies a back bias to the amplification transistor to control the threshold voltage of the amplification transistor,
wherein the second electrode, by the predetermined voltage different from a threshold voltage of the selection transistor being applied, applies a back bias to the selection transistor to control the threshold voltage of the selection transistor, and
wherein the third electrode, by the predetermined voltage different from a threshold voltage of the reset transistor being applied, applies a back bias to the reset transistor to control the threshold voltage of the reset transistor.

16. The solid-state image sensor according to claim 15, wherein
the first to third electrodes apply back biases of different values to the amplification transistor, the selection transistor, and the reset transistor, respectively, to individually control the respective threshold voltages of the amplification transistor, the selection transistor, and the reset transistor.

17. The solid-state image sensor according to claim 2, wherein
the pixel transistor is a selection transistor.

18. The solid-state image sensor according to claim 17, wherein
the electrode applies a back bias to the selection transistor to make on-resistance of the selection transistor different.

19. A solid-state image sensor, comprising:
a first semiconductor substrate having a photoelectric conversion element; and
a second semiconductor substrate facing the first semiconductor substrate with an insulating film interposed therebetween,
wherein the second semiconductor substrate includes:
a pixel transistor that processes an electrical signal output from the photoelectric conversion element on a first main surface; and
an electrode to which a predetermined voltage is applied, the electrode being provided at a position that is near a second main surface opposite to the first main surface and corresponds to a gate electrode of the pixel transistor,
wherein a distance between the first main surface and the second main surface of the second semiconductor substrate is one hundred nanometers or less.

20. The solid-state image sensor according to claim 19, further comprising
a wiring that applies the predetermined voltage to the electrode.

* * * * *